(12) United States Patent
Hahn et al.

(10) Patent No.: US 12,422,440 B2
(45) Date of Patent: Sep. 23, 2025

(54) NEWBORN SCREENING FOR PRIMARY IMMUNODEFICIENCIES, CYSTINOSIS, AND WILSON DISEASE

(71) Applicants: Seattle Children's Hospital, Seattle, WA (US); Fred Hutchinson Cancer Center, Seattle, WA (US)

(72) Inventors: Sihoun Hahn, Clyde Hill, WA (US); Sunhee Jung, Seattle, WA (US); Jeffrey Whiteaker, Seattle, WA (US); Troy Torgerson, Seattle, WA (US); Amanda Paulovich, Seattle, WA (US); Christopher Collins, Seattle, WA (US); Remwilyn Dayuha, Lynnwood, WA (US)

(73) Assignees: Seattle Children's Hospital, Seattle, WA (US); Fred Hutchinson Cancer Research Center, Seattle, WA (US)

( * ) Notice: Subject to any disclaimer, the term of this patent is extended or adjusted under 35 U.S.C. 154(b) by 934 days.

(21) Appl. No.: 17/282,989

(22) PCT Filed: Oct. 4, 2019

(86) PCT No.: PCT/US2019/054856
§ 371 (c)(1),
(2) Date: Apr. 5, 2021

(87) PCT Pub. No.: WO2020/072996
PCT Pub. Date: Apr. 9, 2020

(65) Prior Publication Data
US 2021/0341492 A1    Nov. 4, 2021

Related U.S. Application Data

(60) Provisional application No. 62/742,161, filed on Oct. 5, 2018.

(51) Int. Cl.
*G01N 33/68*    (2006.01)
*C07K 16/28*    (2006.01)

(52) U.S. Cl.
CPC ..... *G01N 33/6893* (2013.01); *C07K 16/2809* (2013.01); *G01N 33/6848* (2013.01); *C07K 2317/34* (2013.01); *C07K 2317/565* (2013.01); *G01N 2800/24* (2013.01); *G01N 2800/60* (2013.01)

(58) Field of Classification Search
CPC ............................ G01N 2800/60; C07K 16/18
See application file for complete search history.

(56) References Cited

U.S. PATENT DOCUMENTS

| | | |
|---|---|---|
| 7,632,686 B2 | 12/2009 | Anderson |
| 8,383,417 B2 | 2/2013 | Lopez et al. |
| 9,588,126 B2 | 3/2017 | Anderson |
| 10,590,190 B2 | 3/2020 | Rosenthal et al. |
| 2007/0099251 A1 | 5/2007 | Zhang et al. |
| 2007/0243119 A1 | 10/2007 | Mao et al. |
| 2007/0265432 A1 | 11/2007 | Meikle et al. |
| 2010/0003239 A1 | 1/2010 | Scales |
| 2010/0009463 A1 | 1/2010 | Hornbeck et al. |
| 2011/0217790 A1 | 9/2011 | Pass et al. |
| 2012/0156710 A1 | 6/2012 | Nakayama et al. |
| 2012/0184050 A1 | 7/2012 | Meikle et al. |
| 2012/0225060 A1 | 9/2012 | Lee et al. |
| 2013/0105684 A1 | 5/2013 | Louette et al. |
| 2013/0137595 A1 | 5/2013 | Zangar et al. |
| 2013/0302399 A1 | 11/2013 | Feldhaus et al. |
| 2014/0106981 A1 | 4/2014 | Hood et al. |
| 2014/0273275 A1 | 9/2014 | Jacobs et al. |
| 2015/0322423 A1 | 11/2015 | Kosugi et al. |
| 2016/0083458 A1 | 3/2016 | Katsuragi et al. |
| 2016/0319005 A1 | 11/2016 | Lopez-Girona et al. |
| 2018/0086846 A1 | 3/2018 | Wiltzius et al. |
| 2018/0164301 A1 | 6/2018 | Anderson |
| 2019/0031754 A1 | 1/2019 | Rader et al. |
| 2019/0134164 A1 | 5/2019 | DeRosa et al. |
| 2021/0285965 A1 | 9/2021 | Hahn et al. |
| 2021/0302435 A1 | 9/2021 | Hahn et al. |
| 2023/0194545 A1 | 6/2023 | Hahn |
| 2024/0248096 A1 | 7/2024 | Hahn et al. |

FOREIGN PATENT DOCUMENTS

| | | | |
|---|---|---|---|
| CN | 1367830 A | 9/2002 | |
| CN | 1635908 A | 7/2005 | |
| EP | 2072527 A1 | 6/2009 | |
| JP | WO2014037977 A1 | 3/2014 | |
| WO | WO-2009033743 A1 * | 3/2009 | ............. C07K 16/18 |
| WO | WO2011015602 A2 | 2/2011 | |

(Continued)

OTHER PUBLICATIONS

Mariuzza (Annu. Rev. Biophys. Biophys. Chem., 16: 139-159, 1987) (Year: 1987).*
McCarthy et al. (J. Immunol. Methods, 251(1-2): 137-149, 2001) (Year: 2001).*
Lin et al. (African Journal of Biotechnology, 10(79):18294-18302, 2011) (Year: 2011).*
Chinese Office Action mailed Dec. 8, 2023 for Chinese Application No. 201980065851.5, a foreign counterpart to U.S. Appl. No. 17/282,989, 18 pages.
Japanese Office Action mailed Oct. 10, 2023 for Japanese Application No. 2021-518442, a foreign counterpart to U.S. Appl. No. 17/282,989, 7 pages.
Office Action for Japan Application No. 2021-518442, issued Jul. 9, 2024, 6pp.

(Continued)

*Primary Examiner* — Gregory S Emch
*Assistant Examiner* — Ashley H. Gao
(74) *Attorney, Agent, or Firm* — Lee & Hayes, P.C.

(57) ABSTRACT

Newborn screening for primary immunodeficiencies, cystinosis, and Wilson disease is described. The newborn screening can detect these disorders from dried blood spots already routinely collected at the time of birth. Early detection of these disorders will greatly improve patient outcome as each of them can be fatal once symptoms emerge.

16 Claims, 59 Drawing Sheets

Specification includes a Sequence Listing.

(56) References Cited

FOREIGN PATENT DOCUMENTS

| WO | WO2013106603 A1 | 7/2013 |
| --- | --- | --- |
| WO | WO2013148284 A1 | 10/2013 |
| WO | 2016110584 A1 | 7/2016 |
| WO | WO2017062672 A2 | 4/2017 |
| WO | WO2017106292 A2 | 6/2017 |
| WO | WO2018097951 A1 | 5/2018 |
| WO | WO2019030377 A1 | 2/2019 |
| WO | WO2019126647 A1 | 6/2019 |
| WO | WO2019149816 A1 | 8/2019 |
| WO | WO2019173291 A1 | 9/2019 |
| WO | WO2021178545 A1 | 9/2021 |

OTHER PUBLICATIONS

Almannai, et al., "Newborn screening: a review of history, recent advancements, and future perspectives in the era of next generation sequencing," Current Opinion in Pediatrics, vol. 28, No. 6, 2016, pp. 694-699.

Anderson, et al., "Mass spectrometric quantitation of peptides and proteins using Stable Isotope Standards and Capture by Anti-Peptide Antibodies (SISCAPA)," Journal of Proteome Research, vol. 3, No. 2, 2004, pp. 235-244.

Anderson, et al., "SISCAPA peptide enrichment on magnetic beads using an in-line bead trap device," Molecular & Cellular Proteomics, vol. 8, No. 5, 2009, pp. 995-1005.

Beynon, et al., "Multiplexed absolute quantification in proteomics using artificial QCAT proteins of concatenated signature peptides," Nature Methods, vol. 2, No. 8, 2005, pp. 587-589.

Brun, et al., "Isotope-labeled Protein Standards: Toward Absolute Quantitative Proteomics," Molecular & Cellular Proteomics, vol. 6, No. 12, 2007, pp. 2139-2149.

Carroll, et al., "Absolute quantification of the glycolytic pathway in yeast: deployment of a complete QconCAT approach," Molecular & Cellular Proteomics, vol. 10, No. 12, 2011, 15 pages.

Chace & Kalas, "A biochemical perspective on the use of tandem mass spectrometry for newborn screening and clinical testing," Clinical Biochemistry, vol. 38, No. 4, 2005, pp. 296-309.

Chase, et al., "Mass spectrometry in newborn and metabolic screening: historical perspective and future directions," Journal of Mass Spectrometry, vol. 44, No. 2, 2009, pp. 163-170.

Chase, et al., "Rapid diagnosis of phenylketonuria by quantitative analysis for phenylalanine and tyrosine in neonatal blood spots by tandem mass spectrometry," Clinical Chemistry, vol. 39, No. 1, 1993, pp. 66-71.

Cutillas, "Principles of Nanoflow Liquid Chromatography and Applications to Proteomics," Current Nanoscience, vol. 1, No. 1, 2005, pp. 65-71.

Ding, et al., "Quantitative analysis of cohesin complex stoichiometry and SMC3 modification-dependent protein Interactions," Journal of Proteome Research, vol. 10, No. 8, 2011, pp. 3652-3659.

Dott, et al., "Metabolic disorders detectable by tandem mass spectrometry and unexpected early childhood mortality: a population-based study," American Journal of Medical Genetics Part A, vol. 140, No. 8, 2006, pp. 837-842.

Gerber, et al., "Absolute quantification of proteins and phosphoproteins from cell lysates by tandem MS," PNAS USA, vol. 100, No. 12, 2003, pp. 6940-6945.

Holman, et al., "The use of selected reaction monitoring in quantitative proteomics," Bioanalysis, vol. 4, No. 14, 2012, pp. 1763-1786.

Holzmann, et al., "Stoichiometry determination of the MP1-p14 complex using a novel and cost-efficient method to produce an equimolar mixture of standard peptides," Analytical Chemistry, vol. 81, No. 24, 2009, pp. 10254-10261.

Hoofnagle, et al., "Quantification of thyroglobulin, a low-abundance serum protein, by immunoaffinity peptide enrichment and tandem mass spectrometry," Clinical Chemistry, vol. 54, No. 11, 2008, pp. 1796-1804.

Hoofnagle, et al., "Recommendations for the Generation, Quantification, Storage, and Handling of Peptides Used for Mass Spectrometry-Based Assays" Clinical Chemistry, vol. 62, No. 1, 2016, pp. 48-69.

Johnson, et al., "Rigorous determination of the stoichiometry of protein phosphorylation using mass spectrometry," Journal of the American Society for Mass Spectrometry, vol. 20, No. 12, 2009, pp. 2211-2220.

Kennedy, et al., "Demonstrating the feasibility of large-scale development of standardized assays to quantify human proteins," Nature Methods, vol. 11, No. 2, 2014, pp. 149-155.

Kirkpatrick, et al., "The absolute quantification strategy: a general procedure for the quantification of proteins and post-translational modifications," Methods, vol. 35, No. 3, 2005, pp. 265-273.

Kito, et al., "A synthetic protein approach toward accurate mass spectrometric quantification of component stoichiometry of multiprotein complexes," Journal of Proteome Research, vol. 6, No. 2, 2007, pp. 792-800.

Kuhn, et al., "Developing Multiplexed Assays for Troponin I and Interleukin-33 in Plasma by Peptide Immunoaffinity Enrichment and Targeted Mass Spectrometry" Clinical Chemistry, vol. 55, No. 6, 2009, pp. 1108-1117.

Lange, et al., "Selected reaction monitoring for quantitative proteomics: a tutorial," Molecular Systems Biology, vol. 4, No. 1, 2008, 14 pages.

Lundgren, et al., "Role of spectral counting in quantitative proteomics," Expert Review of Proteomics, vol. 7, No. 1, 2010, pp. 39-53.

Mallick, et al., "Computational prediction of proteotypic peptides for quantitative proteomics," Nature Biotechnology, vol. 25, 2007, pp. 125-131.

Millington, et al., "Tandem mass spectrometry: a new method for acylcarnitine profiling with potential for neonatal screening for inborn errors of metabolism," Journal of Inherited Metabolic Disease, vol. 13, 1990, pp. 321-324.

Nelson, et al., "Mass spectrometric immunoassay," Analytical Chemistry, vol. 67, No. 7, 1995, pp. 1153-1158.

PCT Search Report and Written Opinion mailed on Jun. 4, 2021 for PCT Application No. PCT/US2021/0206797, 26 pages.

Sweetman, et al., "Naming and counting disorders (conditions) included in newborn screening panels," Pediatrics, vol. 117, No. 5, 2006, pp. S308-S314.

Watson, et al., "Main Report," Genetics in Medicine, vol. 8, No. 5, 2006, pp. 12S-252S.

Whiteaker & Paulovich, "Peptide immunoaffinity enrichment coupled with mass spectrometry for peptide and protein quantification" Clinics in Laboratory Medicine, vol. 31, No. 3, 2011, pp. 385-396.

Whiteaker, et al., "An automated and multiplexed method for high throughput peptide immunoaffinity enrichment and multiple reaction monitoring mass spectrometry-based quantification of protein biomarkers," Molecular & Cellular Proteomics, vol. 9, No. 1, 2010, pp. 184-196.

Zhao, et al., "Quantification of proteins using peptide immunoaffinity enrichment coupled with mass spectrometry," Journal of Visualized Experiments, vol. 53, 2011, 5 pages.

Roos, et al., "X-CGDbase: a database of X-CGD-causing mutations", Immunology Today, vol. 17, Issue 11, Nov. 1996, pp. 517-521.

Schmalstieg, et al., "Effect of RBC Transfusions on Adenosine Deaminase(ADA) Deficient Severe Combined Immunodeficiency(SCID)," Pediatric Research, vol. 11, No. 4, 1977, 1 page.

Partial European Search Report for European Application No. 21780186.9, Dated Apr. 29, 2024, 13 pages.

Staal, et al., "Autologous Stem-Cell-Based Gene Therapy for Inherited Disorders: State of the Art and Perspectives," Frontiers in Pediatrics, vol. 7, No. 443, 2019, 9 pages.

Tangye, et al., "Human Inborn Errors of Immunity: 2019 Update on the Classification from the International Union of Immunological Societies Expert Committee," Journal of Clinical Immunology, vol. 40, 2020, pp. 24-64.

United States Centers for Disease Control and Prevention, "Interim Guidelines for Collecting and Handling of Clinical Specimens for COVID-19 Testing," retrieved on Apr. 22, 2021 at <<https://www.

(56) References Cited

OTHER PUBLICATIONS cdc.gov/coronavirus/2019-ncov/lab/guidelines-clinical-specimens.html>>, United States Centers for Disease Control and Prevention, 2021, 6 pages.
Whiteaker, et al., "High-affinity recombinant antibody fragments (Fabs) can be applied in peptide enrichment immuno-MRM assays," Journal of Proteome Research, vol. 13, No. 4, 2014, pp. 2187-2196.
Whitmore & Gaspar, "Adenosine Deaminase Deficiency—More Than Just an Immunodeficiency," Frontiers in Immunology, vol. 7, No. 314, 2016, 13 pages.
Zhou, et al., "Impact of human granulocyte and monocyte isolation procedures on functional studies," Clinical and Vaccine Immunology, vol. 19, 7, 2012, pp. 1065-1074.
"Buccal Swab Collection Procedure," retrieved on Apr. 22, 2021 at <<https://www.chla.org/sites/default/files/atoms/files/CHLA-Clinical-Pathology-Buccal-Swab-Collection-Procedure.pdf>>, 1 page.
America & Cordewener, "Comparative LC-MS: A landscape of peaks and valleys," Bioinformatics, vol. 8, No. 4, 2008, pp. 731-749.
Anderson & Hunter, "Quantitative Mass Spectrometric Multiple Reaction Monitoring Assays for Major Plasma Proteins," Molecular & Cellular Proteomics, vol. 5, No. 4, 2006, pp. 573-588.
Aydin, et al., "DOCK8 deficiency: clinical and immunological phenotype and treatment options—a review of 136 patients," Journal of Clinical Immunology, vol. 35, No. 2, 2015, 10 pages.
Baker, et al., "Development of a routine newborn screening protocol for severe combined immunodeficiency," The Journal of Allergy and Clinical Immunology, vol. 124, No. 3, 2009, pp. 522-527.
Baron, et al., "Epigenetic immune cell counting in human blood samples for immunodiagnostics," Science Translational Medicine, vol. 10, No. 452, 2018, 12 pages.
BD Biosciences, "BD Vacutainer(CR) CPT(TM) Mononuclear Cell Preparation Tube—Sodium Citrate," retrieved on May 6, 2021 at <<https://www.bdbiosciences.com/us/applications/blood-collection/cell-biomarker-preservation/bd-vacutainerreg-cpttrade-mononuclear-cell-preparation-tube---sodium-citrate/p/362760>>, BD Vacutainer, 2021, 4 pages.
Bonilla, et al., "Practice parameter for the diagnosis and management of primary immunodeficiency," The Journal of Allergy and Clinical Immunology, vol. 136, No. 5, 2015, pp. 1186-1205.E78.
Booth & Gaspar, "Pegademase bovine (PEG-ADA) for the treatment of infants and children with severe combined immunodeficiency (SCID)," Biologics, vol. 3, 2009, pp. 349-358.
Chan & Puck, "Development of population-based newborn screening for severe combined immunodeficiency," The Journal of Allergy and Clinical Immunology, vol. 115, No. 2, 2005, pp. 391-398.
Chase, et al., "Newborn screening for T-cell deficiency," Current Opinion in Allergy and Clinical Immunology, vol. 10, No. 6, 2010, pp. 521-525.
Chen, et al., "Development of a Multiplexed Liquid Chromatography Multiple-Reaction-Monitoring Mass Spectrometry (LC-MRM/MS) Method for Evaluation of Salivary Proteins as Oral Cancer Biomarkers", Molecular & Cellular Proteomics, vol. 16, No. 5, May 1, 2017, pp. 799-811.
Collins, et al., "Multiplexed Proteomic Analysis for Diagnosis and Screening of Five Primary Immunodeficiency Disorders From Dried Blood Spots," Frontiers in Immunology, vol. 11, No. 464, 2020, 16 pages.
Collins, et al., "Rapid Multiplexed Proteomic Screening for Primary Immunodeficiency Disorders From Dried Blood Spots," Frontiers in Immunology, vol. 9, 2018, 17 pages.
Corkum, et al., "Immune cell subsets and their gene expression profiles from human PBMC isolated by Vacutainer Cell Preparation Tube (CP[TM]) and standard density gradient," BMC Immunology, vol. 16, No. 48, 2015, 18 pages.
De Saint Basile, et al., "Severe combined immunodeficiency caused by deficiency in either the delta or the epsilon subunit of CD3," Journal of Clinical Investigation, vol. 114, No. 10, 2004, pp. 1512-1517.

Engelhardt, et al., "Large deletions and point mutations involving the dedicator of cytokinesis 8 (DOCK8) in the autosomal-recessive form of hyper-IgE syndrome," The Journal of Allergy and Clinical Immunology, vol. 124, No. 6, 2009, pp. 1289-1302.e4.
Search Report and Written Opinion for European Application No. 21764238.8, Dated Jun. 17, 2024, 14 pages.
Search Report and Written Opinion for European Application No. 21780186.9, Dated Jul. 22, 2024, 10 pages.
Search Report and Written Opinion for European Application No. 21779339.7, Dated Jul. 8, 2024, 12 pages.
Espinosa-de Aquino, et al., "Protein and RNA extraction from mucosal swabs: a minimally invasive source of ecological data for studies of natural populations," Methods in Ecology and Evolution, vol. 8, No. 3, 2017, pp. 370-378.
Fargo, et al., "Erythrocyte adenosine deaminase: diagnostic value for Diamond-Blackfan anaemia," British Journal of Haematology, vol. 160, No. 4, 2013, pp. 547-554.
Ferrua, et al., "Lentiviral haemopoietic stem/progenitor cell gene therapy for treatment of Wiskott-Aldrich syndrome: interim results of a non-randomised, open-label, phase 1/2 clinical study," Lancet Haematology, vol. 6, No. 5, 2019, pp. E239-E253.
Flinn & Gennery, "Adenosine deaminase deficiency: a review," Orphanet Journal of Rare Diseases, vol. 13, No. 1, 2018, 7 pages.
Gaspar, et al., "How I treat ADA deficiency," Blood, vol. 114, No. 17, 2009, pp. 3524-3532.
Grievink, et al., "Comparison of Three Isolation Techniques for Human Peripheral Blood Mononuclear Cells: Cell Recovery and Viability, Population Composition, and Cell Functionality," Biopreservation and Biobanking, vol. 14, No. 5, 2016, pp. 410-415.
Grunebaum, et al., "Bone marrow transplantation for severe combined immune deficiency," JAMA, vol. 295, No. 5, 2006, pp. 508-518.
Jia, et al., "A Modified Ficoll-Paque Gradient Method for Isolating Mononuclear Cells from the Peripheral and Umbilical Cord Blood of Humans for Biobanks and Clinical Laboratories," Biopreservation and Biobanking, vol. 16, No. 2, 2018, pp. 82-91.
Jin, et al., "Mutations of the Wiskott-Aldrich Syndrome Protein (WASP): hotspots, effect on transcription, and translation and phenotype/genotype correlation," Blood, vol. 104, No. 13, 2004, pp. 4010-4019.
Jing, et al., "Somatic reversion in dedicator of cytokinesis 8 immunodeficiency modulates disease phenotype," The Journal of Allergy and Clinical Immunology, vol. 133, No. 6, 2014, pp. 1667-1675.
Kanariou, et al., "Long-term observational studies of chronic granulomatous disease," Current Opinion in Hematology, vol. 25, No. 1, 2018, pp. 7-12.
Kaveri, et al., "Intravenous immunoglobulins in immunodeficiencies: more than mere replacement therapy," Clinical and Experimental Immunology, vol. 164, No. 2, 2011, pp. 2-5.
Kobrynski, et al., "Prevalence and morbidity of primary immunodeficiency diseases, United States 2001-2007," Journal of Clinical Immunology, vol. 34, No. 8, 2014, pp. 954-961.
Kwan, et al., "Newborn screening for severe combined immunodeficiency in 11 screening programs in the United States," JAMA, vol. 312, No. 7, 2014, pp. 729-738.
La Marca, et al., "Diagnosis of immunodeficiency caused by a purine nucleoside phosphorylase defect by using tandem mass spectrometry on dried blood spots," Journal of Allergy and Clinical Immunology, vol. 134, No. 1, 2014, pp. 155.e3-159.e3.
La Marca, et al., "Tandem mass spectrometry, but not T-cell receptor excision circle analysis, identifies newborns with late-onset adenosine deaminase deficiency," Journal of Allergy and Clinical Immunology, vol. 131, No. 6, 2013, pp. 1604-1610.
La Marca, et al., "The inclusion of ADA-SCID in expanded newborn screening by tandem mass spectrometry," Journal of Pharmaceutical and Biomedical Analysis, vol. 88, 2014, pp. 201-206.
MacCoss Lab Software, "SkyLine," retrieved on May 6, 2021 at <https://skyline.ms/project/home/begin.view>, MacCoss Lab Software, 2021, 1 page.
McCusker, et al., "Primary immunodeficiency," Allergy, Asthma & Clinical Immunology, vol. 14, No. 2, 2018, 12 pages.

(56) References Cited

OTHER PUBLICATIONS

Michalczyk, et al., "Fresh and cultured buccal cells as a source of mRNA and protein for molecular analysis," Bio Techniques, vol. 37, No. 2, 2004, pp. 262-269.

Moratto, et al., "Long-term outcome and lineage-specific chimerism in 194 patients with Wiskott-Aldrich syndrome treated by hematopoietic cell transplantation in the period 1980-2009: an international collaborative study," Blood, vol. 118, No. 6, 2011, pp. 1675-1684.

Otogenetics Corporation, "Instruction for Buccal Swab Sample Collection," retrieved on Apr. 22, 2021 at <<https://www.otogenetics.com/wp-content/uploads/2018/01/buccal-swab-collection-instructions.pdf>>, 1 page.

Parta, et al., "Allogeneic Reduced-Intensity Hematopoietic Stem Cell Transplantation for Chronic Granulomatous Disease: a Single-Center Prospective Trial," Journal of Clinical Immunology, vol. 37, No. 6, 2017, pp. 548-558.

Pathway Genomics, "Buccal DNA Collection Instructions," retrieved on Apr. 22, 2021 at <<https://www.pathway.com/wp-content/uploads/2017/06/Buccal-Swab-Collection-Instructions.pdf>>, 1 page.

PersonalizeDx Labs, "Buccal Swab collection procedure," Youtube uploaded by PersonalizeDx Labs, Nov. 28, 2017, https://www.youtube.com/watch?v=3ftvHkfM710&t=152s, 4 pages.

Puleo, et al., "Isolation of Peripheral Blood Mononuclear Cells Using Vacutainer"CR" Cellular Preparation Tubes (CPTTM)," Bio-Protocol, vol. 7, No. 2, 2017, 6 pages.

Qasim, et al., "Protein assays for diagnosis of Wiskott-Aldrich syndrome and X-linked thrombocytopenia," British Journal of Haematology, vol. 113, No. 4, 2001, pp. 861-865.

Raje & Dinakar, "Overview of Immunodeficiency Disorders," Immunology and Allergy Clinics of North America, vol. 35, No. 4, 2015, pp. 599-623.

De Mello et al. Feasibility of using cryopreserved lymphoblastoid cells to diagnose some lysosomal storage diseases, Cell Proliferation, Feb. 26, 2010 (Feb. 26, 2010). vol. 43, No. 2, pp. 164-169.

Invitation to Pay Fees Dated Jul. 13, 2021 in International Application No. PCT/US2021/025627, 3 Pages.

Search Report and Written Opinion Dated Jul. 22, 2021 in International Application No. PCT/US2021/025270, 20 pages.

Search Report and Written Opinion Dated Sep. 21, 2021 for International Application No. PCT/US2021/025627, 14 pages.

Van Doorn et al. "Salivary a-Iduronidase Activity as a Potential New Biomarker for the Diagnosis and Monitoring the Effect of Therapy in Mucopolysaccharidosis Type I," Biology of Blood and Marrow Transplantation, Sep. 30, 2018 (Sep. 30, 2018), vol. 24, Iss. 9, pp. 1808-1813.

Invitation to Pay Addition Fees Dated Dec. 26, 2019 in International Application No. PCT/US2019/054856, 8 pages.

Jung, et al., "Quanitification of ATP7B Protein in Dried Blood Spots by Peptide Immuno-SRM as a Potential Screen for Wilson's Disease," J. Proteome. Res., vol. 16, No. 2, 2017, pp. 862-871.

Kerfoot, et al., "Tryptic peptide screening for primary immunodeficiency disease by LC/MS-MS," Proteomics Clin. Appl, vol. 6, No. 7-8, 2012, pp. 394-402.

Search Report & Written Opinion Dated Feb. 21, 2019 in International Application No. PCT/US19/54856, 14 pages.

Extended European Search Report mailed Sep. 27, 2022 for European Application No. 19869877.1, 25 pages.

Partial European Search Report Dated Jun. 24, 2022 for European Patent Application No. 19869877.1, 28 pages.

Whiteaker, et al., "Antibody-based enrichment of peptides on magnetic beads for mass-spectrometry-based quantification of serum biomarkers", Analytical Biochemistry, vol. 362, Issue 1, Dec. 20, 2006, pp. 44-54.

\* cited by examiner

FIG. 1

| Disease | Protein Target | Peptides | Sequence | Total Mass | Parent Ion Mass (m/z) | Daughter Ion Masses (m/z) | | |
|---|---|---|---|---|---|---|---|---|
| Severe Combined Immuno-deficiency (SCID) | CD3ε | CD3ε 197-205 ("CD3ε 197") | DLYSGLNQR (SEQ ID NO: 1) | 1066.54 | 533.27 ++ | L [y8] - 950.5054+<br>Y [y7] - 837.4213+<br>S [y6] - 674.3580+<br>G [y5] - 587.3260+<br>L [y4] - 530.3045+<br>N [y3] - 417.2205+ | L [y8] - 475.7563++<br>Y [y7] - 419.2143++<br>S [y6] - 337.6826++<br>G [y5] - 294.1666++<br>L [y4] - 265.6559++<br>N [y3] - 209.1139++ | Y [b3] - 392.1816+<br>S [b4] - 479.2136+<br>G [b5] - 536.2351+<br>L [b6] - 649.3192+<br>N [b7] - 763.3621+<br>Q [b8] - 891.4207+ | Y [b3] - 196.5944++<br>S [b4] - 240.1105++<br>G [b5] - 268.6212++<br>L [b6] - 325.1632++<br>N [b7] - 382.1847++<br>Q [b8] - 446.2140++ |
| Wiskott-Aldrich Syndrome (WAS) | WASp | WASp 274-288 ("WASp 274") | AGISEAQLTDAETSK (SEQ ID NO: 2) | 1521.76 | 760.88 ++ | G [y14] - 1449.7067+<br>I [y13] - 1392.6853+<br>S [y12] - 1279.6012+<br>E [y11] - 1192.5692+<br>A [y10] - 1063.5266+<br>Q [y9] - 992.4895+<br>L [y8] - 864.4309+<br>T [y7] - 751.3468+<br>D [y6] - 650.2992+<br>A [y5] - 535.2722+ | G [y14] - 725.3570++<br>I [y13] - 696.8463++<br>S [y12] - 640.3042++<br>E [y11] - 596.7882++<br>A [y10] - 532.2669++<br>Q [y9] - 496.7484++<br>L [y8] - 432.7191++<br>T [y7] - 376.1771++<br>D [y6] - 325.6532++<br>A [y5] - 268.1397++ | I [b3] - 242.1499+<br>S [b4] - 329.1819+<br>E [b5] - 458.2245+<br>A [b6] - 529.2617+<br>Q [b7] - 657.3202+<br>L [b8] - 770.4043+<br>T [b9] - 871.4520+<br>D [b10] - 986.4789+<br>A [b11] - 1057.5160+<br>E [b12] - 1186.5586+ | I [b3] - 121.5786++<br>S [b4] - 165.0946++<br>E [b5] - 229.6159++<br>A [b6] - 265.1345++<br>Q [b7] - 329.1638++<br>L [b8] - 385.7058++<br>T [b9] - 436.2296++<br>D [b10] - 493.7431++<br>A [b11] - 529.2617++<br>E [b12] - 593.7829++ |

FIG. 1 cont'd

| Disease | Protein Target | Peptides | Sequence | Total Mass | Parent Ion Mass (m/z) | Daughter Ion Masses (m/z) | | |
|---|---|---|---|---|---|---|---|---|
| WAS | WASp | WASp 274 | AGISEAQL TDAETSK (SEQ ID NO: 2) | 1521.76 | 760.88 ++ | E [y4] - 464.2351+<br>T [y3] - 335.1925+ | E [y4] - 232.6212++<br>T [y3] - 168.0999++ | T [b13] - 1287.6063+<br>S [b14] - 1374.6383+ |
| Wiskott-Aldrich Syndrome (WAS) | WASp | WASp 289-304 ("WASp 289") | LIYDFIED QGGLEAV R (SEQ ID NO: 3) | 1838.94 | 919.47 ++ | D [y13] - 1448.7016+<br>F [y12] - 1333.6747+<br>I [y11] - 1186.6062+<br>E [y10] - 1073.5222+<br>D [y9] - 944.4796+<br>Q [y8] - 829.4526+<br>G [y7] - 701.3941+<br>G [y6] - 644.3726+<br>L [y5] - 587.3511+<br>E [y4] - 474.2671+<br>A [y3] - 345.2245+ | I [y15] - 862.9281++<br>Y [y14] - 806.3861++<br>D [y13] - 724.8544++<br>F [y12] - 667.3410++<br>I [y11] - 593.8068++<br>E [y10] - 537.2647++<br>D [y9] - 472.7434++<br>Q [y8] - 415.2300++<br>G [y7] - 351.2007++<br>G [y6] - 322.6899++<br>L [y5] - 294.1792++<br>E [y4] - 237.6372++<br>A [y3] - 173.1159++ | Y [b3] - 390.2387+<br>D [b4] - 505.2657+<br>F [b5] - 652.3341+<br>I [b6] - 765.4182+<br>E [b7] - 894.4607+<br>D [b8] - 1009.4877+<br>Q [b9] - 1137.5463+<br>G [b10] - 1194.5677+<br>G [b11] - 1251.5892+<br>L [b12] - 1364.6733+<br>E [b13] - 1493.7159+ |

(Third daughter ion column for WASp 289, continued): Y [b3] - 195.6230++, D [b4] - 253.1365++, F [b5] - 326.6707++, I [b6] - 383.2127++, E [b7] - 447.7340++, D [b8] - 505.2475++, Q [b9] - 569.2768++, G [b10] - 597.7875++, G [b11] - 626.2982++, L [b12] - 682.8403++, E [b13] - 747.3616++, A [b14] - 782.8801++, V [b15] - 832.4143++

(Third daughter ion column for WASp 274): T [b13] - 644.3068++, S [b14] - 687.8228++

FIG. 1 cont'd

| Disease | Protein Target | Peptides | Sequence | Total Mass | Parent Ion Mass (m/z) | Daughter Ion Masses (m/z) | | |
|---|---|---|---|---|---|---|---|---|
| X-Linked Agamma-Globulinemia (XLA) | BTK | BTK 407-417 ("BTK 407") | ELGTGQFGVVK (SEQ ID NO: 4) | 1135.63 | 567.81 ++ | L [y10]- 1005.5728+<br>G [y9]- 892.4887+<br>T [y8]- 835.4672+<br>G [y7]- 734.4196+<br>Q [y6]- 677.3981+<br>F [y5]- 549.3395+<br>G [y4]- 402.2711+<br>V [y3]- 345.2496+ | L [y10]- 503.2900++<br>G [y9]- 446.7480++<br>T [y8]- 418.2373++<br>G [y7]- 367.7134++<br>Q [y6]- 339.2027++<br>F [y5]- 275.1734++<br>G [y4]- 201.6392++<br>V [y3]- 173.1285++ | G [b3]- 300.1554+<br>T [b4]- 401.2031+<br>G [b5]- 458.2245+<br>Q [b6]- 586.2831+<br>F [b7]- 733.3515+<br>G [b8]- 790.3730+<br>V [b9]- 889.4414+ | G [b3]- 150.5813++<br>T [b4]- 201.1052++<br>G [b5]- 229.6159++<br>Q [b6]- 293.6452++<br>F [b7]- 367.1794++<br>G [b8]- 395.6901++<br>V [b9]- 445.2243++<br>V [b10]- 494.7585++ |
| X-Linked Agamma-Globulinemia (XLA) | BTK | BTK 545-558 ("BTK 545") | YVLDDEYTSSVGSK (SEQ ID NO: 5) | 1563.72 | 781.86 ++ | V [y13]- 1399.6587+<br>L [y12]- 1300.5903+<br>D [y11]- 1187.5063+<br>D [y10]- 1072.4793+<br>E [y9]- 957.4524+<br>Y [y8]- 828.4098+<br>T [y7]- 665.3464+<br>S [y6]- 564.2988+ | V [y13]- 700.3330++<br>L [y12]- 650.7988++<br>D [y11]- 594.2568++<br>D [y10]- 536.7433++<br>E [y9]- 479.2298++<br>Y [y8]- 414.7085++<br>T [y7]- 333.1769++<br>S [y6]- 282.6530++ | L [b3]- 376.2231+<br>D [b4]- 491.2500+<br>D [b5]- 606.2770+<br>E [b6]- 735.3196+<br>Y [b7]- 898.3829+<br>T [b8]- 999.4306+<br>S [b9]- 1086.4626+<br>S [b10]- 1173.4946+ | L [b3]- 188.6152++<br>D [b4]- 246.1287++<br>D [b5]- 303.6421++<br>E [b6]- 368.1634++<br>Y [b7]- 449.6951++<br>T [b8]- 500.2189++<br>S [b9]- 543.7349++<br>S [b10]- 587.2510++ |

FIG. 1 cont'd

| Disease | Protein Target | Peptides | Sequence | Total Mass | Parent Ion Mass (m/z) | Daughter Ion Masses (m/z) | | |
|---|---|---|---|---|---|---|---|---|
| XLA | BTK | BTK 545 | YVLDDEYTSSVGSK (SEQ ID NO: 5) | 1563.72 | 781.86 ++ | S [y5]- 477.2667+<br>V [y4]- 390.2347+<br>G [y3]- 291.1663+ | S [y5]- 239.1370++<br>V [y4]- 195.6210++<br>G [y3]- 146.0868++ | V [b11]- 1272.5630+<br>G [b12]- 1329.5845+<br>S [b13]- 1416.6165+ | V [b11]- 636.7852++<br>G [b12]- 665.2959++<br>S [b13]- 708.8119++ |
| Cystinosis | CTNS | CTNS 115-119 ("CTNS 115") | FLVIR (SEQ ID NO: 6) | 646.41 | 324.21++ | L [y4]- 500.3555+<br>V [y3]- 387.2714+<br>I [y2]- 288.2030+ | L [y4]- 250.6814++<br>V [y3]- 194.1394++<br>I [y2]- 144.6051++ | L [b2]- 261.1598+<br>V [b3]- 360.2282+<br>I [b4]- 473.3122+ | L [b2]- 131.0835++<br>V [b3]- 180.6177++<br>I [b4]- 237.1598++ |
| Cystinosis | CTNS | CTNS 360-367 ("CTNS 360") | RPGYDQLN (SEQ ID NO: 7) | 961.46 | 481.74++ | P [y7]- 806.3679+<br>G [y6]- 709.3151+<br>Y [y5]- 652.2937+<br>D [y4]- 489.2304+<br>Q [y3]- 374.2034+ | P [y7]- 403.6876++<br>G [y6]- 355.1612++<br>Y [y5]- 326.6505++<br>D [y4]- 245.1188++<br>Q [y3]- 187.6053++ | G [b3]- 311.1826+<br>Y [b4]- 474.2459+<br>D [b5]- 589.2729+<br>Q [b6]- 717.3315+<br>L [b7]- 830.4155+ | G [b3]- 156.0949++<br>Y [b4]- 237.6266++<br>D [b5]- 295.1401++<br>Q [b6]- 359.1694++<br>L [b7]- 415.7114++ |

FIG. 1 cont'd

| Disease | Protein Target | Peptides | Sequence | Total Mass | Parent Ion Mass (m/z) | Daughter Ion Masses (m/z) | | |
|---|---|---|---|---|---|---|---|---|
| Cystinosis | CTNS | CTNS 360 | KRPGYDQLN (SEQ ID NO: 8)* | 1089.56 * | 545.29++* | R [y8]- 962.4690+<br>P [y7]- 806.3679+<br>G [y6]- 709.3151+<br>Y [y5]- 652.2937+<br>D [y4]- 489.2304+<br>Q [y3]- 374.2034+ | R [y8]- 481.7381++<br>P [y7]- 403.6876++<br>G [y6]- 355.1612++<br>Y [y5]- 326.6505++<br>D [y4]- 245.1188++<br>Q [y3]- 187.6053++ | P [b3]- 382.2561+<br>G [b4]- 439.2776+<br>Y [b5]- 602.3409+<br>D [b6]- 717.3678+<br>Q [b7]- 845.4264+<br>L [b8]- 958.5105+ | P [b3]- 191.6317++<br>G [b4]- 220.1424++<br>Y [b5]- 301.6741++<br>D [b6]- 359.1876++<br>Q [b7]- 423.2169++<br>L [b8]- 479.7589++ |
| Cystinosis | SHPK | SHPK 363-376 ("SHPK 363") | DTHLTITPTVLGER (SEQ ID NO: 9) | 1551.83 | 518.28 | T [y13]- 1437.8060+<br>H [y12]- 1336.7583+<br>L [y11]- 1199.6994+<br>T [y10]- 1086.6153+<br>I [y9]- 985.5677+<br>T [y8]- 872.4836+<br>P [y7]- 771.4359+<br>T [y6]- 674.3832+<br>V [y5]- 573.3355+<br>L [y4]- 474.2671+ | T [y13]- 719.4066++<br>H [y12]- 668.8828++<br>L [y11]- 600.3533++<br>T [y10]- 543.8113++<br>I [y9]- 493.2875++<br>T [y8]- 436.7454++<br>P [y7]- 386.2216++<br>T [y6]- 337.6952++<br>V [y5]- 287.1714++<br>L [y4]- 237.6372++ | H [b3]- 354.1408+<br>L [b4]- 467.2249+<br>T [b5]- 568.2726+<br>I [b6]- 681.3566+<br>T [b7]- 782.4043+<br>P [b8]- 879.4571+<br>T [b9]- 980.5047+<br>V [b10]- 1079.5732+<br>L [b11]- 1192.6572+<br>G [b12]- 1249.6787+ | H [b3]- 177.5740++<br>L [b4]- 234.1161++<br>T [b5]- 284.6399++<br>I [b6]- 341.1819++<br>T [b7]- 391.7058++<br>P [b8]- 440.2322++<br>T [b9]- 490.7560++<br>V [b10]- 540.2902++<br>L [b11]- 596.8322++<br>G [b12]- 625.3430++ |

FIG. 1 cont'd

| Disease | Protein Target | Peptides | Sequence | Total Mass | Parent Ion Mass (m/z) | Daughter Ion Masses (m/z) | | |
|---|---|---|---|---|---|---|---|---|
| Cystinosis | SHPK | SHPK 363-376 ("SHPK 363") | DTHLTITP TVLGER (SEQ ID NO: 9) | 1551.83 | 518.28 | G [y3]- 361.1830+ | G [y3]- 181.0951++ | E [b13]- 689.8643++ |
| Wilson Disease | ATP7B | ATP7B 325-339 ("ATP7B 325") | VSLPDGA EGSGTDH R (SEQ ID NO: 10) | 1496.7 | 499.9 | S [y14]- 1398.6244+<br>L [y13]- 1311.5924+<br>P [y12]- 1198.5083+<br>D [y11]- 1101.4556+<br>G [y10]- 986.4286+<br>A [y9]- 929.4071+<br>E [y8]- 858.3700+<br>G [y7]- 729.3274+<br>S [y6]- 672.3060+<br>G [y5]- 585.2739+<br>T [y4]- 528.2525+<br>D [y3]- 427.2048+ | S [y14]- 699.8158++<br>L [y13]- 656.2998++<br>P [y12]- 599.7578++<br>D [y11]- 551.2314++<br>G [y10]- 493.7179++<br>A [y9]- 465.2072++<br>E [y8]- 429.6887++<br>G [y7]- 365.1674++<br>S [y6]- 336.6566++<br>G [y5]- 293.1406++<br>T [y4]- 264.6299++<br>D [y3]- 214.1060++ | E [b13]- 1378.7213+<br>L [b3]- 300.1918+<br>P [b4]- 397.2445+<br>D [b5]- 512.2715+<br>G [b6]- 569.2930+<br>A [b7]- 640.3301+<br>E [b8]- 769.3727+<br>G [b9]- 826.3941+<br>S [b10]- 913.4262+<br>G [b11]- 970.4476+<br>T [b12]- 1071.4953+<br>D [b13]- 1186.5222+<br>H [b14]- 1323.5811+ | L [b3]- 150.5995++<br>P [b4]- 199.1259++<br>D [b5]- 256.6394++<br>G [b6]- 285.1501++<br>A [b7]- 320.6687++<br>E [b8]- 385.1900++<br>G [b9]- 413.7007++<br>S [b10]- 457.2167++<br>G [b11]- 485.7274++<br>T [b12]- 536.2513++<br>D [b13]- 593.7648++<br>H [b14]- 662.2942++ |
| Wilson Disease | ATP7B | ATP7B 1056-1077 ("ATP7B 1056") | VLAVVGT AEASSEH PLGVAVT K (SEQ ID NO: 11) | 2134.2 | 712.4 | 827.4 (y17+2), 876.9 (y18+2), 926.5 (y19+2), 966.0 (y20+2) | | |

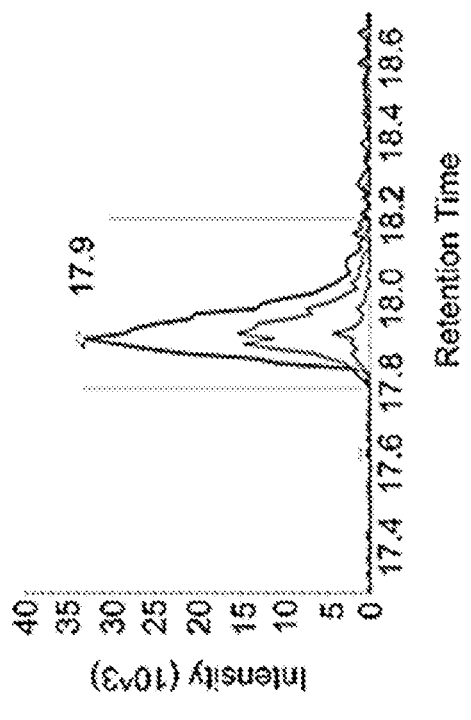
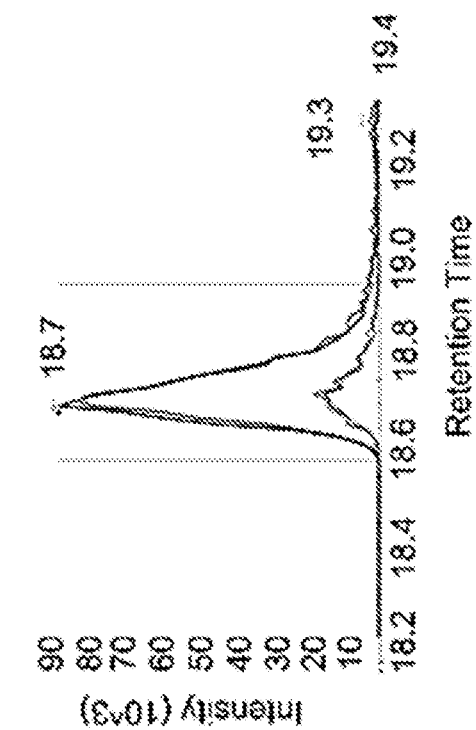
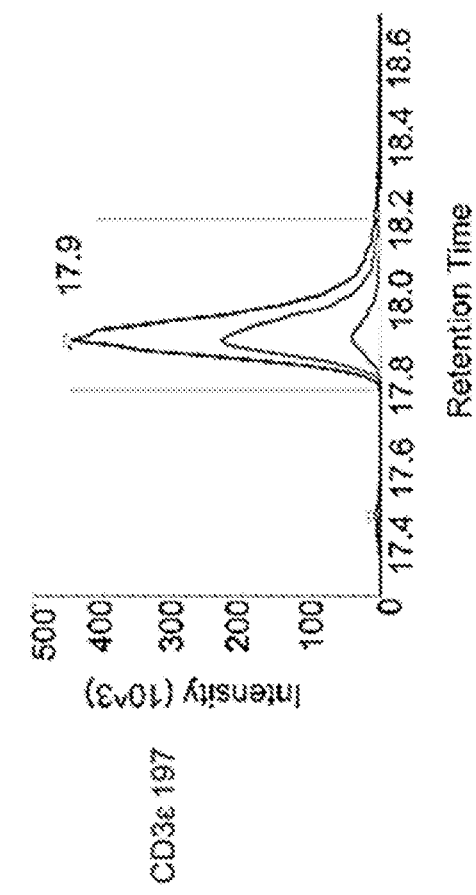
FIG. 3A
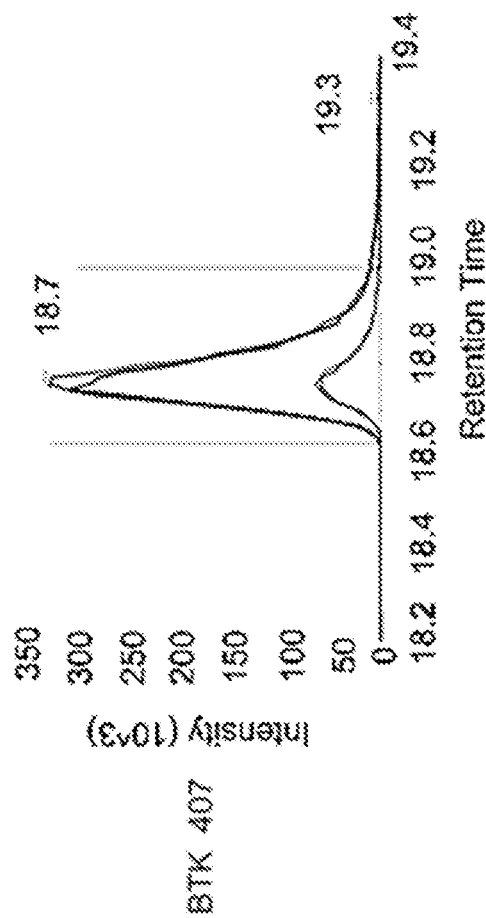
FIG. 3B

BTK 545

WASp 274

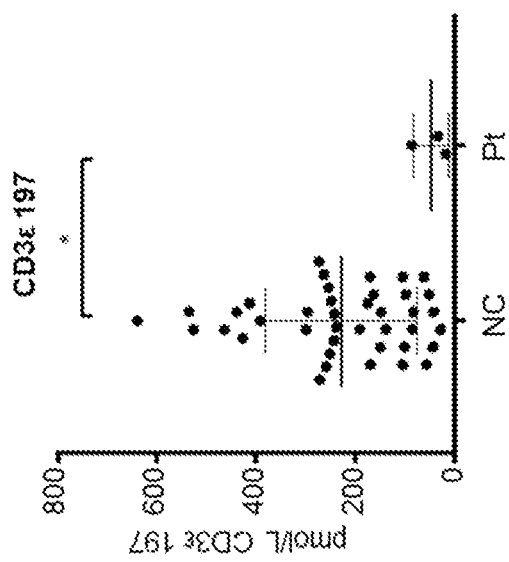
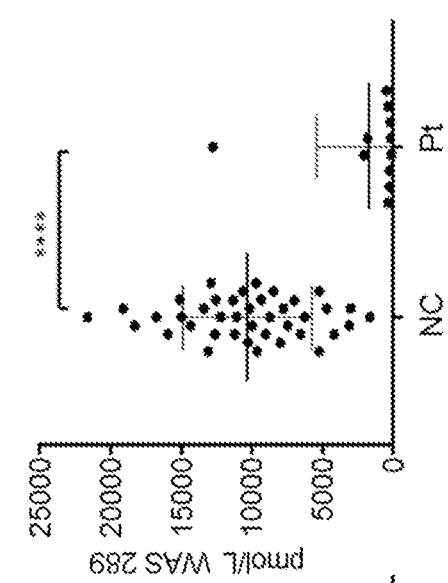
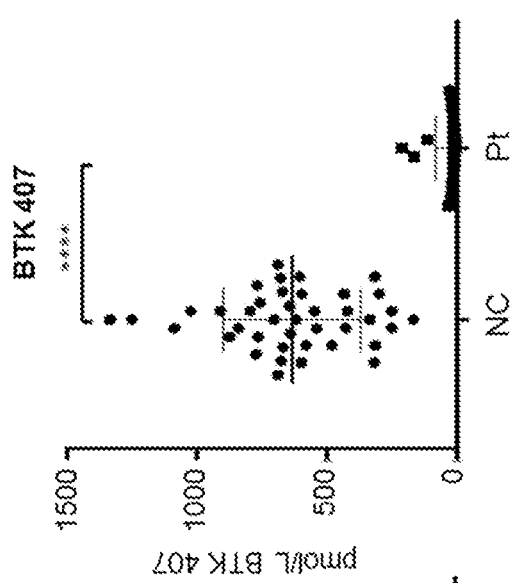
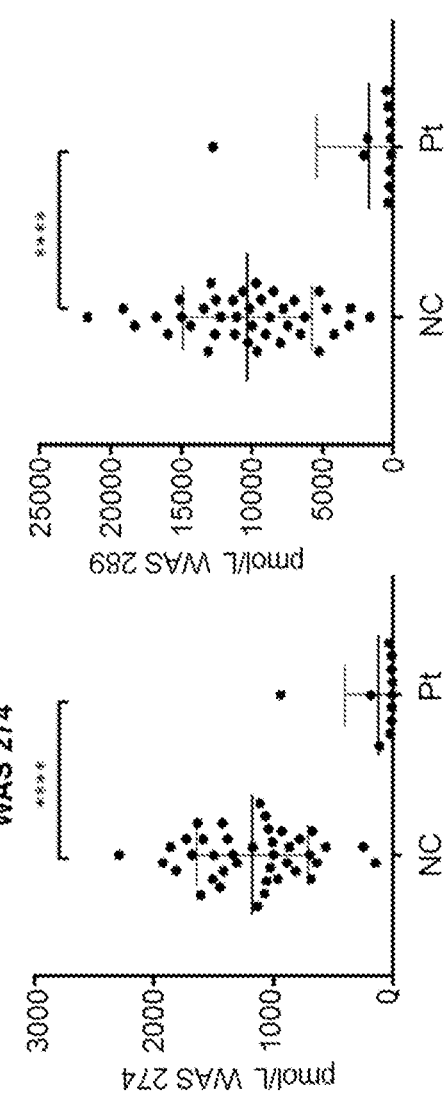
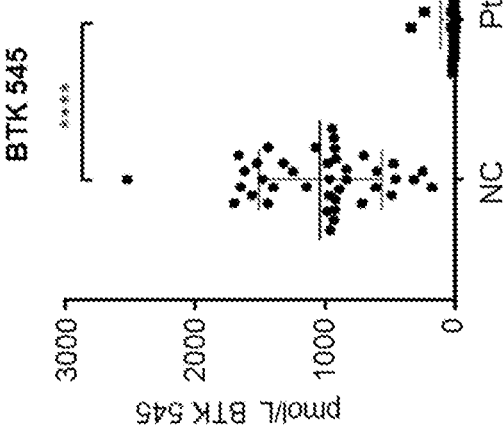

FIG. 7

| Control Sample | ATP7B 1056 (pmol/L) | Patient | ATP7B 1056 (pmol/L) | Immuno-SRM Diagnosis | Clinical Diagnosis | Genotype | Notes |
|---|---|---|---|---|---|---|---|
| NC 1 | 114.29 | 1 | 113.07 | Normal | X-linked CGD | CYBB Mutation | |
| NC 2 | 130.07 | 2 | 136.36 | Normal | X-linked CGD | CYBB Mutation | |
| NC 3 | 110.14 | 3 | 217.07 | BTK | BTK | BTK c.1587_1589delA (p.N530Tfs26*) | Brother of #4 |
| NC 4 | 129.00 | 4 | 107.79 | BTK | BTK | BTK c.1587_1589delA (p.N530Tfs26*) | Brother of #3 |
| NC 5 | 65.36 | 5 | 183.46 | BTK | BTK | BTK c.1940T>C (p.L647P) | |
| NC 6 | 96.93 | 6 | 30.29 | BTK | BTK | BTK c.763C>T (p.R255*) | |
| NC 7 | 162.79 | 7 | 123.21 | BTK | BTK | BTK c.1940T>C (p.L647P) | |
| NC 8 | 116.07 | 8 | 188.61 | BTK | BTK | BTK c.1889T>A (p.M630K) | |
| NC 9 | 138.79 | 9 | 20.00 | BTK | BTK | BTK c.1908+2delTAAGTGCTT (splice) | |
| NC 10 | 98.07 | 10 | 28.43 | Normal | BTK | No mutation identified | |
| NC 11 | 115.14 | 11 | 21.57 | BTK | BTK | BTK c.1768A>T (p.I590F) | |
| NC 12 | 127.57 | 12 | 32.21 | BTK | BTK | No mutation identified | |
| NC 13 | 77.86 | 13 | 30.93 | Normal | BTK | No mutation identified | |

FIG. 7 cont'd

| Control Sample | ATP7B 1056 (pmol/L) | Patient | ATP7B 1056 (pmol/L) | Immuno-SRM Diagnosis | Clinical Diagnosis | Genotype | Notes |
|---|---|---|---|---|---|---|---|
| NC 14 | 108.57 | 14 | 19.43 | BTK | BTK | BTK c.1714_1715delTA (p.S572Ifs14*) | |
| NC 15 | 162.14 | 15 | 25.21 | BTK | BTK | BTK c.953C>T (p.S318F) | |
| NC 16 | 203.71 | 16 | 30.36 | BTK | BTK | BTK c.11811028T>G (p.Y40D) | |
| NC 17 | 179.93 | 17 | 36.29 | BTK | BTK | BTK c.629insA (p.P210Tfs5*) | |
| NC 18 | 127.36 | 18 | 33.50 | BTK | BTK | BTK c.1651T>A (p.Y551N) | |
| NC 19 | 130.64 | 19 | 25.07 | BTK | BTK | BTK c.1735G>C (p.D579H) | |
| NC 20 | 130.00 | 20 | 48.86 | BTK | BTK | BTK c.752G>A (p.W251*) | |
| NC 21 | 101.64 | 21 | 50.71 | BTK | BTK | BTK c.117_119delCTA (p.del40Y) | |
| NC 22 | 115.21 | 22 | 33.64 | BTK | BTK | BTK c.521-1G>A (splice) | |
| NC 23 | 109.14 | 23 | 31.93 | BTK | BTK | BTK c.1876delG (p.A582Lfs4*) | |
| NC 24 | 100.71 | 24 | 30.86 | BTK | BTK | BTK c.763C>T (p.R255*) | |
| NC 25 | 134.64 | 25 | 62.71 | BTK | BTK | BTK c.1782delG (p.K595Rfs52*) | |
| NC 26 | 89.07 | 26 | 46.14 | BTK | BTK | BTK c.1657delA (p.S553Afs2*) | |
| NC 27 | 121.43 | 27 | 44.79 | BTK | BTK | BTK c.1610delT (p.V537Dfs18*) | |
| NC 28 | 96.07 | 28 | 69.71 | BTK | BTK | BTK c.37C>T (p.R13*) | |
| NC 29 | 88.36 | 29 | 90.25 | WAS | WAS | WAS c.1453+2T>A | Same as Pt. #30 (Pre-BMT) |

FIG. 7 cont'd

| Control Sample | ATP7B 1056 (pmol/L) | Patient | ATP7B 1056 (pmol/L) | Immuno-SRM Diagnosis | Clinical Diagnosis | Genotype | Notes |
|---|---|---|---|---|---|---|---|
| NC 30 | 118.64 | 30 | 112.57 | Normal | WAS | Normal BMT donor | Same as Pt. #29 (Post-BMT) |
| NC 31 | 131.86 | 31 | 168.64 | WAS | WAS/XLT | WAS c.223G>A (p.V75M) | |
| NC 32 | 132.64 | 32 | 108.79 | WAS | WAS | WAS c.631C>T (p.R211*) | |
| NC 33 | 106.79 | 33 | 47.71 | WAS | WAS | WAS c.838C>T (p.Q280*) | |
| NC 34 | 139.36 | 34 | 30.07 | WAS | WAS | WAS c.838delC (p.Q280Sfs28*) | |
| NC 35 | 92.93 | 35 | 31.14 | WAS | WAS | WAS c.631C>T (p.R211*) | Brother of Pt. #36 |
| NC 36 | 120.29 | 36 | 60.14 | WAS | WAS | WAS c.631C>T (p.R211*) | Brother of Pt. #35 |
| NC 37 | 85.86 | 37 | 55.79 | WAS | WAS | WAS c.1264_1267insCCTTGCCTGCCTCT (P.G422Pfs20*) | |
| NC 38 | 124.00 | 38 | 7.21 | WAS | WAS | WAS c.332_336insCC (p.F113Pfs15*) | |
| NC 39 | 99.50 | 39 | 63.36 | WAS | WAS | WAS c.756G>A (p.W252*) | |
| NC 40 | 117.43 | 40 | 139.50 | SCID | T-B-NK+ SCID | RAG1 c.2159G>A (p.G720D) - Homozygous | |
| | | 41 | 182.79 | Normal | X-SCID - Hypomorphic | IL2RG c.460C>T (p.T154S) | |
| | | 42 | 176.79 | SCID | T-B+NK+ SCID | Unknown - Gene panel & Exome negative | |

FIG. 8

| Sample | BTK 545 (pmol/L) | BTK 407 (pmol/L) | WASp 274 (pmol/L) | WASp 289 (pmol/L) | CD3ε 197 (pmol/L) | Sample | BTK 545 ATP7B Ratio | BTK 407 ATP7B Ratio | WASp 274 ATP7B Ratio | WASp 289 ATP7B Ratio | CD3ε 197 ATP7B Ratio |
|---|---|---|---|---|---|---|---|---|---|---|---|
| 1 | 251.07 | 252.07 | 699.43 | 5245.29 | 175.14 | 1 | 2.20 | 2.21 | 6.12 | 45.90 | 1.53 |
| 2 | 1485.71 | 796.57 | 1504.79 | 11111.50 | 149.43 | 2 | 11.42 | 6.12 | 11.57 | 85.43 | 1.15 |
| 3 | 926.79 | 679.86 | 966.21 | 6995.86 | 242.07 | 3 | 8.41 | 6.17 | 8.77 | 63.52 | 2.20 |
| 4 | 177.93 | 169.71 | 145.93 | 1674.93 | 51.29 | 4 | 1.38 | 1.32 | 1.13 | 12.98 | 0.40 |
| 5 | 923.00 | 597.29 | 1076.21 | 12230.57 | 259.71 | 5 | 14.12 | 9.14 | 16.47 | 187.13 | 3.97 |
| 6 | 1322.79 | 690.50 | 1445.07 | 14981.07 | 427.07 | 6 | 13.65 | 7.12 | 14.91 | 154.56 | 4.41 |
| 7 | 1700.64 | 1253.00 | 1928.43 | 9975.57 | 104.07 | 7 | 10.45 | 7.70 | 11.85 | 61.28 | 0.64 |
| 8 | 609.36 | 299.57 | 684.50 | 6569.93 | 84.86 | 8 | 5.25 | 2.58 | 5.90 | 56.60 | 0.73 |
| 9 | 927.43 | 642.14 | 1029.29 | 10630.00 | 272.07 | 9 | 6.68 | 4.63 | 7.42 | 76.59 | 1.96 |
| 10 | 1145.71 | 599.36 | 1068.93 | 12893.64 | 392.79 | 10 | 11.68 | 6.11 | 10.90 | 131.47 | 4.01 |
| 11 | 970.29 | 690.50 | 886.07 | 9373.64 | 536.00 | 11 | 8.43 | 6.00 | 7.70 | 81.41 | 4.66 |
| 12 | 916.93 | 673.79 | 927.79 | 12554.64 | 413.71 | 12 | 7.19 | 5.28 | 7.27 | 98.41 | 3.24 |
| 13 | 1071.86 | 582.71 | 1817.00 | 15947.21 | 82.71 | 13 | 13.77 | 7.48 | 23.34 | 204.83 | 1.06 |
| 14 | 834.86 | 429.21 | 1861.93 | 18301.64 | 57.07 | 14 | 7.69 | 3.95 | 17.15 | 168.57 | 0.53 |
| 15 | 1527.86 | 705.07 | 1499.36 | 11235.71 | 148.00 | 15 | 9.42 | 4.35 | 9.25 | 69.30 | 0.91 |
| 16 | 932.64 | 677.64 | 1171.71 | 14357.29 | 251.07 | 16 | 4.58 | 3.33 | 5.75 | 70.48 | 1.23 |
| 17 | 1667.21 | 764.93 | 1634.29 | 19107.36 | 98.07 | 17 | 9.27 | 4.25 | 9.08 | 106.19 | 0.55 |
| 18 | 601.71 | 317.00 | 814.00 | 8712.79 | 162.71 | 18 | 4.72 | 2.49 | 6.39 | 68.41 | 1.28 |
| 19 | 2520.93 | 1336.43 | 2293.86 | 21659.43 | 104.14 | 19 | 19.30 | 10.23 | 17.56 | 204.83 | 0.80 |
| 20 | 967.36 | 644.50 | 1059.14 | 7774.50 | 27.64 | 20 | 7.44 | 4.96 | 8.15 | 59.80 | 0.21 |
| 21 | 984.00 | 606.50 | 1111.43 | 6288.00 | 254.43 | 21 | 9.68 | 5.97 | 10.93 | 61.86 | 2.50 |
| 22 | 981.14 | 549.00 | 1043.43 | 13103.14 | 526.86 | 22 | 8.52 | 4.77 | 9.06 | 113.73 | 4.57 |
| 23 | 1398.86 | 770.71 | 1341.07 | 12621.43 | 439.79 | 23 | 12.82 | 7.06 | 12.29 | 115.64 | 4.03 |
| 24 | 489.71 | 319.57 | 674.57 | 4735.50 | 138.29 | 24 | 4.86 | 3.17 | 6.70 | 47.02 | 1.37 |

FIG. 8 cont'd

| Sample | BTK 545 (pmol/L) | BTK 407 (pmol/L) | WASp 274 (pmol/L) | WASp 289 (pmol/L) | CD3ε 197 (pmol/L) | Sample | BTK 545 ATP7B Ratio | BTK 407 ATP7B Ratio | WASp 274 ATP7B Ratio | WASp 289 ATP7B Ratio | CD3ε 197 ATP7B Ratio |
|---|---|---|---|---|---|---|---|---|---|---|---|
| 25 | 892.29 | 541.00 | 867.29 | 7971.86 | 296.29 | 25 | 6.63 | 4.02 | 6.44 | 59.21 | 2.20 |
| 26 | 1620.93 | 911.79 | 1682.29 | 16762.21 | 263.57 | 26 | 18.20 | 10.24 | 18.89 | 188.19 | 2.96 |
| 27 | 317.93 | 251.50 | 248.21 | 3036.50 | 100.43 | 27 | 2.62 | 2.07 | 2.04 | 25.01 | 0.83 |
| 28 | 701.71 | 422.14 | 1588.29 | 15102.14 | 42.29 | 28 | 7.30 | 4.39 | 16.53 | 157.20 | 0.44 |
| 29 | 1562.21 | 876.14 | 1386.14 | 10278.71 | 639.79 | 29 | 17.68 | 9.92 | 15.69 | 116.33 | 7.24 |
| 30 | 935.43 | 483.57 | 1007.29 | 10191.71 | 249.21 | 30 | 7.88 | 4.08 | 8.49 | 85.90 | 2.10 |
| 31 | 461.21 | 336.86 | 639.00 | 4190.21 | 191.57 | 31 | 3.50 | 2.55 | 4.85 | 31.78 | 1.45 |
| 32 | 835.93 | 671.86 | 780.14 | 5269.57 | 243.14 | 32 | 6.30 | 5.07 | 5.88 | 39.73 | 1.83 |
| 33 | 1248.43 | 759.00 | 1419.71 | 11329.57 | 273.50 | 33 | 11.69 | 7.11 | 13.29 | 106.10 | 2.56 |
| 34 | 474.43 | 314.86 | 563.57 | 3114.79 | 171.14 | 34 | 3.40 | 2.26 | 4.04 | 22.35 | 1.23 |
| 35 | 1648.64 | 1088.07 | 1730.00 | 9638.43 | 238.57 | 35 | 17.74 | 11.71 | 18.62 | 103.72 | 2.57 |
| 36 | 959.50 | 773.43 | 1002.36 | 9043.00 | 170.21 | 36 | 7.98 | 6.43 | 8.33 | 75.18 | 1.42 |
| 37 | 1440.57 | 1026.86 | 1427.57 | 7468.00 | 61.79 | 37 | 16.78 | 11.96 | 16.63 | 86.98 | 0.72 |
| 38 | 948.21 | 620.29 | 1135.29 | 8484.86 | 299.50 | 38 | 7.65 | 5.00 | 9.16 | 68.43 | 2.42 |
| 39 | 717.21 | 435.71 | 1610.86 | 13417.57 | 43.07 | 39 | 7.21 | 4.38 | 16.19 | 134.85 | 0.43 |
| 40 | 1437.36 | 843.00 | 1306.07 | 9699.21 | 464.00 | 40 | 12.24 | 7.18 | 11.12 | 82.60 | 3.95 |

FIG. 9

| Patient | BTK 545 (pmol/L) | BTK 407 (pmol/L) | WASp 274 (pmol/L) | WASp 289 (pmol/L) | CD3ε 197 (pmol/L) | Immuno-SRM Diagnosis | Clinical Diagnosis | Genotype | Notes |
|---|---|---|---|---|---|---|---|---|---|
| 1 | 2221.71 | 1362.07 | 2609.43 | 27763.21 | 246.07 | Normal | X-linked CGD | CYBB Mutation | |
| 2 | 1148.86 | 744.21 | 1028.71 | 11880.21 | 231.00 | Normal | X-linked CGD | CYBB Mutation | |
| 3 | 3.79 | 13.79 | 1919.71 | 23893.21 | 86.29 | BTK | BTK | BTK c.1587_1589delA (p.N530Tfs26*) | Brother of #4 |
| 4 | 11.79 | 13.93 | 1623.07 | 17947.86 | 200.43 | BTK | BTK | BTK c.1587_1589delA (p.N530Tfs26*) | Brother of #3 |
| 5 | 26.96 | 16.96 | 1280.39 | 17413.25 | 99.11 | BTK | BTK | BTK c.1940T>C (p.L647P) | |
| 6 | 20.21 | 11.36 | 257.00 | 4310.21 | 177.50 | BTK | BTK | BTK c.763C>T (p.R255*) | |
| 7 | 19.64 | 12.43 | 1121.29 | 18177.57 | 71.57 | BTK | BTK | BTK c.1940T>C (p.L647P) | |
| 8 | 23.36 | 23.82 | 637.00 | 8699.25 | 103.86 | BTK | BTK | BTK c.1889T>A (p.M630K) | |
| 9 | 21.71 | 13.36 | 495.00 | 6009.64 | 63.50 | BTK | BTK | BTK c.1908+2delTAAGTGCTT | |
| 10 | 237.64 | 113.14 | 548.00 | 7162.29 | 65.79 | Normal | BTK | No mutation identified | |
| 11 | 10.86 | 10.93 | 781.79 | 9599.00 | 81.71 | BTK | BTK | BTK c.1768A>T (p.I590F) | |
| 12 | 13.79 | 11.36 | 618.50 | 7024.36 | 65.64 | BTK | BTK | No mutation identified | |
| 13 | 339.21 | 213.00 | 760.64 | 7695.14 | 110.07 | Normal | BTK | No mutation identified | |
| 14 | 12.71 | 15.50 | 776.93 | 6535.57 | 94.00 | BTK | BTK | BTK c.1714_1715delTA (p.S572Ifs14*) | |
| 15 | 10.36 | 12.07 | 444.21 | 3723.29 | 57.43 | BTK | BTK | BTK c.953C>T (p.S318F) | |
| 16 | 8.79 | 13.29 | 745.00 | 6118.79 | 65.93 | BTK | BTK | BTK c.1811028T>G (p.Y40D) | |

FIG. 9 cont'd

| Patient | BTK 545 (pmol/L) | BTK 407 (pmol/L) | WASp 274 (pmol/L) | WASp 289 (pmol/L) | CD3ε 197 (pmol/L) | Immuno-SRM Diagnosis | Clinical Diagnosis | Genotype | Notes |
|---|---|---|---|---|---|---|---|---|---|
| 17 | 24.29 | 32.36 | 1001.79 | 7820.93 | 109.71 | BTK | BTK | BTK c.629insA (p.P210Tfs5*) | |
| 18 | 7.93 | 167.86 | 609.71 | 5347.21 | 85.57 | BTK | BTK | BTK c.1651T>A (p.Y551N) | |
| 19 | 25.93 | 28.50 | 427.29 | 4181.00 | 80.07 | BTK | BTK | BTK c.1735G>C (p.D579H) | |
| 20 | 16.36 | 23.86 | 786.50 | 5407.93 | 100.57 | BTK | BTK | BTK c.752G>A (p.W251*) | |
| 21 | 6.93 | 19.00 | 801.07 | 8769.71 | 77.21 | BTK | BTK | BTK c.117_119delCTA (p.del40Y) | |
| 22 | 18.50 | 9.29 | 684.64 | 5988.29 | 76.57 | BTK | BTK | BTK c.521-1G>A (splice) | |
| 23 | 4.93 | 8.29 | 508.79 | 5970.86 | 77.71 | BTK | BTK | BTK c.1876delG (p.A582Lfs4*) | |
| 24 | 10.57 | 19.64 | 537.50 | 7728.86 | 91.00 | BTK | BTK | BTK c.763C>T (p.R255*) | |
| 25 | 13.50 | 20.36 | 602.29 | 6838.79 | 65.00 | BTK | BTK | BTK c.1782delG (p.K595Rfs52*) | |
| 26 | 9.21 | 20.36 | 1030.00 | 8832.43 | 147.07 | BTK | BTK | BTK c.1657delA (p.S553Afs2*) | |
| 27 | 10.36 | 21.71 | 751.29 | 6371.79 | 93.64 | BTK | BTK | BTK c.1610delT (p.V537Dfs18*) | |
| 28 | 14.43 | 8.21 | 557.93 | 5896.29 | 50.57 | BTK | BTK | BTK c.37C>T (p.R13*) | |
| 29 | 784.25 | 547.86 | 182.68 | 2041.46 | 360.21 | WAS | WAS | WAS c.1453+2T>A | Pt. #30 (Pre-BMT) |
| 30 | 1397.93 | 786.00 | 938.93 | 12758.86 | 105.64 | Normal | WAS (Post-BMT) | Normal BMT donor | Pt. #29 (Post-BMT) |

FIG. 9 cont'd

| Patient | BTK 545 (pmol/L) | BTK 407 (pmol/L) | WASp 274 (pmol/L) | WASp 289 (pmol/L) | CD3ε 197 (pmol/L) | Immuno-SRM Diagnosis | Clinical Diagnosis | Genotype | Notes |
|---|---|---|---|---|---|---|---|---|---|
| 31 | 415.00 | 202.36 | 113.86 | 1812.00 | 69.21 | WAS | WAS/XLT | WAS c.223G>A (p.V75M) | |
| 32 | 768.93 | 492.21 | 11.29 | 375.86 | 82.07 | WAS | WAS | WAS c.631C>T (p.R211*) | |
| 33 | 342.36 | 346.86 | 11.71 | 248.14 | 77.43 | WAS | WAS | WAS c.838C>T (p.Q280*) | |
| 34 | 275.57 | 206.57 | 10.64 | 238.50 | 42.29 | WAS | WAS | WAS c.838delC (p.Q280Sfs28*) | |
| 35 | 258.79 | 187.50 | 10.29 | 204.64 | 55.43 | WAS | WAS | WAS c.631C>T (p.R211*) | Brother of Pt. #36 |
| 36 | 448.07 | 236.00 | 4.71 | 237.43 | 46.29 | WAS | WAS | WAS c.631C>T (p.R211*) | Brother of Pt. #35 |
| 37 | 307.79 | 167.00 | 33.14 | 476.79 | 126.14 | WAS | WAS | WAS c.1264_1267insCCTT GCCTGCCTCT (P.G422Pfs20*) | |
| 38 | 123.64 | 106.21 | 6.79 | 148.79 | 132.36 | WAS | WAS | WAS c.332_336insCC (p.F113Pfs15*) | |
| 39 | 788.79 | 520.50 | 20.71 | 359.36 | 36.00 | WAS | WAS | WAS c.756G>A (p.W252*) | |
| 40 | 851.71 | 648.71 | 624.43 | 6892.07 | 33.93 | SCID | T-B-NK+ SCID | RAG1 c.2159G>A (p.G720D), Homozygous | |
| 41 | 1012.36 | 567.14 | 1295.93 | 20174.64 | 86.29 | Normal | X-SCID - Hypomorphic | IL2RG c.460C>T (p.T154S) | |
| 42 | 1414.36 | 872.43 | 1898.29 | 16707.14 | 17.57 | SCID | T-B+NK+ SCID | Unknown - Gene panel & Exome negative | |

FIG. 10B

| Peptide | Area Under Curve | p-value |
|---|---|---|
| BTK 407 | 0.999 | <0.0001 |
| BTK 545 | 0.999 | <0.0001 |
| WASp 274 | 0.971 | <0.0001 |
| WASp 289 | 0.930 | <0.0001 |
| CD3ε 197 | 0.925 | <0.0150 |

FIG. 11

| Sample | BTK 545 (pmol/L) | BTK 407 (pmol/L) | WASp 274 (pmol/L) | WASp 289 (nmol/L) | CD3ε (pmol/L) | Sample | BTK 545 (pmol/L) | BTK 407 (pmol/L) | WASp 274 (pmol/L) | WASp 289 (nmol/L) | CD3ε (pmol/L) |
|---|---|---|---|---|---|---|---|---|---|---|---|
| 1 | 355.71 | 623.28 | 1579.24 | 31.99 | 82.85 | 32 | 224.50 | 426.40 | 1009.47 | 20.97 | 76.84 |
| 2 | 358.71 | 649.43 | 1587.71 | 16.74 | 55.14 | 33 | 138.51 | 257.70 | 668.07 | 12.57 | 65.82 |
| 3 | 242.96 | 424.54 | 856.51 | 17.72 | 98.01 | 34 | 219.06 | 440.13 | 1221.81 | 24.63 | 85.14 |
| 4 | 301.43 | 522.86 | 928.86 | 11.06 | 64.00 | 35 | 263.99 | 482.34 | 1316.96 | 27.65 | 89.00 |
| 5 | 209.14 | 366.14 | 703.14 | 8.33 | 49.43 | 36 | 213.20 | 397.64 | 763.65 | 15.04 | 69.54 |
| 6 | 123.86 | 258.57 | 601.43 | 7.44 | 66.29 | 37 | 120.76 | 205.76 | 447.29 | 3.41 | 51.22 |
| 7 | 196.74 | 369.88 | 900.01 | 6.68 | 56.52 | 38 | 108.89 | 199.60 | 433.98 | 9.06 | 66.82 |
| 8 | 265.86 | 486.00 | 740.00 | 9.15 | 71.86 | 39 | 107.60 | 201.18 | 566.91 | 12.00 | 62.53 |
| 9 | 165.41 | 345.98 | 696.68 | 5.40 | 76.69 | 40 | 220.50 | 379.03 | 758.07 | 15.72 | 69.40 |
| 10 | 231.29 | 430.14 | 880.86 | 10.19 | 88.14 | 41 | 161.69 | 310.50 | 671.93 | 13.94 | 70.11 |
| 11 | 207.33 | 352.99 | 732.31 | 14.46 | 73.40 | 42 | 249.11 | 390.48 | 999.88 | 6.56 | 61.10 |
| 12 | 186.14 | 316.29 | 690.00 | 8.27 | 78.14 | 43 | 264.57 | 505.38 | 1119.36 | 23.85 | 95.01 |
| 13 | 260.42 | 606.97 | 1117.93 | 19.75 | 90.14 | 44 | 759.79 | 1255.58 | 2862.29 | 52.00 | 137.65 |
| 14 | 252.55 | 452.72 | 932.35 | 18.15 | 86.42 | 45 | 120.48 | 222.93 | 432.41 | 9.28 | 78.98 |
| 15 | 203.61 | 393.91 | 940.65 | 17.82 | 99.30 | 46 | 816.16 | 1234.69 | 2550.93 | 19.17 | 255.98 |
| 16 | 261.13 | 398.35 | 668.64 | 4.96 | 50.94 | 47 | 823.46 | 1307.23 | 3021.83 | 22.77 | 250.97 |
| 17 | 519.83 | 903.73 | 933.06 | 5.65 | 71.54 | 48 | 838.91 | 1241.70 | 2014.65 | 15.96 | 203.18 |
| 18 | 456.87 | 553.17 | 963.40 | 6.19 | 71.40 | 49 | 623.42 | 905.88 | 1295.50 | 9.37 | 62.67 |
| 19 | 641.17 | 1019.63 | 1579.24 | 10.76 | 100.45 | 50 | 789.83 | 1219.09 | 2700.03 | 19.75 | 112.32 |
| 20 | 167.55 | 334.39 | 607.69 | 4.77 | 52.23 | 51 | 454.58 | 736.89 | 1234.69 | 8.24 | 65.53 |
| 21 | 329.81 | 614.70 | 1072.14 | 7.41 | 67.54 | 52 | 624.14 | 810.87 | 805.00 | 6.36 | 54.94 |
| 22 | 427.25 | 656.19 | 1086.45 | 7.25 | 75.84 | 53 | 360.58 | 498.08 | 785.40 | 5.39 | 58.81 |
| 23 | 325.95 | 447.72 | 587.37 | 3.20 | 93.29 | 54 | 166.55 | 300.91 | 712.42 | 4.89 | 64.82 |
| 24 | 233.52 | 385.19 | 486.06 | 3.55 | 73.83 | 55 | 141.23 | 267.43 | 811.15 | 5.52 | 72.97 |
| 25 | 255.69 | 381.47 | 703.27 | 5.07 | 92.72 | 56 | 263.71 | 438.99 | 975.13 | 6.85 | 108.46 |

FIG. 11 cont'd

| Sample | BTK 545 (pmol/L) | BTK 407 (pmol/L) | WASp 274 (pmol/L) | WASp 289 (nmol/L) | CD3ε (pmol/L) | Sample | BTK 545 (pmol/L) | BTK 407 (pmol/L) | WASp 274 (pmol/L) | WASp 289 (nmol/L) | CD3ε (pmol/L) |
|---|---|---|---|---|---|---|---|---|---|---|---|
| 26 | 246.39 | 365.30 | 937.78 | 5.95 | 86.42 | 57 | 163.12 | 290.75 | 767.37 | 5.19 | 67.11 |
| 27 | 185.30 | 291.04 | 786.97 | 6.13 | 104.74 | 58 | 253.55 | 448.86 | 1016.05 | 6.82 | 62.53 |
| 28 | 208.91 | 387.19 | 755.35 | 5.42 | 116.33 | 59 | 267.28 | 507.53 | 1207.50 | 7.79 | 71.69 |
| 29 | 253.98 | 358.43 | 865.81 | 6.67 | 129.92 | 60 | 149.10 | 269.29 | 698.54 | 4.99 | 63.96 |
| 30 | 168.27 | 289.03 | 565.05 | 4.42 | 111.03 | 61 | 118.33 | 240.81 | 555.17 | 3.92 | 71.54 |
| 31 | 139.37 | 274.44 | 580.07 | 12.01 | 52.37 | 62 | 244.68 | 288.03 | 326.81 | 2.49 | 72.12 |
|  |  |  |  |  |  | Mean | 300.86 | 499.05 | 997.04 | 11.37 | 85.25 |
|  |  |  |  |  |  | SD | 191.74 | 281.62 | 563.07 | 8.47 | 39.49 |

FIG. 12

| Patient | BTK 545 ATP7B Ratio | BTK 407 ATP7B Ratio | WASp 274 ATP7B Ratio | WASp 289 ATP7B Ratio | CD3ε 197 ATP7B Ratio | Immuno-SRM Diagnosis | Clinical Diagnosis | Genotype | Notes |
|---|---|---|---|---|---|---|---|---|---|
| 1 | 19.65 | 12.05 | 23.08 | 245.54 | 2.18 | Normal | X-linked CGD | CYBB Mutation | |
| 2 | 8.43 | 5.46 | 7.54 | 87.13 | 1.69 | Normal | X-linked CGD | CYBB Mutation | |
| 3 | 0.02 | 0.06 | 8.84 | 110.07 | 0.40 | BTK | BTK | BTK c.1587_1589delA (p.N530Tfs26*) | Brother of #4 |
| 4 | 0.11 | 0.13 | 15.06 | 166.51 | 1.86 | BTK | BTK | BTK c.1587_1589delA (p.N530Tfs26*) | Brother of #3 |
| 5 | 0.15 | 0.09 | 6.98 | 94.91 | 0.54 | BTK | BTK | BTK c.1940T>C (p.L647P) | |
| 6 | 0.67 | 0.38 | 8.49 | 142.32 | 5.86 | BTK | BTK | BTK c.763C>T (p.R255*) | |
| 7 | 0.16 | 0.10 | 9.10 | 147.53 | 0.58 | BTK | BTK | BTK c.1940T>C (p.L647P) | |
| 8 | 0.12 | 0.13 | 3.38 | 46.12 | 0.55 | BTK | BTK | BTK c.1889T>A (p.M630K) | |
| 9 | 1.09 | 0.67 | 24.75 | 300.48 | 3.18 | BTK | BTK | BTK c.1908+2delTAAGTGCTT | |
| 10 | 8.36 | 3.98 | 19.28 | 251.94 | 2.31 | Normal | BTK | No mutation identified | |
| 11 | 0.50 | 0.51 | 36.24 | 444.99 | 3.79 | BTK | BTK | BTK c.1768A>T (p.I590F) | |
| 12 | 0.43 | 0.35 | 19.20 | 218.05 | 2.04 | BTK | BTK | No mutation identified | |
| 13 | 10.97 | 6.89 | 24.59 | 248.80 | 3.56 | Normal | BTK | No mutation identified | |
| 14 | 0.65 | 0.80 | 39.99 | 336.39 | 4.84 | BTK | BTK | BTK c.1714_1715delTA (p.S572Ifs14*) | |
| 15 | 0.41 | 0.48 | 17.62 | 147.67 | 2.28 | BTK | BTK | BTK c.953C>T (p.S318F) | |
| 16 | 0.29 | 0.44 | 24.54 | 201.56 | 2.17 | BTK | BTK | BTK c.11811028T>G (p.Y40D) | |
| 17 | 0.67 | 0.89 | 27.61 | 215.54 | 3.02 | BTK | BTK | BTK c.629insA (p.P210Tfs5*) | |
| 18 | 0.24 | 5.01 | 18.20 | 159.62 | 2.55 | BTK | BTK | BTK c.1651T>A (p.Y551N) | |
| 19 | 1.03 | 1.14 | 17.04 | 166.76 | 3.19 | BTK | BTK | BTK c.1735G>C (p.D579H) | |
| 20 | 0.33 | 0.49 | 16.10 | 110.69 | 2.06 | BTK | BTK | BTK c.752G>A (p.W251*) | |
| 21 | 0.14 | 0.37 | 15.80 | 172.92 | 1.52 | BTK | BTK | BTK c.117_119delCTA (p.del40Y) | |
| 22 | 0.55 | 0.28 | 20.35 | 178.00 | 2.28 | BTK | BTK | BTK c.521-1G>A (splice) | |
| 23 | 0.15 | 0.26 | 15.94 | 187.01 | 2.43 | BTK | BTK | BTK c.1876delG (p.A582Lfs4*) | |
| 24 | 0.34 | 0.64 | 17.42 | 250.47 | 2.95 | BTK | BTK | BTK c.763C>T (p.R255*) | |
| 25 | 0.22 | 0.32 | 9.60 | 109.05 | 1.04 | BTK | BTK | BTK c.1782delG (p.K595Rfs52*) | |
| 26 | 0.20 | 0.44 | 22.32 | 191.41 | 3.19 | BTK | BTK | BTK c.1657delA (p.S553Afs2*) | |
| 27 | 0.23 | 0.48 | 16.78 | 142.27 | 2.09 | BTK | BTK | BTK c.1610delT (p.V537Dfs18*) | |

FIG. 12 cont'd

| Patient | BTK 545 ATP7B Ratio | BTK 407 ATP7B Ratio | WASp 274 ATP7B Ratio | WASp 289 ATP7B Ratio | CD3ε 197 ATP7B Ratio | Immuno-SRM Diagnosis | Clinical Diagnosis | Genotype | Notes |
|---|---|---|---|---|---|---|---|---|---|
| 28 | 0.21 | 0.12 | 8.00 | 84.58 | 0.73 | BTK | BTK | BTK c.37C>T (p.R13*) | |
| 29 | 8.69 | 6.07 | 2.02 | 22.62 | 3.99 | WAS | WAS | WAS c.1453+2T>A | Same as Pt. #30 (Pre-BMT) |
| 30 | 12.42 | 6.98 | 8.34 | 113.34 | 0.94 | Normal | WAS (Post-BMT) | Normal BMT donor | Same as Pt. #29 (Post-BMT) |
| 31 | 2.46 | 1.20 | 0.68 | 10.74 | 0.41 | WAS | WAS/XLT | WAS c.223G>A (p.V75M) | |
| 32 | 7.07 | 4.52 | 0.10 | 3.46 | 0.75 | WAS | WAS | WAS c.631C>T (p.R211*) | |
| 33 | 7.18 | 7.27 | 0.25 | 5.20 | 1.62 | WAS | WAS | WAS c.838C>T (p.Q280*) | |
| 34 | 9.16 | 6.87 | 0.35 | 7.93 | 1.41 | WAS | WAS | WAS c.838delC (p.Q280Sfs28*) | |
| 35 | 8.31 | 6.02 | 0.33 | 6.57 | 1.78 | WAS | WAS | WAS c.631C>T (p.R211*) | Brother of Pt. #36 |
| 36 | 7.45 | 3.92 | 0.08 | 3.95 | 0.77 | WAS | WAS | WAS c.631C>T (p.R211*) | Brother of Pt. #35 |
| 37 | 5.52 | 2.99 | 0.59 | 8.55 | 2.26 | WAS | WAS | WAS c.1264_1267insCCTTGCCTGCCTCT (p.G422Pfs20*) | |
| 38 | 17.14 | 14.72 | 0.94 | 20.62 | 18.35 | WAS | WAS | WAS c.332_336insCC (p.F113Pfs15*) | |
| 39 | 12.45 | 8.22 | 0.33 | 5.67 | 0.57 | WAS | WAS | WAS c.756G>A (p.W252*) | |
| 40 | 6.11 | 4.65 | 4.48 | 49.41 | 0.24 | SCID | T-B-NK+ SCID | RAG1 c.2159G>A (p.G720D), Homozygous | |
| 41 | 5.54 | 3.10 | 7.09 | 110.37 | 0.47 | Normal | X-SCID - Hypomorphic | IL2RG c.460C>T (p.T154S) | |
| 42 | 8.00 | 4.93 | 10.74 | 94.51 | 0.10 | SCID | T-B+NK+ SCID | Unknown - Gene panel & Exome negative | |

FIG. 15

| Sample | CTNS 115 (pmol/L) | SHPK 363 (pmol/L) | Genotype | Mutation |
|---|---|---|---|---|
| 1 | N.D. | N.D. | Homozygous | 57-kb Deletion |
| 2 | N.D. | N.D. | Homozygous | 57-kb Deletion |
| 3 | N.D. | N.D. | Homozygous | 57-kb Deletion |
| 4 | N.D. | 939.02 | Heterozygous | c.314_317delACTC; p.H105PfsxX12 / 57-kb Deletion |
| 5 | 9.43 | 1278.88 | Heterozygous | c.473T>C; p.L158P / 57-kb Deletion |
| 6 | 18.00 | 1198.74 | Heterozygous | c.473T>C; p.L158P / 57-kb Deletion |
| 7 | N.D. | N.D. | * | Predicted: Homozygous 57-kb Deletion |
| 8 | N.D. | N.D. | * | Predicted: Homozygous 57-kb Deletion |
| 9 | N.D. | N.D. | * | Predicted: Homozygous 57-kb Deletion |
| NC1 | 20.14 | 2658.48 | - | |
| NC2 | 42.43 | 2842.34 | - | |
| NC3 | 31.71 | 2835.91 | - | |
| NC4 | 26.86 | 1710.32 | - | |
| NC Average | 30.29 | 2511.76 | | |
| NC SD | 8.13 | 468.56 | | |

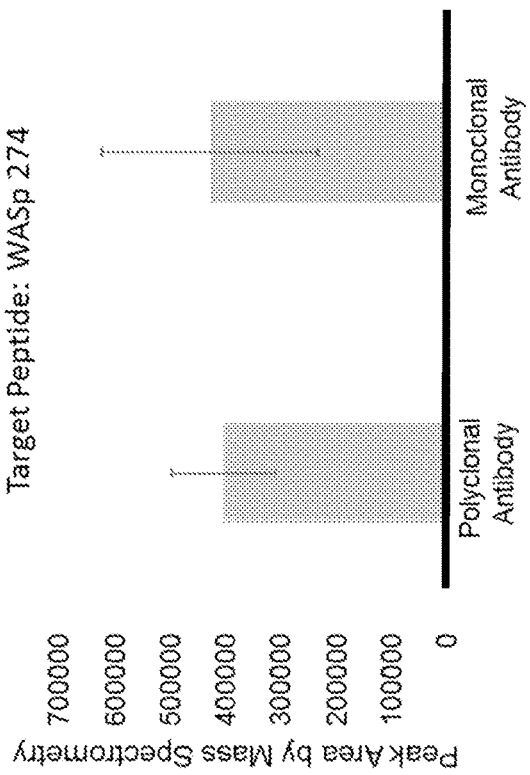
FIG. 16A
Target Peptide: BTK 407
FIG. 16B
Target Peptide: WASp 274
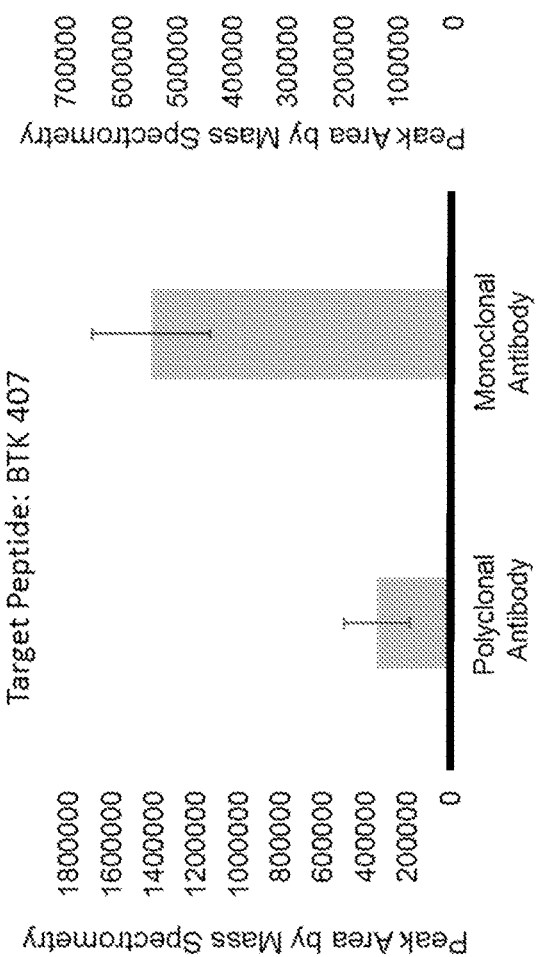
FIG. 16C
Target Peptide: BTK 407
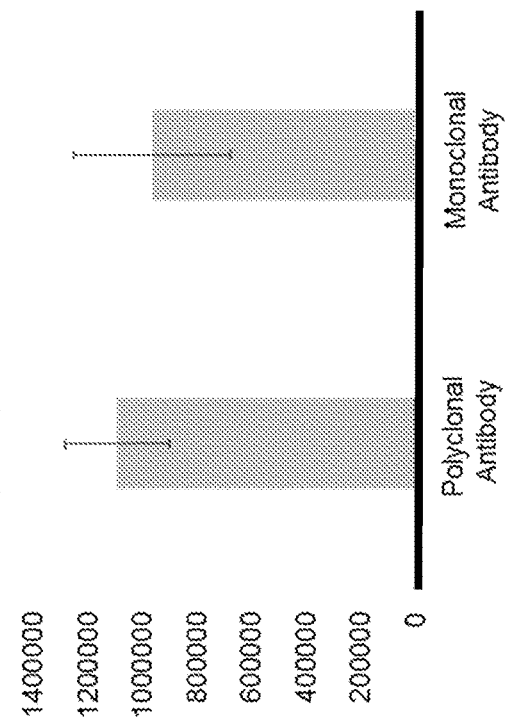
FIG. 16D
Target Peptide: WASp 274
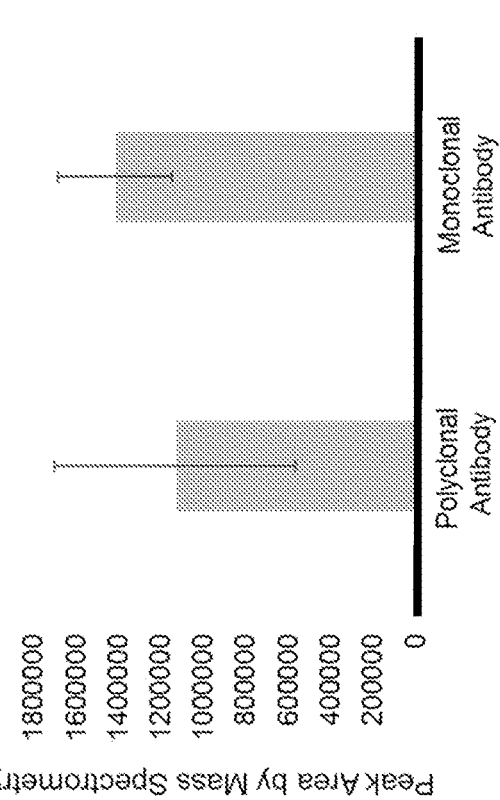

FIG. 19

>Anti-CD3ε 197 VH CDR1
EYVIH (SEQ ID NO: 22)

>Anti-CD3ε 197 VH CDR2
GFNPNIGGTNYNQRFKG (SEQ ID NO: 23)

>Anti-CD3ε 197 VH CDR3
GGPYYYAMDY (SEQ ID NO: 24)

>Anti-CD3ε 197 variable heavy domain coding sequence with leader sequence. The leader sequence is underlined.
<u>ATGGGATGGAGCTGGATCTTTCTCTTTCTCCTGTCAGGAACTGCAGGTGTCCTCTCTGAGG</u>TCCAGCTGCAGCAGTCTGGACCTGACCTGGTGAAGCCTGGGGCCTCAGTGAAGATTTCCTGCAAGACTTCTGGATACATATTCATTGAATACGTCATACACTGGGTGAAGCAGAGCCATGGAAAGAGCCTTGAGTGGATTGGAGGTTTTAATCCTAACATTGGTGGTACTAACTACAACCAGAGGTTCAAGGGCAAGGCCACATTGACTGTAGACAAGTCCTCCAGCACAGCCTACATGGAGCTCCGCAGCCTGACATCTGAGGATTCTGCAGTCTATTACTGTGTAAGGGGGGGACCCTATTACTATGCTATGGACTACTGGGGTCAAGGAACCTCAGTCACCGTCTCCTCA (SEQ ID NO: 78)

>Anti-CD3ε 197 variable heavy domain amino acid sequence with leader sequence. The leader sequence is underlined and the CDRs are bolded.
<u>MGWSWIFLFLLSGTAGVLS</u>EVQLQQSGPDLVKPGASVKISCKTSGYIFIEYVIHWVKQSHGKSLEWIGGFNPNIGGTNYNQRFKGKATLTVDKSSSTAYMELRSLTSEDSAVYYCVRGGPYYYAMDYWGQGTSVTVSS (SEQ ID NO: 79)

>Anti-CD3ε 197 variable heavy domain amino acid sequence without leader sequence. The CDRs are bolded.
EVQLQQSGPDLVKPGASVKISCKTSGYIFIEYVIHWVKQSHGKSLEWIGGFNPNIGGTNYNQRFKGKATLTVDKSSSTAYMELRSLTSEDSAVYYCVRGGPYYYAMDYWGQGTSVTVSS (SEQ ID NO: 63)

FIG. 19 cont'd

>Anti-CD3ε 197 VL CDR1
RSSQSIVHSSGNTYLE (SEQ ID NO: 25)

>Anti-CD3ε 197 VL CDR2
KVSNRFS (SEQ ID NO: 26)

>Anti-CD3ε 197 VL CDR3
FQGSHVPWT (SEQ ID NO: 27)

>Anti-CD3ε 197 variable light domain coding sequence with leader sequence. The leader sequence is underlined.
<u>ATGAAGTTGCCTGTTAGGCTGTTGGTGCTGATGTTCTGGATTCCTGTTTTCAGCAGTGATG</u>TTTTGATGACCCAAAATCCACTCTCCCTGCCTGTCAGTCTTGGAGATCAAGCCTCCATCTCTTGCAGATCTAGTCAGAGCATTGTACATAGTAGTGGAAACACCTATTTAGAATGGTACCTGCAGAAACCAGGCCAGTCTCCAAAGGTCCTGATCTACAAAGTTTCCAACCGATTTCTGGGGTCCCAGACAGGTTCAGTGGCAGTGGATCAGGGACAGATTTCACACTCAAGATCAGCAGAGTGGAGGCTGAGGATCTGGGAGTTTATTACTGCTTTCAAGGTTCACATGTTCCGTGGACGTTCGGTGGAGGCACCAAGCTGGAAATCAAA (SEQ ID NO: 80)

>Anti-CD3ε 197 variable light domain amino acid sequence with leader sequence. The leader sequence is underlined and the CDRs are bolded.
<u>MKLPVRLLVLMFWIPVFSS</u>DVLMTQNPLSLPVSLGDQASISCRSSQSIVHSSGNTYLEWYLQKPGQSPKVLIYKVSNRFSGVPDRFSGSGSGTDFTLKISRVEAEDLGVYYCFQGSHVPWTFGGGTKLEIK (SEQ ID NO: 81)

>Anti-CD3ε 197 variable light domain amino acid sequence without leader sequence. The CDRs are bolded.
DVLMTQNPLSLPVSLGDQASISCRSSQSIVHSSGNTYLEWYLQKPGQSPKVLIYKVSNRFSGVPDRFSGSGSGTDFTLKISRVEAEDLGVYYCFQGSHVPWTFGGGTKLEIK (SEQ ID NO: 64)

FIG. 19 cont'd

>Anti-WASp 274 VH CDR1
TYAMT (SEQ ID NO: 28)

>Anti-WASp 274 VH CDR2
SFYIEGSASYANWANGR (SEQ ID NO: 29)

>Anti-WASp 274 VH CDR3
GNPGGSSAV (SEQ ID NO: 30)

>Anti-WASp 274 heavy chain coding sequence (EB0603-2F8-H2) with leader sequence. The leader sequence is underlined.
<u>ATGGAGACTGGGCTGCGCTGGCTTCTCCTGGTCGCTGTGCTCAAAGGTGTCCAGTGTCAG</u>TCGGTGGAGGAGTCCGGGGGTCGCCTGGTCACGCCTGGGACACCCCTGACACTCACCTGCACAGTCTCTGGATTCTCCCTCAGTACCTATGCAATGACCTGGGTCCGCCAGGCTCCAGGGAAGGGGCTACAATGGATCGGATCCTTTTATATTGAGGGTAGCGCATCCTACGCGAACTGGGCGAATGGTCGATTCACCATCTCCAAAACCTCGAGTACGGTGAATCTGAAAATGACCAGTCCGACAGTCGCGGACACGGCCAGTTATTTCTGTGCCAGAGGCAATCCTGGTGGTAGTAGTGCTGTGTGGGGCCAAGGCACCCTGGTCACCGTCTCCTCAGGGCAACCTAAGGCTCCATCAGTCTTCCCACTGGCCCCCTGCTGCGGGGACACACCCAGCTCCACGGTGACCCTGGGCTGCCTGGTCAAAGGCTACCTCCCGGAGCCAGTGACCGTGACCTGGAACTCGGGCACCCTCACCAATGGGGTACGCACCTTCCCGTCCGTCCGGCAGTCCTCAGGCCTCTACTCGCTGAGCAGCGTGGTGAGCGTGACCTCAAGCAGCCAGCCCGTCACCTGCAACGTGGCCCACCCAGCCACCAACACCAAAGTGGACAAGACCGTTGCGCCCTCGACATGCAGCAAGCCCATGTGCCCACCCCCTGAACTCCTGGGGGGACCGTCTGTCTTCATCTTCCCCCCAAAACCCAAGGACACCCTCATGATCTCACGCACCCCCGAGGTCACATGCGTGGTGGTGGACGTGAGCCAGGATGACCCCGAGGTGCAGTTCACATGGTACATAAACAACGAGCAGGTGCGCACCGCCCGGCCGCCGCTACGGGAGCAGCAGTTCAACAGCACGATCCGCGTGGTCAGCACCCTCCCCATCGCGCACCAGGACTGGCTGAGGGGCAAGGAGTTCAAGTGCAAAGTCCACAACAAGGCACTCCCGGCCCCCATCGAGAAAACCATCTCCAAAGCCAGAGGGCAGCCCCTGGAGCCGAAGGTCTACACCATGGGCCCTCCCCGGGAGGAGCTGAGCAGCAGGTCGGTCAGCCTGACCTGCATGATCAACGGCTTCTACCCTTCCGACATCTCGGTGGAGTGGGAGAAGAACGGGAAGGCAGAGGACAACTACAAGACCACGCCGGCCGTGCTGGACAGCGACGGCTCCTACTTCCTCTACAGCAAGCTCTCAGTGCCCACGAGTGAGTGGCAGCGGGGCGACGTCTTCACCTGCTCCGTGATGCACGAGGCCTTGCACAACCACTACACGCAGAAGTCCATCTCCCGCTCTCCGGGTAAATGA (SEQ ID NO: 82)

>Anti-WASp 274 heavy chain amino acid sequence with leader sequence. The leader sequence is underlined and the CDRs are bolded.
<u>METGLRWLLLVAVLKGVQC</u>QSVEESGGRLVTPGTPLTLTCTVSGFSLSTYAMTWVRQAPGKGLQWIGSFYIEGSASYANWANGRFTISKTSSTVNLKMTSPTVADTASYFCARGNPGGSSAVWGQGTLVTVSSGQPKAPSVFPLAPCCGDTPSSTVTLGCLVKGYLPEPVTVTWNSGTLTNGVRTFPSVRQSSGLYSLSSVVSVTSSSQPVTCNVAHPATNTKVDKTVAPSTCSKPMCPPPELLGGPSVFIFPPKPKDTLMISRTPEVTCVVVDVSQDDPEVQFTWYINNEQVRTARPPLREQQFNSTIRVVSTLPIAHQDWLRGKEFKCKVHNKALPAPIEKTISKARGQPLEPKVYTMGPPREELSSRSVSLTCMINGFYPSDISVEWEKNGKAEDNYKTTPAVLDSDGSYFLYSKLSVPTSEWQRGDVFTCSVMHEALHNHYTQKSISRSPGK (SEQ ID NO: 83)

FIG. 19 cont'd

>Anti-WASp 274 variable heavy domain coding sequence with leader sequence. The leader sequence is underlined.
<u>ATGGAGACTGGGCTGCGCTGGCTTCTCCTGGTCGCTGTGCTCAAAGGTGTCCAGTGT</u>CAG
TCGGTGGAGGAGTCCGGGGGTCGCCTGGTCACGCCTGGGACACCCCTGACACTCACCTG
CACAGTCTCTGGATTCTCCCTCAGTACCTATGCAATGACCTGGGTCCGCCAGGCTCCAGG
GAAGGGGCTACAATGGATCGGATCCTTTTATATTGAGGGTAGCGCATCCTACGCGAACTG
GGCGAATGGTCGATTCACCATCTCCAAAACCTCGAGTACGGTGAATCTGAAAATGACCAGT
CCGACAGTCGCGGACACGGCCAGTTATTTCTGTGCCAGAGGCAATCCTGGTGGTAGTAGT
GCTGTGTGGGGCCAAGGCACCCTGGTCACCGTCTCCTCA (SEQ ID NO: 84)

>Anti-WASp 274 variable heavy domain amino acid sequence with leader sequence. The leader sequence is underlined and the CDRs are bolded.
<u>METGLRWLLLVAVLKGVQC</u>QSVEESGGRLVTPGTPLTLTCTVSGFSLSTYAMTWVRQAPGKG
LQWIGSFYIEGSASYANWANGRFTISKTSSTVNLKMTSPTVADTASYFCARGNPGGSSAVWG
QGTLVTVSS (SEQ ID NO: 85)

>Anti-WASp 274 heavy chain amino acid sequence without leader sequence. The CDRs are bolded.
QSVEESGGRLVTPGTPLTLTCTVSGFSLSTYAMTWVRQAPGKGLQWIG**SFYIEGSASYANWA
NGRFTISKTSSTVNLKMTSPTVADTASYFCARGNPGGSSAV**WGQGTLVTVSSGQPKAPSVFP
LAPCCGDTPSSTVTLGCLVKGYLPEPVTVTWNSGTLTNGVRTFPSVRQSSGLYSLSSVVSVTS
SSQPVTCNVAHPATNTKVDKTVAPSTCSKPMCPPPELLGGPSVFIFPPKPKDTLMISRTPEVTC
VVVDVSQDDPEVQFTWYINNEQVRTARPPLREQQFNSTIRVVSTLPIAHQDWLRGKEFKCKVH
NKALPAPIEKTISKARGQPLEPKVYTMGPPREELSSRSVSLTCMINGFYPSDISVEWEKNGKAE
DNYKTTPAVLDSDGSYFLYSKLSVPTSEWQRGDVFTCSVMHEALHNHYTQKSISRSPGK (SEQ
ID NO: 86)

>Anti-WASp 274 variable heavy domain amino acid sequence without leader sequence. The CDRs are bolded.
QSVEESGGRLVTPGTPLTLTCTVSGFSLSTYAMTWVRQAPGKGLQWIG**SFYIEGSASYANWA
NGRFTISKTSSTVNLKMTSPTVADTASYFCARGNPGGSSAV**WGQGTLVTVSS (SEQ ID NO:
65)

FIG. 19 cont'd

>Anti-WASp 274 VL CDR1
QSSETVYKNNYLA (SEQ ID NO: 31)

>Anti-WASp 274 VL CDR2
WASKLAS (SEQ ID NO: 32)

>Anti-WASp 274 VL CDR3
AGYQSNIVDGTA (SEQ ID NO: 33)

>Anti-WASp 274 light chain coding sequence (EB0603-2F8-K2) with leader sequence. The leader sequence is underlined.
<u>ATGGACACGAGGGCCCCCACTCAGCTGCTGGGGCTCCTGCTGCTCTGGCTCCCAGGTGCCACATTTGCC</u>ATCGTGCTGACCCAGACTCCAGCCTCCGTGTCTGCAGCTGTGGGAGGCACAGTCACCATCAGTTGCCAGTCCAGTGAGACTGTTTATAAGAATAACTACTTAGCCTGGTATCAGCAGAAACTAGGGCAGCCTCCCAAGCTCCTGATCTACTGGGCATCCAAACTGGCATCTGGGGTCCCATCGCGGTTCAAAGGCAGTGGATCTGGGACACAGTTCACTCTCACCATCAGCGATGTGGTGTGTGCCGATGCTGGCACTTACTACTGTGCAGGATATCAAAGTAATATTGTTGATGGTACGGCTTTCGGCGGAGGGACCGAGGTGGTGGTCAACGGTGATCCAGTTGCACCTACTGTCCTCATCTTCCCACCAGCTGCTGATCAGGTGGCAACTGGAACAGTCACCATCGTGTGTGTGGCGAATAAATACTTTCCCGATGTCACCGTCACCTGGGAGGTGGATGGCACCACCCAAACAACTGGCATCGAGAACAGTAAAACACCGCAGAATTCTGCAGATTGTACCTACAACCTCAGCAGCACTCTGACACTGACCAGCACACAGTACAACAGCCACAAAGAGTACACCTGCAAGGTGACCCAGGGCACGACCTCAGTCGTCCAGAGCTTCAATAGGGGTGACTGTTAG (SEQ ID NO: 87)

>Anti-WASp 274 light chain amino acid sequence with leader sequence. The leader sequence is underlined and the CDRs are bolded.
<u>MDTRAPTQLLGLLLLWLPGATFA</u>IVLTQTPASVSAAVGGTVTISCQSSETVYKNNYLAWYQQKLGQPPKLLIYWASKLASGVPSRFKGSGSGTQFTLTISDVVCADAGTYYCAGYQSNIVDGTAFGGGTEVVVNGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC (SEQ ID NO: 88)

>Anti-WASp 274 variable light domain coding sequence with leader sequence. The leader sequence is underlined.
<u>ATGGACACGAGGGCCCCCACTCAGCTGCTGGGGCTCCTGCTGCTCTGGCTCCCAGGTGCCACATTTGCC</u>ATCGTGCTGACCCAGACTCCAGCCTCCGTGTCTGCAGCTGTGGGAGGCACAGTCACCATCAGTTGCCAGTCCAGTGAGACTGTTTATAAGAATAACTACTTAGCCTGGTATCAGCAGAAACTAGGGCAGCCTCCCAAGCTCCTGATCTACTGGGCATCCAAACTGGCATCTGGGGTCCCATCGCGGTTCAAAGGCAGTGGATCTGGGACACAGTTCACTCTCACCATCAGCGATGTGGTGTGTGCCGATGCTGGCACTTACTACTGTGCAGGATATCAAAGTAATATTGTTGATGGTACGGCTTTCGGCGGAGGGACCGAGGTGGTGGTCAAC (SEQ ID NO: 89)

>Anti-WASp 274 variable light domain amino acid sequence with leader sequence. The leader sequence is underlined and the CDRs are bolded.
<u>MDTRAPTQLLGLLLLWLPGATFA</u>IVLTQTPASVSAAVGGTVTISCQSSETVYKNNYLAWYQQKLGQPPKLLIYWASKLASGVPSRFKGSGSGTQFTLTISDVVCADAGTYYCAGYQSNIVDGTAFGGGTEVVVN (SEQ ID NO: 90)

FIG. 19 cont'd

>Anti-WASp 274 light chain amino acid sequence without the leader sequence. The CDRs are bolded.
IVLTQTPASVSAAVGGTVTISCQSSETVYKNNYLAWYQQKLGQPPKLLIYWASKLASGVPSRFKGSGSGTQFTLTISDVVCADAGTYYCAGYQSNIVDGTAFGGGTEVVVNGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC (SEQ ID NO: 91)

>Anti-WASp 274 variable light domain amino acid sequence without the leader sequence. The CDRs are bolded.
IVLTQTPASVSAAVGGTVTISCQSSETVYKNNYLAWYQQKLGQPPKLLIYWASKLASGVPSRFKGSGSGTQFTLTISDVVCADAGTYYCAGYQSNIVDGTAFGGGTEVVVN (SEQ ID NO: 66)

FIG. 19 cont'd

>Anti-BTK 407 VH CDR1
RNEIS (SEQ ID NO: 34)

>Anti-BTK 407 VH CDR2
GIGSPGRAYYATWAKSR (SEQ ID NO: 35)

>Anti BTK 407 VH CDR3
GDI

>Anti-BTK 407 heavy chain coding sequence (EB0602-1G5-H2) with leader sequence. The leader sequence is underlined.
<u>ATGGAGACTGGGCTGCGCTGGCTTCTCCTGGTCGCTGTGCTCAAAGGTGTCCAGTGTCAG</u>TCGGTGAAGGAGTCCGAGGGAGGTCTCTTCAAGCCAACGGATACCCTGACAGTCACCTGCACAGTCTCTGGATTCTCCCTCAGTAGGAATGAAATAAGCTGGTTCCGCCAGGCTCCAGGGAACGGGCTGGAATGGATCGGGGGCATTGGTAGTCCTGGACGCGCATACTACGCGACCTGGGCGAAAAGCCGATCCACCATCACCAGAAACACCAACCTGAATACGGTGACTCTGAAAATGACCAGTCTGACAGCCGCGGACACGGCCACCTATTTCTGTGCGAGAGGGGACATCTGGGGCCCAGGCACCGTGGTCACCGTCTCCTCAGGGCAACCTAAGGCTCCATCAGTCTTCCCACTGGCCCCCTGCTGCGGGGACACACCCAGCTCCACGGTGACCCTGGGCTGCCTGGTCAAAGGCTACCTCCCGGAGCCAGTGACCGTGACCTGGAACTCGGGCACCCTCACCAATGGGGTACGCACCTTCCCGTCCGTCCGGCAGTCCTCAGGCCTCTACTCGCTGAGCAGCGTGGTGAGCGTGACCTCAAGCAGCCAGCCCGTCACCTGCAACGTGGCCCACCCAGCCACCAACACCAAAGTGGACAAGACCGTTGCGCCCTCGACATGCAGCAAGCCCATGTGCCCACCCCCTGAACTCCTGGGGGGACCGTCTGTCTTCATCTTCCCCCCAAAACCCAAGGACACCCTCATGATCTCACGCACCCCCGAGGTCACATGCGTGGTGGTGGACGTGAGCCAGGATGACCCCGAGGTGCAGTTCACATGGTACATAAACAACGAGCAGGTGCGCACCGCCCGGCCGCCGCTACGGGAGCAGCAGTTCAACAGCACGATCCGCGTGGTCAGCACCCTCCCCATCGCGCACCAGGACTGGCTGAGGGGCAAGGAGTTCAAGTGCAAAGTCCACAACAAGGCACTCCCGGCCCCCATCGAGAAAACCATCTCCAAAGCCAGAGGGCAGCCCCTGGAGCCGAAGGTCTACACCATGGGCCCTCCCCGGGAGGAGCTGAGCAGCAGGTCGGTCAGCCTGACCTGCATGATCAACGGCTTCTACCCTTCCGACATCTCGGTGGAGTGGGAGAAGAACGGGAAGGCAGAGGACAACTACAAGACCACGCCGGCCGTGCTGGACAGCGACGGCTCCTACTTCCTCTACAGCAAGCTCTCAGTGCCCACGAGTGAGTGGCAGCGGGGCGACGTCTTCACCTGCTCCGTGATGCACGAGGCCTTGCACAACCACTACACGCAGAAGTCCATCTCCCGCTCTCCGGGTAAATGA (SEQ ID NO: 92)

>Anti-BTK 407 heavy chain amino acid sequence with leader sequence. The leader sequence is underlined and the CDRs are bolded.
<u>METGLRWLLLVAVLKGVQC</u>QSVKESEGGLFKPTDTLTVTCTVSGFSLSRNEISWFRQAPGNGLEWIGGIGSPGRAYYATWAKSRSTITRNTNLNTVTLKMTSLTAADTATYFCARGDIWGPGTVVTVSSGQPKAPSVFPLAPCCGDTPSSTVTLGCLVKGYLPEPVTVTWNSGTLTNGVRTFPSVRQSSGLYSLSSVVSVTSSSQPVTCNVAHPATNTKVDKTVAPSTCSKPMCPPPELLGGPSVFIFPPKPKDTLMISRTPEVTCVVVDVSQDDPEVQFTWYINNEQVRTARPPLREQQFNSTIRVVSTLPIAHQDWLRGKEFKCKVHNKALPAPIEKTISKARGQPLEPKVYTMGPPREELSSRSVSLTCMINGFYPSDISVEWEKNGKAEDNYKTTPAVLDSDGSYFLYSKLSVPTSEWQRGDVFTCSVMHEALHNHYTQKSISRSPGK (SEQ ID NO: 93)

FIG. 19 cont'd

>Anti-BTK 407 variable heavy domain coding sequence with leader sequence. The leader sequence is underlined.
<u>ATGGAGACTGGGCTGCGCTGGCTTCTCCTGGTCGCTGTGCTCAAAGGTGTCCAGTGT</u>CAG
TCGGTGAAGGAGTCCGAGGGAGGTCTCTTCAAGCCAACGGATACCCTGACAGTCACCTGC
ACAGTCTCTGGATTCTCCCTCAGTAGGAATGAAATAAGCTGGTTCCGCCAGGCTCCAGGG
AACGGGCTGGAATGGATCGGGGGCATTGGTAGTCCTGGACGCGCATACTACGCGACCTG
GGCGAAAAGCCGATCCACCATCACCAGAAACACCAACCTGAATACGGTGACTCTGAAAAT
GACCAGTCTGACAGCCGCGGACACGGCCACCTATTTCTGTGCGAGAGGGGACATCTGGG
GCCCAGGCACCGTGGTCACCGTCTCCTCA (SEQ ID NO: 94)

>Anti-BTK 407 variable heavy domain amino acid sequence with leader sequence. The leader sequence is underlined and the CDRs are bolded.
<u>METGLRWLLLVAVLKGVQC</u>QSVKESEGGLFKPTDTLTVTCTVSGFSLSRNEISWFRQAPGNGL
EWIGGIGSPGRAYYATWAKSRSTITRNTNLNTVTLKMTSLTAADTATYFCARGDIWGPGTVVT
VSS (SEQ ID NO: 95)

>Anti-BTK 407 heavy chain amino acid sequence without leader sequence. The CDRs are bolded.
QSVKESEGGLFKPTDTLTVTCTVSGFSLSRNEISWFRQAPGNGLEWIG**GIGSPGRAYYATWA
KSRSTITRNTNLNTVTLKMTSLTAADTATYFCARGDI**WGPGTVVTVSSGQPKAPSVFPLAPCCG
DTPSSTVTLGCLVKGYLPEPVTVTWNSGTLTNGVRTFPSVRQSSGLYSLSSVVSVTSSSQPVT
CNVAHPATNTKVDKTVAPSTCSKPMCPPPELLGGPSVFIFPPKPKDTLMISRTPEVTCVVVDVS
QDDPEVQFTWYINNEQVRTARPPLREQQFNSTIRVVSTLPIAHQDWLRGKEFKCKVHNKALPA
PIEKTISKARGQPLEPKVYTMGPPREELSSRSVSLTCMINGFYPSDISVEWEKNGKAEDNYKTT
PAVLDSDGSYFLYSKLSVPTSEWQRGDVFTCSVMHEALHNHYTQKSISRSPGK (SEQ ID NO: 96)

>Anti-BTK 407 variable heavy domain amino acid sequence without leader sequence. The CDRs are bolded.
QSVKESEGGLFKPTDTLTVTCTVSGFSLSRNEISWFRQAPGNGLEWIG**GIGSPGRAYYATWA
KSRSTITRNTNLNTVTLKMTSLTAADTATYFCARGDI**WGPGTVVTVSS (SEQ ID NO: 67)

FIG. 19 cont'd

>Anti-BTK 407 VL CDR1
QSSQSVYNNNRLA (SEQ ID NO: 36)

>Anti-BTK 407 VL CDR2
SASTLAS (SEQ ID NO: 37)

>Anti-BTK 407 VL CDR3
LGSYDCSTADCNA (SEQ ID NO: 38)

>Anti-BTK 407 light chain coding sequence (EB0602-1G5-K1) with leader sequence. The leader sequence is underlined.
<u>ATGGACACGAGGGCCCCCACTCAGCTGCTGGGGCTCCTGCTGCTCTGGCTCCCAGGTGC
CACATTTGCCC</u>AAGTGCTGACCCAGACTGTATCGCCCGTGTCTGCAGCTGTGGGAAGCAC
AGTCACCATCAATTGCCAGTCCAGTCAGAGTGTTTATAATAACAACCGCTTAGCCTGGTATC
AGCAGAAACCAGGGCAGCCTCCCAAAGGCCTGATCTATTCTGCATCCACTCTGGCATCTG
GGGTCTCATCGCGGTTCAAAGGCAGTGGATCTGGGACACAGTTCACTCTCACCATCAGCG
ACGTGCAGTGTGACGATGCTGCCACTTACTACTGTCTAGGCAGTTATGATTGTAGTACTGC
TGATTGTAATGCTTTCGGCGGAGGGACCGAGGTGGTGGTCAAAGGTGATCCAGTTGCACC
TACTGTCCTCATCTTCCCACCAGCTGCTGATCAGGTGGCAACTGGAACAGTCACCATCGTG
TGTGTGGCGAATAAATACTTTCCCGATGTCACCGTCACCTGGGAGGTGGATGGCACCACC
CAAACAACTGGCATCGAGAACAGTAAAACACCGCAGAATTCTGCAGATTGTACCTACAACC
TCAGCAGCACTCTGACACTGACCAGCACACAGTACAACAGCCACAAAGAGTACACCTGCA
AGGTGACCCAGGGCACGACCTCAGTCGTCCAGAGCTTCAATAGGGGTGACTGTTAG (SEQ
ID NO: 97)

>Anti-BTK 407 light chain amino acid sequence with leader sequence. The leader sequence is underlined and the CDRs are bolded.
<u>MDTRAPTQLLGLLLLWLPGATFA</u>QVLTQTVSPVSAAVGSTVTINCQSSQSVYNNNRLAWYQQ
KPGQPPKGLIYSASTLASGVSSRFKGSGSGTQFTLTISDVQCDDAATYYCLGSYDCSTADCNA
FGGGTEVVVKGDPVAPTVLIFPPAADQVATGTVTIVCVANKYFPDVTVTWEVDGTTQTTGIENS
KTPQNSADCTYNLSSTLTLTSTQYNSHKEYTCKVTQGTTSVVQSFNRGDC (SEQ ID NO: 98)

>Anti-BTK 407 variable light domain coding sequence with leader sequence. The leader sequence is underlined.
<u>ATGGACACGAGGGCCCCCACTCAGCTGCTGGGGCTCCTGCTGCTCTGGCTCCCAGGTGC
CACATTTGCCC</u>AAGTGCTGACCCAGACTGTATCGCCCGTGTCTGCAGCTGTGGGAAGCAC
AGTCACCATCAATTGCCAGTCCAGTCAGAGTGTTTATAATAACAACCGCTTAGCCTGGTATC
AGCAGAAACCAGGGCAGCCTCCCAAAGGCCTGATCTATTCTGCATCCACTCTGGCATCTG
GGGTCTCATCGCGGTTCAAAGGCAGTGGATCTGGGACACAGTTCACTCTCACCATCAGCG
ACGTGCAGTGTGACGATGCTGCCACTTACTACTGTCTAGGCAGTTATGATTGTAGTACTGC
TGATTGTAATGCTTTCGGCGGAGGGACCGAGGTGGTGGTCAAA (SEQ ID NO: 99)

>Anti-BTK 407 variable light domain amino acid sequence with leader sequence. The leader sequence is underlined and the CDRs are bolded.
<u>MDTRAPTQLLGLLLLWLPGATFA</u>QVLTQTVSPVSAAVGSTVTINCQSSQSVYNNNRLAWYQQ
KPGQPPKGLIYSASTLASGVSSRFKGSGSGTQFTLTISDVQCDDAATYYCLGSYDCSTADCNA
FGGGTEVVVK (SEQ ID NO: 100)

FIG. 19 cont'd

>Anti-BTK 407 light chain amino acid sequence without leader sequence. The CDRs are bolded.
QVLTQTVSPVSAAVGSTVTINCQSSQSVYNNNRLAWYQQKPGQPPKGLIYSASTLASGVSSR FKGSGSGTQFTLTISDVQCDDAATYYCLGSYDCSTADCNAFGGGTEVVVKGDPVAPTVLIFPP AADQVATGTVTIVCVANKYFPDVTVTWEVDGTTQTTGIENSKTPQNSADCTYNLSSTLTLTSTQ YNSHKEYTCKVTQGTTSVVQSFNRGDC (SEQ ID NO: 101)

>Anti-BTK 407 variable light domain amino acid sequence without leader sequence. The CDRs are bolded.
QVLTQTVSPVSAAVGSTVTINCQSSQSVYNNNRLAWYQQKPGQPPKGLIYSASTLASGVSSR FKGSGSGTQFTLTISDVQCDDAATYYCLGSYDCSTADCNAFGGGTEVVVK (SEQ ID NO: 68)

FIG. 19 cont'd

>Anti-CTNS 115 VH CDR1
TRDGVC (SEQ ID NO: 39)

>Anti-CTNS 115 VH CDR2
CIYRGISATTSYASWAKGR (SEQ ID NO: 40)

>Anti-CTNS 115 VH CDR3
AWDL (SEQ ID NO: 41)

>Anti-CTNS 115 heavy chain coding sequence (EB0606-3H8-H5) with leader sequence. The leader sequence is underlined.
<u>ATGGAGACTGGGCTGCGCTGGCTTCTCCTGGTCGCTGTGCTCAAAGGTGTCCAGTGT</u>CAG
GAGCAGCTGGTGGAGTCCGGGGGAGGCCTGGTCCAGCCTGAGGGATCCCTGACACTCAC
CTGCAAAGCCTCTGGATTCTCCTTCAGTACCAGAGATGGCGTATGCTGGGTCCGCCAGGC
TCCAGGGAAGGGGCTGGAGTGGATCGCATGCATTTATCGTGGTATTAGTGCTACCACTTC
CTACGCGAGCTGGGCGAAAGGCCGATTCACCATCTCCAAAACCTCGTCGACCACGGTGAC
TCTGCAAATGACCAGTCTGACAGCCGCGGACACGGCCACCTATTTCTGTGCGAGAGCCTG
GGACTTATGGGGCCCAGGCACCCTGGTCACCGTCTCCTCAGGGCAACCTAAGGCTCCATC
AGTCTTCCCACTGGCCCCCTGCTGCGGGGACACACCCAGCTCCACGGTGACCCTGGGCT
GCCTGGTCAAAGGCTACCTCCCGGAGCCAGTGACCGTGACCTGGAACTCGGGCACCCTC
ACCAATGGGGTACGCACCTTCCCGTCCGTCCGGCAGTCCTCAGGCCTCTACTCGCTGAGC
AGCGTGGTGAGCGTGACCTCAAGCAGCCAGCCCGTCACCTGCAACGTGGCCCACCCAGC
CACCAACACCAAAGTGGACAAGACCGTTGCGCCCTCGACATGCAGCAAGCCCATGTGCCC
ACCCCCTGAACTCCTGGGGGGACCGTCTGTCTTCATCTTCCCCCCAAAACCCAAGGACAC
CCTCATGATCTCACGCACCCCCGAGGTCACATGCGTGGTGGTGGACGTGAGCCAGGATGA
CCCCGAGGTGCAGTTCACATGGTACATAAACAACGAGCAGGTGCGCACCGCCCGGCCGC
CGCTACGGGAGCAGCAGTTCAACAGCACGATCCGCGTGGTCAGCACCCTCCCCATCGCG
CACCAGGACTGGCTGAGGGGCAAGGAGTTCAAGTGCAAAGTCCACAACAAGGCACTCCC
GGCCCCCATCGAGAAAACCATCTCCAAAGCCAGAGGGCAGCCCCTGGAGCCGAAGGTCT
ACACCATGGGCCCTCCCCGGGAGGAGCTGAGCAGCAGGTCGGTCAGCCTGACCTGCATG
ATCAACGGCTTCTACCCTTCCGACATCTCGGTGGAGTGGGAGAAGAACGGGAAGGCAGAG
GACAACTACAAGACCACGCCGGCCGTGCTGGACAGCGACGGCTCCTACTTCCTCTACAGC
AAGCTCTCAGTGCCCACGAGTGAGTGGCAGCGGGGCGACGTCTTCACCTGCTCCGTGAT
GCACGAGGCCTTGCACAACCACTACACGCAGAAGTCCATCTCCCGCTCTCCGGGTAAATG
A (SEQ ID NO: 102)

>Anti-CTNS 115 heavy chain amino acid sequence with leader sequence. The leader sequence is underlined and the CDRs are bolded.
<u>METGLRWLLLVAVLKGVQC</u>QEQLVESGGGLVQPEGSLTLTCKASGFSFSTRDGVCWVRQAP
GKGLEWIACIYRGISATTSYASWAKGRFTISKTSSTTVTLQMTSLAADTATYFCARAWDLWG
PGTLVTVSSGQPKAPSVFPLAPCCGDTPSSTVTLGCLVKGYLPEPVTVTWNSGTLTNGVRTFP
SVRQSSGLYSLSSVVSVTSSSQPVTCNVAHPATNTKVDKTVAPSTCSKPMCPPPELLGGPSVF
IFPPKPKDTLMISRTPEVTCVVVDVSQDDPEVQFTWYINNEQVRTARPPLREQQFNSTIRVVST
LPIAHQDWLRGKEFKCKVHNKALPAPIEKTISKARGQPLEPKVYTMGPPREELSSRSVSLTCMI
NGFYPSDISVEWEKNGKAEDNYKTTPAVLDSDGSYFLYSKLSVPTSEWQRGDVFTCSVMHEA
LHNHYTQKSISRSPGK (SEQ ID NO: 103)

FIG. 19 cont'd

>Anti-CTNS 115 variable heavy domain coding sequence with leader sequence. The leader sequence is underlined.
<u>ATGGAGACTGGGCTGCGCTGGCTTCTCCTGGTCGCTGTGCTCAAAGGTGTCCAGTGT</u>CAG
GAGCAGCTGGTGGAGTCCGGGGGAGGCCTGGTCCAGCCTGAGGGATCCCTGACACTCAC
CTGCAAAGCCTCTGGATTCTCCTTCAGTACCAGAGATGGCGTATGCTGGGTCCGCCAGGC
TCCAGGGAAGGGGCTGGAGTGGATCGCATGCATTTATCGTGGTATTAGTGCTACCACTTC
CTACGCGAGCTGGGCGAAAGGCCGATTCACCATCTCCAAAACCTCGTCGACCACGGTGAC
TCTGCAAATGACCAGTCTGACAGCCGCGGACACGGCCACCTATTTCTGTGCGAGAGCCTG
GGACTTATGGGGCCCAGGCACCCTGGTCACCGTCTCCTCA (SEQ ID NO: 104)

>Anti-CTNS 115 variable heavy domain amino acid sequence with leader sequence. The leader sequence is underlined and the CDRs are bolded.
<u>METGLRWLLLVAVLKGVQC</u>QEQLVESGGGLVQPEGSLTLTCKASGFSFSTRDGVCWVRQAP
GKGLEWIACIYRGISATTSYASWAKGRFTISKTSSTTVTLQMTSLTAADTATYFCARAWDLWG
PGTLVTVSS (SEQ ID NO: 105)

>Anti-CTNS 115 heavy chain amino acid sequence without leader sequence. The CDRs are bolded.
QEQLVESGGGLVQPEGSLTLTCKASGFSFSTRDGVCWVRQAPGKGLEWIA**CIYRGISATTSYA
SWAKGRFTISKTSSTTVTLQMTSLTAADTATYFCARAWDL**WGPGTLVTVSSQPKAPSVFPLA
PCCGDTPSSTVTLGCLVKGYLPEPVTVTWNSGTLTNGVRTFPSVRQSSGLYSLSSVVSVTSSS
QPVTCNVAHPATNTKVDKTVAPSTCSKPMCPPPELLGGPSVFIFPPKPKDTLMISRTPEVTCVV
VDVSQDDPEVQFTWYINNEQVRTARPPLREQQFNSTIRVVSTLPIAHQDWLRGKEFKCKVHNK
ALPAPIEKTISKARGQPLEPKVYTMGPPREELSSRSVSLTCMINGFYPSDISVEWEKNGKAEDN
YKTTPAVLDSDGSYFLYSKLSVPTSEWQRGDVFTCSVMHEALHNHYTQKSISRSPGK (SEQ ID
NO: 106)

>Anti-CTNS 115 variable heavy domain amino acid sequence without leader sequence. The CDRs are bolded.
QEQLVESGGGLVQPEGSLTLTCKASGFSFSTRDGVCWVRQAPGKGLEWIA**CIYRGISATTSYA
SWAKGRFTISKTSSTTVTLQMTSLTAADTATYFCARAWDL**WGPGTLVTVSS (SEQ ID NO: 69)

FIG. 19 cont'd

>Anti-CTNS 115 VL CDR1
QASQSIGSDLS (SEQ ID NO: 42)

>Anti-CTNS 115 VL CDR2
KASKVET (SEQ ID NO: 43)

>Anti-CTNS 115 VL CDR3
QSIDFSKSYIGGA (SEQ ID NO: 44)

>Anti-CTNS 115 light chain coding sequence (EB0606-3H8-K7) with leader sequence. The leader sequence is underlined.
<u>ATGGACACGAGGGCCCCCACTCAGCTGCTGGGGCTCCTGCTGCTCTGGCTCCCAGGTGC
CAGATGT</u>GATGTTGTGATGACCCAGACTCCAGCCTCCGTGTCTGAACCTGTGGGAGGCAC
AGTCACCATCAAGTGCCAGGCCAGTCAGAGCATTGGTAGCGACTTATCCTGGTATCAGCA
GAAACCAGGGCAGCCTCCCAAGCGCCTGATCTACAAGGCATCCAAAGTGGAAACTGGGGT
CCCATCGCGGTTCAGCGGCAGTGGATCTGGGACAGAGTTCACTCTCACCATCAGCGACCT
GGAGTGTGCCGATGCTAGCACTTACTACTGTCAATCTATTGATTTTAGTAAAAGTTATATAG
GGGGTGCTTTCGGCGGAGGGACCGAGGTGGTGGTCAAAGGTGATCCAGTTGCACCTACT
GTCCTCATCTTCCCACCAGCTGCTGATCAGGTGGCAACTGGAACAGTCACCATCGTGTGT
GTGGCGAATAAATACTTTCCCGATGTCACCGTCACCTGGGAGGTGGATGGCACCACCCAA
ACAACTGGCATCGAGAACAGTAAAACACCGCAGAATTCTGCAGATTGTACCTACAACCTCA
GCAGCACTCTGACACTGACCAGCACACAGTACAACAGCCACAAAGAGTACACCTGCAAGG
TGACCCAGGGCACGACCTCAGTCGTCCAGAGCTTCAATAGGGGTGACTGTTAG (SEQ ID
NO: 107)

>Anti-CTNS 115 light chain amino acid sequence with leader sequence. The leader sequence is underlined and the CDRs are bolded.
<u>MDTRAPTQLLGLLLLWLPGARC</u>DVVMTQTPASVSEPVGGTVTIKQASQSIGSDLSWYQQKP
GQPPKRLIYKASKVETGVPSRFSGSGSGTEFTLTISDLECADASTYYCQSIDFSKSYIGGAFGG
GTEVVVKGDPVAPTVLIFPPAADQVATGTVTIVCVANKYFPDVTVTWEVDGTTQTTGIENSKTP
QNSADCTYNLSSTLTLTSTQYNSHKEYTCKVTQGTTSVVQSFNRGDC (SEQ ID NO: 108)

>Anti-CTNS 115 variable light domain coding sequence with leader sequence. The leader sequence is underlined.
<u>ATGGACACGAGGGCCCCCACTCAGCTGCTGGGGCTCCTGCTGCTCTGGCTCCCAGGTGC
CAGATGT</u>GATGTTGTGATGACCCAGACTCCAGCCTCCGTGTCTGAACCTGTGGGAGGCAC
AGTCACCATCAAGTGCCAGGCCAGTCAGAGCATTGGTAGCGACTTATCCTGGTATCAGCA
GAAACCAGGGCAGCCTCCCAAGCGCCTGATCTACAAGGCATCCAAAGTGGAAACTGGGGT
CCCATCGCGGTTCAGCGGCAGTGGATCTGGGACAGAGTTCACTCTCACCATCAGCGACCT
GGAGTGTGCCGATGCTAGCACTTACTACTGTCAATCTATTGATTTTAGTAAAAGTTATATAG
GGGGTGCTTTCGGCGGAGGGACCGAGGTGGTGGTCAAA (SEQ ID NO: 109)

>Anti-CTNS 115 variable light domain amino acid sequence with leader sequence. The leader sequence is underlined and the CDRs are bolded.
<u>MDTRAPTQLLGLLLLWLPGARC</u>DVVMTQTPASVSEPVGGTVTIKQASQSIGSDLSWYQQKP
GQPPKRLIYKASKVETGVPSRFSGSGSGTEFTLTISDLECADASTYYCQSIDFSKSYIGGAFGG
GTEVVVK (SEQ ID NO: 110)

FIG. 19 cont'd

>Anti-CTNS 115 light chain amino acid sequence without leader sequence. The CDRs are bolded.
DVVMTQTPASVSEPVGGTVTIKCQASQSIGSDLSWYQQKPGQPPKRLIYKASKVETGVPSRFSGSGSGTEFTLTISDLECADASTYYCQSIDFSKSYIGGAFGGGTEVVVKGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC (SEQ ID NO: 111)

>Anti-CTNS 115 variable light domain amino acid sequence without leader sequence. The CDRs are bolded.
DVVMTQTPASVSEPVGGTVTIKCQASQSIGSDLSWYQQKPGQPPKRLIYKASKVETGVPSRFSGSGSGTEFTLTISDLECADASTYYCQSIDFSKSYIGGAFGGGTEVVVK (SEQ ID NO: 70)

FIG. 19 cont'd

>Anti-CTNS 360 VH CDR1
NNDGIC (SEQ ID NO: 45)

>Anti-CTNS 360 VH CDR2
CIGSTSGRIYYASWAKGR (SEQ ID NO: 46)

>Anti-CTNS 360 VH CDR3
EPYGSGSMAFDL (SEQ ID NO: 47)

>Anti-CTNS 360 heavy chain coding sequence (EB0604-4E3-H4) with leader sequence. The leader sequence is underlined.
<u>ATGGAGACTGGGCTGCGCTGGCTTCTCCTGGTCGCTGTGCTCAAAGGTGTCCAGTGT</u>CAG
TCGTTGGAGGAGTCCGGGGGAGGCCTGTTCCAGCCTGGGGCATCCCTGACACTCACCTG
CACAGCCTCTGGATTCTCCTTCAGTAACAATGACGGGATATGCTGGGTCCGCCAGGCTCC
AGGGAAGGGGCTGGAGTGGATCGGATGTATTGGTAGTACTAGTGGTAGGATTTATTACGC
GAGCTGGGCGAAAGGCCGACTCACCATCTCCAAAACCTCGTCGACCACGGTGATTCTGCA
AATGACCAGTCTGACAGCCGCGGACACGGCCACTTATTTCTGTGCGAGCGAACCCTATGG
TAGTGGTAGTATGGCTTTTGACTTGTGGGGCCCAGGCACTCTGGTCACCGTCTCCTCAGG
GCAACCTAAGGCTCCATCAGTCTTCCCACTGGCCCCCTGCTGCGGGGACACACCCAGCTC
CACGGTGACCCTGGGCTGCCTGGTCAAAGGCTACCTCCCGGAGCCAGTGACCGTGACCT
GGAACTCGGGCACCCTCACCAATGGGGTACGCACCTTCCCGTCCGTCCGGCAGTCCTCA
GGCCTCTACTCGCTGAGCAGCGTGGTGAGCGTGACCTCAAGCAGCCAGCCCGTCACCTG
CAACGTGGCCCACCCAGCCACCAACACCAAAGTGGACAAGACCGTTGCGCCCTCGACATG
CAGCAAGCCCATGTGCCCACCCCTGAACTCCTGGGGGGACCGTCTGTCTTCATCTTCCC
CCCAAAACCCAAGGACACCCTCATGATCTCACGCACCCCCGAGGTCACATGCGTGGTGGT
GGACGTGAGCCAGGATGACCCCGAGGTGCAGTTCACATGGTACATAAACAACGAGCAGGT
GCGCACCGCCCGGCCGCCGCTACGGGAGCAGCAGTTCAACAGCACGATCCGCGTGGTCA
GCACCCTCCCCATCGCGCACCAGGACTGGCTGAGGGGCAAGGAGTTCAAGTGCAAAGTC
CACAACAAGGCACTCCCGGCCCCCATCGAGAAAACCATCTCCAAAGCCAGAGGGCAGCCC
CTGGAGCCGAAGGTCTACACCATGGGCCCTCCCGGGAGGAGCTGAGCAGCAGGTCGGT
CAGCCTGACCTGCATGATCAACGGCTTCTACCCTTCCGACATCTCGGTGGAGTGGGAGAA
GAACGGGAAGGCAGAGGACAACTACAAGACCACGCCGGCCGTGCTGGACAGCGACGGCT
CCTACTTCCTCTACAGCAAGCTCTCAGTGCCCACGAGTGAGTGGCAGCGGGGCGACGTCT
TCACCTGCTCCGTGATGCACGAGGCCTTGCACAACCACTACACGCAGAAGTCCATCTCCC
GCTCTCCGGGTAAATGA (SEQ ID NO: 112)

>Anti-CTNS 360 heavy chain amino acid sequence with leader sequence. The leader sequence is underlined and the CDRs are bolded.
<u>METGLRWLLLVAVLKGVQC</u>QSLEESGGGLFQPGASLTLTCTASGFSFSNNDGICWVRQAPGK
GLEWIGCIGSTSGRIYYASWAKGRLTISKTSSTTVILQMTSLTAADTATYFCAS**EPYGSGSMAF
DL**WGPGTLVTVSSGQPKAPSVFPLAPCCGDTPSSTVTLGCLVKGYLPEPVTVTWNSGTLTNG
VRTFPSVRQSSGLYSLSSVVSVTSSSQPVTCNVAHPATNTKVDKTVAPSTCSKPMCPPPELLG
GPSVFIFPPKPKDTLMISRTPEVTCVVVDVSQDDPEVQFTWYINNEQVRTARPPLREQQFNSTI
RVVSTLPIAHQDWLRGKEFKCKVHNKALPAPIEKTISKARGQPLEPKVYTMGPPREELSSRSVS
LTCMINGFYPSDISVEWEKNGKAEDNYKTTPAVLDSDGSYFLYSKLSVPTSEWQRGDVFTCSV
MHEALHNHYTQKSISRSPGK (SEQ ID NO: 113)

FIG. 19 cont'd

>Anti-CTNS 360 variable heavy domain coding sequence with leader sequence. The leader sequence is underlined.
<u>ATGGAGACTGGGCTGCGCTGGCTTCTCCTGGTCGCTGTGCTCAAAGGTGTCCAGTGT</u>CAG
TCGTTGGAGGAGTCCGGGGGAGGCCTGTTCCAGCCTGGGGCATCCCTGACACTCACCTG
CACAGCCTCTGGATTCTCCTTCAGTAACAATGACGGGATATGCTGGGTCCGCCAGGCTCC
AGGGAAGGGGCTGGAGTGGATCGGATGTATTGGTAGTACTAGTGGTAGGATTTATTACGC
GAGCTGGGCGAAAGGCCGACTCACCATCTCCAAAACCTCGTCGACCACGGTGATTCTGCA
AATGACCAGTCTGACAGCCGCGGACACGGCCACTTATTTCTGTGCGAGCGAACCCTATGG
TAGTGGTAGTATGGCTTTTGACTTGTGGGGCCCAGGCACTCTGGTCACCGTCTCCTCA
(SEQ ID NO: 114)

>Anti-CTNS 360 variable heavy domain amino acid sequence with leader sequence. The leader sequence is underlined and the CDRs are bolded.
<u>METGLRWLLLVAVLKGVQC</u>QSLEESGGGLFQPGASLTLTCTASGFSFSNNDGICWVRQAPGK
GLEWIGCIGSTSGRIYYASWAKGRLTISKTSSTTVILQMTSLTAADTATYFCAS**EPYGSGSMAF
DL**WGPGTLVTVSS (SEQ ID NO: 115)

>Anti-CTNS 360 heavy chain amino acid sequence without leader sequence. The CDRs are bolded.
QSLEESGGGLFQPGASLTLTCTASGFSFSNNDGICWVRQAPGKGLEWIG**CIGSTSGRIYYASW
AKGRLTISKTSSTTVILQMTSLTAADTATYFCASEPYGSGSMAFDL**WGPGTLVTVSSGQPKAP
SVFPLAPCCGDTPSSTVTLGCLVKGYLPEPVTVTWNSGTLTNGVRTFPSVRQSSGLYSLSSVV
SVTSSSQPVTCNVAHPATNTKVDKTVAPSTCSKPMCPPPELLGGPSVFIFPPKPKDTLMISRTP
EVTCVVVDVSQDDPEVQFTWYINNEQVRTARPPLREQQFNSTIRVVSTLPIAHQDWLRGKEFK
CKVHNKALPAPIEKTISKARGQPLEPKVYTMGPPREELSSRSVSLTCMINGFYPSDISVEWEKN
GKAEDNYKTTPAVLDSDGSYFLYSKLSVPTSEWQRGDVFTCSVMHEALHNHYTQKSISRSPG
K (SEQ ID NO: 116)

>Anti-CTNS 360 variable heavy domain amino acid sequence without leader sequence. The CDRs are bolded.
QSLEESGGGLFQPGASLTLTCTASGFSFSNNDGICWVRQAPGKGLEWIG**CIGSTSGRIYYASW
AKGRLTISKTSSTTVILQMTSLTAADTATYFCASEPYGSGSMAFDL**WGPGTLVTVSS (SEQ ID
NO: 71)

FIG. 19 cont'd

>Anti-CTNS 360 VL CDR1
QASQSIWNNNFLS (SEQ ID NO: 48)

>Anti-CTNS 360 VL CDR2
EASKLAS (SEQ ID NO: 49)

>Anti-CTNS 360 VL CDR3
QGEFSCSIADCVA (SEQ ID NO: 50)

>Anti-CTNS 360 light chain coding sequence (EB0604-4E3-K1) with leader sequence. The leader sequence is underlined.
<u>ATGGACACGAGGGCCCCCACTCAGCTGCTGGGGCTCCTGCTGCTCTGGCTCCCAGGTGC
CACATTTGCCC</u>AAGTGCTGACCCAGACTGCATCGTCCGTGTCTGCAGCTGTGGGAGGCAC
AGTCACCGTCAATTGCCAGGCCAGTCAGAGTATTTGGAATAACAACTTCTTATCCTGGTATC
AGCAGAAACCAGGGCAGCCTCCCAAGCTCCTGATCTACGAAGCATCCAAACTGGCATCTG
GGGTCCCATCGCGGTTTAGCGGCAGTGGATCTGGGACACAGTTCACTCTCACCATCAGCG
GCGTGCAGTGTGACGATGCTGCCACTTACTACTGTCAGGGCGAATTTAGTTGTAGTATTGC
TGATTGTGTTGCTTTCGGCGGAGGGACCGAGGTGGTGGTCAGAGGTGATCCAGTTGCACC
TACTGTCCTCATCTTCCCACCAGCTGCTGATCAGGTGGCAACTGGAACAGTCACCATCGTG
TGTGTGGCGAATAAATACTTTCCCGATGTCACCGTCACCTGGGAGGTGGATGGCACCACC
CAAACAACTGGCATCGAGAACAGTAAAACACCGCAGAATTCTGCAGATTGTACCTACAACC
TCAGCAGCACTCTGACACTGACCAGCACACAGTACAACAGCCACAAAGAGTACACCTGCA
AGGTGACCCAGGGCACGACCTCAGTCGTCCAGAGCTTCAATAGGGGTGACTGTTAG (SEQ
ID NO: 117)

>Anti-CTNS 360 light chain amino acid sequence with leader sequence. The leader sequence is underlined and the CDRs are bolded.
<u>MDTRAPTQLLGLLLLWLPGATFA</u>QVLTQTASSVSAAVGGTVTVNCQASQSIWNNNFLSWYQQ
KPGQPPKLLIYEASKLASGVPSRFSGSGSGTQFTLTISGVQCDDAATYYCQGEFSCSIADCVA
FGGGTEVVVRGDPVAPTVLIFPPAADQVATGTVTIVCVANKYFPDVTVTWEVDGTTQTTGIENS
KTPQNSADCTYNLSSTLTLTSTQYNSHKEYTCKVTQGTTSVVQSFNRGDC (SEQ ID NO: 118)

>Anti-CTNS 360 variable light domain coding sequence with leader sequence. The leader sequence is underlined.
<u>ATGGACACGAGGGCCCCCACTCAGCTGCTGGGGCTCCTGCTGCTCTGGCTCCCAGGTGC
CACATTTGCCC</u>AAGTGCTGACCCAGACTGCATCGTCCGTGTCTGCAGCTGTGGGAGGCAC
AGTCACCGTCAATTGCCAGGCCAGTCAGAGTATTTGGAATAACAACTTCTTATCCTGGTATC
AGCAGAAACCAGGGCAGCCTCCCAAGCTCCTGATCTACGAAGCATCCAAACTGGCATCTG
GGGTCCCATCGCGGTTTAGCGGCAGTGGATCTGGGACACAGTTCACTCTCACCATCAGCG
GCGTGCAGTGTGACGATGCTGCCACTTACTACTGTCAGGGCGAATTTAGTTGTAGTATTGC
TGATTGTGTTGCTTTCGGCGGAGGGACCGAGGTGGTGGTCAGA (SEQ ID NO: 119)

>Anti-CTNS 360 variable light domain amino acid sequence with leader sequence. The leader sequence is underlined and the CDRs are bolded.
<u>MDTRAPTQLLGLLLLWLPGATFA</u>QVLTQTASSVSAAVGGTVTVNCQASQSIWNNNFLSWYQQ
KPGQPPKLLIYEASKLASGVPSRFSGSGSGTQFTLTISGVQCDDAATYYCQGEFSCSIADCVA
FGGGTEVVVR (SEQ ID NO: 120)

FIG. 19 cont'd

>Anti-CTNS 360 light chain amino acid sequence without leader sequence. The CDRs are bolded.
QVLTQTASSVSAAVGGTVTVNCQASQSIWNNNFLSWYQQKPGQPPKLLIYEASKLASGVPSRFSGSGSGTQFTLTISGVQCDDAATYYCQGEFSCSIADCVAFGGGTEVVVRGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC (SEQ ID NO: 121)

>Anti-CTNS 360 variable light domain amino acid sequence without leader sequence. The CDRs are bolded.
QVLTQTASSVSAAVGGTVTVNCQASQSIWNNNFLSWYQQKPGQPPKLLIYEASKLASGVPSRFSGSGSGTQFTLTISGVQCDDAATYYCQGEFSCSIADCVAFGGGTEVVVR (SEQ ID NO: 72)

FIG. 19 cont'd

>Anti-SHPK 363 VH CDR1
SNYFMC (SEQ ID NO: 51)

>Anti-SHPK 363 VH CDR2
CILVGSGRTTFASWAKGR (SEQ ID NO: 52)

>Anti-SHPK 363 VH CDR3
AWAL (SEQ ID NO: 53)

>Anti-SHPK 363 heavy chain coding sequence (EB0605B-6G12-H1) with leader sequence. The leader sequence is underlined.
<u>ATGGAGACTGGGCTGCGCTGGCTTCTCCTGGTCGCTGTGCTCAAAGGTGTCCAGTGT</u>CAG
GAGCAGATAGAGGAGTCCGGGGGAGGCCTGGTCAAGCCTGAGGGATCCCTGACACTCAC
CTGCAAAGTCTCTGGATTCGACTTCAGTAGTAACTATTTCATGTGCTGGGTCCGCCAGGCT
CCAGGGAAGGGGCTGGAGTGGATCGGATGTATTCTTGTTGGTAGTGGTAGGACTACTTTC
GCGAGCTGGGCGAAAGGCCGATTCACCATCTCCAAAACCTCGTCGACCACGGTGACTCTG
CAAATGACCAGTCTGACAGCCGCGGACACGGCCACCTATTTCTGTGCGAGGGCCTGGGC
CTTGTGGGGCCCCGGCACCCTGGTCACCGTCTCCTCAGGGCAACCTAAGGCTCCATCAGT
CTTCCCACTGGCCCCCTGCTGCGGGGACACACCCAGCTCCACGGTGACCCTGGGCTGCC
TGGTCAAAGGCTACCTCCCGGAGCCAGTGACCGTGACCTGGAACTCGGGCACCCTCACCA
ATGGGGTACGCACCTTCCCGTCCGTCCGGCAGTCCTCAGGCCTCTACTCGCTGAGCAGCG
TGGTGAGCGTGACCTCAAGCAGCCAGCCCGTCACCTGCAACGTGGCCCACCCAGCCACC
AACACCAAAGTGGACAAGACCGTTGCGCCCTCGACATGCAGCAAGCCCATGTGCCCACCC
CCTGAACTCCTGGGGGGACCGTCTGTCTTCATCTTCCCCCCAAAACCCAAGGACACCCTC
ATGATCTCACGCACCCCCGAGGTCACATGCGTGGTGGTGGACGTGAGCCAGGATGACCC
CGAGGTGCAGTTCACATGGTACATAAACAACGAGCAGGTGCGCACCGCCCGGCCGCCGC
TACGGGAGCAGCAGTTCAACAGCACGATCCGCGTGGTCAGCACCCTCCCCATCGCGCAC
CAGGACTGGCTGAGGGGCAAGGAGTTCAAGTGCAAAGTCCACAACAAGGCACTCCCGGC
CCCCATCGAGAAAACCATCTCCAAAGCCAGAGGGCAGCCCCTGGAGCCGAAGGTCTACAC
CATGGGCCCTCCCCGGGAGGAGCTGAGCAGCAGGTCGGTCAGCCTGACCTGCATGATCA
ACGGCTTCTACCCTTCCGACATCTCGGTGGAGTGGGAGAAGAACGGGAAGGCAGAGGAC
AACTACAAGACCACGCCGGCCGTGCTGGACAGCGACGGCTCCTACTTCCTCTACAGCAAG
CTCTCAGTGCCCACGAGTGAGTGGCAGCGGGGCGACGTCTTCACCTGCTCCGTGATGCA
CGAGGCCTTGCACAACCACTACACGCAGAAGTCCATCTCCCGCTCTCCGGGTAAATGA
(SEQ ID NO: 122)

>Anti-SHPK 363 heavy chain amino acid sequence with leader sequence. The leader sequence is underlined and the CDRs are bolded.
<u>METGLRWLLLVAVLKGVQC</u>QEQIEESGGGLVKPEGSLTLTCKVSGFDFSSNYFMCWVRQAPG
KGLEWIGCILVGSGRTTFASWAKGRFTISKTSSTTVTLQMTSLTAADTATYFCARAWALWGPG
TLVTVSSGQPKAPSVFPLAPCCGDTPSSTVTLGCLVKGYLPEPVTVTWNSGTLTNGVRTFPSV
RQSSGLYSLSSVVSVTSSSQPVTCNVAHPATNTKVDKTVAPSTCSKPMCPPPELLGGPSVFIF
PPKPKDTLMISRTPEVTCVVVDVSQDDPEVQFTWYINNEQVRTARPPLREQQFNSTIRVVSTLP
IAHQDWLRGKEFKCKVHNKALPAPIEKTISKARGQPLEPKVYTMGPPREELSSRSVSLTCMING
FYPSDISVEWEKNGKAEDNYKTTPAVLDSDGSYFLYSKLSVPTSEWQRGDVFTCSVMHEALH
NHYTQKSISRSPGK (SEQ ID NO: 123)

FIG. 19 cont'd

>Anti-SHPK 363 variable heavy domain coding sequence with leader. The leader sequence is underlined.
<u>ATGGAGACTGGGCTGCGCTGGCTTCTCCTGGTCGCTGTGCTCAAAGGTGTCCAGTGT</u>CAG
GAGCAGATAGAGGAGTCCGGGGGAGGCCTGGTCAAGCCTGAGGGATCCCTGACACTCAC
CTGCAAAGTCTCTGGATTCGACTTCAGTAGTAACTATTTCATGTGCTGGGTCCGCCAGGCT
CCAGGGAAGGGGCTGGAGTGGATCGGATGTATTCTTGTTGGTAGTGGTAGGACTACTTTC
GCGAGCTGGGCGAAAGGCCGATTCACCATCTCCAAAACCTCGTCGACCACGGTGACTCTG
CAAATGACCAGTCTGACAGCCGCGGACACGGCCACCTATTTCTGTGCGAGGGCCTGGGC
CTTGTGGGGCCCCGGCACCCTGGTCACCGTCTCCTCA (SEQ ID NO: 124)

>Anti-SHPK 363 variable heavy domain amino acid sequence with leader sequence. The leader sequence is underlined and the CDRs are bolded.
<u>METGLRWLLLVAVLKGVQC</u>QEQIEESGGGLVKPEGSLTLTCKVSGFDFSSNYFMCWVRQAPG
KGLEWIGCILVGSGRTTFASWAKGRFTISKTSSTTVTLQMTSLTAADTATYFCARAWALWGPG
TLVTVSS (SEQ ID NO: 125)

>Anti-SHPK 363 heavy chain amino acid sequence without leader sequence. The CDRs are bolded.
QEQIEESGGGLVKPEGSLTLTCKVSGFDFSSNYFMCWVRQAPGKGLEWIG**CILVGSGRTTFAS
WAKGRFTISKTSSTTVTLQMTSLTAADTATYFCARAWAL**WGPGTLVTVSSGQPKAPSVFPLAP
CCGDTPSSTVTLGCLVKGYLPEPVTVTWNSGTLTNGVRTFPSVRQSSGLYSLSSVVSVTSSSQ
PVTCNVAHPATNTKVDKTVAPSTCSKPMCPPPELLGGPSVFIFPPKPKDTLMISRTPEVTCVVV
DVSQDDPEVQFTWYINNEQVRTARPPLREQQFNSTIRVVSTLPIAHQDWLRGKEFKCKVHNKA
LPAPIEKTISKARGQPLEPKVYTMGPPREELSSRSVSLTCMINGFYPSDISVEWEKNGKAEDNY
KTTPAVLDSDGSYFLYSKLSVPTSEWQRGDVFTCSVMHEALHNHYTQKSISRSPGK (SEQ ID NO: 126)

>Anti-SHPK 363 variable heavy domain amino acid sequence without leader sequence. The CDRs are bolded.
QEQIEESGGGLVKPEGSLTLTCKVSGFDFSSNYFMCWVRQAPGKGLEWIG**CILVGSGRTTFAS
WAKGRFTISKTSSTTVTLQMTSLTAADTATYFCARAWAL**WGPGTLVTVSS (SEQ ID NO: 73)

FIG. 19 cont'd

>Anti-SHPK 363 VL CDR1
QASQSVYNNNDLA (SEQ ID NO: 54)

>Anti-SHPK 363 VL CDR2
GASTLVS (SEQ ID NO: 55)

>Anti-SHPK 363 VL CDR3
QGGYDPRNYP (SEQ ID NO: 56)

>Anti-SHPK 363 light chain coding sequence (EB0605B-6G12-K1) with leader sequence. The leader sequence is underlined.
<u>ATGGACACGAGGGCCCCCACTCAGCTGCTGGGGCTCCTGCTGCTCTGGCTCCCAGGTGCCACATTTGCG</u>CAAGTGCTGACCCAGACTCCATCCCCTGTGTCTGCAGCTGTGGGAGGCACAGTCACCATCAGTTGCCAGGCCAGTCAGAGTGTTTATAATAACAACGACTTAGCCTGGTATCAGCAGAAACCAGGGCAGCCTCCCAAGCTCCTGATCTATGGTGCATCCACTCTGGTATCTGGGGTCCCGTCGCGGTTCAGCGGCAGTGGATCTGGGGCACAGTTCACTCTCACCATCAGCGACCTGGAGTGTGACGATGCTGCCACTTACTACTGTCAAGGCGGATATGATCCTCGTAATTATCCTTTCGGCGGAGGGACCGAGGTGGTGGTCAAAGGTGATCCAGTTGCACCTACTGTCCTCATCTTCCCACCAGCTGCTGATCAGGTGGCAACTGGAACAGTCACCATCGTGTGTGTGGCGAATAAATACTTTCCCGATGTCACCGTCACCTGGGAGGTGGATGGCACCACCCAAACAACTGGCATCGAGAACAGTAAAACACCGCAGAATTCTGCAGATTGTACCTACAACCTCAGCAGCACTCTGACACTGACCAGCACACAGTACAACAGCCACAAAGAGTACACCTGCAAGGTGACCCAGGGCACGACCTCAGTCGTCCAGAGCTTCAATAGGGGTGACTGTTAG (SEQ ID NO: 127)

>Anti-SHPK 363 light chain amino acid sequence with leader sequence. The leader sequence is underlined and the CDRs are bolded.
<u>MDTRAPTQLLGLLLLWLPGATFA</u>QVLTQTPSPVSAAVGGTVTISCQASQSVYNNNDLAWYQQKPGQPPKLLIYGASTLVSGVPSRFSGSGSGAQFTLTISDLECDDAATYYCQGGYDPRNYPFGGGTEVVVKGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC (SEQ ID NO: 128)

>Anti-SHPK 363 variable light domain coding sequence with leader sequence. The leader sequence is underlined.
<u>ATGGACACGAGGGCCCCCACTCAGCTGCTGGGGCTCCTGCTGCTCTGGCTCCCAGGTGCCACATTTGCG</u>CAAGTGCTGACCCAGACTCCATCCCCTGTGTCTGCAGCTGTGGGAGGCACAGTCACCATCAGTTGCCAGGCCAGTCAGAGTGTTTATAATAACAACGACTTAGCCTGGTATCAGCAGAAACCAGGGCAGCCTCCCAAGCTCCTGATCTATGGTGCATCCACTCTGGTATCTGGGGTCCCGTCGCGGTTCAGCGGCAGTGGATCTGGGGCACAGTTCACTCTCACCATCAGCGACCTGGAGTGTGACGATGCTGCCACTTACTACTGTCAAGGCGGATATGATCCTCGTAATTATCCTTTCGGCGGAGGGACCGAGGTGGTGGTCAAA (SEQ ID NO: 129)

>Anti-SHPK 363 variable light domain amino acid sequence with leader sequence. The leader sequence is underlined and the CDRs are bolded.
<u>MDTRAPTQLLGLLLLWLPGATFA</u>QVLTQTPSPVSAAVGGTVTISCQASQSVYNNNDLAWYQQKPGQPPKLLIYGASTLVSGVPSRFSGSGSGAQFTLTISDLECDDAATYYCQGGYDPRNYPFGGGTEVVVK (SEQ ID NO: 130)

FIG. 19 cont'd

>Anti-SHPK 363 light chain amino acid sequence without leader sequence. The CDRs are bolded.
QVLTQTPSPVSAAVGGTVTISCQASQSVYNNNDLAWYQQKPGQPPKLLIYGASTLVSGVPSRFSGSGSGAQFTLTISDLECDDAATYYCQGGYDPRNYPFGGGTEVVVKGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC (SEQ ID NO: 131)

>Anti-SHPK 363 variable light domain amino acid sequence without leader sequence. The CDRs are bolded.
QVLTQTPSPVSAAVGGTVTISCQASQSVYNNNDLAWYQQKPGQPPKLLIYGASTLVSGVPSRFSGSGSGAQFTLTISDLECDDAATYYCQGGYDPRNYPFGGGTEVVVK (SEQ ID NO: 74)

FIG. 19 cont'd

>Anti-ATP7B 1056 VH CDR1
SYWII (SEQ ID NO: 57)

>Anti-ATP7B 1056 VH CDR2
SSGPSGSAYYTSWVKG (SEQ ID NO: 58)

>Anti-ATP7B 1056 VH CDR3
AGGSDYDWFDL (SEQ ID NO: 59)

>Anti-ATP7B 1056 heavy chain coding sequence (EB0601-H3-1) with leader sequence. The leader sequence is underlined.
<u>ATGGAGACTGGGCTGCGCTGGCTTCTCCTGGTCGCTGTGCTCAAAGGTGTCCAGTGT</u>CAG
TCGCTGGAGGAGTCCGGGGGTCGCCTGGTCACGCCTGGAGGATCCCTGACAGTCACCTG
TACAGTCTCTGGATTCTCCCTCAGTAGCTATTGGATAATCTGGGTCCGCCAGGCTCCAGGG
GAGGGGCTGGAATGGATCGGAAGCAGTGGTCCTAGTGGTAGCGCATACTACACGAGCTG
GGTGAAAGGCCGATTCACCATCTCCAAGACCTCGACTACGGTGGATCTGAAAATGACCGG
TCTGACAACCGAGGACACGGCCACCTATTTCTGTGCCAGAGCTGGTGGTAGTGACTACGA
CTGGTTTGATCTCTGGGGCCAGGGCACCCTGGTCACCGTCTCTTCAGGGCAACCTAAGGC
TCCATCAGTCTTCCCACTGGCCCCCTGCTGCGGGGACACACCCAGCTCCACGGTGACCCT
GGGCTGCCTGGTCAAAGGCTACCTCCCGGAGCCAGTGACCGTGACCTGGAACTCGGGCA
CCCTCACCAATGGGGTACGCACCTTCCCGTCCGTCCGGCAGTCCTCAGGCCTCTACTCGC
TGAGCAGCGTGGTGAGCGTGACCTCAAGCAGCCAGCCCGTCACCTGCAACGTGGCCCAC
CCAGCCACCAACACCAAAGTGGACAAGACCGTTGCGCCCTCGACATGCAGCAAGCCCACG
TGCCCACCCCCTGAACTCCTGGGGGGACCGTCTGTCTTCATCTTCCCCCCAAAACCCAAG
GACACCCTCATGATCTCACGCACCCCCGAGGTCACATGCGTGGTGGTGGACGTGAGCCA
GGATGACCCCGAGGTGCAGTTCACATGGTACATAAACAACGAGCAGGTGCGCACCGCCC
GGCCGCCGCTACGGGAGCAGCAGTTCAACAGCACGATCCGCGTGGTCAGCACCCTCCCC
ATCGCGCACCAGGACTGGCTGAGGGGCAAGGAGTTCAAGTGCAAAGTCCACAACAAGGC
ACTCCCGGCCCCCATCGAGAAAACCATCTCCAAAGCCAGAGGGCAGCCCCTGGAGCCGA
AGGTCTACACCATGGGCCCTCCCCGGGAGGAGCTGAGCAGCAGGTCGGTCAGCCTGACC
TGCATGATCAACGGCTTCTACCCTTCCGACATCTCGGTGGAGTGGGAGAAGAACGGGAAG
GCAGAGGACAACTACAAGACCACGCCGGCCGTGCTGGACAGCGACGGCTCCTACTTCCT
CTACAGCAAGCTCTCAGTGCCCACGAGTGAGTGGCAGCGGGGCGACGTCTTCACCTGCTC
CGTGATGCACGAGGCCTTGCACAACCACTACACGCAGAAGTCCATCTCCCGCTCTCCGGG
TAAATGA (SEQ ID NO: 132)

>Anti-ATP7B 1056 heavy chain amino acid sequence with leader sequence. The leader sequence is underlined and the CDRs are bolded.
<u>METGLRWLLLVAVLKGVQC</u>QSLEESGGRLVTPGGSLTVTCTVSGFSLSSYWIIWVRQAPGEGL
EWIGSSGPSGSAYYTSWVKGRFTISKTSTTVDLKMTGLTTEDTATYFCARAGGSDYDWFDLW
GQGTLVTVSSGQPKAPSVFPLAPCCGDTPSSTVTLGCLVKGYLPEPVTVTWNSGTLTNGVRTF
PSVRQSSGLYSLSSVVSVTSSSQPVTCNVAHPATNTKVDKTVAPSTCSKPTCPPPELLGGPSV
FIFPPKPKDTLMISRTPEVTCVVVDVSQDDPEVQFTWYINNEQVRTARPPLREQQFNSTIRVVS
TLPIAHQDWLRGKEFKCKVHNKALPAPIEKTISKARGQPLEPKVYTMGPPREELSSRSVSLTCM
INGFYPSDISVEWEKNGKAEDNYKTTPAVLDSDGSYFLYSKLSVPTSEWQRGDVFTCSVMHEA
LHNHYTQKSISRSPGK (SEQ ID NO: 133)

FIG. 19 cont'd

>Anti-ATP7B 1056 variable heavy domain coding sequence with leader sequence. The leader sequence is underlined.
<u>ATGGAGACTGGGCTGCGCTGGCTTCTCCTGGTCGCTGTGCTCAAAGGTGTCCAGTGT</u>CAG
TCGCTGGAGGAGTCCGGGGGTCGCCTGGTCACGCCTGGAGGATCCCTGACAGTCACCTG
TACAGTCTCTGGATTCTCCCTCAGTAGCTATTGGATAATCTGGGTCCGCCAGGCTCCAGGG
GAGGGGCTGGAATGGATCGGAAGCAGTGGTCCTAGTGGTAGCGCATACTACACGAGCTG
GGTGAAAGGCCGATTCACCATCTCCAAGACCTCGACTACGGTGGATCTGAAAATGACCGG
TCTGACAACCGAGGACACGGCCACCTATTTCTGTGCCAGAGCTGGTGGTAGTGACTACGA
CTGGTTTGATCTCTGGGGCCAGGGCACCCTGGTCACCGTCTCTTCA (SEQ ID NO: 134)

>Anti-ATP7B 1056 variable heavy domain amino acid sequence with leader sequence. The leader sequence is underlined and the CDRs are bolded.
<u>METGLRWLLLVAVLKGVQC</u>QSLEESGGRLVTPGGSLTVTCTVSGFSLSSYWIIWVRQAPGEGL
EWIGSSGPSGSAYYTSWVKGRFTISKTSTTVDLKMTGLTTEDTATYFCARAGGSDYDWFDLW
GQGTLVTVSS (SEQ ID NO: 135)

>Anti-ATP7B 1056 heavy chain amino acid sequence without leader sequence. The CDRs are bolded.
QSLEESGGRLVTPGGSLTVTCTVSGFSLSSYWIIWVRQAPGEGLEWIG**SSGPSGSAYYTSWV
KGRFTISKTSTTVDLKMTGLTTEDTATYFCARAGGSDYDWFDL**WGQGTLVTVSSGQPKAPSV
FPLAPCCGDTPSSTVTLGCLVKGYLPEPVTVTWNSGTLTNGVRTFPSVRQSSGLYSLSSVVSV
TSSSQPVTCNVAHPATNTKVDKTVAPSTCSKPTCPPPELLGGPSVFIFPPKPKDTLMISRTPEV
TCVVVDVSQDDPEVQFTWYINNEQVRTARPPLREQQFNSTIRVVSTLPIAHQDWLRGKEFKCK
VHNKALPAPIEKTISKARGQPLEPKVYTMGPPREELSSRSVSLTCMINGFYPSDISVEWEKNGK
AEDNYKTTPAVLDSDGSYFLYSKLSVPTSEWQRGDVFTCSVMHEALHNHYTQKSISRSPGK
(SEQ ID NO: 136)

>Anti-ATP7B 1056 variable heavy domain amino acid sequence without the leader sequence. The CDRs are bolded.
QSLEESGGRLVTPGGSLTVTCTVSGFSLSSYWIIWVRQAPGEGLEWIG**SSGPSGSAYYTSWV
KGRFTISKTSTTVDLKMTGLTTEDTATYFCARAGGSDYDWFDL**WGQGTLVTVSS (SEQ ID
NO: 75)

FIG. 19 cont'd

>Anti-ATP7B 1056 VL CDR1
QSSPSVANNNWLS (SEQ ID NO: 60)

>Anti-ATP7B 1056 VL CDR2
GASTLAS (SEQ ID NO: 61)

>Anti-ATP7B 1056 VL CDR3
AGGHKTAEKNP (SEQ ID NO: 62)

>Anti-ATP7B 1056 light chain coding sequence (EB0601-K3-2) with leader sequence. The leader sequence is underlined.
<u>ATGGACACGAGGGCCCCCACTCAGCTGCTGGGGCTCCTGCTGCTCTGGCTCCCAGGTGCCACATTTGCC</u>CAAGTGCTGACCCAGACTCCATCTCCCGTGTCTGCGGCTGTGGGAGGCACAGTCACCATCAACTGCCAGTCCAGTCCGAGTGTTGCTAATAACAACTGGTTATCCTGGTTTCAGCAGAAACCAGGGCAGCGTCCCAAGCTCCTGATCTATGGTGCATCCACTCTGGCATCTGGGGTCCCATCGCGGTTCAAAGGCAGTGGATCTGGGACACAGTTCACTCTCACCATCAGCGACGTGCAGTGTGACGATGCTGCCACTTACTACTGTGCAGGCGGTCATAAAACTGCTGAAAAAAATCCTTTCGGCGGAGGGACCGAGGTGGTGGTCAAAGGTGATCCAGTTGCACCTACTGTCCTCATCTTCCCACCAGCTGCTGATCAGGTGGCAACTGGAACAGTCACCATCGTGTGTGTGGCGAATAAATACTTTCCCGATGTCACCGTCACCTGGGAGGTGGATGGCACCACCCAAACAACTGGCATCGAGAACAGTAAAACACCGCAGAATTCTGCAGATTGTACCTACAACCTCAGCAGCACTCTGACACTGACCAGCACACAGTACAACAGCCACAAGAGTACACCTGCAAGGTGACCCAGGGCACGACCTCAGTCGTCCAGAGCTTCAATAGGGGTGACTGTTAG (SEQ ID NO: 137)

>Anti-ATP7B 1056 light chain amino acid sequence with leader sequence. The leader sequence is underlined and the CDRs are bolded.
<u>MDTRAPTQLLGLLLLWLPGATFA</u>QVLTQTPSPVSAAVGGTVTINCQSSPSVANNNWLSWFQQKPGQRPKLLIYGASTLASGVPSRFKGSGSGTQFTLTISDVQCDDAATYYCAGGHKTAEKNPFGGGTEVVVKGDPVAPTVLIFPPAADQVATGTVTIVCVANKYFPDVTVTWEVDGTTQTTGIENSKTPQNSADCTYNLSSTLTLTSTQYNSHKEYTCKVTQGTTSVVQSFNRGDC (SEQ ID NO: 138)

>Anti-ATP7B 1056 variable light domain coding sequence with leader sequence. The leader sequence is underlined.
<u>ATGGACACGAGGGCCCCCACTCAGCTGCTGGGGCTCCTGCTGCTCTGGCTCCCAGGTGCCACATTTGCC</u>CAAGTGCTGACCCAGACTCCATCTCCCGTGTCTGCGGCTGTGGGAGGCACAGTCACCATCAACTGCCAGTCCAGTCCGAGTGTTGCTAATAACAACTGGTTATCCTGGTTTCAGCAGAAACCAGGGCAGCGTCCCAAGCTCCTGATCTATGGTGCATCCACTCTGGCATCTGGGGTCCCATCGCGGTTCAAAGGCAGTGGATCTGGGACACAGTTCACTCTCACCATCAGCGACGTGCAGTGTGACGATGCTGCCACTTACTACTGTGCAGGCGGTCATAAAACTGCTGAAAAAAATCCTTTCGGCGGAGGGACCGAGGTGGTGGTCAAA (SEQ ID NO: 139)

>Anti-ATP7B 1056 variable light domain amino acid sequence with leader sequence. The leader sequence is underlined and the CDRs are bolded.
<u>MDTRAPTQLLGLLLLWLPGATFA</u>QVLTQTPSPVSAAVGGTVTINCQSSPSVANNNWLSWFQQKPGQRPKLLIYGASTLASGVPSRFKGSGSGTQFTLTISDVQCDDAATYYCAGGHKTAEKNPFGGGTEVVVK (SEQ ID NO: 140)

FIG. 19 cont'd

>Anti-ATP7B 1056 light chain amino acid sequence without leader sequence. The CDRs are bolded.
QVLTQTPSPVSAAVGGTVTINCQSSPSVANNNWLSWFQQKPGQRPKLLIYGASTLASGVPSR
FKGSGSGTQFTLTISDVQCDDAATYYCAGGHKTAEKNPFGGGTEVVVKGDPVAPTVLIFPPAA
DQVATGTVTIVCVANKYFPDVTVTWEVDGTTQTTGIENSKTPQNSADCTYNLSSTLTLTSTQYN
SHKEYTCKVTQGTTSVVQSFNRGDC (SEQ ID NO: 141)

>Anti-ATP7B 1056 variable light domain amino acid sequence without the leader sequence. The CDRs are bolded.
QVLTQTPSPVSAAVGGTVTINCQSSPSVANNNWLSWFQQKPGQRPKLLIYGASTLASGVPSR
FKGSGSGTQFTLTISDVQCDDAATYYCAGGHKTAEKNPFGGGTEVVVK (SEQ ID NO: 76)

SEQUENCE LISTING

<160> NUMBER OF SEQ ID NOS: 147

<210> SEQ ID NO 1
<211> LENGTH: 9
<212> TYPE: PRT
<213> ORGANISM: Homo sapiens

<400> SEQUENCE: 1

Asp Leu Tyr Ser Gly Leu Asn Gln Arg
1               5

<210> SEQ ID NO 2
<211> LENGTH: 15
<212> TYPE: PRT
<213> ORGANISM: Homo sapiens

<400> SEQUENCE: 2

Ala Gly Ile Ser Glu Ala Gln Leu Thr Asp Ala Glu Thr Ser Lys
1               5                   10                  15

<210> SEQ ID NO 3
<211> LENGTH: 16
<212> TYPE: PRT
<213> ORGANISM: Homo sapiens

<400> SEQUENCE: 3

Leu Ile Tyr Asp Phe Ile Glu Asp Gln Gly Gly Leu Glu Ala Val Arg
1               5                   10                  15

<210> SEQ ID NO 4
<211> LENGTH: 11
<212> TYPE: PRT
<213> ORGANISM: Homo sapiens

<400> SEQUENCE: 4

Glu Leu Gly Thr Gly Gln Phe Gly Val Val Lys
1               5                   10

<210> SEQ ID NO 5
<211> LENGTH: 14
<212> TYPE: PRT
<213> ORGANISM: Homo sapiens

<400> SEQUENCE: 5

Tyr Val Leu Asp Asp Glu Tyr Thr Ser Ser Val Gly Ser Lys
1               5                   10

<210> SEQ ID NO 6
<211> LENGTH: 5
<212> TYPE: PRT
<213> ORGANISM: Homo sapiens

<400> SEQUENCE: 6

Phe Leu Val Ile Arg
1               5

<210> SEQ ID NO 7
<211> LENGTH: 8
<212> TYPE: PRT
<213> ORGANISM: Homo sapiens

<400> SEQUENCE: 7

Arg Pro Gly Tyr Asp Gln Leu Asn
1               5

```
<210> SEQ ID NO 8
<211> LENGTH: 9
<212> TYPE: PRT
<213> ORGANISM: Homo sapiens

<400> SEQUENCE: 8

Lys Arg Pro Gly Tyr Asp Gln Leu Asn
1               5

<210> SEQ ID NO 9
<211> LENGTH: 14
<212> TYPE: PRT
<213> ORGANISM: Homo sapiens

<400> SEQUENCE: 9

Asp Thr His Leu Thr Ile Thr Pro Thr Val Leu Gly Glu Arg
1               5                   10

<210> SEQ ID NO 10
<211> LENGTH: 15
<212> TYPE: PRT
<213> ORGANISM: Homo sapiens

<400> SEQUENCE: 10

Val Ser Leu Pro Asp Gly Ala Glu Gly Ser Gly Thr Asp His Arg
1               5                   10                  15

<210> SEQ ID NO 11
<211> LENGTH: 22
<212> TYPE: PRT
<213> ORGANISM: Homo sapiens

<400> SEQUENCE: 11

Val Leu Ala Val Val Gly Thr Ala Glu Ala Ser Ser Glu His Pro Leu
1               5                   10                  15

Gly Val Ala Val Thr Lys
            20

<210> SEQ ID NO 12
<211> LENGTH: 32
<212> TYPE: PRT
<213> ORGANISM: Homo sapiens

<400> SEQUENCE: 12

Ser Ser Ala Ile Ser Ile Ile Asn Gln Val Ile Gly Trp Ile Tyr Phe
1               5                   10                  15

Val Ala Trp Ser Ile Ser Phe Tyr Pro Gln Val Ile Met Asn Trp Arg
            20                  25                  30

<210> SEQ ID NO 13
<211> LENGTH: 35
<212> TYPE: PRT
<213> ORGANISM: Homo sapiens
<220> FEATURE:
<221> NAME/KEY: MISC_FEATURE
<222> LOCATION: (30)..(31)
<223> OTHER INFORMATION: Cys residues at residue 30 and residue 31 are
      each S-carboxymethylated

<400> SEQUENCE: 13

Tyr Pro Asn Gly Val Asn Pro Val Asn Ser Asn Asp Val Phe Phe Ser
1               5                   10                  15

Leu His Ala Val Val Leu Thr Leu Ile Ile Ile Val Gln Cys Cys Leu
            20                  25                  30
```

Tyr Glu Arg
        35

<210> SEQ ID NO 14
<211> LENGTH: 15
<212> TYPE: PRT
<213> ORGANISM: Homo sapiens

<400> SEQUENCE: 14

Ala Glu Ala Ala Val Glu Ser Ala Val Ala Gly Pro Gln Gly Arg
1               5                   10                  15

<210> SEQ ID NO 15
<211> LENGTH: 13
<212> TYPE: PRT
<213> ORGANISM: Homo sapiens

<400> SEQUENCE: 15

Ile Ser Ser Ser Asp Leu Ser Leu Gly His Val Thr Arg
1               5                   10

<210> SEQ ID NO 16
<211> LENGTH: 13
<212> TYPE: PRT
<213> ORGANISM: Homo sapiens

<400> SEQUENCE: 16

Val Ala Pro Leu Ser Leu Gly Pro Ile Asp Ile Glu Arg
1               5                   10

<210> SEQ ID NO 17
<211> LENGTH: 12
<212> TYPE: PRT
<213> ORGANISM: Homo sapiens

<400> SEQUENCE: 17

Leu Pro Ala Asn His Ala Pro Asp Ile Leu Ala Lys
1               5                   10

<210> SEQ ID NO 18
<211> LENGTH: 15
<212> TYPE: PRT
<213> ORGANISM: Homo sapiens

<400> SEQUENCE: 18

Thr Asn Gly Ile Thr Tyr Ala Ser Val Ala Leu Ala Thr Ser Lys
1               5                   10                  15

<210> SEQ ID NO 19
<211> LENGTH: 14
<212> TYPE: PRT
<213> ORGANISM: Homo sapiens

<400> SEQUENCE: 19

Ile Ile Glu Glu Ile Gly Phe His Ala Ser Leu Ala Gln Arg
1               5                   10

<210> SEQ ID NO 20
<211> LENGTH: 15
<212> TYPE: PRT
<213> ORGANISM: Homo sapiens

<400> SEQUENCE: 20

Ala Thr His Val Gly Asn Asp Thr Thr Leu Ala Gln Ile Val Lys

<210> SEQ ID NO 21
<211> LENGTH: 17
<212> TYPE: PRT
<213> ORGANISM: Homo sapiens

<400> SEQUENCE: 21

Gly Thr Ala Glu Ala Ser Ser Glu His Pro Leu Gly Val Ala Val Thr
1               5                   10                  15
Lys

<210> SEQ ID NO 22
<211> LENGTH: 5
<212> TYPE: PRT
<213> ORGANISM: Artificial Sequence
<220> FEATURE:
<223> OTHER INFORMATION: Anti-CD3e 197 VH CDR1

<400> SEQUENCE: 22

Glu Tyr Val Ile His
1               5

<210> SEQ ID NO 23
<211> LENGTH: 17
<212> TYPE: PRT
<213> ORGANISM: Artificial Sequence
<220> FEATURE:
<223> OTHER INFORMATION: Anti-CD3e 197 VH CDR2

<400> SEQUENCE: 23

Gly Phe Asn Pro Asn Ile Gly Gly Thr Asn Tyr Asn Gln Arg Phe Lys
1               5                   10                  15
Gly

<210> SEQ ID NO 24
<211> LENGTH: 10
<212> TYPE: PRT
<213> ORGANISM: Artificial Sequence
<220> FEATURE:
<223> OTHER INFORMATION: Anti-CD3e 197 VH CDR3

<400> SEQUENCE: 24

Gly Gly Pro Tyr Tyr Tyr Ala Met Asp Tyr
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Anti-CD3e 197 VL CDR1

<400> SEQUENCE: 25

Arg Ser Ser Gln Ser Ile Val His Ser Ser Gly Asn Thr Tyr Leu Glu
1               5                   10                  15

<210> SEQ ID NO 26
<211> LENGTH: 7
<212> TYPE: PRT
<213> ORGANISM: Artificial Sequence
<220> FEATURE:
<223> OTHER INFORMATION: Anti-CD3e 197 VL CDR2

<400> SEQUENCE: 26

Lys Val Ser Asn Arg Phe Ser
1               5

<210> SEQ ID NO 27
<211> LENGTH: 9
<212> TYPE: PRT
<213> ORGANISM: Artificial Sequence
<220> FEATURE:
<223> OTHER INFORMATION: Anti-CD3e 197 VL CDR3

<400> SEQUENCE: 27

Phe Gln Gly Ser His Val Pro Trp Thr
1               5

<210> SEQ ID NO 28
<211> LENGTH: 5
<212> TYPE: PRT
<213> ORGANISM: Artificial Sequence
<220> FEATURE:
<223> OTHER INFORMATION: Anti-WASp 274 VH CDR1

<400> SEQUENCE: 28

Thr Tyr Ala Met Thr
1               5

<210> SEQ ID NO 29
<211> LENGTH: 17
<212> TYPE: PRT
<213> ORGANISM: Artificial Sequence
<220> FEATURE:
<223> OTHER INFORMATION: Anti-WASp 274 VH CDR2

<400> SEQUENCE: 29

Ser Phe Tyr Ile Glu Gly Ser Ala Ser Tyr Ala Asn Trp Ala Asn Gly
1               5                   10                  15

Arg

<210> SEQ ID NO 30
<211> LENGTH: 9
<212> TYPE: PRT
<213> ORGANISM: Artificial Sequence
<220> FEATURE:
<223> OTHER INFORMATION: Anti-WASp 274 VH CDR3

<400> SEQUENCE: 30

Gly Asn Pro Gly Gly Ser Ser Ala Val
1               5

<210> SEQ ID NO 31
<211> LENGTH: 13
<212> TYPE: PRT
<213> ORGANISM: Artificial Sequence
<220> FEATURE:
<223> OTHER INFORMATION: Anti-WASp 274 VL CDR1

<400> SEQUENCE: 31

Gln Ser Ser Glu Thr Val Tyr Lys Asn Asn Tyr Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Anti-WASp 274 VL CDR2

<400> SEQUENCE: 32

Trp Ala Ser Lys Leu Ala Ser
1               5

<210> SEQ ID NO 33
<211> LENGTH: 12
<212> TYPE: PRT
<213> ORGANISM: Artificial Sequence
<220> FEATURE:
<223> OTHER INFORMATION: Anti-WASp 274 VL CDR3

<400> SEQUENCE: 33

Ala Gly Tyr Gln Ser Asn Ile Val Asp Gly Thr Ala
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Anti-BTK 407 VH CDR1

<400> SEQUENCE: 34

Arg Asn Glu Ile Ser
1               5

<210> SEQ ID NO 35
<211> LENGTH: 17
<212> TYPE: PRT
<213> ORGANISM: Artificial Sequence
<220> FEATURE:
<223> OTHER INFORMATION: Anti-BTK 407 VH CDR2

<400> SEQUENCE: 35

Gly Ile Gly Ser Pro Gly Arg Ala Tyr Tyr Ala Thr Trp Ala Lys Ser
1               5                   10                  15

Arg

<210> SEQ ID NO 36
<211> LENGTH: 13
<212> TYPE: PRT
<213> ORGANISM: Artificial Sequence
<220> FEATURE:
<223> OTHER INFORMATION: Anti-BTK 407 VL CDR1

<400> SEQUENCE: 36

Gln Ser Ser Gln Ser Val Tyr Asn Asn Asn Arg Leu Ala
1               5                   10

<210> SEQ ID NO 37
<211> LENGTH: 7
<212> TYPE: PRT
<213> ORGANISM: Artificial Sequence
<220> FEATURE:
<223> OTHER INFORMATION: Anti-BTK 407 VL CDR2

<400> SEQUENCE: 37

Ser Ala Ser Thr Leu Ala Ser
1               5

<210> SEQ ID NO 38
<211> LENGTH: 13
<212> TYPE: PRT
<213> ORGANISM: Artificial Sequence
<220> FEATURE:
<223> OTHER INFORMATION: Anti-BTK 407 VL CDR3

```
<400> SEQUENCE: 38

Leu Gly Ser Tyr Asp Cys Ser Thr Ala Asp Cys Asn Ala
1               5                   10

<210> SEQ ID NO 39
<211> LENGTH: 6
<212> TYPE: PRT
<213> ORGANISM: Artificial Sequence
<220> FEATURE:
<223> OTHER INFORMATION: Anti-CTNS 115 VH CDR1

<400> SEQUENCE: 39

Thr Arg Asp Gly Val Cys
1               5

<210> SEQ ID NO 40
<211> LENGTH: 19
<212> TYPE: PRT
<213> ORGANISM: Artificial Sequence
<220> FEATURE:
<223> OTHER INFORMATION: Anti-CTNS 115 VH CDR2

<400> SEQUENCE: 40

Cys Ile Tyr Arg Gly Ile Ser Ala Thr Thr Ser Tyr Ala Ser Trp Ala
1               5                   10                  15

Lys Gly Arg

<210> SEQ ID NO 41
<211> LENGTH: 4
<212> TYPE: PRT
<213> ORGANISM: Artificial Sequence
<220> FEATURE:
<223> OTHER INFORMATION: Anti-CTNS 115 VH CDR3

<400> SEQUENCE: 41

Ala Trp Asp Leu
1

<210> SEQ ID NO 42
<211> LENGTH: 11
<212> TYPE: PRT
<213> ORGANISM: Artificial Sequence
<220> FEATURE:
<223> OTHER INFORMATION: Anti-CTNS 115 VL CDR1

<400> SEQUENCE: 42

Gln Ala Ser Gln Ser Ile Gly Ser Asp Leu Ser
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Anti-CTNS 115 VL CDR2

<400> SEQUENCE: 43

Lys Ala Ser Lys Val Glu Thr
1               5

<210> SEQ ID NO 44
<211> LENGTH: 13
<212> TYPE: PRT
<213> ORGANISM: Artificial Sequence
<220> FEATURE:
<223> OTHER INFORMATION: Anti-CTNS 115 VL CDR3
```

```
<400> SEQUENCE: 44

Gln Ser Ile Asp Phe Ser Lys Ser Tyr Ile Gly Gly Ala
1               5                   10

<210> SEQ ID NO 45
<211> LENGTH: 6
<212> TYPE: PRT
<213> ORGANISM: Artificial Sequence
<220> FEATURE:
<223> OTHER INFORMATION: Anti-CTNS 360 VH CDR1

<400> SEQUENCE: 45

Asn Asn Asp Gly Ile Cys
1               5

<210> SEQ ID NO 46
<211> LENGTH: 18
<212> TYPE: PRT
<213> ORGANISM: Artificial Sequence
<220> FEATURE:
<223> OTHER INFORMATION: Anti-CTNS 360 VH CDR2

<400> SEQUENCE: 46

Cys Ile Gly Ser Thr Ser Gly Arg Ile Tyr Tyr Ala Ser Trp Ala Lys
1               5                   10                  15

Gly Arg

<210> SEQ ID NO 47
<211> LENGTH: 12
<212> TYPE: PRT
<213> ORGANISM: Artificial Sequence
<220> FEATURE:
<223> OTHER INFORMATION: Anti-CTNS 360 VH CDR3

<400> SEQUENCE: 47

Glu Pro Tyr Gly Ser Gly Ser Met Ala Phe Asp Leu
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Anti-CTNS 360 VL CDR1

<400> SEQUENCE: 48

Gln Ala Ser Gln Ser Ile Trp Asn Asn Asn Phe Leu Ser
1               5                   10

<210> SEQ ID NO 49
<211> LENGTH: 7
<212> TYPE: PRT
<213> ORGANISM: Artificial Sequence
<220> FEATURE:
<223> OTHER INFORMATION: Anti-CTNS 360 VL CDR2

<400> SEQUENCE: 49

Glu Ala Ser Lys Leu Ala Ser
1               5

<210> SEQ ID NO 50
<211> LENGTH: 13
<212> TYPE: PRT
<213> ORGANISM: Artificial Sequence
<220> FEATURE:
```

```
<223> OTHER INFORMATION: Anti-CTNS 360 VL CDR3

<400> SEQUENCE: 50

Gln Gly Glu Phe Ser Cys Ser Ile Ala Asp Cys Val Ala
1               5                   10

<210> SEQ ID NO 51
<211> LENGTH: 6
<212> TYPE: PRT
<213> ORGANISM: Artificial Sequence
<220> FEATURE:
<223> OTHER INFORMATION: Anti-SHPK 363 VH CDR1

<400> SEQUENCE: 51

Ser Asn Tyr Phe Met Cys
1               5

<210> SEQ ID NO 52
<211> LENGTH: 18
<212> TYPE: PRT
<213> ORGANISM: Artificial Sequence
<220> FEATURE:
<223> OTHER INFORMATION: Anti-SHPK 363 VH CDR2

<400> SEQUENCE: 52

Cys Ile Leu Val Gly Ser Gly Arg Thr Thr Phe Ala Ser Trp Ala Lys
1               5                   10                  15

Gly Arg

<210> SEQ ID NO 53
<211> LENGTH: 4
<212> TYPE: PRT
<213> ORGANISM: Artificial Sequence
<220> FEATURE:
<223> OTHER INFORMATION: Anti-SHPK 363 VH CDR3

<400> SEQUENCE: 53

Ala Trp Ala Leu
1

<210> SEQ ID NO 54
<211> LENGTH: 13
<212> TYPE: PRT
<213> ORGANISM: Artificial Sequence
<220> FEATURE:
<223> OTHER INFORMATION: Anti-SHPK 363 VL CDR1

<400> SEQUENCE: 54

Gln Ala Ser Gln Ser Val Tyr Asn Asn Asn Asp Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Anti-SHPK 363 VL CDR2

<400> SEQUENCE: 55

Gly Ala Ser Thr Leu Val Ser
1               5

<210> SEQ ID NO 56
<211> LENGTH: 10
<212> TYPE: PRT
<213> ORGANISM: Artificial Sequence
```

<220> FEATURE:
<223> OTHER INFORMATION: Anti-SHPK 363 VL CDR3

<400> SEQUENCE: 56

Gln Gly Gly Tyr Asp Pro Arg Asn Tyr Pro
1               5                   10

<210> SEQ ID NO 57
<211> LENGTH: 5
<212> TYPE: PRT
<213> ORGANISM: Artificial Sequence
<220> FEATURE:
<223> OTHER INFORMATION: Anti-ATP7B 1056 VH CDR1

<400> SEQUENCE: 57

Ser Tyr Trp Ile Ile
1               5

<210> SEQ ID NO 58
<211> LENGTH: 16
<212> TYPE: PRT
<213> ORGANISM: Artificial Sequence
<220> FEATURE:
<223> OTHER INFORMATION: Anti-ATP7B 1056 VH CDR2

<400> SEQUENCE: 58

Ser Ser Gly Pro Ser Gly Ser Ala Tyr Tyr Thr Ser Trp Val Lys Gly
1               5                   10                  15

<210> SEQ ID NO 59
<211> LENGTH: 11
<212> TYPE: PRT
<213> ORGANISM: Artificial Sequence
<220> FEATURE:
<223> OTHER INFORMATION: Anti-ATP7B 1056 VH CDR3

<400> SEQUENCE: 59

Ala Gly Gly Ser Asp Tyr Asp Trp Phe Asp Leu
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Anti-ATP7B 1056 VL CDR1

<400> SEQUENCE: 60

Gln Ser Ser Pro Ser Val Ala Asn Asn Asn Trp Leu Ser
1               5                   10

<210> SEQ ID NO 61
<211> LENGTH: 7
<212> TYPE: PRT
<213> ORGANISM: Artificial Sequence
<220> FEATURE:
<223> OTHER INFORMATION: Anti-ATP7B 1056 VL CDR2

<400> SEQUENCE: 61

Gly Ala Ser Thr Leu Ala Ser
1               5

<210> SEQ ID NO 62
<211> LENGTH: 11
<212> TYPE: PRT
<213> ORGANISM: Artificial Sequence
<220> FEATURE:

<223> OTHER INFORMATION: Anti-ATP7B 1056 VL CDR3

<400> SEQUENCE: 62

Ala Gly Gly His Lys Thr Ala Glu Lys Asn Pro
1               5                   10

<210> SEQ ID NO 63
<211> LENGTH: 119
<212> TYPE: PRT
<213> ORGANISM: Artificial Sequence
<220> FEATURE:
<223> OTHER INFORMATION: Anti-CD3epsilon 197 variable heavy domain

<400> SEQUENCE: 63

Glu Val Gln Leu Gln Gln Ser Gly Pro Asp Leu Val Lys Pro Gly Ala
1               5                   10                  15

Ser Val Lys Ile Ser Cys Lys Thr Ser Gly Tyr Ile Phe Ile Glu Tyr
                20                  25                  30

Val Ile His Trp Val Lys Gln Ser His Gly Lys Ser Leu Glu Trp Ile
            35                  40                  45

Gly Gly Phe Asn Pro Asn Ile Gly Gly Thr Asn Tyr Asn Gln Arg Phe
        50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Val Arg Gly Gly Pro Tyr Tyr Tyr Ala Met Asp Tyr Trp Gly Gln Gly
                100                 105                 110

Thr Ser Val Thr Val Ser Ser
        115

<210> SEQ ID NO 64
<211> LENGTH: 112
<212> TYPE: PRT
<213> ORGANISM: Artificial Sequence
<220> FEATURE:
<223> OTHER INFORMATION: Anti-CD3epsilon 197 variable light domain

<400> SEQUENCE: 64

Asp Val Leu Met Thr Gln Asn Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Ser Gly Asn Thr Tyr Leu Glu Trp Tyr Leu Gln Lys Pro Gly Gln Ser
            35                  40                  45

Pro Lys Val Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
                100                 105                 110

<210> SEQ ID NO 65
<211> LENGTH: 114
<212> TYPE: PRT
<213> ORGANISM: Artificial Sequence
<220> FEATURE:
<223> OTHER INFORMATION: Anti-WASp 274 variable heavy domain

```
<400> SEQUENCE: 65

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Met Thr Trp Val Arg Gln Ala Pro Gly Lys Gly Leu Gln Trp Ile Gly
        35                  40                  45

Ser Phe Tyr Ile Glu Gly Ser Ala Ser Tyr Ala Asn Trp Ala Asn Gly
    50                  55                  60

Arg Phe Thr Ile Ser Lys Thr Ser Ser Thr Val Asn Leu Lys Met Thr
65                  70                  75                  80

Ser Pro Thr Val Ala Asp Thr Ala Ser Tyr Phe Cys Ala Arg Gly Asn
                85                  90                  95

Pro Gly Gly Ser Ser Ala Val Trp Gly Gln Gly Thr Leu Val Thr Val
            100                 105                 110

Ser Ser

<210> SEQ ID NO 66
<211> LENGTH: 111
<212> TYPE: PRT
<213> ORGANISM: Artificial Sequence
<220> FEATURE:
<223> OTHER INFORMATION: Anti-WASp 274 variable light domain

<400> SEQUENCE: 66

Ile Val Leu Thr Gln Thr Pro Ala Ser Val Ser Ala Ala Val Gly Gly
1               5                   10                  15

Thr Val Thr Ile Ser Cys Gln Ser Ser Glu Thr Val Tyr Lys Asn Asn
            20                  25                  30

Tyr Leu Ala Trp Tyr Gln Gln Lys Leu Gly Gln Pro Pro Lys Leu Leu
        35                  40                  45

Ile Tyr Trp Ala Ser Lys Leu Ala Ser Gly Val Pro Ser Arg Phe Lys
    50                  55                  60

Gly Ser Gly Ser Gly Thr Gln Phe Thr Leu Thr Ile Ser Asp Val Val
65                  70                  75                  80

Cys Ala Asp Ala Gly Thr Tyr Tyr Cys Ala Gly Tyr Gln Ser Asn Ile
                85                  90                  95

Val Asp Gly Thr Ala Phe Gly Gly Gly Thr Glu Val Val Val Asn
            100                 105                 110

<210> SEQ ID NO 67
<211> LENGTH: 110
<212> TYPE: PRT
<213> ORGANISM: Artificial Sequence
<220> FEATURE:
<223> OTHER INFORMATION: Anti-BTK 407 variable heavy domain

<400> SEQUENCE: 67

Gln Ser Val Lys Glu Ser Glu Gly Gly Leu Phe Lys Pro Thr Asp Thr
1               5                   10                  15

Leu Thr Val Thr Cys Thr Val Ser Gly Phe Ser Leu Ser Arg Asn Glu
            20                  25                  30

Ile Ser Trp Phe Arg Gln Ala Pro Gly Asn Gly Leu Glu Trp Ile Gly
        35                  40                  45

Gly Ile Gly Ser Pro Gly Arg Ala Tyr Tyr Ala Thr Trp Ala Lys Ser
    50                  55                  60
```

Arg Ser Thr Ile Thr Arg Asn Thr Asn Leu Asn Val Thr Leu Lys
65                  70                  75                  80

Met Thr Ser Leu Thr Ala Ala Asp Thr Ala Tyr Phe Cys Ala Arg
                85                  90                  95

Gly Asp Ile Trp Gly Pro Gly Thr Val Val Thr Val Ser Ser
            100                 105                 110

<210> SEQ ID NO 68
<211> LENGTH: 112
<212> TYPE: PRT
<213> ORGANISM: Artificial Sequence
<220> FEATURE:
<223> OTHER INFORMATION: Anti-BTK 407 variable light domain

<400> SEQUENCE: 68

Gln Val Leu Thr Gln Thr Val Ser Pro Val Ser Ala Ala Val Gly Ser
1               5                   10                  15

Thr Val Thr Ile Asn Cys Gln Ser Ser Gln Ser Val Tyr Asn Asn Asn
                20                  25                  30

Arg Leu Ala Trp Tyr Gln Gln Lys Pro Gly Gln Pro Pro Lys Gly Leu
            35                  40                  45

Ile Tyr Ser Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Leu Gly Ser Tyr Asp Cys Ser
                85                  90                  95

Thr Ala Asp Cys Asn Ala Phe Gly Gly Gly Thr Glu Val Val Val Lys
            100                 105                 110

<210> SEQ ID NO 69
<211> LENGTH: 114
<212> TYPE: PRT
<213> ORGANISM: Artificial Sequence
<220> FEATURE:
<223> OTHER INFORMATION: Anti-CTNS 115 variable heavy domain

<400> SEQUENCE: 69

Gln Glu Gln Leu Val Glu Ser Gly Gly Gly Leu Val Gln Pro Glu Gly
1               5                   10                  15

Ser Leu Thr Leu Thr Cys Lys Ala Ser Gly Phe Ser Phe Ser Thr Arg
                20                  25                  30

Asp Gly Val Cys Trp Val Arg Gln Ala Pro Gly Lys Gly Leu Glu Trp
            35                  40                  45

Ile Ala Cys Ile Tyr Arg Gly Ile Ser Ala Thr Thr Ser Tyr Ala Ser
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Ala Trp Asp Leu Trp Gly Pro Gly Thr Leu Val Thr Val
            100                 105                 110

Ser Ser

<210> SEQ ID NO 70
<211> LENGTH: 111
<212> TYPE: PRT
<213> ORGANISM: Artificial Sequence
<220> FEATURE:

<223> OTHER INFORMATION: Anti-CTNS 115 variable light domain

<400> SEQUENCE: 70

Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Asp
            20                  25                  30

Leu Ser Trp Tyr Gln Gln Lys Pro Gly Gln Pro Pro Lys Arg Leu Ile
        35                  40                  45

Tyr Lys Ala Ser Lys Val Glu Thr Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ser Thr Tyr Tyr Cys Gln Ser Ile Asp Phe Ser Lys Ser
                85                  90                  95

Tyr Ile Gly Gly Ala Phe Gly Gly Thr Glu Val Val Val Lys
            100                 105                 110

<210> SEQ ID NO 71
<211> LENGTH: 120
<212> TYPE: PRT
<213> ORGANISM: Artificial Sequence
<220> FEATURE:
<223> OTHER INFORMATION: Anti-CTNS 360 variable heavy domain

<400> SEQUENCE: 71

Gln Ser Leu Glu Glu Ser Gly Gly Gly Leu Phe Gln Pro Gly Ala Ser
1               5                   10                  15

Leu Thr Leu Thr Cys Thr Ala Ser Gly Phe Ser Phe Ser Asn Asn Asp
            20                  25                  30

Gly Ile Cys Trp Val Arg Gln Ala Pro Gly Lys Gly Leu Glu Trp Ile
        35                  40                  45

Gly Cys Ile Gly Ser Thr Ser Gly Arg Ile Tyr Tyr Ala Ser Trp Ala
    50                  55                  60

Lys Gly Arg Leu Thr Ile Ser Lys Thr Ser Thr Thr Val Ile Leu
65                  70                  75                  80

Gln Met Thr Ser Leu Thr Ala Ala Asp Thr Ala Thr Tyr Phe Cys Ala
                85                  90                  95

Ser Glu Pro Tyr Gly Ser Gly Ser Met Ala Phe Asp Leu Trp Gly Pro
            100                 105                 110

Gly Thr Leu Val Thr Val Ser Ser
        115                 120

<210> SEQ ID NO 72
<211> LENGTH: 112
<212> TYPE: PRT
<213> ORGANISM: Artificial Sequence
<220> FEATURE:
<223> OTHER INFORMATION: Anti-CTNS 360 variable light domain

<400> SEQUENCE: 72

Gln Val Leu Thr Gln Thr Ala Ser Ser Val Ser Ala Ala Val Gly Gly
1               5                   10                  15

Thr Val Thr Val Asn Cys Gln Ala Ser Gln Ser Ile Trp Asn Asn Asn
            20                  25                  30

Phe Leu Ser Trp Tyr Gln Gln Lys Pro Gly Gln Pro Pro Lys Leu Leu
        35                  40                  45

Ile Tyr Glu Ala Ser Lys Leu Ala Ser Gly Val Pro Ser Arg Phe Ser

```
                    50                  55                  60
Gly Ser Gly Ser Gly Thr Gln Phe Thr Leu Thr Ile Ser Gly Val Gln
 65                  70                  75                  80

Cys Asp Asp Ala Ala Thr Tyr Tyr Cys Gln Gly Glu Phe Ser Cys Ser
                 85                  90                  95

Ile Ala Asp Cys Val Ala Phe Gly Gly Gly Thr Glu Val Val Val Arg
                100                 105                 110
```

<210> SEQ ID NO 73
<211> LENGTH: 113
<212> TYPE: PRT
<213> ORGANISM: Artificial Sequence
<220> FEATURE:
<223> OTHER INFORMATION: Anti-SHPK 363 variable heavy domain

<400> SEQUENCE: 73

```
Gln Glu Gln Ile Glu Glu Ser Gly Gly Gly Leu Val Lys Pro Glu Gly
  1               5                  10                  15

Ser Leu Thr Leu Thr Cys Lys Val Ser Gly Phe Asp Phe Ser Ser Asn
                 20                  25                  30

Tyr Phe Met Cys Trp Val Arg Gln Ala Pro Gly Lys Gly Leu Glu Trp
             35                  40                  45

Ile Gly Cys Ile Leu Val Gly Ser Gly Arg Thr Thr Phe Ala Ser Trp
 50                  55                  60

Ala Lys Gly Arg Phe Thr Ile Ser Lys Thr Ser Ser Thr Thr Val Thr
 65                  70                  75                  80

Leu Gln Met Thr Ser Leu Thr Ala Ala Asp Thr Ala Thr Tyr Phe Cys
                 85                  90                  95

Ala Arg Ala Trp Ala Leu Trp Gly Pro Gly Thr Leu Val Thr Val Ser
                100                 105                 110

Ser
```

<210> SEQ ID NO 74
<211> LENGTH: 109
<212> TYPE: PRT
<213> ORGANISM: Artificial Sequence
<220> FEATURE:
<223> OTHER INFORMATION: Anti-SHPK 363 variable light domain

<400> SEQUENCE: 74

```
Gln Val Leu Thr Gln Thr Pro Ser Pro Val Ser Ala Ala Val Gly Gly
  1               5                  10                  15

Thr Val Thr Ile Ser Cys Gln Ala Ser Gln Ser Val Tyr Asn Asn Asn
                 20                  25                  30

Asp Leu Ala Trp Tyr Gln Gln Lys Pro Gly Gln Pro Lys Leu Leu
             35                  40                  45

Ile Tyr Gly Ala Ser Thr Leu Val Ser Gly Val Pro Ser Arg Phe Ser
 50                  55                  60

Gly Ser Gly Ser Gly Ala Gln Phe Thr Leu Thr Ile Ser Asp Leu Glu
 65                  70                  75                  80

Cys Asp Asp Ala Ala Thr Tyr Tyr Cys Gln Gly Gly Tyr Asp Pro Arg
                 85                  90                  95

Asn Tyr Pro Phe Gly Gly Gly Thr Glu Val Val Val Lys
                100                 105
```

<210> SEQ ID NO 75
<211> LENGTH: 116
<212> TYPE: PRT

<213> ORGANISM: Artificial Sequence
<220> FEATURE:
<223> OTHER INFORMATION: Anti-ATP7B 1056 variable heavy domain

<400> SEQUENCE: 75

Gln Ser Leu Glu Glu Ser Gly Gly Arg Leu Val Thr Pro Gly Ser
1               5                   10                  15

Leu Thr Val Thr Cys Thr Val Ser Gly Phe Ser Leu Ser Ser Tyr Trp
                20                  25                  30

Ile Ile Trp Val Arg Gln Ala Pro Gly Glu Gly Leu Glu Trp Ile Gly
            35                  40                  45

Ser Ser Gly Pro Ser Gly Ser Ala Tyr Tyr Thr Ser Trp Val Lys Gly
50                  55                  60

Arg Phe Thr Ile Ser Lys Thr Ser Thr Val Asp Leu Lys Met Thr
65                  70                  75                  80

Gly Leu Thr Thr Glu Asp Thr Ala Thr Tyr Phe Cys Ala Arg Ala Gly
                85                  90                  95

Gly Ser Asp Tyr Asp Trp Phe Asp Leu Trp Gly Gln Gly Thr Leu Val
                100                 105                 110

Thr Val Ser Ser
        115

<210> SEQ ID NO 76
<211> LENGTH: 110
<212> TYPE: PRT
<213> ORGANISM: Artificial Sequence
<220> FEATURE:
<223> OTHER INFORMATION: Anti-ATP7B 1056 variable light domain

<400> SEQUENCE: 76

Gln Val Leu Thr Gln Thr Pro Ser Pro Val Ser Ala Ala Val Gly Gly
1               5                   10                  15

Thr Val Thr Ile Asn Cys Gln Ser Ser Pro Ser Val Ala Asn Asn Asn
                20                  25                  30

Trp Leu Ser Trp Phe Gln Gln Lys Pro Gly Gln Arg Pro Lys Leu Leu
            35                  40                  45

Ile Tyr Gly Ala Ser Thr Leu Ala Ser Gly Val Pro Ser Arg Phe Lys
50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Ala Gly Gly His Lys Thr Ala
                85                  90                  95

Glu Lys Asn Pro Phe Gly Gly Gly Thr Glu Val Val Val Lys
                100                 105                 110

<210> SEQ ID NO 77
<211> LENGTH: 4
<212> TYPE: PRT
<213> ORGANISM: Artificial Sequence
<220> FEATURE:
<223> OTHER INFORMATION: C-terminal extension for signature peptides

<400> SEQUENCE: 77

Gly Ser Gly Cys
1

<210> SEQ ID NO 78
<211> LENGTH: 414
<212> TYPE: DNA
<213> ORGANISM: Artificial Sequence

```
<220> FEATURE:
<223> OTHER INFORMATION: Anti-CD3epsilon 197 variable heavy domain
      coding sequence with leader sequence

<400> SEQUENCE: 78
atgggatgga gctggatctt tctctttctc ctgtcaggaa ctgcaggtgt cctctctgag       60
gtccagctgc agcagtctgg acctgacctg gtgaagcctg ggcctcagt gaagatttcc      120 tgcaagactt ctggatacat attcattgaa tacgtcatac actgggtgaa gcagagccat      180
ggaaagagcc ttgagtggat tggaggtttt aatcctaaca ttggtggtac taactacaac      240
cagaggttca aggcaaggc cacattgact gtagacaagt cctccagcac agcctacatg       300
gagctccgca gcctgacatc tgaggattct gcagtctatt actgtgtaag ggggggaccc      360
tattactatg ctatggacta ctggggtcaa ggaacctcag tcaccgtctc ctca            414

<210> SEQ ID NO 79
<211> LENGTH: 138
<212> TYPE: PRT
<213> ORGANISM: Artificial Sequence
<220> FEATURE:
<223> OTHER INFORMATION: Anti-CD3epsilon 197 variable heavy domain amino
      acid sequence with leader sequence

<400> SEQUENCE: 79

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Asp Leu Val Lys
            20                  25                  30

Pro Gly Ala Ser Val Lys Ile Ser Cys Lys Thr Ser Gly Tyr Ile Phe
        35                  40                  45

Ile Glu Tyr Val Ile His Trp Val Lys Gln Ser His Gly Lys Ser Leu
    50                  55                  60

Glu Trp Ile Gly Gly Phe Asn Pro Asn Ile Gly Gly Thr Asn Tyr Asn
65                  70                  75                  80

Gln Arg Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Val Arg Gly Gly Pro Tyr Tyr Tyr Ala Met Asp Tyr Trp
        115                 120                 125

Gly Gln Gly Thr Ser Val Thr Val Ser Ser
    130                 135

<210> SEQ ID NO 80
<211> LENGTH: 393
<212> TYPE: DNA
<213> ORGANISM: Artificial Sequence
<220> FEATURE:
<223> OTHER INFORMATION: Anti-CD3epsilon 197 variable light domain
      coding sequence with leader sequence

<400> SEQUENCE: 80
atgaagttgc ctgttaggct gttggtgctg atgttctgga ttcctgtttt cagcagtgat       60
gttttgatga cccaaaatcc actctccctg cctgtcagtc ttggagatca agcctccatc      120
tcttgcagat ctagtcagag cattgtacat agtagtggaa acacctattt gaatggtac      180 ctgcagaaac caggccagtc tccaaaggtc ctgatctaca agtttccaa ccgattttct       240 ggggtcccag acaggttcag tggcagtgga tcagggacag atttcacact caagatcagc      300
```
agagtggagg ctgaggatct gggagtttat tactgctttc aaggttcaca tgttccgtgg    360
acgttcggtg gaggcaccaa gctggaaatc aaa                                 393

<210> SEQ ID NO 81
<211> LENGTH: 131
<212> TYPE: PRT
<213> ORGANISM: Artificial Sequence
<220> FEATURE:
<223> OTHER INFORMATION: Anti-CD3epsilon 197 variable light domain amino
      acid sequence with leader sequence

<400> SEQUENCE: 81

Met Lys Leu Pro Val Arg Leu Leu Val Leu Met Phe Trp Ile Pro Val
1               5                   10                  15

Phe Ser Ser Asp Val Leu Met Thr Gln Asn Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Ser Gly Asn Thr Tyr Leu Glu Trp Tyr Leu Gln Lys Pro
    50                  55                  60

Gly Gln Ser Pro Lys Val Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Trp Thr Phe Gly Gly Gly Thr Lys Leu
        115                 120                 125

Glu Ile Lys
    130

<210> SEQ ID NO 82
<211> LENGTH: 1371
<212> TYPE: DNA
<213> ORGANISM: Artificial Sequence
<220> FEATURE:
<223> OTHER INFORMATION: Anti-WASp 274 heavy chain coding sequence
      (EB0603-2F8-H2) with leader sequence

<400> SEQUENCE: 82
atggagactg ggctgcgctg gcttctcctg gtcgctgtgc tcaaaggtgt ccagtgtcag    60
tcggtggagg agtccggggg tcgcctggtc acgcctggga caccctgac actcacctgc    120 acagtctctg gattctccct cagtacctat gcaatgacct gggtccgcca ggctccaggg    180
aaggggctac aatggatcgg atcctttat attgagggta gcgcatccta cgcgaactgg    240
gcgaatggtc gattcaccat ctccaaaacc tcgagtacgg tgaatctgaa aatgaccagt    300
ccgacagtcg cggacacggc cagttatttc tgtgccagag caatcctgg tggtagtagt    360 gctgtgtggg gccaaggcac cctggtcacc gtctcctcag gcaacctaa gctccatca    420 gtcttcccac tggccccctg ctgcggggac acacccagct ccacggtgac cctgggctgc    480
ctggtcaaag gctacctccc ggagccagtg accgtgacct ggaactcggg caccctcacc    540 aatgggtac gcaccttccc gtccgtcgg cagtcctcag gcctctactc gctgagcagc    600
gtggtgagcg tgacctcaag cagccagccc gtcacctgca acgtggccca cccagccacc    660
aacaccaaag tggacaagac cgttgcgccc tcgacatgca gcagcccat gtgcccaccc    720 cctgaactcc tggggggacc gtctgtcttc atcttccccc caaaacccaa ggacaccctc    780

```
atgatctcac gcaccccccga ggtcacatgc gtggtggtgg acgtgagcca ggatgacccc    840
gaggtgcagt tcacatggta cataaacaac gagcaggtgc gcaccgcccg gccgccgcta    900
cgggagcagc agttcaacag cacgatccgc gtggtcagca ccctcccat cgcgcaccag     960 gactggctga ggggcaagga gttcaagtgc aaagtccaca acaaggcact cccggccccc   1020
atcgagaaaa ccatctccaa agccagaggg cagcccctgg agccgaaggt ctacaccatg   1080
ggccctcccc gggaggagct gagcagcagg tcggtcagcc tgacctgcat gatcaacggc   1140 ttctacccctt ccgacatctc ggtggagtgg gagaagaacg ggaaggcaga ggacaactac   1200
aagaccacgc cggccgtgct ggacagcgac ggctccctact cctctacag caagctctca   1260 gtgcccacga gtgagtggca gcggggcgac gtcttcacct gctccgtgat gcacgaggcc   1320
ttgcacaacc actacacgca gaagtccatc tcccgctctc cgggtaaatg a             1371
```

<210> SEQ ID NO 83
<211> LENGTH: 456
<212> TYPE: PRT
<213> ORGANISM: Artificial Sequence
<220> FEATURE:
<223> OTHER INFORMATION: Anti-WASp 274 heavy chain amino acid sequence with leader sequence

<400> SEQUENCE: 83

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Thr Tyr Ala Met Thr Trp Val Arg Gln Ala Pro Gly Lys Gly Leu Gln
    50                  55                  60

Trp Ile Gly Ser Phe Tyr Ile Glu Gly Ser Ala Ser Tyr Ala Asn Trp
65                  70                  75                  80

Ala Asn Gly Arg Phe Thr Ile Ser Lys Thr Ser Ser Thr Val Asn Leu
                85                  90                  95

Lys Met Thr Ser Pro Thr Val Ala Asp Thr Ala Ser Tyr Phe Cys Ala
            100                 105                 110

Arg Gly Asn Pro Gly Gly Ser Ser Ala Val Trp Gly Gln Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
        195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Met Cys Pro Pro
225                 230                 235                 240

Pro Glu Leu Leu Gly Gly Pro Ser Val Phe Ile Phe Pro Pro Lys Pro
                245                 250                 255
```

-continued

```
Lys Asp Thr Leu Met Ile Ser Arg Thr Pro Glu Val Thr Cys Val Val
            260                 265                 270

Val Asp Val Ser Gln Asp Asp Pro Glu Val Gln Phe Thr Trp Tyr Ile
        275                 280                 285

Asn Asn Glu Gln Val Arg Thr Ala Arg Pro Leu Arg Glu Gln Gln
290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                325                 330                 335

Leu Pro Ala Pro Ile Glu Lys Thr Ile Ser Lys Ala Arg Gly Gln Pro
            340                 345                 350

Leu Glu Pro Lys Val Tyr Thr Met Gly Pro Pro Arg Glu Glu Leu Ser
        355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                405                 410                 415

Ser Lys Leu Ser Val Pro Thr Ser Glu Trp Gln Arg Gly Asp Val Phe
            420                 425                 430

Thr Cys Ser Val Met His Glu Ala Leu His Asn His Tyr Thr Gln Lys
        435                 440                 445

Ser Ile Ser Arg Ser Pro Gly Lys
    450                 455
```

<210> SEQ ID NO 84
<211> LENGTH: 399
<212> TYPE: DNA
<213> ORGANISM: Artificial Sequence
<220> FEATURE:
<223> OTHER INFORMATION: Anti-WASp 274 variable heavy domain coding
      sequence with leader sequence

<400> SEQUENCE: 84

```
atggagactg ggctgcgctg gcttctcctg gtcgctgtgc tcaaaggtgt ccagtgtcag      60
tcggtggagg agtccggggg tcgcctggtc acgcctggga cacccctgac actcacctgc     120
acagtctctg gattctccct cagtacctat gcaatgacct gggtccgcca ggctccaggg     180
aaggggctac aatggatcgg atccttttat attgagggta gcgcatccta cgcgaactgg     240
gcgaatggtc gattcaccat ctccaaaacc tcgagtacgg tgaatctgaa aatgaccagt     300
ccgacagtcg cggacacggc cagttatttc tgtgccagag gcaatcctgg tggtagtagt     360
gctgtgtggg gccaaggcac cctggtcacc gtctcctca                            399
```

<210> SEQ ID NO 85
<211> LENGTH: 133
<212> TYPE: PRT
<213> ORGANISM: Artificial Sequence
<220> FEATURE:
<223> OTHER INFORMATION: Anti-WASp 274 variable heavy domain amino acid
      sequence with leader sequence

<400> SEQUENCE: 85

```
Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
```

```
                20                  25                  30
Gly Thr Pro Leu Thr Leu Thr Cys Thr Val Ser Gly Phe Ser Leu Ser
            35                  40                  45
Thr Tyr Ala Met Thr Trp Val Arg Gln Ala Pro Gly Lys Gly Leu Gln
        50                  55                  60
Trp Ile Gly Ser Phe Tyr Ile Glu Gly Ser Ala Ser Tyr Ala Asn Trp
65                  70                  75                  80
Ala Asn Gly Arg Phe Thr Ile Ser Lys Thr Ser Ser Thr Val Asn Leu
                85                  90                  95
Lys Met Thr Ser Pro Thr Val Ala Asp Thr Ala Ser Tyr Phe Cys Ala
            100                 105                 110
Arg Gly Asn Pro Gly Gly Ser Ser Ala Val Trp Gly Gln Gly Thr Leu
        115                 120                 125
Val Thr Val Ser Ser
    130

<210> SEQ ID NO 86
<211> LENGTH: 437
<212> TYPE: PRT
<213> ORGANISM: Artificial Sequence
<220> FEATURE:
<223> OTHER INFORMATION: Anti-WASp 274 heavy chain amino acid sequence
      without leader sequence

<400> SEQUENCE: 86

Gln Ser Val Glu Glu Ser Gly Gly Arg Leu Val Thr Pro Gly Thr Pro
1               5                   10                  15
Leu Thr Leu Thr Cys Thr Val Ser Gly Phe Ser Leu Ser Thr Tyr Ala
                20                  25                  30
Met Thr Trp Val Arg Gln Ala Pro Gly Lys Gly Leu Gln Trp Ile Gly
            35                  40                  45
Ser Phe Tyr Ile Glu Gly Ser Ala Ser Tyr Ala Asn Trp Ala Asn Gly
        50                  55                  60
Arg Phe Thr Ile Ser Lys Thr Ser Ser Thr Val Asn Leu Lys Met Thr
65                  70                  75                  80
Ser Pro Thr Val Ala Asp Thr Ala Ser Tyr Phe Cys Ala Arg Gly Asn
                85                  90                  95
Pro Gly Gly Ser Ser Ala Val Trp Gly Gln Gly Thr Leu Val Thr Val
            100                 105                 110
Ser Ser Gly Gln Pro Lys Ala Pro Ser Val Phe Pro Leu Ala Pro Cys
        115                 120                 125
Cys Gly Asp Thr Pro Ser Ser Thr Val Thr Leu Gly Cys Leu Val Lys
    130                 135                 140
Gly Tyr Leu Pro Glu Pro Val Thr Val Thr Trp Asn Ser Gly Thr Leu
145                 150                 155                 160
Thr Asn Gly Val Arg Thr Phe Pro Ser Val Arg Gln Ser Ser Gly Leu
                165                 170                 175
Tyr Ser Leu Ser Ser Val Val Ser Val Thr Ser Ser Ser Gln Pro Val
            180                 185                 190
Thr Cys Asn Val Ala His Pro Ala Thr Asn Thr Lys Val Asp Lys Thr
        195                 200                 205
Val Ala Pro Ser Thr Cys Ser Lys Pro Met Cys Pro Pro Pro Glu Leu
    210                 215                 220
Leu Gly Gly Pro Ser Val Phe Ile Phe Pro Pro Lys Pro Lys Asp Thr
225                 230                 235                 240
```

Leu Met Ile Ser Arg Thr Pro Glu Val Thr Cys Val Val Val Asp Val
                245                 250                 255

Ser Gln Asp Asp Pro Glu Val Gln Phe Thr Trp Tyr Ile Asn Asn Glu
        260                 265                 270

Gln Val Arg Thr Ala Arg Pro Pro Leu Arg Glu Gln Gln Phe Asn Ser
    275                 280                 285

Thr Ile Arg Val Val Ser Thr Leu Pro Ile Ala His Gln Asp Trp Leu
290                 295                 300

Arg Gly Lys Glu Phe Lys Cys Lys Val His Asn Lys Ala Leu Pro Ala
305                 310                 315                 320

Pro Ile Glu Lys Thr Ile Ser Lys Ala Arg Gly Gln Pro Leu Glu Pro
                325                 330                 335

Lys Val Tyr Thr Met Gly Pro Pro Arg Glu Glu Leu Ser Ser Arg Ser
            340                 345                 350

Val Ser Leu Thr Cys Met Ile Asn Gly Phe Tyr Pro Ser Asp Ile Ser
        355                 360                 365

Val Glu Trp Glu Lys Asn Gly Lys Ala Glu Asp Asn Tyr Lys Thr Thr
    370                 375                 380

Pro Ala Val Leu Asp Ser Asp Gly Ser Tyr Phe Leu Tyr Ser Lys Leu
385                 390                 395                 400

Ser Val Pro Thr Ser Glu Trp Gln Arg Gly Asp Val Phe Thr Cys Ser
                405                 410                 415

Val Met His Glu Ala Leu His Asn His Tyr Thr Gln Lys Ser Ile Ser
            420                 425                 430

Arg Ser Pro Gly Lys
        435

<210> SEQ ID NO 87
<211> LENGTH: 717
<212> TYPE: DNA
<213> ORGANISM: Artificial Sequence
<220> FEATURE:
<223> OTHER INFORMATION: Anti-WASp 274 light chain coding sequence
      (EB0603-2F8-K2) with leader sequence

<400> SEQUENCE: 87
atggacacga gggcccccac tcagctgctg gggctcctgc tgctctggct cccaggtgcc      60
acatttgcca tcgtgctgac ccagactcca gcctccgtgt ctgcagctgt gggaggcaca     120
gtcaccatca gttgccagtc cagtgagact gtttataaga taactacttt agcctggtat     180
cagcagaaac tagggcagcc tcccaagctc ctgatctact gggcatccaa actggcatct     240
ggggtcccat cgcggttcaa aggcagtgga tctgggacac agttcactct caccatcagc     300
gatgtggtgt gtgccgatgc tggcacttac tactgtgcag gatatcaaag taatattgtt     360
gatggtacgg ctttcggcgg agggaccgag gtggtggtca acggtgatcc agttgcacct     420
actgtcctca tcttcccacc agctgctgat caggtggcaa ctggaacagt caccatcgtg     480
tgtgtggcga ataaatactt tcccgatgtc accgtcacct gggaggtgga tggcaccacc     540
caaacaactg gcatcgagaa cagtaaaaca ccgcagaatt ctgcagattg tacctacaac     600
ctcagcagca ctctgacact gaccagcaca cagtacaaca gccacaaaga gtacacctgc     660
aaggtgaccc agggcacgac ctcagtcgtc cagagcttca taggggtga ctgttag       717

<210> SEQ ID NO 88
<211> LENGTH: 238
<212> TYPE: PRT
<213> ORGANISM: Artificial Sequence
<220> FEATURE:
<223> OTHER INFORMATION: Anti-WASp 274 light chain amino acid sequence
with leader sequence

<400> SEQUENCE: 88

Met Asp Thr Arg Ala Pro Thr Gln Leu Leu Gly Leu Leu Leu Leu Trp
1               5                   10                  15

Leu Pro Gly Ala Thr Phe Ala Ile Val Leu Thr Gln Thr Pro Ala Ser
            20                  25                  30

Val Ser Ala Ala Val Gly Gly Thr Val Thr Ile Ser Cys Gln Ser Ser
        35                  40                  45

Glu Thr Val Tyr Lys Asn Asn Tyr Leu Ala Trp Tyr Gln Gln Lys Leu
    50                  55                  60

Gly Gln Pro Pro Lys Leu Leu Ile Tyr Trp Ala Ser Lys Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Val Cys Ala Asp Ala Gly Thr Tyr Tyr Cys
            100                 105                 110

Ala Gly Tyr Gln Ser Asn Ile Val Asp Gly Thr Ala Phe Gly Gly Gly
        115                 120                 125

Thr Glu Val Val Val Asn Gly Asp Pro Val Ala Pro Thr Val Leu Ile
130                 135                 140

Phe Pro Pro Ala Ala Asp Gln Val Ala Thr Gly Thr Val Thr Ile Val
145                 150                 155                 160

Cys Val Ala Asn Lys Tyr Phe Pro Asp Val Thr Val Thr Trp Glu Val
                165                 170                 175

Asp Gly Thr Thr Gln Thr Thr Gly Ile Glu Asn Ser Lys Thr Pro Gln
            180                 185                 190

Asn Ser Ala Asp Cys Thr Tyr Asn Leu Ser Ser Thr Leu Thr Leu Thr
        195                 200                 205

Ser Thr Gln Tyr Asn Ser His Lys Glu Tyr Thr Cys Lys Val Thr Gln
    210                 215                 220

Gly Thr Thr Ser Val Val Gln Ser Phe Asn Arg Gly Asp Cys
225                 230                 235

<210> SEQ ID NO 89
<211> LENGTH: 402
<212> TYPE: DNA
<213> ORGANISM: Artificial Sequence
<220> FEATURE:
<223> OTHER INFORMATION: Anti-WASp 274 variable light domain coding
sequence with leader sequence

<400> SEQUENCE: 89
atggacacga gggcccccac tcagctgctg gggctcctgc tgctctggct cccaggtgcc    60
acatttgcca tcgtgctgac ccagactcca gcctccgtgt ctgcagctgt gggaggcaca   120
gtcaccatca gttgccagtc cagtgagact gtttataaga ataactactt agcctggtat   180
cagcagaaac tagggcagcc tcccaagctc ctgatctact gggcatccaa actggcatct   240
ggggtcccat cgcggttcaa aggcagtgga tctgggacac agttcactct caccatcagc   300
gatgtggtgt gtgccgatgc tggcacttac tactgtgcag gatatcaaag taatattgtt   360
gatggtacgg ctttcggcgg agggaccgag gtggtggtca ac                      402

<210> SEQ ID NO 90
<211> LENGTH: 134

```
<212> TYPE: PRT
<213> ORGANISM: Artificial Sequence
<220> FEATURE:
<223> OTHER INFORMATION: Anti-WASp 274 variable light domain amino acid
      sequence with leader sequence

<400> SEQUENCE: 90

Met Asp Thr Arg Ala Pro Thr Gln Leu Leu Gly Leu Leu Leu Trp
1               5                   10                  15

Leu Pro Gly Ala Thr Phe Ala Ile Val Leu Thr Gln Thr Pro Ala Ser
            20                  25                  30

Val Ser Ala Ala Val Gly Gly Thr Val Thr Ile Ser Cys Gln Ser Ser
            35                  40                  45

Glu Thr Val Tyr Lys Asn Asn Tyr Leu Ala Trp Tyr Gln Gln Lys Leu
        50                  55                  60

Gly Gln Pro Pro Lys Leu Leu Ile Tyr Trp Ala Ser Lys Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Val Cys Ala Asp Ala Gly Thr Tyr Tyr Cys
            100                 105                 110

Ala Gly Tyr Gln Ser Asn Ile Val Asp Gly Thr Ala Phe Gly Gly Gly
            115                 120                 125

Thr Glu Val Val Val Asn
            130

<210> SEQ ID NO 91
<211> LENGTH: 215
<212> TYPE: PRT
<213> ORGANISM: Artificial Sequence
<220> FEATURE:
<223> OTHER INFORMATION: Anti-WASp 274 light chain amino acid sequence
      without the leader sequence

<400> SEQUENCE: 91

Ile Val Leu Thr Gln Thr Pro Ala Ser Val Ser Ala Ala Val Gly Gly
1               5                   10                  15

Thr Val Thr Ile Ser Cys Gln Ser Ser Glu Thr Val Tyr Lys Asn Asn
            20                  25                  30

Tyr Leu Ala Trp Tyr Gln Gln Lys Leu Gly Gln Pro Pro Lys Leu Leu
            35                  40                  45

Ile Tyr Trp Ala Ser Lys Leu Ala Ser Gly Val Pro Ser Arg Phe Lys
        50                  55                  60

Gly Ser Gly Ser Gly Thr Gln Phe Thr Leu Thr Ile Ser Asp Val Val
65                  70                  75                  80

Cys Ala Asp Ala Gly Thr Tyr Tyr Cys Ala Gly Tyr Gln Ser Asn Ile
                85                  90                  95

Val Asp Gly Thr Ala Phe Gly Gly Gly Thr Glu Val Val Val Asn Gly
            100                 105                 110

Asp Pro Val Ala Pro Thr Val Leu Ile Phe Pro Pro Ala Ala Asp Gln
            115                 120                 125

Val Ala Thr Gly Thr Val Thr Ile Val Cys Val Ala Asn Lys Tyr Phe
            130                 135                 140

Pro Asp Val Thr Val Thr Trp Glu Val Asp Gly Thr Thr Gln Thr Thr
145                 150                 155                 160

Gly Ile Glu Asn Ser Lys Thr Pro Gln Asn Ser Ala Asp Cys Thr Tyr
                165                 170                 175
```

Asn Leu Ser Ser Thr Leu Thr Leu Thr Ser Thr Gln Tyr Asn Ser His
            180                 185                 190

Lys Glu Tyr Thr Cys Lys Val Thr Gln Gly Thr Thr Ser Val Val Gln
            195                 200                 205

Ser Phe Asn Arg Gly Asp Cys
            210                 215

<210> SEQ ID NO 92
<211> LENGTH: 1359
<212> TYPE: DNA
<213> ORGANISM: Artificial Sequence
<220> FEATURE:
<223> OTHER INFORMATION: Anti-BTK 407 heavy chain coding sequence
      (EB0602-1G5-H2) with leader sequence

<400> SEQUENCE: 92
atggagactg ggctgcgctg gcttctcctg gtcgctgtgc tcaaaggtgt ccagtgtcag    60
tcggtgaagg agtccgaggg aggtctcttc aagccaacgg ataccctgac agtcacctgc   120
acagtctctg gattctccct cagtaggaat gaaataagct ggttccgcca ggctccaggg   180
aacgggctgg aatggatcgg ggcattggt agtcctggac gcgcatacta cgcgacctgg   240
gcgaaaagcc gatccaccat caccagaaac accaacctga atacggtgac tctgaaaatg   300
accagtctga cagccgcgga cacggccacc tatttctgtg cgagagggga catctggggc   360
ccaggcaccg tggtcaccgt ctcctcaggg caacctaagg ctccatcagt cttcccactg   420
gccccctgct gcggggacac acccagctcc acggtgaccc tgggctgcct ggtcaaaggc   480
tacctcccgg agccagtgac cgtgacctgg aactcgggca ccctcaccaa tggggtacgc   540
accttcccgt ccgtccggca gtcctcaggc ctctactcgc tgagcagcgt ggtgagcgtg   600
acctcaagca gccagcccgt cacctgcaac gtggcccacc cagccaccaa caccaaagtg   660
gacaagaccg ttgcgccctc gacatgcagc aagcccatgt gcccaccccc tgaactcctg   720
gggggaccgt ctgtcttcat cttccccccc aaacccaagg acacccctcat gatctcacgc   780 accccccgagg tcacatgcgt ggtggtggac gtgagccagg atgaccccga ggtgcagttc   840
acatggtaca taaacaacga gcaggtgcgc accgcccggc cgccgctacg ggagcagcag   900
ttcaacagca cgatccgcgt ggtcagcacc ctccccatcg cgcaccagga ctggctgagg   960
ggcaaggagt tcaagtgcaa agtccacaac aaggcactcc cggcccccat cgagaaaacc   1020
atctccaaag ccagagggca gccctggag ccgaaggtct acaccatggg ccctcccgg   1080 gaggagctga gcagcaggtc ggtcagcctg acctgcatga tcaacggctt ctacccttcc   1140
gacatctcgg tggagtggga agaacgggg aaggcagagg acaactacaa gaccacgccg   1200
gccgtgctgg acagcgacgg ctcctacttc ctctacagca agctctcagt gcccacgagt   1260
gagtggcagc ggggcgacgt cttcacctgc tccgtgatgc acgaggcctt gcacaaccac   1320
tacacgcaga agtccatctc ccgctctccg ggtaaatga                        1359

<210> SEQ ID NO 93
<211> LENGTH: 452
<212> TYPE: PRT
<213> ORGANISM: Artificial Sequence
<220> FEATURE:
<223> OTHER INFORMATION: Anti-BTK 407 heavy chain amino acid sequence
      with leader sequence

<400> SEQUENCE: 93

Met Glu Thr Gly Leu Arg Trp Leu Leu Leu Val Ala Val Leu Lys Gly
1               5                   10                  15

```
Val Gln Cys Gln Ser Val Lys Glu Ser Glu Gly Gly Leu Phe Lys Pro
             20                  25                  30

Thr Asp Thr Leu Thr Val Thr Cys Thr Val Ser Gly Phe Ser Leu Ser
         35                  40                  45

Arg Asn Glu Ile Ser Trp Phe Arg Gln Ala Pro Gly Asn Gly Leu Glu
50                  55                  60

Trp Ile Gly Gly Ile Gly Ser Pro Gly Arg Ala Tyr Tyr Ala Thr Trp
65                  70                  75                  80

Ala Lys Ser Arg Ser Thr Ile Thr Arg Asn Thr Asn Leu Asn Thr Val
             85                  90                  95

Thr Leu Lys Met Thr Ser Leu Thr Ala Ala Asp Thr Ala Thr Tyr Phe
            100                 105                 110

Cys Ala Arg Gly Asp Ile Trp Gly Pro Gly Thr Val Thr Val Ser
            115                 120                 125

Ser Gly Gln Pro Lys Ala Pro Ser Val Phe Pro Leu Ala Pro Cys Cys
130                 135                 140

Gly Asp Thr Pro Ser Ser Thr Val Thr Leu Gly Cys Leu Val Lys Gly
145                 150                 155                 160

Tyr Leu Pro Glu Pro Val Thr Val Thr Trp Asn Ser Gly Thr Leu Thr
                165                 170                 175

Asn Gly Val Arg Thr Phe Pro Ser Val Arg Gln Ser Ser Gly Leu Tyr
            180                 185                 190

Ser Leu Ser Ser Val Val Ser Val Thr Ser Ser Gln Pro Val Thr
            195                 200                 205

Cys Asn Val Ala His Pro Ala Thr Asn Thr Lys Val Asp Lys Thr Val
210                 215                 220

Ala Pro Ser Thr Cys Ser Lys Pro Met Cys Pro Pro Glu Leu Leu
225                 230                 235                 240

Gly Gly Pro Ser Val Phe Ile Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Asp Asp Pro Glu Val Gln Phe Thr Trp Tyr Ile Asn Asn Glu Gln
            275                 280                 285

Val Arg Thr Ala Arg Pro Pro Leu Arg Glu Gln Gln Phe Asn Ser Thr
            290                 295                 300

Ile Arg Val Val Ser Thr Leu Pro Ile Ala His Gln Asp Trp Leu Arg
305                 310                 315                 320

Gly Lys Glu Phe Lys Cys Lys Val His Asn Lys Ala Leu Pro Ala Pro
                325                 330                 335

Ile Glu Lys Thr Ile Ser Lys Ala Arg Gly Gln Pro Leu Glu Pro Lys
            340                 345                 350

Val Tyr Thr Met Gly Pro Pro Arg Glu Glu Leu Ser Ser Arg Ser Val
            355                 360                 365

Ser Leu Thr Cys Met Ile Asn Gly Phe Tyr Pro Ser Asp Ile Ser Val
            370                 375                 380

Glu Trp Glu Lys Asn Gly Lys Ala Glu Asp Asn Tyr Lys Thr Thr Pro
385                 390                 395                 400

Ala Val Leu Asp Ser Asp Gly Ser Tyr Phe Leu Tyr Ser Lys Leu Ser
                405                 410                 415

Val Pro Thr Ser Glu Trp Gln Arg Gly Asp Val Phe Thr Cys Ser Val
            420                 425                 430
```

Met His Glu Ala Leu His Asn His Tyr Thr Gln Lys Ser Ile Ser Arg
            435                 440                 445

Ser Pro Gly Lys
    450

<210> SEQ ID NO 94
<211> LENGTH: 387
<212> TYPE: DNA
<213> ORGANISM: Artificial Sequence
<220> FEATURE:
<223> OTHER INFORMATION: Anti-BTK 407 variable heavy domain coding
      sequence with leader sequence

<400> SEQUENCE: 94
atggagactg ggctgcgctg gcttctcctg gtcgctgtgc tcaaaggtgt ccagtgtcag    60
tcggtgaagg agtccgaggg aggtctcttc aagccaacgg ataccctgac agtcacctgc   120
acagtctctg gattctcccc cagtaggaat gaaataagct ggttccgcca ggctccaggg   180
aacgggctgg aatggatcgg gggcattggt agtcctggac gcgcatacta cgcgacctgg   240
gcgaaaagcc gatccaccat caccagaaac accaacctga atacggtgac tctgaaaatg   300
accagtctga cagccgcgga cacggccacc tatttctgtg cgagagggga catctggggc   360
ccaggcaccg tggtcaccgt ctcctca                                       387

<210> SEQ ID NO 95
<211> LENGTH: 129
<212> TYPE: PRT
<213> ORGANISM: Artificial Sequence
<220> FEATURE:
<223> OTHER INFORMATION: Anti-BTK 407 variable heavy domain amino acid
      sequence with leader sequence

<400> SEQUENCE: 95

Met Glu Thr Gly Leu Arg Trp Leu Leu Leu Val Ala Val Leu Lys Gly
1               5                   10                  15

Val Gln Cys Gln Ser Val Lys Glu Ser Glu Gly Gly Leu Phe Lys Pro
            20                  25                  30

Thr Asp Thr Leu Thr Val Thr Cys Thr Val Ser Gly Phe Ser Leu Ser
        35                  40                  45

Arg Asn Glu Ile Ser Trp Phe Arg Gln Ala Pro Gly Asn Gly Leu Glu
    50                  55                  60

Trp Ile Gly Gly Ile Gly Ser Pro Gly Arg Ala Tyr Tyr Ala Thr Trp
65                  70                  75                  80

Ala Lys Ser Arg Ser Thr Ile Thr Arg Asn Thr Asn Leu Asn Thr Val
                85                  90                  95

Thr Leu Lys Met Thr Ser Leu Thr Ala Ala Asp Thr Ala Thr Tyr Phe
            100                 105                 110

Cys Ala Arg Gly Asp Ile Trp Gly Pro Gly Thr Val Val Thr Val Ser
        115                 120                 125

Ser

<210> SEQ ID NO 96
<211> LENGTH: 433
<212> TYPE: PRT
<213> ORGANISM: Artificial Sequence
<220> FEATURE:
<223> OTHER INFORMATION: Anti-BTK 407 heavy chain amino acid sequence
      without leader sequence

<400> SEQUENCE: 96

-continued

```
Gln Ser Val Lys Glu Ser Glu Gly Gly Leu Phe Lys Pro Thr Asp Thr
 1               5                  10                  15
Leu Thr Val Thr Cys Thr Val Ser Gly Phe Ser Leu Ser Arg Asn Glu
            20                  25                  30
Ile Ser Trp Phe Arg Gln Ala Pro Gly Asn Gly Leu Glu Trp Ile Gly
        35                  40                  45
Gly Ile Gly Ser Pro Gly Arg Ala Tyr Tyr Ala Thr Trp Ala Lys Ser
    50                  55                  60
Arg Ser Thr Ile Thr Arg Asn Thr Asn Leu Thr Val Thr Leu Lys
 65                  70                  75                  80
Met Thr Ser Leu Thr Ala Ala Asp Thr Ala Thr Tyr Phe Cys Ala Arg
                85                  90                  95
Gly Asp Ile Trp Gly Pro Gly Thr Val Val Thr Val Ser Ser Gly Gln
            100                 105                 110
Pro Lys Ala Pro Ser Val Phe Pro Leu Ala Pro Cys Cys Gly Asp Thr
        115                 120                 125
Pro Ser Ser Thr Val Thr Leu Gly Cys Leu Val Lys Gly Tyr Leu Pro
    130                 135                 140
Glu Pro Val Thr Val Thr Trp Asn Ser Gly Thr Leu Thr Asn Gly Val
145                 150                 155                 160
Arg Thr Phe Pro Ser Val Arg Gln Ser Ser Gly Leu Tyr Ser Leu Ser
                165                 170                 175
Ser Val Val Ser Val Thr Ser Ser Ser Gln Pro Val Thr Cys Asn Val
            180                 185                 190
Ala His Pro Ala Thr Asn Thr Lys Val Asp Lys Thr Val Ala Pro Ser
        195                 200                 205
Thr Cys Ser Lys Pro Met Cys Pro Pro Pro Glu Leu Leu Gly Gly Pro
    210                 215                 220
Ser Val Phe Ile Phe Pro Pro Lys Pro Lys Asp Thr Leu Met Ile Ser
225                 230                 235                 240
Arg Thr Pro Glu Val Thr Cys Val Val Val Asp Val Ser Gln Asp Asp
                245                 250                 255
Pro Glu Val Gln Phe Thr Trp Tyr Ile Asn Asn Glu Gln Val Arg Thr
            260                 265                 270
Ala Arg Pro Pro Leu Arg Glu Gln Gln Phe Asn Ser Thr Ile Arg Val
        275                 280                 285
Val Ser Thr Leu Pro Ile Ala His Gln Asp Trp Leu Arg Gly Lys Glu
    290                 295                 300
Phe Lys Cys Lys Val His Asn Lys Ala Leu Pro Ala Pro Ile Glu Lys
305                 310                 315                 320
Thr Ile Ser Lys Ala Arg Gly Gln Pro Leu Glu Pro Lys Val Tyr Thr
                325                 330                 335
Met Gly Pro Pro Arg Glu Glu Leu Ser Ser Arg Ser Val Ser Leu Thr
            340                 345                 350
Cys Met Ile Asn Gly Phe Tyr Pro Ser Asp Ile Ser Val Glu Trp Glu
        355                 360                 365
Lys Asn Gly Lys Ala Glu Asp Asn Tyr Lys Thr Thr Pro Ala Val Leu
    370                 375                 380
Asp Ser Asp Gly Ser Tyr Phe Leu Tyr Ser Lys Leu Ser Val Pro Thr
385                 390                 395                 400
Ser Glu Trp Gln Arg Gly Asp Val Phe Thr Cys Ser Val Met His Glu
                405                 410                 415
Ala Leu His Asn His Tyr Thr Gln Lys Ser Ile Ser Arg Ser Pro Gly
```

Lys

<210> SEQ ID NO 97
<211> LENGTH: 720
<212> TYPE: DNA
<213> ORGANISM: Artificial Sequence
<220> FEATURE:
<223> OTHER INFORMATION: Anti-BTK 407 light chain coding sequence
    (EB0602-1G5-K1) with leader sequence

<400> SEQUENCE: 97

```
atggacacga gggcccccac tcagctgctg gggctcctgc tgctctggct cccaggtgcc    60
acatttgccc aagtgctgac ccagactgta tcgcccgtgt ctgcagctgt gggaagcaca   120
gtcaccatca attgccagtc cagtcagagt gtttataata caaccgctt agcctggtat   180
cagcagaaac cagggcagcc tcccaaaggc ctgatctatt ctgcatccac tctggcatct   240
ggggtctcat cgcggttcaa aggcagtgga tctgggacac agttcactct caccatcagc   300
gacgtgcagt gtgacgatgc tgccacttac tactgtctag cagttatga ttgtagtact   360
gctgattgta atgctttcgg cggagggacc gaggtggtgg tcaaaggtga tccagttgca   420
cctactgtcc tcatcttccc accagctgct gatcaggtgg caactggaac agtcaccatc   480
gtgtgtgtgg cgaataaata ctttcccgat gtcaccgtca cctgggaggt ggatggcacc   540
acccaaacaa ctggcatcga gaacagtaaa acaccgcaga attctgcaga ttgtacctac   600
aacctcagca gcactctgac actgaccagc acacagtaca cagccacaa agagtacacc   660
tgcaaggtga cccagggcac gacctcagtc gtccagagct caatagggg tgactgttag   720
```

<210> SEQ ID NO 98
<211> LENGTH: 239
<212> TYPE: PRT
<213> ORGANISM: Artificial Sequence
<220> FEATURE:
<223> OTHER INFORMATION: Anti-BTK 407 light chain amino acid sequence
    with leader sequence

<400> SEQUENCE: 98

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Val Ser Pro
            20                  25                  30

Val Ser Ala Ala Val Gly Ser Thr Val Thr Ile Asn Cys Gln Ser Ser
        35                  40                  45

Gln Ser Val Tyr Asn Asn Arg Leu Ala Trp Tyr Gln Gln Lys Pro
    50                  55                  60

Gly Gln Pro Pro Lys Gly Leu Ile Tyr Ser Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Ser Tyr Asp Cys Ser Thr Ala Asp Cys Asn Ala Phe Gly Gly
        115                 120                 125

Gly Thr Glu Val Val Val Lys Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160
```

```
Val Cys Val Ala Asn Lys Tyr Phe Pro Asp Val Thr Val Thr Trp Glu
            165                 170                 175

Val Asp Gly Thr Thr Gln Thr Gly Ile Glu Asn Ser Lys Thr Pro
        180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235
```

<210> SEQ ID NO 99
<211> LENGTH: 405
<212> TYPE: DNA
<213> ORGANISM: Artificial Sequence
<220> FEATURE:
<223> OTHER INFORMATION: Anti-BTK 407 variable light domain coding
      sequence with leader sequence

<400> SEQUENCE: 99

```
atggacacga gggcccccac tcagctgctg gggctcctgc tgctctggct cccaggtgcc    60
acatttgccc aagtgctgac ccagactgta tcgcccgtgt ctgcagctgt gggaagcaca   120
gtcaccatca attgccagtc cagtcagagt gtttataata caaccgctt agcctggtat    180 cagcagaaac cagggcagcc tcccaaaggc ctgatctatt ctgcatccac tctggcatct   240
ggggtctcat cgcggttcaa aggcagtgga tctgggacac agttcactct caccatcagc   300
gacgtgcagt gtgacgatgc tgccacttac tactgtctag cagttatga ttgtagtact    360 gctgattgta atgctttcgg cggagggacc gaggtggtgg tcaaa                   405
```

<210> SEQ ID NO 100
<211> LENGTH: 135
<212> TYPE: PRT
<213> ORGANISM: Artificial Sequence
<220> FEATURE:
<223> OTHER INFORMATION: Anti-BTK 407 variable light domain amino acid
      sequence with leader sequence

<400> SEQUENCE: 100

```
Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Thr Val Ser Pro
            20                  25                  30

Val Ser Ala Ala Val Gly Ser Thr Val Thr Ile Asn Cys Gln Ser Ser
        35                  40                  45

Gln Ser Val Tyr Asn Asn Arg Leu Ala Trp Tyr Gln Gln Lys Pro
    50                  55                  60

Gly Gln Pro Pro Lys Gly Leu Ile Tyr Ser Ala Ser Thr Leu Ala Ser
65                  70                  75                  80

Gly Val Ser Ser Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Ser Tyr Asp Cys Ser Thr Ala Asp Cys Asn Ala Phe Gly Gly
            115                 120                 125

Gly Thr Glu Val Val Val Lys
        130                 135
```

<210> SEQ ID NO 101
<211> LENGTH: 216
<212> TYPE: PRT
<213> ORGANISM: Artificial Sequence
<220> FEATURE:
<223> OTHER INFORMATION: Anti-BTK 407 light chain amino acid sequence without leader sequence

<400> SEQUENCE: 101

```
Gln Val Leu Thr Gln Thr Val Ser Pro Val Ser Ala Ala Val Gly Ser
 1               5                  10                  15

Thr Val Thr Ile Asn Cys Gln Ser Ser Gln Ser Val Tyr Asn Asn Asn
            20                  25                  30

Arg Leu Ala Trp Tyr Gln Gln Lys Pro Gly Gln Pro Pro Lys Gly Leu
        35                  40                  45

Ile Tyr Ser Ala Ser Thr Leu Ala Ser Gly Val Ser Ser Arg Phe Lys
    50                  55                  60

Gly Ser Gly Ser Gly Thr Gln Phe Thr Leu Thr Ile Ser Asp Val Gln
 65                  70                  75                  80

Cys Asp Asp Ala Ala Thr Tyr Tyr Cys Leu Gly Ser Tyr Asp Cys Ser
                85                  90                  95

Thr Ala Asp Cys Asn Ala Phe Gly Gly Gly Thr Glu Val Val Val Lys
            100                 105                 110

Gly Asp Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215
```

<210> SEQ ID NO 102
<211> LENGTH: 1371
<212> TYPE: DNA
<213> ORGANISM: Artificial Sequence
<220> FEATURE:
<223> OTHER INFORMATION: Anti-CTNS 115 heavy chain coding sequence (EB0606-3H8-H5) with leader sequence

<400> SEQUENCE: 102

| | |
|---|---|
| atggagactg ggctgcgctg gcttctcctg gtcgctgtgc tcaaaggtgt ccagtgtcag | 60 |
| gagcagctgg tggagtccgg gggaggcctg gtccagcctg agggatccct gacactcacc | 120 |
| tgcaaagcct ctggattctc cttcagtacc agagatggcg tatgctgggt ccgccaggct | 180 |
| ccagggaagg ggctggagtg gatcgcatgc atttatcgtg gtattagtgc taccacttcc | 240 |
| tacgcgagct gggcgaaagg ccgattcacc atctccaaaa cctcgtcgac cacggtgact | 300 |
| ctgcaaatga ccagtctgac agccgcggac acggccacct atttctgtgc gagagcctgg | 360 |
| gacttatggg gccaggcac cctggtcacc gtctcctcag gcaacctaa ggctccatca | 420 |
| gtcttcccac tggccccctg ctgcgggac acacccagct ccacggtgac cctgggctgc | 480 |

```
ctggtcaaag gctacctccc ggagccagtg accgtgacct ggaactcggg caccctcacc    540
aatggggtac gcaccttccc gtccgtccgg cagtcctcag gcctctactc gctgagcagc    600
gtggtgagcg tgacctcaag cagccagccc gtcacctgca acgtggccca cccagccacc    660
aacaccaaag tggacaagac cgttgcgccc tcgacatgca caagccat gtgcccaccc      720 cctgaactcc tggggggacc gtctgtcttc atcttccccc caaaacccaa ggacaccctc    780
atgatctcac gcaccccga ggtcacatgc gtggtggtgg acgtgagcca ggatgacccc    840
gaggtgcagt tcacatggta cataaacaac gagcaggtgc gcaccgcccg ccgccgcta     900 cgggagcagc agttcaacag cacgatccgc gtggtcagca ccctccccat cgcgcaccag    960
gactggctga ggggcaagga gttcaagtgc aaagtccaca acaaggcact cccggccccc   1020
atcgagaaaa ccatctccaa agccagaggg cagcccctgg agccgaaggt ctacaccatg   1080
ggccctcccc gggaggagct gagcagcagg tcggtcagcc tgacctgcat gatcaacggc   1140
ttctacccct tccgacatctc ggtggagtgg gagaagaacg ggaaggcaga ggacaactac   1200
aagaccacgc cggccgtgct ggacagcgac ggctcctact cctctacag caagctctca    1260 gtgcccacga gtgagtggca gcggggcgac gtcttcacct gctccgtgat gcacgaggcc   1320
ttgcacaacc actacacgca gaagtccatc tcccgctctc cgggtaaatg a            1371
```

<210> SEQ ID NO 103
<211> LENGTH: 456
<212> TYPE: PRT
<213> ORGANISM: Artificial Sequence
<220> FEATURE:
<223> OTHER INFORMATION: Anti-CTNS 115 heavy chain amino acid sequence
      with leader sequence

<400> SEQUENCE: 103

```
Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Lys Ala Ser Gly Phe Ser Phe
        35                  40                  45

Ser Thr Arg Asp Gly Val Cys Trp Val Arg Gln Ala Pro Gly Lys Gly
    50                  55                  60

Leu Glu Trp Ile Ala Cys Ile Tyr Arg Gly Ile Ser Ala Thr Thr Ser
65                  70                  75                  80

Tyr Ala Ser Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Ala Trp Asp Leu Trp Gly Pro Gly Thr Leu
        115                 120                 125

Val Thr Val Ser Ser Gly Gln Pro Lys Ala Pro Ser Val Phe Pro Leu
    130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                165                 170                 175

Gly Thr Leu Thr Asn Gly Val Arg Thr Phe Pro Ser Val Arg Gln Ser
            180                 185                 190

Ser Gly Leu Tyr Ser Leu Ser Ser Val Val Ser Val Thr Ser Ser Ser
```

```
              195                 200                 205
Gln Pro Val Thr Cys Asn Val Ala His Pro Ala Thr Asn Thr Lys Val
    210                 215                 220
Asp Lys Thr Val Ala Pro Ser Thr Cys Ser Lys Pro Met Cys Pro Pro
225                 230                 235                 240
Pro Glu Leu Leu Gly Gly Pro Ser Val Phe Ile Phe Pro Pro Lys Pro
                245                 250                 255
Lys Asp Thr Leu Met Ile Ser Arg Thr Pro Glu Val Thr Cys Val Val
                260                 265                 270
Val Asp Val Ser Gln Asp Asp Pro Glu Val Gln Phe Thr Trp Tyr Ile
            275                 280                 285
Asn Asn Glu Gln Val Arg Thr Ala Arg Pro Pro Leu Arg Glu Gln Gln
        290                 295                 300
Phe Asn Ser Thr Ile Arg Val Val Ser Thr Leu Pro Ile Ala His Gln
305                 310                 315                 320
Asp Trp Leu Arg Gly Lys Glu Phe Lys Cys Lys Val His Asn Lys Ala
                325                 330                 335
Leu Pro Ala Pro Ile Glu Lys Thr Ile Ser Lys Ala Arg Gly Gln Pro
                340                 345                 350
Leu Glu Pro Lys Val Tyr Thr Met Gly Pro Pro Arg Glu Glu Leu Ser
            355                 360                 365
Ser Arg Ser Val Ser Leu Thr Cys Met Ile Asn Gly Phe Tyr Pro Ser
        370                 375                 380
Asp Ile Ser Val Glu Trp Glu Lys Asn Gly Lys Ala Glu Asp Asn Tyr
385                 390                 395                 400
Lys Thr Thr Pro Ala Val Leu Asp Ser Asp Gly Ser Tyr Phe Leu Tyr
                405                 410                 415
Ser Lys Leu Ser Val Pro Thr Ser Glu Trp Gln Arg Gly Asp Val Phe
                420                 425                 430
Thr Cys Ser Val Met His Glu Ala Leu His Asn His Tyr Thr Gln Lys
            435                 440                 445
Ser Ile Ser Arg Ser Pro Gly Lys
    450                 455

<210> SEQ ID NO 104
<211> LENGTH: 399
<212> TYPE: DNA
<213> ORGANISM: Artificial Sequence
<220> FEATURE:
<223> OTHER INFORMATION: Anti-CTNS 115 variable heavy domain coding
      sequence with leader sequence

<400> SEQUENCE: 104
atggagactg ggctgcgctg gcttctcctg gtcgctgtgc tcaaaggtgt ccagtgtcag      60
gagcagctgg tggagtccgg gggaggcctg gtccagcctg agggatccct gacactcacc     120
tgcaaagcct ctggattctc cttcagtacc agagatggcg tatgctgggt ccgccaggct     180
ccagggaagg ggctggagtg gatcgcatgc atttatcgtg gtattagtgc taccacttcc     240
tacgcgagct gggcgaaagg ccgattcacc atctccaaaa cctcgtcgac cacggtgact     300
ctgcaaatga ccagtctgac agccgcggac acggccacct atttctgtgc gagagcctgg     360
gacttatggg gcccaggcac cctggtcacc gtctcctca                            399

<210> SEQ ID NO 105
<211> LENGTH: 133
<212> TYPE: PRT
```

```
<213> ORGANISM: Artificial Sequence
<220> FEATURE:
<223> OTHER INFORMATION: Anti-CTNS 115 variable heavy domain amino acid
      sequence with leader sequence

<400> SEQUENCE: 105

Met Glu Thr Gly Leu Arg Trp Leu Leu Leu Val Ala Val Leu Lys Gly
1               5                   10                  15

Val Gln Cys Gln Glu Gln Leu Val Glu Ser Gly Gly Gly Leu Val Gln
            20                  25                  30

Pro Glu Gly Ser Leu Thr Leu Thr Cys Lys Ala Ser Gly Phe Ser Phe
        35                  40                  45

Ser Thr Arg Asp Gly Val Cys Trp Val Arg Gln Ala Pro Gly Lys Gly
    50                  55                  60

Leu Glu Trp Ile Ala Cys Ile Tyr Arg Gly Ile Ser Ala Thr Thr Ser
65                  70                  75                  80

Tyr Ala Ser Trp Ala Lys Gly Arg Phe Thr Ile Ser Lys Thr Ser Ser
                85                  90                  95

Thr Thr Val Thr Leu Gln Met Thr Ser Leu Thr Ala Ala Asp Thr Ala
            100                 105                 110

Thr Tyr Phe Cys Ala Arg Ala Trp Asp Leu Trp Gly Pro Gly Thr Leu
        115                 120                 125

Val Thr Val Ser Ser
        130

<210> SEQ ID NO 106
<211> LENGTH: 437
<212> TYPE: PRT
<213> ORGANISM: Artificial Sequence
<220> FEATURE:
<223> OTHER INFORMATION: Anti-CTNS 115 heavy chain amino acid sequence
      without leader sequence

<400> SEQUENCE: 106

Gln Glu Gln Leu Val Glu Ser Gly Gly Gly Leu Val Gln Pro Glu Gly
1               5                   10                  15

Ser Leu Thr Leu Thr Cys Lys Ala Ser Gly Phe Ser Phe Ser Thr Arg
            20                  25                  30

Asp Gly Val Cys Trp Val Arg Gln Ala Pro Gly Lys Gly Leu Glu Trp
        35                  40                  45

Ile Ala Cys Ile Tyr Arg Gly Ile Ser Ala Thr Thr Ser Tyr Ala Ser
    50                  55                  60

Trp Ala Lys Gly Arg Phe Thr Ile Ser Lys Thr Ser Ser Thr Thr Val
65                  70                  75                  80

Thr Leu Gln Met Thr Ser Leu Thr Ala Ala Asp Thr Ala Thr Tyr Phe
                85                  90                  95

Cys Ala Arg Ala Trp Asp Leu Trp Gly Pro Gly Thr Leu Val Thr Val
            100                 105                 110

Ser Ser Gly Gln Pro Lys Ala Pro Ser Val Phe Pro Leu Ala Pro Cys
        115                 120                 125

Cys Gly Asp Thr Pro Ser Ser Thr Val Thr Leu Gly Cys Leu Val Lys
    130                 135                 140

Gly Tyr Leu Pro Glu Pro Val Thr Val Thr Trp Asn Ser Gly Thr Leu
145                 150                 155                 160

Thr Asn Gly Val Arg Thr Phe Pro Ser Val Arg Gln Ser Ser Gly Leu
                165                 170                 175

Tyr Ser Leu Ser Ser Val Val Ser Val Thr Ser Ser Ser Gln Pro Val
```

```
            180                 185                 190
Thr Cys Asn Val Ala His Pro Ala Thr Asn Thr Lys Val Asp Lys Thr
            195                 200                 205

Val Ala Pro Ser Thr Cys Ser Lys Pro Met Cys Pro Pro Glu Leu
    210                 215                 220

Leu Gly Gly Pro Ser Val Phe Ile Phe Pro Pro Lys Pro Lys Asp Thr
225                 230                 235                 240

Leu Met Ile Ser Arg Thr Pro Glu Val Thr Cys Val Val Val Asp Val
            245                 250                 255

Ser Gln Asp Asp Pro Glu Val Gln Phe Thr Trp Tyr Ile Asn Asn Glu
        260                 265                 270

Gln Val Arg Thr Ala Arg Pro Pro Leu Arg Glu Gln Gln Phe Asn Ser
    275                 280                 285

Thr Ile Arg Val Val Ser Thr Leu Pro Ile Ala His Gln Asp Trp Leu
        290                 295                 300

Arg Gly Lys Glu Phe Lys Cys Lys Val His Asn Lys Ala Leu Pro Ala
305                 310                 315                 320

Pro Ile Glu Lys Thr Ile Ser Lys Ala Arg Gly Gln Pro Leu Glu Pro
            325                 330                 335

Lys Val Tyr Thr Met Gly Pro Pro Arg Glu Glu Leu Ser Ser Arg Ser
        340                 345                 350

Val Ser Leu Thr Cys Met Ile Asn Gly Phe Tyr Pro Ser Asp Ile Ser
    355                 360                 365

Val Glu Trp Glu Lys Asn Gly Lys Ala Glu Asn Tyr Lys Thr Thr
    370                 375                 380

Pro Ala Val Leu Asp Ser Asp Gly Ser Tyr Phe Leu Tyr Ser Lys Leu
385                 390                 395                 400

Ser Val Pro Thr Ser Glu Trp Gln Arg Gly Asp Val Phe Thr Cys Ser
            405                 410                 415

Val Met His Glu Ala Leu His Asn His Tyr Thr Gln Lys Ser Ile Ser
            420                 425                 430

Arg Ser Pro Gly Lys
        435

<210> SEQ ID NO 107
<211> LENGTH: 714
<212> TYPE: DNA
<213> ORGANISM: Artificial Sequence
<220> FEATURE:
<223> OTHER INFORMATION: Anti-CTNS 115 light chain coding sequence
      (EB0606-3H8-K7) with leader sequence

<400> SEQUENCE: 107
atggacacga gggcccccac tcagctgctg gggctcctgc tgctctggct cccaggtgcc     60
agatgtgatg ttgtgatgac ccagactcca gcctccgtgt ctgaacctgt gggaggcaca    120
gtcaccatca gtgccaggc cagtcagagc attggtagcg acttatcctg gtatcagcag     180
aaaccagggc agcctcccaa gcgcctgatc tacaaggcat ccaaagtgga aactggggtc    240
ccatcgcggt tcagcggcag tggatctggg acagagttca ctctcaccat cagcgacctg    300
gagtgtgccg atgctagcac ttactactgt caatctattg attttagtaa agttatata    360 gggggtgctt tcggcggagg gaccgaggtg gtggtcaaag tgatccagt tgcacctact     420 gtcctcatct tcccaccagc tgctgatcag gtggcaactg gaacagtcac catcgtgtgt    480
gtggcgaata atactttccc cgatgtcacc gtcacctggg aggtggatgg caccacccaa    540
```

```
acaactggca tcgagaacag taaaacaccg cagaattctg cagattgtac ctacaacctc    600
agcagcactc tgacactgac cagcacacag tacaacagcc acaaagagta cacctgcaag    660
gtgacccagg gcacgacctc agtcgtccag agcttcaata ggggtgactg ttag          714
```

<210> SEQ ID NO 108
<211> LENGTH: 237
<212> TYPE: PRT
<213> ORGANISM: Artificial Sequence
<220> FEATURE:
<223> OTHER INFORMATION: Anti-CTNS 115 light chain amino acid sequence
      with leader sequence

<400> SEQUENCE: 108

```
Met Asp Thr Arg Ala Pro Thr Gln Leu Leu Gly Leu Leu Leu Trp
1               5                   10                  15

Leu Pro Gly Ala Arg Cys Asp Val Val Met Thr Gln Thr Pro Ala Ser
            20                  25                  30

Val Ser Glu Pro Val Gly Gly Thr Val Thr Ile Lys Cys Gln Ala Ser
        35                  40                  45

Gln Ser Ile Gly Ser Asp Leu Ser Trp Tyr Gln Gln Lys Pro Gly Gln
    50                  55                  60

Pro Pro Lys Arg Leu Ile Tyr Lys Ala Ser Lys Val Glu Thr Gly Val
65                  70                  75                  80

Pro Ser Arg Phe Ser Gly Ser Gly Ser Gly Thr Glu Phe Thr Leu Thr
                85                  90                  95

Ile Ser Asp Leu Glu Cys Ala Asp Ala Ser Thr Tyr Tyr Cys Gln Ser
            100                 105                 110

Ile Asp Phe Ser Lys Ser Tyr Ile Gly Gly Ala Phe Gly Gly Gly Thr
        115                 120                 125

Glu Val Val Val Lys Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235
```

<210> SEQ ID NO 109
<211> LENGTH: 399
<212> TYPE: DNA
<213> ORGANISM: Artificial Sequence
<220> FEATURE:
<223> OTHER INFORMATION: Anti-CTNS 115 variable light domain coding
      sequence with leader sequence

<400> SEQUENCE: 109

```
atggacacga gggcccccac tcagctgctg ggctcctgc tgctctggct cccaggtgcc     60
agatgtgatg ttgtgatgac ccagactcca gcctccgtgt ctgaacctgt gggaggcaca   120
gtcaccatca agtgccaggc cagtcagagc attggtagcg acttatcctg gtatcagcag   180
```

```
aaaccagggc agcctcccaa gcgcctgatc tacaaggcat ccaaagtgga aactggggtc    240
ccatcgcggt tcagcggcag tggatctggg acagagttca ctctcaccat cagcgacctg    300
gagtgtgccg atgctagcac ttactactgt caatctattg attttagtaa aagttatata    360
gggggtgctt tcggcggagg gaccgaggtg gtggtcaaa                           399
```

<210> SEQ ID NO 110
<211> LENGTH: 133
<212> TYPE: PRT
<213> ORGANISM: Artificial Sequence
<220> FEATURE:
<223> OTHER INFORMATION: Anti-CTNS 115 variable light domain amino acid
      sequence with leader sequence

<400> SEQUENCE: 110

```
Met Asp Thr Arg Ala Pro Thr Gln Leu Leu Gly Leu Leu Leu Leu Trp
1               5                   10                  15

Leu Pro Gly Ala Arg Cys Asp Val Val Met Thr Gln Thr Pro Ala Ser
            20                  25                  30

Val Ser Glu Pro Val Gly Gly Thr Val Thr Ile Lys Cys Gln Ala Ser
        35                  40                  45

Gln Ser Ile Gly Ser Asp Leu Ser Trp Tyr Gln Gln Lys Pro Gly Gln
    50                  55                  60

Pro Pro Lys Arg Leu Ile Tyr Lys Ala Ser Lys Val Glu Thr Gly Val
65                  70                  75                  80

Pro Ser Arg Phe Ser Gly Ser Gly Ser Gly Thr Glu Phe Thr Leu Thr
                85                  90                  95

Ile Ser Asp Leu Glu Cys Ala Asp Ala Ser Thr Tyr Tyr Cys Gln Ser
            100                 105                 110

Ile Asp Phe Ser Lys Ser Tyr Ile Gly Gly Ala Phe Gly Gly Gly Thr
        115                 120                 125

Glu Val Val Val Lys
    130
```

<210> SEQ ID NO 111
<211> LENGTH: 215
<212> TYPE: PRT
<213> ORGANISM: Artificial Sequence
<220> FEATURE:
<223> OTHER INFORMATION: Anti-CTNS 115 light chain amino acid sequence
      without leader sequence

<400> SEQUENCE: 111

```
Asp Val Val Met Thr Gln Thr Pro Ala Ser Val Ser Glu Pro Val Gly
1               5                   10                  15

Gly Thr Val Thr Ile Lys Cys Gln Ala Ser Gln Ser Ile Gly Ser Asp
            20                  25                  30

Leu Ser Trp Tyr Gln Gln Lys Pro Gly Gln Pro Pro Lys Arg Leu Ile
        35                  40                  45

Tyr Lys Ala Ser Lys Val Glu Thr Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ser Thr Tyr Tyr Cys Gln Ser Ile Asp Phe Ser Lys Ser
                85                  90                  95

Tyr Ile Gly Gly Ala Phe Gly Gly Gly Thr Glu Val Val Val Lys Gly
            100                 105                 110

Asp Pro Val Ala Pro Thr Val Leu Ile Phe Pro Pro Ala Ala Asp Gln
```

|  | | | | 115 | | | | 120 | | | | 125 | | |
|---|---|---|---|---|---|---|---|---|---|---|---|---|---|---|
| Val | Ala | Thr | Gly | Thr | Val | Thr | Ile | Val | Cys | Val | Ala | Asn | Lys | Tyr | Phe |
| | | | | 130 | | | | | 135 | | | | 140 | | |

| Pro | Asp | Val | Thr | Val | Thr | Trp | Glu | Val | Asp | Gly | Thr | Thr | Gln | Thr | Thr |
|---|---|---|---|---|---|---|---|---|---|---|---|---|---|---|---|
| 145 | | | | | 150 | | | | 155 | | | | | 160 | |

| Gly | Ile | Glu | Asn | Ser | Lys | Thr | Pro | Gln | Asn | Ser | Ala | Asp | Cys | Thr | Tyr |
|---|---|---|---|---|---|---|---|---|---|---|---|---|---|---|---|
| | | | | 165 | | | | 170 | | | | | 175 | | |

| Asn | Leu | Ser | Ser | Thr | Leu | Thr | Leu | Thr | Ser | Thr | Gln | Tyr | Asn | Ser | His |
|---|---|---|---|---|---|---|---|---|---|---|---|---|---|---|---|
| | | | 180 | | | | 185 | | | | 190 | | | | |

| Lys | Glu | Tyr | Thr | Cys | Lys | Val | Thr | Gln | Gly | Thr | Thr | Ser | Val | Val | Gln |
|---|---|---|---|---|---|---|---|---|---|---|---|---|---|---|---|
| | | | 195 | | | | 200 | | | | 205 | | | | |

| Ser | Phe | Asn | Arg | Gly | Asp | Cys |
|---|---|---|---|---|---|---|
| 210 | | | | | 215 | |

<210> SEQ ID NO 112
<211> LENGTH: 1389
<212> TYPE: DNA
<213> ORGANISM: Artificial Sequence
<220> FEATURE:
<223> OTHER INFORMATION: Anti-CTNS 360 heavy chain coding sequence (EB0604-4E3-H4) with leader sequence

<400> SEQUENCE: 112

| | |
|---|---|
| atggagactg ggctgcgctg gcttctcctg gtcgctgtgc tcaaaggtgt ccagtgtcag | 60 |
| tcgttggagg agtccggggg aggcctgttc agcctgggg catccctgac actcacctgc | 120 |
| acagcctctg gattctcctt cagtaacaat gacgggatat gctgggtccg ccaggctcca | 180 |
| gggaaggggc tggagtggat cggatgtatt ggtagtacta gtggtaggat ttattacgcg | 240 |
| agctgggcga aaggccgact caccatctcc aaaacctcgt cgaccacggt gattctgcaa | 300 |
| atgaccagtc tgacagccgc ggacacggcc acttatttct gtgcgagcga accctatggt | 360 |
| agtggtagta tggcttttga cttgtggggc ccaggcactc tggtcaccgt ctcctcaggg | 420 |
| caacctaagg ctccatcagt cttcccactg gccccctgct gcgggacac acccagctcc | 480 |
| acggtgaccc tgggctgcct ggtcaaaggc tacctcccgg agccagtgac cgtgacctgg | 540 |
| aactcgggca ccctcaccaa tggggtacgc accttcccgt ccgtcggca gtcctcaggc | 600 |
| ctctactcgc tgagcagcgt ggtgagcgtg acctcaagca gccagcccgt cacctgcaac | 660 |
| gtggcccacc cagccaccaa caccaaagtg gacaagaccg ttgcgccctc gacatgcagc | 720 |
| aagcccatgt gcccaccccc tgaactcctg ggggaccgt ctgtcttcat cttcccccca | 780 |
| aaacccaagg acaccctcat gatctcacgc accccgagg tcacatgcgt ggtggtggac | 840 |
| gtgagccagg atgaccccga ggtgcagttc acatggtaca taaacaacga gcaggtgcgc | 900 |
| accgcccggc cgccgctacg ggagcagcag ttcaacagca cgatccgcgt ggtcagcacc | 960 |
| ctccccatcg cgcaccagga ctggctgagg ggcaaggagt tcaagtgcaa agtccacaac | 1020 |
| aaggcactcc cggcccccat cgagaaaacc atctccaaag ccagagggca gccctggag | 1080 |
| ccgaaggtct acaccatggg ccctccccgg gaggagctga gcagcaggtc ggtcagcctg | 1140 |
| acctgcatga tcaacggctt ctaccttcc gacatctcgg tggagtggga agaacgggg | 1200 |
| aaggcagaga caactacaa gaccacgccg ccgtgctgg acagcgacgg ctcctacttc | 1260 |
| ctctacagca agctctcagt gcccacgagt gagtggcagc ggggcgacgt cttcacctgc | 1320 |
| tccgtgatgc acgaggcctt gcacaaccac tacacgcaga agtccatctc ccgctctccg | 1380 |
| ggtaaatga | 1389 |

<210> SEQ ID NO 113
<211> LENGTH: 462
<212> TYPE: PRT
<213> ORGANISM: Artificial Sequence
<220> FEATURE:
<223> OTHER INFORMATION: Anti-CTNS 360 heavy chain amino acid sequence
      with leader sequence

<400> SEQUENCE: 113

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Phe Gln Pro
            20                  25                  30

Gly Ala Ser Leu Thr Leu Thr Cys Thr Ala Ser Gly Phe Ser Phe Ser
        35                  40                  45

Asn Asn Asp Gly Ile Cys Trp Val Arg Gln Ala Pro Gly Lys Gly Leu
    50                  55                  60

Glu Trp Ile Gly Cys Ile Gly Ser Thr Gly Arg Ile Tyr Tyr Ala
65                  70                  75                  80

Ser Trp Ala Lys Gly Arg Leu Thr Ile Ser Lys Thr Ser Ser Thr Thr
                85                  90                  95

Val Ile Leu Gln Met Thr Ser Leu Thr Ala Ala Asp Thr Ala Thr Tyr
            100                 105                 110

Phe Cys Ala Ser Glu Pro Tyr Gly Ser Gly Ser Met Ala Phe Asp Leu
        115                 120                 125

Trp Gly Pro Gly Thr Leu Val Thr Val Ser Ser Gly Gln Pro Lys Ala
    130                 135                 140

Pro Ser Val Phe Pro Leu Ala Pro Cys Cys Gly Asp Thr Pro Ser Ser
145                 150                 155                 160

Thr Val Thr Leu Gly Cys Leu Val Lys Gly Tyr Leu Pro Glu Pro Val
                165                 170                 175

Thr Val Thr Trp Asn Ser Gly Thr Leu Thr Asn Gly Val Arg Thr Phe
            180                 185                 190

Pro Ser Val Arg Gln Ser Ser Gly Leu Tyr Ser Leu Ser Ser Val Val
        195                 200                 205

Ser Val Thr Ser Ser Ser Gln Pro Val Thr Cys Asn Val Ala His Pro
    210                 215                 220

Ala Thr Asn Thr Lys Val Asp Lys Thr Val Ala Pro Ser Thr Cys Ser
225                 230                 235                 240

Lys Pro Met Cys Pro Pro Pro Glu Leu Leu Gly Gly Pro Ser Val Phe
                245                 250                 255

Ile Phe Pro Pro Lys Pro Lys Asp Thr Leu Met Ile Ser Arg Thr Pro
            260                 265                 270

Glu Val Thr Cys Val Val Val Asp Val Ser Gln Asp Asp Pro Glu Val
        275                 280                 285

Gln Phe Thr Trp Tyr Ile Asn Asn Glu Gln Val Arg Thr Ala Arg Pro
    290                 295                 300

Pro Leu Arg Glu Gln Gln Phe Asn Ser Thr Ile Arg Val Val Ser Thr
305                 310                 315                 320

Leu Pro Ile Ala His Gln Asp Trp Leu Arg Gly Lys Glu Phe Lys Cys
                325                 330                 335

Lys Val His Asn Lys Ala Leu Pro Ala Pro Ile Glu Lys Thr Ile Ser
            340                 345                 350

Lys Ala Arg Gly Gln Pro Leu Glu Pro Lys Val Tyr Thr Met Gly Pro
        355                 360                 365

Pro Arg Glu Glu Leu Ser Ser Arg Ser Val Ser Leu Thr Cys Met Ile
    370                 375                 380

Asn Gly Phe Tyr Pro Ser Asp Ile Ser Val Glu Trp Glu Lys Asn Gly
385                 390                 395                 400

Lys Ala Glu Asp Asn Tyr Lys Thr Thr Pro Ala Val Leu Asp Ser Asp
                405                 410                 415

Gly Ser Tyr Phe Leu Tyr Ser Lys Leu Ser Val Pro Thr Ser Glu Trp
                420                 425                 430

Gln Arg Gly Asp Val Phe Thr Cys Ser Val Met His Glu Ala Leu His
            435                 440                 445

Asn His Tyr Thr Gln Lys Ser Ile Ser Arg Ser Pro Gly Lys
    450                 455                 460

<210> SEQ ID NO 114
<211> LENGTH: 417
<212> TYPE: DNA
<213> ORGANISM: Artificial Sequence
<220> FEATURE:
<223> OTHER INFORMATION: Anti-CTNS 360 variable heavy domain coding
      sequence with leader sequence

<400> SEQUENCE: 114
atggagactg ggctgcgctg gcttctcctg gtcgctgtgc tcaaaggtgt ccagtgtcag    60
tcgttggagg agtccggggg aggcctgttc agcctggggg catccctgac actcacctgc   120
acagcctctg gattctcctt cagtaacaat gacgggatat gctgggtccg ccaggctcca   180
gggaaggggc tggagtggat cggatgtatt ggtagtacta gtggtaggat ttattacgcg   240
agctgggcga aaggccgact caccatctcc aaaacctcgt cgaccacggt gattctgcaa   300
atgaccagtc tgacagccgc ggacacggcc acttatttct gtgcgagcga accctatggt   360
agtggtagta tggcttttga cttgtggggc ccaggcactc tggtcaccgt ctcctca      417

<210> SEQ ID NO 115
<211> LENGTH: 139
<212> TYPE: PRT
<213> ORGANISM: Artificial Sequence
<220> FEATURE:
<223> OTHER INFORMATION: Anti-CTNS 360 variable heavy domain amino acid
      sequence with leader sequence

<400> SEQUENCE: 115

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Gly Leu Phe Gln Pro
            20                  25                  30

Gly Ala Ser Leu Thr Leu Thr Cys Thr Ala Ser Gly Phe Ser Phe Ser
        35                  40                  45

Asn Asn Asp Gly Ile Cys Trp Val Arg Gln Ala Pro Gly Lys Gly Leu
    50                  55                  60

Glu Trp Ile Gly Cys Ile Gly Ser Thr Ser Gly Arg Ile Tyr Tyr Ala
65                  70                  75                  80

Ser Trp Ala Lys Gly Arg Leu Thr Ile Ser Lys Thr Ser Ser Thr Thr
                85                  90                  95

Val Ile Leu Gln Met Thr Ser Leu Thr Ala Ala Asp Thr Ala Thr Tyr
            100                 105                 110

Phe Cys Ala Ser Glu Pro Tyr Gly Ser Gly Ser Met Ala Phe Asp Leu
        115                 120                 125

```
Trp Gly Pro Gly Thr Leu Val Thr Val Ser Ser
    130                 135
```

<210> SEQ ID NO 116
<211> LENGTH: 443
<212> TYPE: PRT
<213> ORGANISM: Artificial Sequence
<220> FEATURE:
<223> OTHER INFORMATION: Anti-CTNS 360 heavy chain amino acid sequence
      without leader sequence

<400> SEQUENCE: 116

```
Gln Ser Leu Glu Glu Ser Gly Gly Leu Phe Gln Pro Gly Ala Ser
1               5                   10                  15

Leu Thr Leu Thr Cys Thr Ala Ser Gly Phe Ser Phe Ser Asn Asn Asp
                20                  25                  30

Gly Ile Cys Trp Val Arg Gln Ala Pro Gly Lys Gly Leu Glu Trp Ile
            35                  40                  45

Gly Cys Ile Gly Ser Thr Ser Gly Arg Ile Tyr Tyr Ala Ser Trp Ala
        50                  55                  60

Lys Gly Arg Leu Thr Ile Ser Lys Thr Ser Thr Thr Val Ile Leu
65                  70                  75                  80

Gln Met Thr Ser Leu Thr Ala Ala Asp Thr Ala Thr Tyr Phe Cys Ala
                85                  90                  95

Ser Glu Pro Tyr Gly Ser Gly Ser Met Ala Phe Asp Leu Trp Gly Pro
                100                 105                 110

Gly Thr Leu Val Thr Val Ser Ser Gly Gln Pro Lys Ala Pro Ser Val
            115                 120                 125

Phe Pro Leu Ala Pro Cys Cys Gly Asp Thr Pro Ser Ser Thr Val Thr
        130                 135                 140

Leu Gly Cys Leu Val Lys Gly Tyr Leu Pro Glu Pro Val Thr Val Thr
145                 150                 155                 160

Trp Asn Ser Gly Thr Leu Thr Asn Gly Val Arg Thr Phe Pro Ser Val
                165                 170                 175

Arg Gln Ser Ser Gly Leu Tyr Ser Leu Ser Ser Val Val Ser Val Thr
                180                 185                 190

Ser Ser Ser Gln Pro Val Thr Cys Asn Val Ala His Pro Ala Thr Asn
            195                 200                 205

Thr Lys Val Asp Lys Thr Val Ala Pro Ser Thr Cys Ser Lys Pro Met
210                 215                 220

Cys Pro Pro Pro Glu Leu Leu Gly Gly Pro Ser Val Phe Ile Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Asp Asp Pro Glu Val Gln Phe Thr
                260                 265                 270

Trp Tyr Ile Asn Asn Glu Gln Val Arg Thr Ala Arg Pro Pro Leu Arg
            275                 280                 285

Glu Gln Gln Phe Asn Ser Thr Ile Arg Val Val Ser Thr Leu Pro Ile
290                 295                 300

Ala His Gln Asp Trp Leu Arg Gly Lys Glu Phe Lys Cys Lys Val His
305                 310                 315                 320

Asn Lys Ala Leu Pro Ala Pro Ile Glu Lys Thr Ile Ser Lys Ala Arg
                325                 330                 335

Gly Gln Pro Leu Glu Pro Lys Val Tyr Thr Met Gly Pro Pro Arg Glu
                340                 345                 350
```

```
Glu Leu Ser Ser Arg Ser Val Ser Leu Thr Cys Met Ile Asn Gly Phe
        355                 360                 365

Tyr Pro Ser Asp Ile Ser Val Glu Trp Glu Lys Asn Gly Lys Ala Glu
    370                 375                 380

Asp Asn Tyr Lys Thr Thr Pro Ala Val Leu Asp Ser Asp Gly Ser Tyr
385                 390                 395                 400

Phe Leu Tyr Ser Lys Leu Ser Val Pro Thr Ser Glu Trp Gln Arg Gly
            405                 410                 415

Asp Val Phe Thr Cys Ser Val Met His Glu Ala Leu His Asn His Tyr
        420                 425                 430

Thr Gln Lys Ser Ile Ser Arg Ser Pro Gly Lys
        435                 440

<210> SEQ ID NO 117
<211> LENGTH: 720
<212> TYPE: DNA
<213> ORGANISM: Artificial Sequence
<220> FEATURE:
<223> OTHER INFORMATION: Anti-CTNS 360 light chain coding sequence
      (EB0604-4E3-K1) with leader sequence

<400> SEQUENCE: 117
atggacacga gggcccccac tcagctgctg gggctcctgc tgctctggct cccaggtgcc      60
acatttgccc aagtgctgac ccagactgca tcgtccgtgt ctgcagctgt ggaggcaca     120 gtcaccgtca attgccaggc cagtcagagt atttggaata caacttctt atcctggtat     180 cagcagaaac cagggcagcc tcccaagctc ctgatctacg aagcatccaa actggcatct    240
ggggtcccat cgcggtttag cggcagtgga tctgggacac agttcactct caccatcagc    300
ggcgtgcagt gtgacgatgc tgccacttac tactgtcagg gcgaatttag ttgtagtatt    360
gctgattgtg ttgctttcgg cggagggacc gaggtggtgg tcagaggtga tccagttgca    420
cctactgtcc tcatcttccc accagctgct gatcaggtgg caactggaac agtcaccatc    480
gtgtgtgtgg cgaataaata cttcccgat gtcaccgtca cctgggaggt ggatggcacc    540
acccaaacaa ctggcatcga gaacagtaaa acaccgcaga ttctgcaga ttgtacctac    600 aacctcagca gcactctgac actgaccagc acacagtaca cagccacaa agagtacacc    660 tgcaaggtga cccagggcac gacctcagtc gtccagagct tcaataggg tgactgttag    720

<210> SEQ ID NO 118
<211> LENGTH: 239
<212> TYPE: PRT
<213> ORGANISM: Artificial Sequence
<220> FEATURE:
<223> OTHER INFORMATION: Anti-CTNS 360 light chain amino acid sequence
      with leader sequence

<400> SEQUENCE: 118

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
            20                  25                  30

Val Ser Ala Ala Val Gly Gly Thr Val Thr Val Asn Cys Gln Ala Ser
        35                  40                  45

Gln Ser Ile Trp Asn Asn Phe Leu Ser Trp Tyr Gln Gln Lys Pro
    50                  55                  60

Gly Gln Pro Pro Lys Leu Leu Ile Tyr Glu Ala Ser Lys Leu Ala Ser
65                  70                  75                  80
```

```
Gly Val Pro Ser Arg Phe Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Gln Gly Glu Phe Ser Cys Ser Ile Ala Asp Cys Val Ala Phe Gly Gly
        115                 120                 125

Gly Thr Glu Val Val Val Arg Gly Asp Pro Val Ala Pro Thr Val Leu
    130                 135                 140

Ile Phe Pro Pro Ala Ala Asp Gln Val Ala Thr Gly Thr Val Thr Ile
145                 150                 155                 160

Val Cys Val Ala Asn Lys Tyr Phe Pro Asp Val Thr Val Thr Trp Glu
                165                 170                 175

Val Asp Gly Thr Thr Gln Thr Thr Gly Ile Glu Asn Ser Lys Thr Pro
            180                 185                 190

Gln Asn Ser Ala Asp Cys Thr Tyr Asn Leu Ser Ser Thr Leu Thr Leu
        195                 200                 205

Thr Ser Thr Gln Tyr Asn Ser His Lys Glu Tyr Thr Cys Lys Val Thr
    210                 215                 220

Gln Gly Thr Thr Ser Val Val Gln Ser Phe Asn Arg Gly Asp Cys
225                 230                 235

<210> SEQ ID NO 119
<211> LENGTH: 405
<212> TYPE: DNA
<213> ORGANISM: Artificial Sequence
<220> FEATURE:
<223> OTHER INFORMATION: Anti-CTNS 360 variable light domain coding
      sequence with leader sequence

<400> SEQUENCE: 119
atggacacga gggcccccac tcagctgctg gggctcctgc tgctctggct cccaggtgcc      60
acatttgccc aagtgctgac ccagactgca tcgtccgtgt ctgcagctgt gggaggcaca     120
gtcaccgtca attgccaggc cagtcagagt atttggaata caacttcttt atcctggtat     180
cagcagaaac cagggcagcc tcccaagctc ctgatctacg aagcatccaa actggcatct     240
ggggtcccat cgcggtttag cggcagtgga tctgggacac agttcactct caccatcagc     300
ggcgtgcagt gtgacgatgc tgccacttac tactgtcagg gcgaatttag ttgtagtatt     360
gctgattgtg ttgctttcgg cggagggacc gaggtggtgg tcaga                    405

<210> SEQ ID NO 120
<211> LENGTH: 135
<212> TYPE: PRT
<213> ORGANISM: Artificial Sequence
<220> FEATURE:
<223> OTHER INFORMATION: Anti-CTNS 360 variable light domain amino acid
      sequence with leader sequence

<400> SEQUENCE: 120

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Ala Ser Ser
            20                  25                  30

Val Ser Ala Ala Val Gly Gly Thr Val Thr Val Asn Cys Gln Ala Ser
        35                  40                  45

Gln Ser Ile Trp Asn Asn Asn Phe Leu Ser Trp Tyr Gln Gln Lys Pro
    50                  55                  60
```

Gly Gln Pro Pro Lys Leu Leu Ile Tyr Glu Ala Ser Lys Leu Ala Ser
65                  70                  75                  80

Gly Val Pro Ser Arg Phe Ser Gly Ser Gly Ser Gly Thr Gln Phe Thr
                85                  90                  95

Leu Thr Ile Ser Gly Val Gln Cys Asp Asp Ala Ala Thr Tyr Tyr Cys
            100                 105                 110

Gln Gly Glu Phe Ser Cys Ser Ile Ala Asp Cys Val Ala Phe Gly Gly
        115                 120                 125

Gly Thr Glu Val Val Val Arg
    130                 135

<210> SEQ ID NO 121
<211> LENGTH: 216
<212> TYPE: PRT
<213> ORGANISM: Artificial Sequence
<220> FEATURE:
<223> OTHER INFORMATION: Anti-CTNS 360 light chain amino acid sequence
      without leader sequence

<400> SEQUENCE: 121

Gln Val Leu Thr Gln Thr Ala Ser Ser Val Ser Ala Ala Val Gly Gly
1               5                   10                  15

Thr Val Thr Val Asn Cys Gln Ala Ser Gln Ser Ile Trp Asn Asn Asn
                20                  25                  30

Phe Leu Ser Trp Tyr Gln Gln Lys Pro Gly Gln Pro Pro Lys Leu Leu
            35                  40                  45

Ile Tyr Glu Ala Ser Lys Leu Ala Ser Gly Val Pro Ser Arg Phe Ser
        50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Gln Gly Glu Phe Ser Cys Ser
                85                  90                  95

Ile Ala Asp Cys Val Ala Phe Gly Gly Gly Thr Glu Val Val Val Arg
            100                 105                 110

Gly Asp Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215

<210> SEQ ID NO 122
<211> LENGTH: 1368
<212> TYPE: DNA
<213> ORGANISM: Artificial Sequence
<220> FEATURE:
<223> OTHER INFORMATION: Anti-SHPK 363 heavy chain coding sequence
      (EB0605B-6G12-H1) with leader sequence

<400> SEQUENCE: 122

```
atggagactg gctgcgctg gcttctcctg gtcgctgtgc tcaaaggtgt ccagtgtcag    60
gagcagatag aggagtccgg gggaggcctg gtcaagcctg agggatccct gacactcacc   120
tgcaaagtct ctggattcga cttcagtagt aactatttca tgtgctgggt ccgccaggct   180
ccagggaagg ggctggagtg gatcggatgt attcttgttg gtagtggtag gactactttc   240
gcgagctggg cgaaaggccg attcaccatc tccaaaacct cgtcgaccac ggtgactctg   300
caaatgacca gtctgacagc cgcggacacg gccacctatt tctgtgcgag ggcctgggcc   360
ttgtggggcc ccggcaccct ggtcaccgtc tcctcagggc aacctaaggc tccatcagtc   420
ttcccactgg cccctgctg cggggacaca cccagctcca cggtgaccct gggctgcctg   480
gtcaaaggct acctcccgga gccagtgacc gtgacctgga actcgggcac cctcaccaat   540
ggggtacgca ccttcccgtc cgtccggcag tcctcaggcc tctactcgct gagcagcgtg   600
gtgagcgtga cctcaagcag ccagcccgtc acctgcaacg tggcccaccc agccaccaac   660
accaaagtgg acaagaccgt tgcgccctcg acatgcagca agcccatgtg cccacccct   720 gaactcctgg ggggaccgtc tgtcttcatc ttccccccaa acccaaggga cacccctcatg   780 atctcacgca ccccccgaggt cacatgcgtg gtggtggacg tgagccagga tgaccccgag   840
gtgcagttca catggtacat aaacaacgag caggtgcgca ccgcccggcc gccgctacgg   900
gagcagcagt tcaacagcac gatccgcgtg gtcagcaccc tccccatcgc gccaggac   960 tggctgaggg gcaaggagtt caagtgcaaa gtccacaaca aggcactccc ggcccccatc  1020
gagaaaacca tctccaaagc cagagggcag ccctggagc cgaaggtcta caccatgggc  1080
cctccccggg aggagctgag cagcaggtcg gtcagcctga cctgcatgat caacggcttc  1140 taccttccg acatctcggt ggagtgggag aagaacggga aggcagagga caactacaag  1200
accacgccgg ccgtgctgga cagcgacggc tcctacttcc tctacagcaa gctctcagtg  1260
cccacgagtg agtggcagcg gggcgacgtc ttcacctgct ccgtgatgca cgaggccttg  1320
cacaaccact acacgcagaa gtccatctcc cgctctccgg gtaaatga                1368
```

<210> SEQ ID NO 123
<211> LENGTH: 455
<212> TYPE: PRT
<213> ORGANISM: Artificial Sequence
<220> FEATURE:
<223> OTHER INFORMATION: Anti-SHPK 363 heavy chain amino acid sequence
      with leader sequence

<400> SEQUENCE: 123

Met Glu Thr Gly Leu Arg Trp Leu Leu Leu Val Ala Val Leu Lys Gly
1               5                   10                  15

Val Gln Cys Gln Glu Gln Ile Glu Glu Ser Gly Gly Gly Leu Val Lys
            20                  25                  30

Pro Glu Gly Ser Leu Thr Leu Thr Cys Lys Val Ser Gly Phe Asp Phe
        35                  40                  45

Ser Ser Asn Tyr Phe Met Cys Trp Val Arg Gln Ala Pro Gly Lys Gly
    50                  55                  60

Leu Glu Trp Ile Gly Cys Ile Leu Val Gly Ser Gly Arg Thr Thr Phe
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Ala Trp Ala Leu Trp Gly Pro Gly Thr Leu Val

```
                    115                 120                 125
Thr Val Ser Ser Gly Gln Pro Lys Ala Pro Ser Val Phe Pro Leu Ala
            130                 135                 140
Pro Cys Cys Gly Asp Thr Pro Ser Ser Thr Val Thr Leu Gly Cys Leu
145                 150                 155                 160
Val Lys Gly Tyr Leu Pro Glu Pro Val Thr Val Thr Trp Asn Ser Gly
                165                 170                 175
Thr Leu Thr Asn Gly Val Arg Thr Phe Pro Ser Val Arg Gln Ser Ser
            180                 185                 190
Gly Leu Tyr Ser Leu Ser Ser Val Val Ser Val Thr Ser Ser Ser Gln
                195                 200                 205
Pro Val Thr Cys Asn Val Ala His Pro Ala Thr Asn Thr Lys Val Asp
            210                 215                 220
Lys Thr Val Ala Pro Ser Thr Cys Ser Lys Pro Met Cys Pro Pro Pro
225                 230                 235                 240
Glu Leu Leu Gly Gly Pro Ser Val Phe Ile Phe Pro Pro Lys Pro Lys
                245                 250                 255
Asp Thr Leu Met Ile Ser Arg Thr Pro Glu Val Thr Cys Val Val Val
            260                 265                 270
Asp Val Ser Gln Asp Asp Pro Glu Val Gln Phe Thr Trp Tyr Ile Asn
                275                 280                 285
Asn Glu Gln Val Arg Thr Ala Arg Pro Pro Leu Arg Glu Gln Gln Phe
290                 295                 300
Asn Ser Thr Ile Arg Val Val Ser Thr Leu Pro Ile Ala His Gln Asp
305                 310                 315                 320
Trp Leu Arg Gly Lys Glu Phe Lys Cys Lys Val His Asn Lys Ala Leu
                325                 330                 335
Pro Ala Pro Ile Glu Lys Thr Ile Ser Lys Ala Arg Gly Gln Pro Leu
            340                 345                 350
Glu Pro Lys Val Tyr Thr Met Gly Pro Pro Arg Glu Glu Leu Ser Ser
                355                 360                 365
Arg Ser Val Ser Leu Thr Cys Met Ile Asn Gly Phe Tyr Pro Ser Asp
370                 375                 380
Ile Ser Val Glu Trp Glu Lys Asn Gly Lys Ala Glu Asp Asn Tyr Lys
385                 390                 395                 400
Thr Thr Pro Ala Val Leu Asp Ser Asp Gly Ser Tyr Phe Leu Tyr Ser
                405                 410                 415
Lys Leu Ser Val Pro Thr Ser Glu Trp Gln Arg Gly Asp Val Phe Thr
            420                 425                 430
Cys Ser Val Met His Glu Ala Leu His Asn His Tyr Thr Gln Lys Ser
            435                 440                 445
Ile Ser Arg Ser Pro Gly Lys
            450                 455

<210> SEQ ID NO 124
<211> LENGTH: 396
<212> TYPE: DNA
<213> ORGANISM: Artificial Sequence
<220> FEATURE:
<223> OTHER INFORMATION: Anti-SHPK 363 variable heavy domain coding
      sequence with leader sequence

<400> SEQUENCE: 124
atggagactg ggctgcgctg gcttctcctg gtcgctgtgc tcaaaggtgt ccagtgtcag      60
gagcagatag aggagtccgg gggaggcctg gtcaagcctg aggatccct gacactcacc      120
```

```
tgcaaagtct ctggattcga cttcagtagt aactatttca gtgtgctgggt ccgccaggct    180 ccagggaagg ggctggagtg gatcggatgt attcttgttg gtagtggtag gactactttc    240
gcgagctggg cgaaaggccg attcaccatc tccaaaacct cgtcgaccac ggtgactctg    300
caaatgacca gtctgacagc cgcggacacg gccacctatt tctgtgcgag ggcctgggcc    360
ttgtggggcc ccggcaccct ggtcaccgtc tcctca                              396
```

```
<210> SEQ ID NO 125
<211> LENGTH: 132
<212> TYPE: PRT
<213> ORGANISM: Artificial Sequence
<220> FEATURE:
<223> OTHER INFORMATION: Anti-SHPK 363 variable heavy domain amino acid
      sequence with leader sequence

<400> SEQUENCE: 125

Met Glu Thr Gly Leu Arg Trp Leu Leu Leu Val Ala Val Leu Lys Gly
1               5                   10                  15

Val Gln Cys Gln Glu Gln Ile Glu Glu Ser Gly Gly Gly Leu Val Lys
                20                  25                  30

Pro Glu Gly Ser Leu Thr Leu Thr Cys Lys Val Ser Gly Phe Asp Phe
            35                  40                  45

Ser Ser Asn Tyr Phe Met Cys Trp Val Arg Gln Ala Pro Gly Lys Gly
        50                  55                  60

Leu Glu Trp Ile Gly Cys Ile Leu Val Gly Ser Gly Arg Thr Thr Phe
65                  70                  75                  80

Ala Ser Trp Ala Lys Gly Arg Phe Thr Ile Ser Lys Thr Ser Ser Thr
                85                  90                  95

Thr Val Thr Leu Gln Met Thr Ser Leu Thr Ala Ala Asp Thr Ala Thr
            100                 105                 110

Tyr Phe Cys Ala Arg Ala Trp Ala Leu Trp Gly Pro Gly Thr Leu Val
        115                 120                 125

Thr Val Ser Ser
        130
```

```
<210> SEQ ID NO 126
<211> LENGTH: 436
<212> TYPE: PRT
<213> ORGANISM: Artificial Sequence
<220> FEATURE:
<223> OTHER INFORMATION: Anti-SHPK 363 heavy chain amino acid sequence
      without leader sequence

<400> SEQUENCE: 126

Gln Glu Gln Ile Glu Glu Ser Gly Gly Gly Leu Val Lys Pro Glu Gly
1               5                   10                  15

Ser Leu Thr Leu Thr Cys Lys Val Ser Gly Phe Asp Phe Ser Ser Asn
                20                  25                  30

Tyr Phe Met Cys Trp Val Arg Gln Ala Pro Gly Lys Gly Leu Glu Trp
            35                  40                  45

Ile Gly Cys Ile Leu Val Gly Ser Gly Arg Thr Thr Phe Ala Ser Trp
        50                  55                  60

Ala Lys Gly Arg Phe Thr Ile Ser Lys Thr Ser Ser Thr Thr Val Thr
65                  70                  75                  80

Leu Gln Met Thr Ser Leu Thr Ala Ala Asp Thr Ala Thr Tyr Phe Cys
                85                  90                  95

Ala Arg Ala Trp Ala Leu Trp Gly Pro Gly Thr Leu Val Thr Val Ser
```

```
            100                 105                 110
Ser Gly Gln Pro Lys Ala Pro Ser Val Phe Pro Leu Ala Pro Cys Cys
            115                 120                 125

Gly Asp Thr Pro Ser Ser Thr Val Thr Leu Gly Cys Leu Val Lys Gly
    130                 135                 140

Tyr Leu Pro Glu Pro Val Thr Val Thr Trp Asn Ser Gly Thr Leu Thr
145                 150                 155                 160

Asn Gly Val Arg Thr Phe Pro Ser Val Arg Gln Ser Ser Gly Leu Tyr
                165                 170                 175

Ser Leu Ser Ser Val Val Ser Val Thr Ser Ser Ser Gln Pro Val Thr
            180                 185                 190

Cys Asn Val Ala His Pro Ala Thr Asn Thr Lys Val Asp Lys Thr Val
        195                 200                 205

Ala Pro Ser Thr Cys Ser Lys Pro Met Cys Pro Pro Pro Glu Leu Leu
    210                 215                 220

Gly Gly Pro Ser Val Phe Ile Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

Gln Asp Asp Pro Glu Val Gln Phe Thr Trp Tyr Ile Asn Asn Glu Gln
            260                 265                 270

Val Arg Thr Ala Arg Pro Pro Leu Arg Glu Gln Gln Phe Asn Ser Thr
        275                 280                 285

Ile Arg Val Val Ser Thr Leu Pro Ile Ala His Gln Asp Trp Leu Arg
    290                 295                 300

Gly Lys Glu Phe Lys Cys Lys Val His Asn Lys Ala Leu Pro Ala Pro
305                 310                 315                 320

Ile Glu Lys Thr Ile Ser Lys Ala Arg Gly Gln Pro Leu Glu Pro Lys
                325                 330                 335

Val Tyr Thr Met Gly Pro Pro Arg Glu Glu Leu Ser Ser Arg Ser Val
            340                 345                 350

Ser Leu Thr Cys Met Ile Asn Gly Phe Tyr Pro Ser Asp Ile Ser Val
        355                 360                 365

Glu Trp Glu Lys Asn Gly Lys Ala Glu Asp Asn Tyr Lys Thr Thr Pro
    370                 375                 380

Ala Val Leu Asp Ser Asp Gly Ser Tyr Phe Leu Tyr Ser Lys Leu Ser
385                 390                 395                 400

Val Pro Thr Ser Glu Trp Gln Arg Gly Asp Val Phe Thr Cys Ser Val
                405                 410                 415

Met His Glu Ala Leu His Asn His Tyr Thr Gln Lys Ser Ile Ser Arg
            420                 425                 430

Ser Pro Gly Lys
        435

<210> SEQ ID NO 127
<211> LENGTH: 711
<212> TYPE: DNA
<213> ORGANISM: Artificial Sequence
<220> FEATURE:
<223> OTHER INFORMATION: Anti-SHPK 363 light chain coding sequence
      (EB0605B-6G12-K1) with leader sequence

<400> SEQUENCE: 127
atggacacga gggcccccac tcagctgctg gggctcctgc tgctctggct cccaggtgcc     60
acatttgcgc aagtgctgac ccagactcca tcccctgtgt ctgcagctgt gggaggcaca    120
```

```
gtcaccatca gttgccaggc cagtcagagt gtttataata acaacgactt agcctggtat      180
cagcagaaac cagggcagcc tcccaagctc ctgatctatg gtgcatccac tctggtatct      240
ggggtcccgt cgcggttcag cggcagtgga tctggggcac agttcactct caccatcagc      300
gacctggagt gtgacgatgc tgccacttac tactgtcaag cggatatga tcctcgtaat      360 tatcctttcg gcggagggac cgaggtggtg gtcaaaggtg atccagttgc acctactgtc      420
ctcatcttcc caccagctgc tgatcaggtg caactggaa cagtcaccat cgtgtgtgtg      480
gcgaataaat actttcccga tgtcaccgtc acctgggagg tggatggcac cacccaaaca      540
actggcatcg agaacagtaa aaccccgcag aattctgcag attgtaccta aacctcagc      600 agcactctga cactgaccag cacacagtac aacagccaca agagtacac ctgcaaggtg      660 acccagggca cgacctcagt cgtccagagc ttcaataggg gtgactgtta g              711
```

<210> SEQ ID NO 128
<211> LENGTH: 236
<212> TYPE: PRT
<213> ORGANISM: Artificial Sequence
<220> FEATURE:
<223> OTHER INFORMATION: Anti-SHPK 363 light chain amino acid sequence with leader sequence

<400> SEQUENCE: 128

```
Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Thr Pro Ser Pro
                20                  25                  30

Val Ser Ala Ala Val Gly Gly Thr Val Thr Ile Ser Cys Gln Ala Ser
            35                  40                  45

Gln Ser Val Tyr Asn Asn Asn Asp Leu Ala Trp Tyr Gln Gln Lys Pro
        50                  55                  60

Gly Gln Pro Pro Lys Leu Leu Ile Tyr Gly Ala Ser Thr Leu Val Ser
65                  70                  75                  80

Gly Val Pro Ser Arg Phe Ser Gly Ser Gly Ser Gly Ala Gln Phe Thr
                85                  90                  95

Leu Thr Ile Ser Asp Leu Glu Cys Asp Asp Ala Ala Thr Tyr Tyr Cys
                100                 105                 110

Gln Gly Gly Tyr Asp Pro Arg Asn Tyr Pro Phe Gly Gly Gly Thr Glu
            115                 120                 125

Val Val Val Lys Gly Asp Pro Val Ala Pro Thr Val Leu Ile Phe Pro
        130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190

Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
    210                 215                 220

Thr Ser Val Val Gln Ser Phe Asn Arg Gly Asp Cys
225                 230                 235
```

<210> SEQ ID NO 129

-continued

```
<211> LENGTH: 396
<212> TYPE: DNA
<213> ORGANISM: Artificial Sequence
<220> FEATURE:
<223> OTHER INFORMATION: Anti-SHPK 363 variable light domain coding
      sequence with leader sequence

<400> SEQUENCE: 129
atggacacga gggcccccac tcagctgctg gggctcctgc tgctctggct cccaggtgcc       60
acatttgcgc aagtgctgac ccagactcca tccctgtgt ctgcagctgt gggaggcaca      120
gtcaccatca gttgccaggc cagtcagagt gtttataata acaacgactt agcctggtat      180
cagcagaaac cagggcagcc tcccaagctc ctgatctatg gtgcatccac tctggtatct      240
ggggtcccgt cgcggttcag cggcagtgga tctgggcac agttcactct caccatcagc       300
gacctggagt gtgacgatgc tgccacttac tactgtcaag gcggatatga tcctcgtaat      360
tatcctttcg gcggagggac cgaggtggtg gtcaaa                                396

<210> SEQ ID NO 130
<211> LENGTH: 132
<212> TYPE: PRT
<213> ORGANISM: Artificial Sequence
<220> FEATURE:
<223> OTHER INFORMATION: Anti-SHPK 363 variable light domain amino acid
      sequence with leader sequence

<400> SEQUENCE: 130

Met Asp Thr Arg Ala Pro Thr Gln Leu Leu Gly Leu Leu Leu Leu Trp
1               5                  10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Ser Cys Gln Ala Ser
        35                  40                  45

Gln Ser Val Tyr Asn Asn Asn Asp Leu Ala Trp Tyr Gln Gln Lys Pro
    50                  55                  60

Gly Gln Pro Pro Lys Leu Leu Ile Tyr Gly Ala Ser Thr Leu Val Ser
65                  70                  75                  80

Gly Val Pro Ser Arg Phe Ser Gly Ser Gly Ser Gly Ala Gln Phe Thr
                85                  90                  95

Leu Thr Ile Ser Asp Leu Glu Cys Asp Asp Ala Ala Thr Tyr Tyr Cys
            100                 105                 110

Gln Gly Gly Tyr Asp Pro Arg Asn Tyr Pro Phe Gly Gly Gly Thr Glu
        115                 120                 125

Val Val Val Lys
    130

<210> SEQ ID NO 131
<211> LENGTH: 213
<212> TYPE: PRT
<213> ORGANISM: Artificial Sequence
<220> FEATURE:
<223> OTHER INFORMATION: Anti-SHPK 363 light chain amino acid sequence
      without leader sequence

<400> SEQUENCE: 131

Gln Val Leu Thr Gln Thr Pro Ser Pro Val Ser Ala Ala Val Gly Gly
1               5                  10                  15

Thr Val Thr Ile Ser Cys Gln Ala Ser Gln Ser Val Tyr Asn Asn Asn
            20                  25                  30

Asp Leu Ala Trp Tyr Gln Gln Lys Pro Gly Gln Pro Pro Lys Leu Leu
```

```
                    35                  40                  45
Ile Tyr Gly Ala Ser Thr Leu Val Ser Gly Val Pro Ser Arg Phe Ser
 50                  55                  60

Gly Ser Gly Ser Gly Ala Gln Phe Thr Leu Thr Ile Ser Asp Leu Glu
 65                  70                  75                  80

Cys Asp Asp Ala Ala Thr Tyr Tyr Cys Gln Gly Tyr Asp Pro Arg
                 85                  90                  95

Asn Tyr Pro Phe Gly Gly Gly Thr Glu Val Val Lys Gly Asp Pro
                100                 105                 110

Val Ala Pro Thr Val Leu Ile Phe Pro Pro Ala Ala Asp Gln Val Ala
                115                 120                 125

Thr Gly Thr Val Thr Ile Val Cys Val Ala Asn Lys Tyr Phe Pro Asp
                130                 135                 140

Val Thr Val Thr Trp Glu Val Asp Gly Thr Thr Gln Thr Gly Ile
145                 150                 155                 160

Glu Asn Ser Lys Thr Pro Gln Asn Ser Ala Asp Cys Thr Tyr Asn Leu
                165                 170                 175

Ser Ser Thr Leu Thr Leu Thr Ser Thr Gln Tyr Asn Ser His Lys Glu
                180                 185                 190

Tyr Thr Cys Lys Val Thr Gln Gly Thr Thr Ser Val Val Gln Ser Phe
                195                 200                 205

Asn Arg Gly Asp Cys
    210

<210> SEQ ID NO 132
<211> LENGTH: 1377
<212> TYPE: DNA
<213> ORGANISM: Artificial Sequence
<220> FEATURE:
<223> OTHER INFORMATION: Anti-ATP7B 1056 heavy chain coding sequence
      (EB0601-H3-1) with leader sequence

<400> SEQUENCE: 132
atggagactg ggctgcgctg gcttctcctg gtcgctgtgc tcaaaggtgt ccagtgtcag     60
tcgctggagg agtccggggg tcgcctggtc acgcctggag atccctgac agtcacctgt    120 acagtctctg gattctcccc cagtagctat tggataatct gggtccgcca ggctccaggg    180
gaggggctgg aatggatcgg aagcagtggt cctagtggta gcgcatacta cacgagctgg    240
gtgaaaggcc gattcaccat ctccaagacc tcgactacgg tggatctgaa aatgaccggt    300
ctgacaaccg aggacacggc cacctatttc tgtgccagag ctggtggtag tgactacgac    360
tggtttgatc tctggggcca gggcaccctg gtcaccgtct cttcagggca acctaaggct    420
ccatcagtct tcccactggc ccctgctgc ggggacacac ccagctccac ggtgaccctg    480
ggctgcctgg tcaaaggcta cctcccggag ccagtgaccg tgacctggaa ctcgggcacc    540
ctcaccaatg gggtacgcac cttcccgtcc gtcggcagt cctcaggcct ctactcgctg    600
agcagcgtgg tgagcgtgac ctcaagcagc cagcccgtca cctgcaacgt ggcccaccca    660
gccaccaaca ccaaagtgga caagaccgtt gcgccctcga catgcagcaa gcccacgtgc    720
ccaccccctg aactcctggg gggaccgtct gtcttcatct tcccccccaaa acccaaggac    780 accctcatga tctcacgcac ccccgaggtc acatgcgtgg tggtggacgt gagccaggat    840
gaccccgagg tgcagttcac atggtacata aacaacgagc aggtgcgcac cgcccggccg    900
ccgctacggg agcagcagtt caacagcacg atccgcgtgg tcagcaccct cccccatcgcg    960 caccaggact ggctgagggg caaggagttc aagtgcaaag tccacaacaa ggcactcccg   1020
```

```
gcccccatcg agaaaaccat ctccaaagcc agagggcagc ccctggagcc gaaggtctac    1080
accatgggcc ctccccggga ggagctgagc agcaggtcgg tcagcctgac ctgcatgatc    1140
aacggcttct acccttccga catctcggtg gagtgggaga agaacgggaa ggcagaggac    1200
aactacaaga ccacgccggc cgtgctggac agcgacggct cctacttcct ctacagcaag    1260
ctctcagtgc ccacgagtga gtggcagcgg ggcgacgtct tcacctgctc cgtgatgcac    1320
gaggccttgc acaaccacta cacgcagaag tccatctccc gctctccggg taaatga       1377
```

<210> SEQ ID NO 133
<211> LENGTH: 458
<212> TYPE: PRT
<213> ORGANISM: Artificial Sequence
<220> FEATURE:
<223> OTHER INFORMATION: Anti-ATP7B 1056 heavy chain amino acid sequence
      with leader sequence

<400> SEQUENCE: 133

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Gly Ser Leu Thr Val Thr Cys Thr Val Ser Gly Phe Ser Leu Ser
        35                  40                  45

Ser Tyr Trp Ile Ile Trp Val Arg Gln Ala Pro Gly Glu Gly Leu Glu
    50                  55                  60

Trp Ile Gly Ser Ser Gly Pro Ser Gly Ser Ala Tyr Tyr Thr Ser Trp
65                  70                  75                  80

Val Lys Gly Arg Phe Thr Ile Ser Lys Thr Ser Thr Thr Val Asp Leu
                85                  90                  95

Lys Met Thr Gly Leu Thr Thr Glu Asp Thr Ala Thr Tyr Phe Cys Ala
            100                 105                 110

Arg Ala Gly Gly Ser Asp Tyr Asp Trp Phe Asp Leu Trp Gly Gln Gly
        115                 120                 125

Thr Leu Val Thr Val Ser Ser Gly Gln Pro Lys Ala Pro Ser Val Phe
130                 135                 140

Pro Leu Ala Pro Cys Cys Gly Asp Thr Pro Ser Ser Thr Val Thr Leu
145                 150                 155                 160

Gly Cys Leu Val Lys Gly Tyr Leu Pro Glu Pro Val Thr Val Thr Trp
                165                 170                 175

Asn Ser Gly Thr Leu Thr Asn Gly Val Arg Thr Phe Pro Ser Val Arg
            180                 185                 190

Gln Ser Ser Gly Leu Tyr Ser Leu Ser Ser Val Val Ser Val Thr Ser
        195                 200                 205

Ser Ser Gln Pro Val Thr Cys Asn Val Ala His Pro Ala Thr Asn Thr
    210                 215                 220

Lys Val Asp Lys Thr Val Ala Pro Ser Thr Cys Ser Lys Pro Thr Cys
225                 230                 235                 240

Pro Pro Pro Glu Leu Leu Gly Gly Pro Ser Val Phe Ile Phe Pro Pro
                245                 250                 255

Lys Pro Lys Asp Thr Leu Met Ile Ser Arg Thr Pro Glu Val Thr Cys
            260                 265                 270

Val Val Val Asp Val Ser Gln Asp Asp Pro Glu Val Gln Phe Thr Trp
        275                 280                 285

Tyr Ile Asn Asn Glu Gln Val Arg Thr Ala Arg Pro Pro Leu Arg Glu

```
                290                 295                 300
Gln Gln Phe Asn Ser Thr Ile Arg Val Val Ser Thr Leu Pro Ile Ala
305                 310                 315                 320

His Gln Asp Trp Leu Arg Gly Lys Glu Phe Lys Cys Lys Val His Asn
                325                 330                 335

Lys Ala Leu Pro Ala Pro Ile Glu Lys Thr Ile Ser Lys Ala Arg Gly
                340                 345                 350

Gln Pro Leu Glu Pro Lys Val Tyr Thr Met Gly Pro Pro Arg Glu Glu
            355                 360                 365

Leu Ser Ser Arg Ser Val Ser Leu Thr Cys Met Ile Asn Gly Phe Tyr
        370                 375                 380

Pro Ser Asp Ile Ser Val Glu Trp Glu Lys Asn Gly Lys Ala Glu Asp
385                 390                 395                 400

Asn Tyr Lys Thr Thr Pro Ala Val Leu Asp Ser Asp Gly Ser Tyr Phe
                405                 410                 415

Leu Tyr Ser Lys Leu Ser Val Pro Thr Ser Glu Trp Gln Arg Gly Asp
                420                 425                 430

Val Phe Thr Cys Ser Val Met His Glu Ala Leu His Asn His Tyr Thr
            435                 440                 445

Gln Lys Ser Ile Ser Arg Ser Pro Gly Lys
    450                 455

<210> SEQ ID NO 134
<211> LENGTH: 405
<212> TYPE: DNA
<213> ORGANISM: Artificial Sequence
<220> FEATURE:
<223> OTHER INFORMATION: Anti-ATP7B 1056 variable heavy domain coding
      sequence with leader sequence

<400> SEQUENCE: 134
atggagactg ggctgcgctg gcttctcctg gtcgctgtgc tcaaaggtgt ccagtgtcag    60
tcgctggagg agtccggggg tcgcctggtc acgcctggag gatccctgac agtcacctgt   120
acagtctctg gattctccct cagtagctat tggataatct gggtccgcca ggctccaggg   180 gagggactg aatggatcgg aagcagtggt cctagtggta cgcatacta cacgagctgg    240 gtgaaaggcc gattcaccat ctccaagacc tcgactacgg tggatctgaa aatgaccggt   300
ctgacaaccg aggacacggc cacctatttc tgtgccagag ctggtggtag tgactacgac   360
tggtttgatc tctggggcca gggcaccctg gtcaccgtct cttca                  405

<210> SEQ ID NO 135
<211> LENGTH: 135
<212> TYPE: PRT
<213> ORGANISM: Artificial Sequence
<220> FEATURE:
<223> OTHER INFORMATION: Anti-ATP7B 1056 variable heavy domain amino
      acid sequence with leader sequence

<400> SEQUENCE: 135

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Gly Ser Leu Thr Val Thr Cys Thr Val Ser Gly Phe Ser Leu Ser
        35                  40                  45

Ser Tyr Trp Ile Ile Trp Val Arg Gln Ala Pro Gly Glu Gly Leu Glu
    50                  55                  60
```

```
Trp Ile Gly Ser Ser Gly Pro Ser Gly Ser Ala Tyr Tyr Thr Ser Trp
 65                  70                  75                  80

Val Lys Gly Arg Phe Thr Ile Ser Lys Thr Ser Thr Val Asp Leu
                 85                  90                  95

Lys Met Thr Gly Leu Thr Thr Glu Asp Thr Ala Thr Tyr Phe Cys Ala
                100                 105                 110

Arg Ala Gly Gly Ser Asp Tyr Asp Trp Phe Asp Leu Trp Gly Gln Gly
            115                 120                 125

Thr Leu Val Thr Val Ser Ser
            130             135

<210> SEQ ID NO 136
<211> LENGTH: 439
<212> TYPE: PRT
<213> ORGANISM: Artificial Sequence
<220> FEATURE:
<223> OTHER INFORMATION: Anti-ATP7B 1056 heavy chain amino acid sequence
      without leader sequence

<400> SEQUENCE: 136

Gln Ser Leu Glu Glu Ser Gly Gly Arg Leu Val Thr Pro Gly Gly Ser
 1               5                  10                  15

Leu Thr Val Thr Cys Thr Val Ser Gly Phe Ser Leu Ser Ser Tyr Trp
                 20                  25                  30

Ile Ile Trp Val Arg Gln Ala Pro Gly Glu Gly Leu Glu Trp Ile Gly
             35                  40                  45

Ser Ser Gly Pro Ser Gly Ser Ala Tyr Tyr Thr Ser Trp Val Lys Gly
 50                  55                  60

Arg Phe Thr Ile Ser Lys Thr Ser Thr Val Asp Leu Lys Met Thr
 65                  70                  75                  80

Gly Leu Thr Thr Glu Asp Thr Ala Thr Tyr Phe Cys Ala Arg Ala Gly
                 85                  90                  95

Gly Ser Asp Tyr Asp Trp Phe Asp Leu Trp Gly Gln Gly Thr Leu Val
            100                 105                 110

Thr Val Ser Ser Gly Gln Pro Lys Ala Pro Ser Val Phe Pro Leu Ala
            115                 120                 125

Pro Cys Cys Gly Asp Thr Pro Ser Ser Thr Val Thr Leu Gly Cys Leu
130                 135                 140

Val Lys Gly Tyr Leu Pro Glu Pro Val Thr Val Thr Trp Asn Ser Gly
145                 150                 155                 160

Thr Leu Thr Asn Gly Val Arg Thr Phe Pro Ser Val Arg Gln Ser Ser
                165                 170                 175

Gly Leu Tyr Ser Leu Ser Ser Val Val Ser Val Thr Ser Ser Ser Gln
            180                 185                 190

Pro Val Thr Cys Asn Val Ala His Pro Ala Thr Asn Thr Lys Val Asp
            195                 200                 205

Lys Thr Val Ala Pro Ser Thr Cys Ser Lys Pro Thr Cys Pro Pro Pro
210                 215                 220

Glu Leu Leu Gly Gly Pro Ser Val Phe Ile Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser Gln Asp Asp Pro Glu Val Gln Phe Thr Trp Tyr Ile Asn
            260                 265                 270

Asn Glu Gln Val Arg Thr Ala Arg Pro Pro Leu Arg Glu Gln Gln Phe
```

```
                275                 280                 285
Asn Ser Thr Ile Arg Val Val Ser Thr Leu Pro Ile Ala His Gln Asp
    290                 295                 300

Trp Leu Arg Gly Lys Glu Phe Lys Cys Lys Val His Asn Lys Ala Leu
305                 310                 315                 320

Pro Ala Pro Ile Glu Lys Thr Ile Ser Lys Ala Arg Gly Gln Pro Leu
                325                 330                 335

Glu Pro Lys Val Tyr Thr Met Gly Pro Pro Arg Glu Glu Leu Ser Ser
                340                 345                 350

Arg Ser Val Ser Leu Thr Cys Met Ile Asn Gly Phe Tyr Pro Ser Asp
                355                 360                 365

Ile Ser Val Glu Trp Glu Lys Asn Gly Lys Ala Glu Asp Asn Tyr Lys
            370                 375                 380

Thr Thr Pro Ala Val Leu Asp Ser Asp Gly Ser Tyr Phe Leu Tyr Ser
385                 390                 395                 400

Lys Leu Ser Val Pro Thr Ser Glu Trp Gln Arg Gly Asp Val Phe Thr
                405                 410                 415

Cys Ser Val Met His Glu Ala Leu His Asn His Tyr Thr Gln Lys Ser
                420                 425                 430

Ile Ser Arg Ser Pro Gly Lys
            435

<210> SEQ ID NO 137
<211> LENGTH: 714
<212> TYPE: DNA
<213> ORGANISM: Artificial Sequence
<220> FEATURE:
<223> OTHER INFORMATION: Anti-ATP7B 1056 light chain coding sequence
      (EB0601-K3-2) with leader sequence

<400> SEQUENCE: 137
atggacacga gggcccccac tcagctgctg gggctcctgc tgctctggct cccaggtgcc      60
acatttgccc aagtgctgac ccagactcca tctcccgtgt ctgcggctgt gggaggcaca     120
gtcaccatca actgccagtc cagtccgagt gttgctaata caactggtt atcctggttt      180 cagcagaaac cagggcagcg tcccaagctc ctgatctatg gtgcatccac tctggcatct     240
ggggtcccat cgcggttcaa aggcagtgga tctgggacac agttcactct caccatcagc     300
gacgtgcagt gtgacgatgc tgccacttac tactgtgcag gcggtcataa aactgctgaa     360
aaaaatcctt tcggcggagg gaccgaggtg gtggtcaaag gtgatccagt gcacctact      420 gtcctcatct tcccaccagc tgctgatcag gtggcaactg gaacagtcac catcgtgtgt     480
gtggcgaata atactttcc cgatgtcacc gtcacctggg aggtggatgg caccacccaa     540
acaactggca tcgagaacag taaaacaccg cagaattctg cagattgtac ctacaacctc     600
agcagcactc tgacactgac cagcacacag tacaacagcc acaagagta cacctgcaag     660 gtgacccagg gcacgacctc agtcgtccag agcttcaata ggggtgactg ttag           714

<210> SEQ ID NO 138
<211> LENGTH: 237
<212> TYPE: PRT
<213> ORGANISM: Artificial Sequence
<220> FEATURE:
<223> OTHER INFORMATION: Anti-ATP7B 1056 light chain amino acid sequence
      with leader sequence

<400> SEQUENCE: 138

Met Asp Thr Arg Ala Pro Thr Gln Leu Leu Gly Leu Leu Leu Leu Trp
```

```
             1               5                  10                 15
Leu Pro Gly Ala Thr Phe Ala Gln Val Leu Thr Gln Thr Pro Ser Pro
             20                 25                 30

Val Ser Ala Val Gly Gly Thr Val Thr Ile Asn Cys Gln Ser Ser
             35                 40                 45

Pro Ser Val Ala Asn Asn Trp Leu Ser Trp Phe Gln Gln Lys Pro
 50                 55                 60

Gly Gln Arg Pro Lys Leu Leu Ile Tyr Gly Ala Ser Thr Leu Ala Ser
 65                 70                 75                 80

Gly Val Pro Ser Arg Phe Lys Gly Ser Gly Ser Gly Thr Gln Phe Thr
                 85                 90                 95

Leu Thr Ile Ser Asp Val Gln Cys Asp Asp Ala Ala Thr Tyr Tyr Cys
                 100                105                110

Ala Gly Gly His Lys Thr Ala Glu Lys Asn Pro Phe Gly Gly Thr
                 115                120                125

Glu Val Val Lys Gly Asp Pro Val Ala Pro Thr Val Leu Ile Phe
 130                135                140

Pro Pro Ala Ala Asp Gln Val Ala Thr Gly Thr Val Thr Ile Val Cys
145                150                155                160

Val Ala Asn Lys Tyr Phe Pro Asp Val Thr Val Trp Glu Val Asp
                 165                170                175

Gly Thr Thr Gln Thr Thr Gly Ile Glu Asn Ser Lys Thr Pro Gln Asn
                 180                185                190

Ser Ala Asp Cys Thr Tyr Asn Leu Ser Ser Thr Leu Thr Leu Thr Ser
                 195                200                205

Thr Gln Tyr Asn Ser His Lys Glu Tyr Thr Cys Lys Val Thr Gln Gly
 210                215                220

Thr Thr Ser Val Val Gln Ser Phe Asn Arg Gly Asp Cys
225                230                235
```

<210> SEQ ID NO 139
<211> LENGTH: 399
<212> TYPE: DNA
<213> ORGANISM: Artificial Sequence
<220> FEATURE:
<223> OTHER INFORMATION: Anti-ATP7B 1056 variable light domain coding
      sequence with leader sequence

<400> SEQUENCE: 139
atggacacga gggcccccac tcagctgctg gggctcctgc tgctctggct cccaggtgcc    60
acatttgccc aagtgctgac ccagactcca tctcccgtgt ctgcggctgt gggaggcaca   120
gtcaccatca actgccagtc cagtccgagt gttgctaata caactggttt atcctggttt   180
cagcagaaac cagggcagcg tcccaagctc ctgatctatg gtgcatccac tctggcatct   240
ggggtcccat cgcggttcaa aggcagtgga tctgggacac agttcactct caccatcagc   300
gacgtgcagt gtgacgatgc tgccacttac tactgtgcag gcggtcataa aactgctgaa   360
aaaaatcctt tcggcggagg gaccgaggtg gtggtcaaa                          399

<210> SEQ ID NO 140
<211> LENGTH: 133
<212> TYPE: PRT
<213> ORGANISM: Artificial Sequence
<220> FEATURE:
<223> OTHER INFORMATION: Anti-ATP7B 1056 variable light domain amino
      acid sequence with leader sequence

<400> SEQUENCE: 140

```
Met Asp Thr Arg Ala Pro Thr Gln Leu Leu Gly Leu Leu Leu Trp
1               5                   10                  15

Leu Pro Gly Ala Thr Phe Ala Gln Val Leu Thr Gln Thr Pro Ser Pro
            20                  25                  30

Val Ser Ala Ala Val Gly Gly Thr Val Thr Ile Asn Cys Gln Ser Ser
        35                  40                  45

Pro Ser Val Ala Asn Asn Asn Trp Leu Ser Trp Phe Gln Gln Lys Pro
    50                  55                  60

Gly Gln Arg Pro Lys Leu Leu Ile Tyr Gly Ala Ser Thr Leu Ala Ser
65                  70                  75                  80

Gly Val Pro Ser Arg Phe Lys Gly Ser Gly Ser Gly Thr Gln Phe Thr
                85                  90                  95

Leu Thr Ile Ser Asp Val Gln Cys Asp Asp Ala Ala Thr Tyr Tyr Cys
            100                 105                 110

Ala Gly Gly His Lys Thr Ala Glu Lys Asn Pro Phe Gly Gly Gly Thr
        115                 120                 125

Glu Val Val Val Lys
    130
```

<210> SEQ ID NO 141
<211> LENGTH: 214
<212> TYPE: PRT
<213> ORGANISM: Artificial Sequence
<220> FEATURE:
<223> OTHER INFORMATION: Anti-ATP7B 1056 light chain amino acid sequence
      without leader sequence

<400> SEQUENCE: 141

```
Gln Val Leu Thr Gln Thr Pro Ser Pro Val Ser Ala Ala Val Gly Gly
1               5                   10                  15

Thr Val Thr Ile Asn Cys Gln Ser Ser Pro Ser Val Ala Asn Asn Asn
            20                  25                  30

Trp Leu Ser Trp Phe Gln Gln Lys Pro Gly Gln Arg Pro Lys Leu Leu
        35                  40                  45

Ile Tyr Gly Ala Ser Thr Leu Ala Ser Gly Val Pro Ser Arg Phe Lys
    50                  55                  60

Gly Ser Gly Ser Gly Thr Gln Phe Thr Leu Thr Ile Ser Asp Val Gln
65                  70                  75                  80

Cys Asp Asp Ala Ala Thr Tyr Tyr Cys Ala Gly Gly His Lys Thr Ala
                85                  90                  95

Glu Lys Asn Pro Phe Gly Gly Gly Thr Glu Val Val Val Lys Gly Asp
            100                 105                 110

Pro Val Ala Pro Thr Val Leu Ile Phe Pro Pro Ala Ala Asp Gln Val
        115                 120                 125

Ala Thr Gly Thr Val Thr Ile Val Cys Val Ala Asn Lys Tyr Phe Pro
    130                 135                 140

Asp Val Thr Val Thr Trp Glu Val Asp Gly Thr Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
            180                 185                 190

Glu Tyr Thr Cys Lys Val Thr Gln Gly Thr Thr Ser Val Val Gln Ser
        195                 200                 205

Phe Asn Arg Gly Asp Cys
```

<210> SEQ ID NO 142
<211> LENGTH: 11
<212> TYPE: PRT
<213> ORGANISM: Artificial Sequence
<220> FEATURE:
<223> OTHER INFORMATION: linker

<400> SEQUENCE: 142

Gly Gly Ser Gly Gly Gly Ser Gly Gly Ser Gly
1               5                   10

<210> SEQ ID NO 143
<211> LENGTH: 10
<212> TYPE: PRT
<213> ORGANISM: Artificial Sequence
<220> FEATURE:
<223> OTHER INFORMATION: linker

<400> SEQUENCE: 143

Gly Gly Ser Gly Gly Gly Ser Gly Ser Gly
1               5                   10

<210> SEQ ID NO 144
<211> LENGTH: 8
<212> TYPE: PRT
<213> ORGANISM: Artificial Sequence
<220> FEATURE:
<223> OTHER INFORMATION: linker

<400> SEQUENCE: 144

Gly Gly Ser Gly Gly Gly Ser Gly
1               5

<210> SEQ ID NO 145
<211> LENGTH: 10
<212> TYPE: PRT
<213> ORGANISM: Artificial Sequence
<220> FEATURE:
<223> OTHER INFORMATION: linker

<400> SEQUENCE: 145

Gly Gly Gly Gly Ser Gly Gly Gly Gly Ser
1               5                   10

<210> SEQ ID NO 146
<211> LENGTH: 8
<212> TYPE: PRT
<213> ORGANISM: Artificial Sequence
<220> FEATURE:
<223> OTHER INFORMATION: linker

<400> SEQUENCE: 146

Gly Gly Gly Ser Gly Gly Gly Ser
1               5

<210> SEQ ID NO 147
<211> LENGTH: 6
<212> TYPE: PRT
<213> ORGANISM: Artificial Sequence
<220> FEATURE:
<223> OTHER INFORMATION: linker

```
<400> SEQUENCE: 147

Gly Gly Ser Gly Gly Ser
1               5
```

NEWBORN SCREENING FOR PRIMARY IMMUNODEFICIENCIES, CYSTINOSIS, AND WILSON DISEASE

CROSS-REFERENCE TO RELATED APPLICATIONS

This application is a U.S. National Phase Application based on International Patent Application No. PCT/US2019/054856, filed on Oct. 4, 2019, which claims priority to U.S. Provisional Patent Application No. 62/742,161 filed Oct. 5, 2018, each of which is incorporated herein by reference in its entirety as if fully set forth herein.

STATEMENT REGARDING FEDERALLY SPONSORED RESEARCH OR DEVELOPMENT

This invention was made with government support under HD069890, AI106784, and AI123135, all awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 2GO5265_ST25.txt. The text file is 146 KB, was created on Mar. 24, 2021, and is being submitted electronically via EFS-Web.

FIELD OF THE DISCLOSURE

The current disclosure provides newborn screening for primary immunodeficiencies, cystinosis, and Wilson disease. The newborn screening can detect these disorders from dried blood spots already routinely collected at the time of birth. Early detection of these disorders will greatly improve patient outcome as each of them can be fatal once symptoms emerge.

BACKGROUND OF THE DISCLOSURE

There are a number of diseases with effective treatments available. However, for a number of these diseases, once symptoms emerge, the disease is already fatal or has led to irreversible damage. Examples of such diseases include primary immunodeficiency diseases (PIDD), cystinosis, and Wilson Disease (WD).

PIDD are a group of life-threatening hereditary or genetic congenital diseases characterized by an absent, impaired, or non-functioning immune system. Examples of PIDD include severe combined immunodeficiency (SCID), Wiskott-Aldrich Syndrome (WAS), and X-linked agammaglobulinemia (XLA).

SCID is a group of rare disorders caused by mutations in different genes involved in the development and function of infection-fighting immune cells such as T cells and B cells. SCID patients are usually affected by severe bacterial, viral, or fungal infections early in life and often are afflicted with scarring of the lungs, chronic diarrhea, and failure to thrive. The condition is fatal, usually within the first year or two of life, unless infants receive immune-restoring treatments, such as transplants of blood-forming stem cells, gene therapy, or enzyme therapy.

WAS is an immune deficiency that primarily affect males and is characterized by a reduced ability to form blood clots, due to a decrease in the number and size of platelets. This platelet abnormality, which is typically present from birth, leads to easy bruising and episodes of prolonged bleeding following minor trauma, which in some cases, is life threatening. Individuals with WAS also have an increased risk of developing infections, autoimmune disorders, and certain types of cancer. In WAS patients, immunoglobulin infusions and antibiotics can be used to prevent infections, and in severe cases, stem cell transplantation can provide a cure. Gene therapies are also being explored as another alternative treatment.

XLA is an inherited immunodeficiency that also primarily affect males. In XLA, the body is unable to produce antibodies needed to defend against bacteria, viruses, and other foreign substances. Children with XLA are usually healthy for the first 1 or 2 months of life because they are protected by maternal antibodies acquired before birth. After this time, however, the maternal antibodies are cleared from the body, and the affected child develops recurrent infections that lead to organ damage. Once the disease is detected, immunoglobulin infusions provide a standard therapy to strengthen the immune system, and antibiotics can be given to fight bacterial infections. However, by the time a diagnosis is made, organ damage may have already occurred.

Cystinosis is a rare metabolic disorder in which the amino acid cystine gets into cells but cannot exit due to defects in a cystine-specific transporter called cystinosin. Because of the defect in transportation of cystine, cells accumulate cystine in crystals in lysosomes, organelles inside cells, leading to early cell death. Cystinosis slowly destroys the organs in the body including the kidneys, liver, eyes, muscles and the brain. Children with infantile cystinosis appear normal at birth, but by 9-10 months of age, have symptoms that include excessive thirst and urination and failure to thrive. Cysteamine is a treatment that slows the progression of cystinosis by removing cystine from the cells. If cysteamine treatment is not started early enough in disease progression, however, renal transplantation is usually required.

WD is a copper transport disorder in which copper accumulates in vital organs such as the liver, kidneys, and brain. Diagnosing WD is difficult because its progression is slow and there is a broad spectrum of clinical symptoms. Therefore, despite the fact that treatments are available, many patients still present with irreversible multi-organ damage at the time of diagnosis.

The treatment of each of the above-described diseases would be significantly enhanced if diagnosis could be made before clinical symptoms emerge. Newborn screening (NBS) is a standard public preventive mandatory screening test for the 4 million babies born every year in the U.S. NBS usually involves a blood test performed 24 to 48 hours after birth. The screening uses a few drops of blood from a newborn's heel deposited on filter paper. The paper containing dried blood spots (DBS) can be stored until the tests are conducted.

To conduct NBS assessments, punches of dried blood are taken from the DBS and laboratory tests are performed to detect the presence or absence of specific substances within the blood (called markers or biomarkers) that are indicative of disorders not apparent at birth but that cause serious health problems later in life. Though the disorders screened vary from state to state, most states screen for phenylketonuria, primary congenital hypothyroidism, cystic fibrosis, and sickle cell disease. NBS has proven to be highly effective at improving patient outcomes and avoiding long-term disability in affected individuals, while at the same time reducing healthcare costs.

SCID has recently been added to NBS panels. However, the current molecular test for SCID is not able to reliably identify all patients having SCID-like disorders including late and delayed onset adenosine deaminase (ADA) deficiency, ZAP70 deficiency, and MHC Class II deficiency. Unfortunately, for most of the other life-threatening but treatable "non-SCID" immunodeficiencies, there are currently no broad-based, cost-effective screening methods available.

One reason that many disorders that would be beneficial to screen for lack an available test is that laboratory tests have been unable to reliably measure markers associated with the disorders. One reason for this inability is that the disorders are associated with the absence of or very reduced levels of markers. In this scenario, it can be difficult to reliably detect the absence of markers due to "background noise" associated with many laboratory techniques that can mask clinically relevant results.

Peptide immunoaffinity enrichment coupled to selected reaction monitoring mass spectrometry (immuno-SRM) is a method that enables precise quantification of low abundance markers. Utilization of immuno-SRM generally involves the following steps: (i) selection of markers that are indicative of the presence or absence of a disorder; (ii) treatment of a biological sample that would include the marker, if present, with enzymes to digest all proteins in the biological sample into smaller fragments called peptides; (iii) enrichment for peptides derived from the selected marker and (iv) analysis and quantification of the enriched peptides of interest in a mass spectrometer.

Recently, Jung et al., (J. Proteome Res. 2017; 16: 862-871) described use of immuno-SRM to quantify a protein marker, ATP7B, associated with WD from DBS. This was the first demonstration that immuno-SRM could be used to reliably detect a low-abundant marker from stored DBS, opening the possibility of using the approach to screen for a wider panel of disorders.

Though Jung and colleagues demonstrated the feasibility of using DBS in an immuno-SRM assay to distinguish individuals affected by WD from unaffected individuals, many aspects of such an assay depend on the disorder being diagnosed, the biomarkers available for each disorder, the ability to develop molecular entities that can enrich for peptides of interest, and the behavior of each peptide of interest in the mass spectrometer. All of these aspects and more require careful consideration and experimentation to achieve an assay that can reliably detect disorders in an NBS panel using DBS before clinical symptoms emerge.

SUMMARY OF THE DISCLOSURE

The current disclosure describes development of multiplexed assays that can be used to screen newborns for severe combined immunodeficiency (SCID), Wiskott-Aldrich Syndrome (WAS), X-linked agammaglobulinemia (XLA), cystinosis, and Wilson Disease (WD). The assays can significantly improve the outcome for affected individuals by reliably diagnosing these disorders before devastating and often fatal clinical symptoms emerge. The assays can detect the presence or absence of markers associated with these disorders using dried blood spots (DBS) already routinely collected as part of existing newborn screening (NBS) procedures.

The current disclosure describes peptides associated with each of the disorders that can be reliably detected and quantified using peptide immunoaffinity enrichment coupled to selected reaction monitoring mass spectrometry (immuno-SRM). The current disclosure also provides high affinity antibodies that can be used to enrich for the peptides, as well as methods to tag the peptides to increase the throughput of the assay.

BRIEF DESCRIPTION OF THE SEVERAL VIEWS OF THE DRAWINGS

FIG. 1. Protein targets and peptide sequences used for peptide immunoaffinity enrichment coupled to selected reaction monitoring mass spectrometry (immuno-SRM-MS) to diagnose severe combined immunodeficiency (SCID), Wiskott-Aldrich Syndrome (WAS), X-linked agammaglobulinemia (XLA), cystinosis, and Wilson Disease (WD). Total mass, parent ion mass, and daughter ion masses are also shown. ++ indicates doubly charged parent ions. The ion type for daughter ions are in parenthesis. *Total mass and parent ion mass when detecting ragged end sequence with leading K amino acid residue.

(FIG. 2A) BTK 407; (FIG. 2B) BTK 545; (FIG. 2C) CD3ε 197; (FIG. 2D) WASp 274; (FIG. 2E) WASp 289.

FIGS. 3A-3E. MRM traces for internal standard (left panels) and endogenous (right panels) signature peptides: (FIG. 3A) CD3ε 197; (FIG. 3B) BTK 407; (FIG. 3C) BTK 545; (FIG. 3D) WASp 274; (FIG. 3E) WASp 289.

(FIG. 4A) WASp 274; (FIG. 4B) CD3ε 197; (FIG. 4C) BTK 407; (FIG. 4D) ATP7B 1056.

FIGS. 6A-6E. Differences in signature peptide levels between patients (Pt). (FIG. 6A) BTK 545; (FIG. 6B) BTK 407; (FIG. 6C) CD3ε 197; (FIG. 6D) WASp 274; (FIG. 6E) WASp 289 (SCID: n=3, WAS: n=11, BTK: n=26) and normal controls (NC, n=40). **** $p<0.0001$, * $p<0.05$.

FIG. 7. ATP7B 1056 signature peptide concentrations.

FIG. 8. Quantification of signature peptides in normal controls from a blinded cohort study.

FIG. 9. Concentrations of signature peptides in a blinded patient cohort study.

FIGS. 10A, 10B. Receiver operating characteristic (ROC) plots showing the diagnostic performance of immuno-SRM for PIDDs. (FIG. 10A) ROC plots for BTK 407, BTK 545, CD3ε 197, WASp 274, and WASp 289. True positive and false positive rates are plotted for increasingly stringent cutoff values. Line of identity indicates a test that cannot distinguish patients from controls. (FIG. 10B) Area under the curve (AUC) values and p-values for peptides shown in FIG. 10A.

FIG. 11. Signature peptide levels in DBS obtained from Washington State Newborn Screening Laboratory.

FIG. 12. Ratios of signature peptides against ATP7B peptide and patient diagnosis in a blinded cohort study.

FIG. 15. Measured CTNS 115 and SHPK 363 concentrations in DBS and predicted genotype by immuno-SRM. Peptides were considered not detected (N.D.) if the signal-to-noise ratio for the peptide was less than 10. * indicates unknown mutations at this time.

FIGS. 16A-16D. Internal standard peptide peak areas generated upon peptide capture of both WASp 274 (FIGS. 16B and 16D) and BTK 407 (FIGS. 16A and 16C) using polyclonal and monoclonal antibodies. Peak areas were measured in blank control samples only (i.e. no patient blood, FIGS. 16C, 16D) and in an aggregated set of both patient and blank control samples (FIGS. 16A and 16B).

(FIG. 18A) ATP7B 1056 concentration in NC and WD patients. The 50 NC in the first column were run separately to set the reference range in the lab; the 3 NC in the middle column were run together with all 16 WD patients as quality control. (FIG. 18B) ATP7B 214 concentration in NC and WD patients. (FIG. 18C) ATP7B 887 concentration in NC and WD patients.

FIG. 19. Sequences (SEQ ID NOs: 22-76, and 78-141) supporting the disclosure.

DETAILED DESCRIPTION

Figures 2A, 2B, 2C, 2D, 2E:
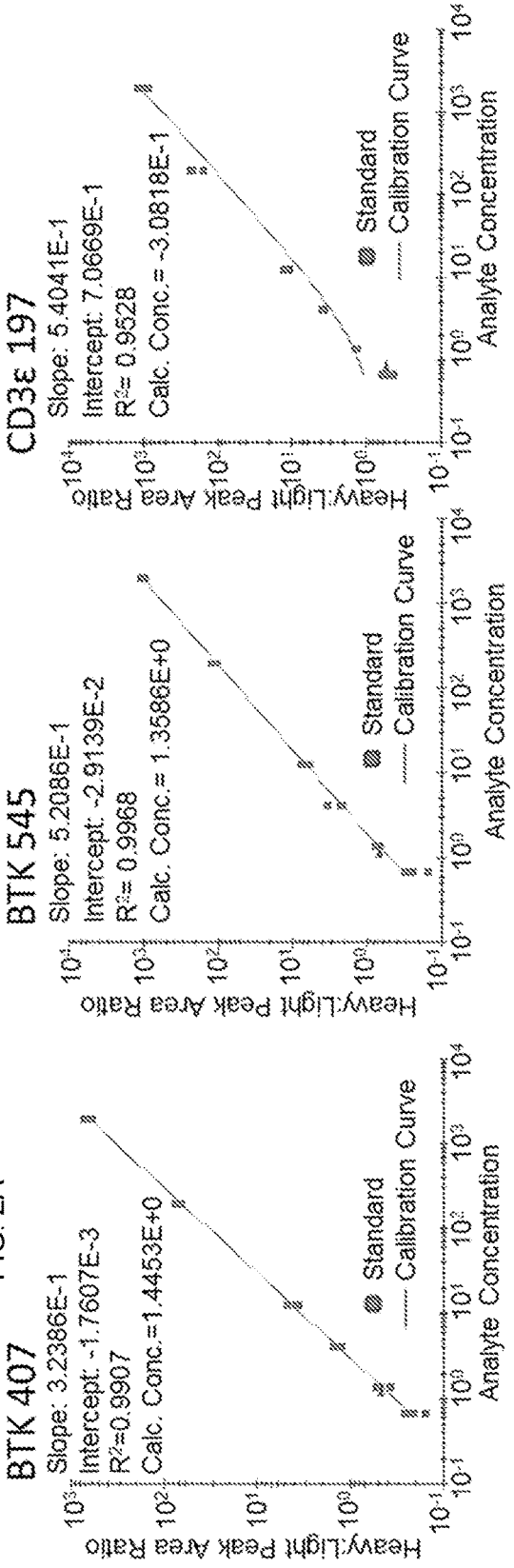
FIGS. 2A-2E. Response curves for peptides measured by the multiplexed immuno-multiple reaction monitoring (MRM) assay. When multiple parent ions are monitored in a single mass spectrometry (MS) run, this type of analysis is known as multiple reaction monitoring (MRM). Using MRM analysis, multiple proteins and multiple regions (signature peptides) of a protein can be monitored in a single mass spectrometry run. Response curves plot the heavy:light peak area ratio as a function of heavy peptide concentration, measured in a background matrix of digested protein extracted from dried blood spots (DBS). The curves allow determination of the linear range and sensitivity of the assay. Each datapoint is plotted as a gray box and linear regression is plotted as a line. Regression fit parameters are reported in the corner of each plot. Weighting for each plot is 1/x.
Figure 3C:
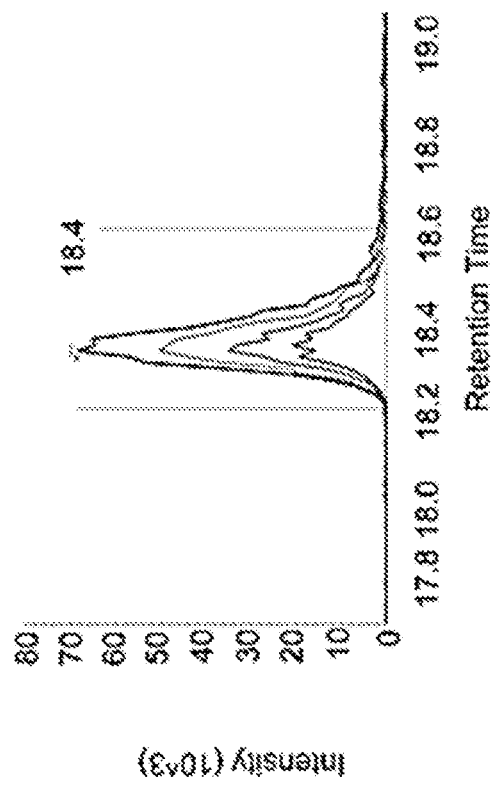
Figure 3D:
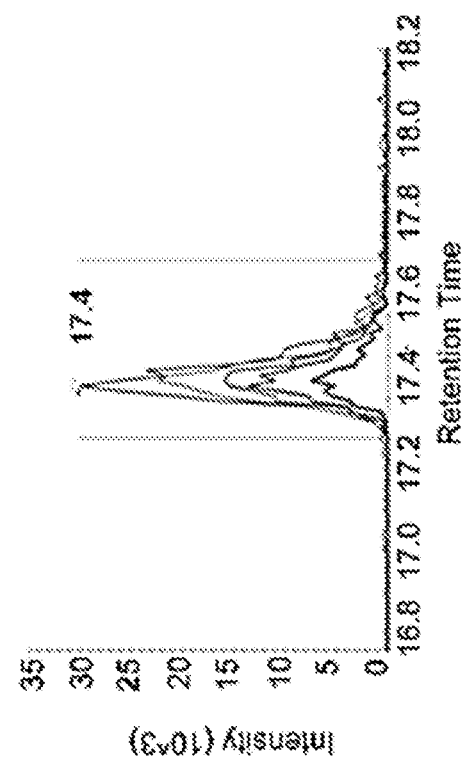
Figure 3E:
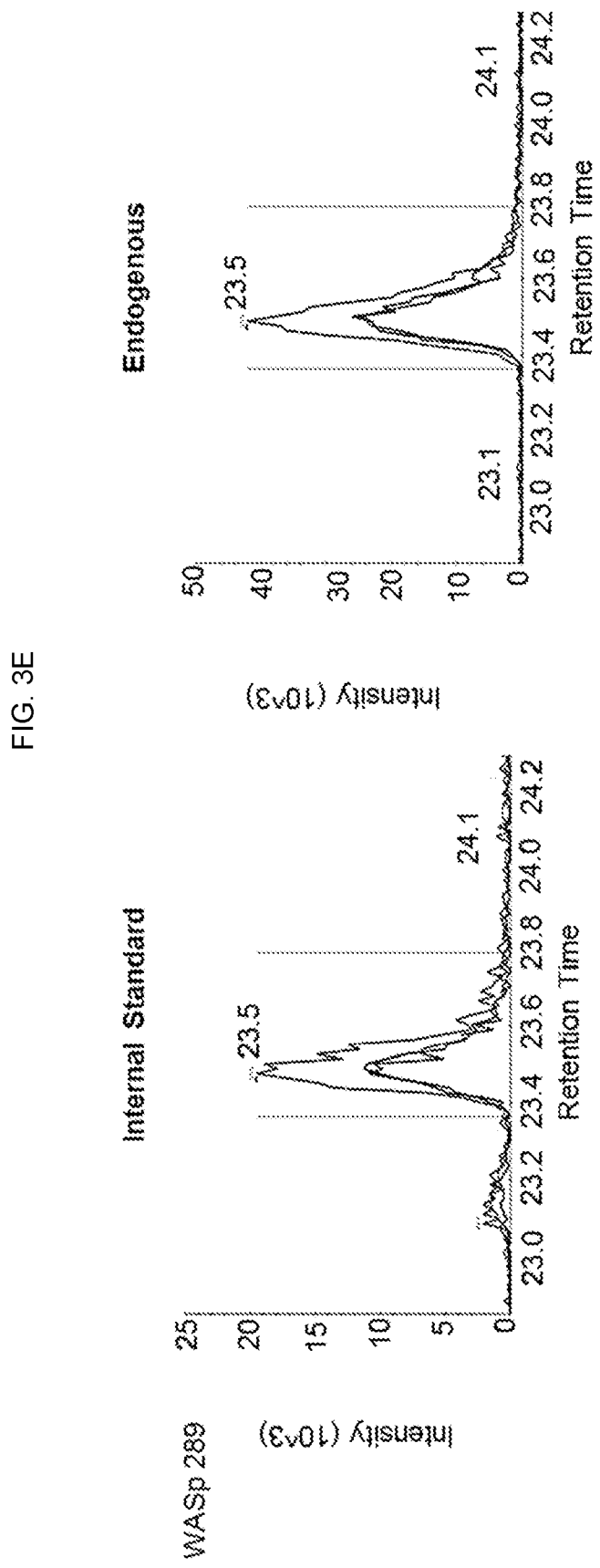

There are a number of diseases with effective treatments available. However, for a number of these diseases, once symptoms emerge, the disease is already fatal or has led to irreversible damage. Examples of such diseases include primary immunodeficiency diseases (PIDD), cystinosis, and Wilson Disease (WD).

PIDD are a collection of diverse congenital diseases characterized by absent or impaired immune responses including: autosomal recessive CD3ε-associated severe combined immunodeficiency (SCID, OMIM #615615); X-linked Wiskott-Aldrich Syndrome (WAS, OMIM #301000); and X-linked agammaglobulinemia (XLA, OMIM #300755). Although genetically and clinically heterogeneous, these disorders lead to fatal infections unless detected and treated early. While early detection of PIDD can be life-saving, unfortunately, most affected infants are diagnosed only after developing devastating infections.

SCID is a group of rare disorders caused by mutations in different genes involved in the development and function of infection-fighting immune cells such as T cells and B cells. More than a dozen genes have been implicated in SCID. Most often SCID is inherited in an autosomal recessive pattern, in which both copies of a particular gene, one inherited from the mother and one from the father, contain defects. The best-known form of autosomal recessive SCID is caused by adenosine deaminase (ADA) deficiency, in which infants lack the ADA enzyme necessary for T-cell survival. X-linked SCID, which is caused by mutations in a gene on the X chromosome, primarily affects males. Boys with this type of SCID have white blood cells that grow and develop abnormally. As a consequence, they have low numbers of T cells and natural killer cells, and their B cells do not function. SCID patients are usually affected by severe bacterial, viral, or fungal infections early in life and often are afflicted with scarring of the lungs, chronic diarrhea, and failure to thrive. The condition is fatal, usually within the first year or two of life, unless infants receive immune-restoring treatments, such as transplants of blood-forming stem cells, gene therapy, or enzyme therapy.

WAS is an immune deficiency that is characterized by a decrease in the number and size of platelets. WAS is caused by mutations in the WAS gene which produces the WAS protein (WASp), and is often considered to be part of a disease spectrum with two other disorders: X-linked thrombocytopenia and severe congenital neutropenia. These conditions have overlapping signs and symptoms and the same genetic cause.

The decrease in the number and size of platelets associated with WAS results in a reduced ability to form blood clots. This leads to easy bruising and episodes of prolonged bleeding following minor trauma, which in some cases, is life threatening. Individuals with WAS also have an increased susceptibility to infection, autoimmune disorders (e.g., eczema) and certain cancers (e.g., lymphoma). Once diagnosed, treatments for WAS are available. Exemplary treatments include immunoglobulin infusions, antibiotics, and stem cell transplants. Gene therapy is also being explored as a treatment option for WAS.

XLA is an inherited immunodeficiency which prevents B cells from developing normally. XLA is caused by mutations in a gene called Bruton's Tyrosine Kinase (BTK). XLA results in an inability to produce antibodies needed to defend against bacteria, viruses, and other foreign substances. Children with XLA are usually healthy for the first 1 or 2 months of life because they are protected by maternal antibodies acquired before birth. After this time, however, the maternal antibodies are cleared from the body, and the affected child develops recurrent infections. Recurrent infections can lead to organ damage. Once diagnosed, treatments in the form of antibody infusions and antibiotics are available to treat XLA.

Cystinosis is a rare metabolic disorder in which the amino acid cystine gets into cells but cannot exit due to defects in a cystine-specific transporter called cystinosin. Because of the defect in transportation of cystine, cells accumulate cystine in crystals in lysosomes, organelles inside cells, leading to early cell death. Over 90 mutations in the cystinosin (CTNS) gene or region have been reported. About half of the cystinosis variant genes in the Western populations are caused by a large chromosomal deletion which extends from part of the CTNS gene through the adjacent SHPK and initial part of the TRPV1 (capsaicin receptor) genes. Cystinosis slowly destroys the organs in the body including the kidneys, liver, eyes, muscles and the brain. Children with infantile cystinosis appear normal at birth, but by 9-10 months of age, have symptoms that include excessive thirst and urination and failure to thrive. If diagnosed early, treatment with cysteamine, a cystine depleting agent that slows the progression of cystinosis by removing cystine from the cells, is possible. If not diagnosed early enough, renal transplantation is often required.

Wilson Disease (WD) is a slow and progressive copper transport disorder in which excess copper is not eliminated properly and accumulates in vital organs such as the liver, kidneys, and brain. WD is caused by a genetic defect in the ATP7B gene. WD leads to irreversible neurological disability and liver cirrhosis if not diagnosed and treated early. Unfortunately, WD remains difficult because of its slow progression and the broad clinical spectrum of symptoms. Therefore, many patients still present with irreversible and sometimes fatal multi-organ damage at the time of diagnosis. When diagnosed early enough, available treatments include D-penicillamine, trientine and zinc salts.

The treatment of each of the above-described diseases would be significantly enhanced if diagnosis could be made before clinical symptoms emerge. Newborn screening (NBS) is a standard public preventive mandatory screening test for the 4 million babies born every year in the U.S. NBS usually involves a blood test performed 24 to 48 hours after birth. The screening uses a few drops of blood from a newborn's heel deposited on filter paper. The paper containing dried blood spots (DBS) can be stored until the tests are conducted.

To conduct NBS assessments, punches of dried blood are taken from the DBS and laboratory tests are performed to detect the presence or absence of specific substances within the blood (called markers or biomarkers) that are indicative of disorders not apparent at birth but that cause serious health problems later in life. Though the disorders screened vary from state to state, most states screen for phenylketonuria, primary congenital hypothyroidism, cystic fibrosis, and sickle cell disease. NBS has proven to be highly effective at improving patient outcomes and avoiding long-term disability in affected individuals, while at the same time reducing healthcare costs.

T-cell receptor excision circle (TREC) analysis and kappa-deleting element recombination circle (KREC) screening from dried blood spots (DBS) on filter paper has recently been introduced for SCID and some X-linked or autosomal recessive agammaglobulinemias. However, NBS methods for other PIDD do not exist.

Tandem mass spectrometry (MS/MS) was first applied to NBS in the 1990s, paving the way for rapid screening of multiple metabolites and thus several diseases from DBS samples collected at birth. Chace J Mass Spectrom. Wiley-Blackwell; 2009; 44: 163-170; Millington et al. J. Inherit. Metab. Dis. 1990; 13: 321-324; Sweetman et al. Pediatrics. 2006; 117: S308-S314; Almannai et al. Curr. Opin. Pediatr. 2016; 28: 694-699; Watson et al. Genet. Med. Nature Publishing Group; 2006. pp. 1S-252S; Chace et al. Clin. Chem. 1993; 39: 66-71. Selected reaction monitoring mass spectrometry (SRM-MS) performed on triple quadrupole mass spectrometers further enabled the precise, high-throughput, and analytically-robust quantification of specific biomarkers; as such, it is now the standard of care at clinical NBS laboratories across the world. Chace D H J Mass Spectrom. Wiley-Blackwell; 2009; 44: 163-170; Chace & Kalas. Clinical Biochemistry. 2005; 38: 296-309. Dott et al. American Journal of Medical Genetics Part A. Wiley Subscription Services, Inc., A Wiley Company; 2006; 140: 837-842.

MS/MS relies on the measurement of concentrated upstream metabolites for detection of various inborn errors of metabolism with specific enzyme deficiencies. This excludes its application to diseases, such as PIDD, where no accumulated metabolites are present or currently verified. For this reason, protein-based assays such as flow cytometry or western blotting have been used as first-line investigative methods for diseases such as WAS and its milder phenotype, X-linked thrombocytopenia (XLT), where most mutations lead to absent or decreased protein products. Qasim et al. Br. J. Haematol. 2001; 113: 861-865; Jin et al. Blood. American Society of Hematology; 2004; 104: 4010-4019. These approaches require that intact blood samples or cells from patients be available, making population-based screening or testing of patients from resource-poor areas impossible.

SRM-MS utilizes proteolytically-generated signature peptides as stoichiometric surrogates of a protein of interest. This may, in turn, be used to estimate the number of a particular cell-type expressing that protein in a sample (i.e. quantification of CD3ε for an indication of the amount of CD3+ T-cells in blood). The high specificity of MS for each signature peptide is conferred by three physiochemical properties—its mass, retention times upon high-performance liquid chromatography (HPLC) separation, and resultant target-specific fragmentation patterns. Kennedy et al. Nat. Methods. 2014; 11: 149-155. Despite these advances, with a typical limit of quantification ranging from 100 to 1000 ng protein/mL, the use of complex matrices such as blood or plasma often precludes accurate quantification of low-abundance targets by SRM-MS based assays. This limits applicability to many PIDD including SCID, WAS, and XLA that result in absent or decreased levels of target proteins expressed only intracellularly. de Saint Basile et al. J. Clin. Invest. American Society for Clinical Investigation; 2004; 114: 1512-1517.

Peptide immunoaffinity enrichment coupled to SRM (immuno-SRM), also referred to as Stable Isotope Standards and Capture by Anti-Peptide Antibodies (SISCAPA), increases the sensitivity of SRM-MS assays by utilizing anti-peptide antibodies to purify and enrich peptides of interest from a complex biologic sample prior to SRM-MS analysis. Zhao et al. J Vis Exp. 2011; 53: 2812; Whiteaker et al. Mol. Cell Proteomics. American Society for Biochemistry and Molecular Biology; 2010; 9: 184-196; Whiteaker et al. Mol. Cell Proteomics. American Society for Biochemistry and Molecular Biology; 2012; 11: M111.015347; Kuhn et al. Clin. Chem. 2009; 55: 1108-1117; Anderson et al. J Proteome Res. 2004; 3(2): 235-244. This additional peptide enrichment step, coupled to SRM-MS, lowers the limit of detection to the low pg protein/mL range from 1 mL of plasma that is suitable for the accurate quantification of very low abundance proteins in complex matrices such as DBS. Whiteaker et al. Mol. Cell Proteomics. American Society for Biochemistry and Molecular Biology; 2010; 9: 184-196; Hoofnagle et al. Clin. Chem. 2008; 54: 1796-1804; Netzel et al. Clin. Chem. 2016; 62: 297-299; Razavi et al. Bioanalysis. Future Science Ltd London, UK; 2016; 8: 1597-1609.

The ability of LC-MS/MS to detect signature peptides from CD3ε, WASp, and BTK in proteolytically digested human peripheral blood mononuclear cell (PMBC) lysates has previously been demonstrated. In a blinded study, peptide levels were quantified in normal control PMBCs but nearly undetectable in a disease-specific fashion in affected patients. Kerfoot et al. Proteomics Clin Appl. 2012; 6: 394-402. The same proteomic method was applied to show elevated levels of α-aminoadipic semialdehyde antiquitin (α-AASA) and piperideine-6-carboxylate (P6C) in DBS of patients with pyridoxine-dependent seizures, revealing the possibility of its application to NBS. Jung et al. Mol. Genet. Metab. 2013; 110: 237-240. To improve the sensitivity and reproducibility of the assay, the immuno-SRM platform was harnessed to allow for the quantification of very low abundance peptides in DBS such as surrogate peptides of the ATP7B protein from patients with Wilson Disease (WD). The results demonstrated the ability of immuno-SRM to detect ATP7B peptides in the low picomolar (pmol) range and to reproducibly differentiate between patients with WD from unaffected individuals. Jung et al. 2017, supra.

Though the feasibility of using DBS in an immuno-SRM assay to distinguish individuals affected by certain diseases from unaffected individuals has been established, many aspects of the assay depend on the disorder being diagnosed, the biomarkers available for each disorder, the ability to develop molecular entities that can enrich for peptides of interest, and the behavior of each peptide of interest in the mass spectrometer. All of these aspects and more require careful consideration and experimentation to achieve a reliable assay that can reliably detect disorders in an NBS panel using DBS before clinical symptoms emerge.

The present disclosure provides a multiplexed immuno-SRM method to reliably diagnose SCID, WAS, XLA, cystinosis, and WD from a dried blood spot (DBS). The multiplexed immuno-SRM assay disclosed herein can utilize anti-peptide antibodies generated against peptides of proteins reduced or absent in SCID, WAS, XLA, cystinosis, and WD.

The following aspects of the disclosure are now described in more detail: (I) Collection and Processing of DBS; (II) Peptide Markers for SCID, WAS, XLA, cystinosis, and Wilson disease; (III) Enzymatic Digestion of Proteins in DBS; (IV) Antibodies to Enrich for the Peptide Markers; (V) Enrichment Strategies for Peptides; (VI) Liquid Chromatography (LC); (VII) Mass Spectrometry (MS); (VIII) Kits; (IX) Methods of Use; (X) Exemplary Embodiments; and (XI) Experimental Examples.

(I) Collection and Processing of DBS

In particular embodiments, samples used in the methods of the present disclosure are DBS. In particular embodiments, whole blood from a subject can be prepared by placing blood onto a filter paper card and allowing the blood to dry.

In particular embodiments, whole blood from a subject can be collected in ACD (acid citrate dextrose) tubes and DBS can be prepared by pipetting 50-100 µL (e.g., 70 µL) blood/spot onto filter paper card (e.g., Protein Saver™ 903® Card, Whatman Inc, Piscataway, N.J.), and allowed to dry at room temperature. In particular embodiments, blood is allowed to dry on filter paper card overnight. DBS can be stored, for example, in sealed plastic bags at −80° C. until use. In particular embodiments, the whole DBS can be used in the immuno-SRM assays of the disclosure. In particular embodiments, one or more 3-mm punches from the DBS can be used in the immuno-SRM assays of the disclosure.

(II) Peptide Markers for SCID, was, XLA, Cystinosis, and WD

There are many theoretical proteolytic peptides from target proteins. Those can be potential candidates for monoclonal antibody production. Nonetheless, the best potential candidate peptides were chosen after screening their characteristics by MS/MS. Those signature peptides with the highest sensitivity and specificity were selected to develop corresponding monoclonal antibodies and validated using clinical samples. In particular embodiments, multiple peptides and antibodies can be included in a multiplex analysis to maximize the sensitivity and specificity of the SRM assay.

Typically, one or two signature proteotypic peptides which are unique to the protein of interest and that are consistently observed in MS experiments are selected to stoichiometrically represent the protein of interest. Mallick et al. Nat Biotechnol 2007; 25: 125-131. Signature peptides can be selected by detection in previous MS experiments, use of computational tools to predict the peptides most likely observable by MS, or a combination of both. In particular embodiments, tryptic peptides 8-22 amino acids in length with moderate hydrophobicity can be selected. Very hydrophilic and very hydrophobic peptides can be less stable due to retention time variation in HPLC and loss to surfaces. In particular embodiments, Methionine residues (oxidation), N-terminal glutamine (cyclization), asparagine followed by glycine or proline (prone to deamidation), and dibasic termini (e.g. neighboring lysine or arginine residues such as KK, KR, RR, RK have the potential for variable digestion efficiency) can be undesirable. Whiteaker and Paulovich Clin Lab Med. 2011; 31(3): 385-396. Shorter peptides and those containing proline residues can be better targets for SRM. Lange et al. Molecular Systems Biology 2008; 4: 222.

In particular embodiments, the peptides include portions of CD3ε, WASp, BTK, CTNS, SHPK and/or ATP7B. In particular embodiments, the peptides include SEQ ID NOs: 1-21.

In particular embodiments, peptides of the present disclosure include: CD3ε 197 for SCID; WASp 274 for WAS; WASp 289 for WAS; BTK 407 for XLA; BTK 545 for XLA; CTNS 115 for cystinosis; CTNS 120 for cystinosis; CTNS 194 for cystinosis; CTNS 360 for cystinosis; SHPK 44 for cystinosis; SHPK 363 for cystinosis; SHPK 388 for cystinosis; ATP7B 214 for WD; ATP7B 325 for WD; ATP7B 466 for WD; ATP7B 589 for WD; ATP7B 621 for WD; ATP7B 887 for WD; ATP7B 1056 for WD; and ATP7B 1061 for WD. In particular embodiments, proteolytically-generated signature peptides useful for methods of the present disclosure include peptides in FIG. 1: CD3ε 197 (DLYSGLNQR, SEQ ID NO: 1); WASp 274 (AGISEAQLTDAETSK, SEQ ID NO: 2); WASp 289 (LIYDFIEDQGGLEAVR, SEQ ID NO: 3); BTK 407 (ELGTGQFGVVK, SEQ ID NO: 4); BTK 545 (YVLDDEYTSSVGSK, SEQ ID NO: 5); CTNS 115 (FLVIR, SEQ ID NO: 6); CTNS 360 (RPGYDQLN (SEQ ID NO: 7) and KRPGYDQLN (SEQ ID NO: 8)); SHPK 363 (DTHLTITPTVLGER, SEQ ID NO: 9); ATP7B 325 (VSLPDGAEGSGTDHR, SEQ ID NO: 10); and ATP7B 1056 (VLAVVGTAEASSEHPLGVAVTK, SEQ ID NO: 11). In particular embodiments, additional peptides useful for methods of the present disclosure include the following in Table 1.

TABLE 1

Additional exemplary peptides of the present disclosure

| Peptide name | Sequence |
| --- | --- |
| CTNS 120-151 "CTNS 120" | SSAISIINQVIGWIYFVAWSISFYPQVIMNWR (SEQ ID NO: 12) |
| CTNS 194-228 "CTNS 194" | YPNGVNPVNSNDVFFSLHAVVLTLIIIVQC (CAM)C(CAM)LYER (SEQ ID NO: 13) |

TABLE 1-continued

Additional exemplary peptides of the present disclosure

| Peptide name | Sequence |
| --- | --- |
| SHPK 44-58 "SHPK 44" | AEAAVESAVAGPQGR (SEQ ID NO: 14) |
| SHPK 388-400 "SHPK 388" | ISSSDLSLGHVTR (SEQ ID NO: 15) |
| ATP7B 214-226 "ATP7B 214" | VAPLSLGPIDIER (SEQ ID NO: 16) |
| ATP7B 466-477 "ATP7B 466" | LPANHAPDILAK (SEQ ID NO: 17) |
| ATP7B 589-603 "ATP7B 589" | TNGITYASVALATSK (SEQ ID NO: 18) |
| ATP7B 621-634 "ATP7B 621" | IIEEIGFHASLAQR (SEQ ID NO: 19) |
| ATP7B 887-901 "ATP7B 887" | ATHVGNDTTLAQIVK (SEQ ID NO: 20) |
| ATP7B 1061-1077 "ATP7B 1061" | GTAEASSEHPLGVAVTK (SEQ ID NO: 21) |

(III) Enzymatic Digestion of Proteins in DBS

Proteins in DBS can be subjected to proteolysis to produce peptides that can be further selected by immunoaffinity purification before analysis by LC-SRM-MS. Proteolysis can be accomplished using site specific endoproteases, such as pepsin, arg-C proteinase, asp-N endopeptidase, BNPS-skatole, caspase 1, caspase 2, caspase 3, caspase 4, caspase 5, caspase 6, caspase 7, caspase 8, caspase 9, caspase 10, chymotrypsin, clostripain (clostridiopeptidase B), enterokinase, factor Xa, glutamyl endopeptidase, granzyme B, lysC, proline-endopeptidase, proteinase K, staphylococcal peptidase I, thermolysin, thrombin, and trypsin. Chemicals which cleave site specifically can also be used. Combinations of enzymes and/or chemicals can be used to obtain desirable analytes.

In particular embodiments, proteins in DBS can be digested into peptides with trypsin. Trypsin cleaves exclusively C-terminal to arginine and lysine residues and can be a preferred choice to generate peptides because the masses of generated peptides are compatible with the detection ability of most mass spectrometers (up to 2000 m/z) and because there are efficient algorithms available for the generation of databases of theoretical trypsin-generated peptides. High cleavage specificity, availability, and cost are other advantages of trypsin. Peptides formed by the treatment of a protein with trypsin are known as tryptic peptides.

(IV) Antibodies to Enrich for the Peptide Markers

An antibody includes a polypeptide ligand substantially encoded by an immunoglobulin gene or immunoglobulin genes, or fragments thereof, whether natural, or partially or wholly synthetically produced. An antibody specifically (or selectively) binds and recognizes an epitope (e.g., an antigen). An antibody can include any protein having a binding domain that is homologous or largely homologous to an immunoglobulin binding domain. An antibody may be monoclonal or polyclonal. The antibody may be a member of any immunoglobulin class, including any of the human classes: IgG, IgM, IgA, IgD, and IgE, etc. The recognized immunoglobulin genes include the kappa and lambda light chain constant region genes, the alpha, gamma, delta, epsilon and mu heavy chain constant region genes, and the myriad immunoglobulin variable region genes. "Fc" portion of an antibody refers to that portion of an immunoglobulin heavy chain that includes one or more heavy chain constant region domains, CH1, CH2 and CH3, but does not include the heavy chain variable region.

An intact antibody can include at least two heavy (H) chains and two light (L) chains inter-connected by disulfide bonds. Each heavy chain is composed of a heavy chain variable region (abbreviated herein as VH or VH) and a heavy chain constant region. The heavy chain constant region includes three domains, CH1, CH2 and CH3. Each light chain is composed of a light chain variable region (abbreviated herein as VL or VL) and a light chain constant region. The light chain constant region includes one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Clq) of the classical complement system.

The precise amino acid sequence boundaries of a given CDR or FR can be readily determined using any of a number of well-known schemes, including those described by: Kabat et al. (1991) "Sequences of Proteins of Immunological Interest," 5th Ed. Public Health Service, National Institutes of Health, Bethesda, Md. (Kabat numbering scheme); Al-Lazikani et al. (1997) J Mol Biol 273: 927-948 (Chothia numbering scheme); Maccallum et al. (1996) J Mol Biol 262: 732-745 (Contact numbering scheme); Martin et al. (1989) Proc. Natl. Acad. Sci., 86: 9268-9272 (AbM numbering scheme); Lefranc M P et al. (2003) Dev Comp Immunol 27(1): 55-77 (IMGT numbering scheme); and Honegger and Pluckthun (2001) J Mol Biol 309(3): 657-670 ("Aho" numbering scheme). The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. In particular embodiments, the antibody CDR sequences disclosed herein are according to Kabat numbering.

An antibody fragment includes any derivative or portion of an antibody that is less than full-length. In particular embodiments, the antibody fragment retains at least a significant portion of the full-length antibody's specific binding ability as a binding partner. Examples of antibody fragments include Fab, Fab', Fab'-SH, F(ab')$_2$, single chain variable fragment (scFv), Fv, dsFv diabody, and Fd fragments, and/or any biologically effective fragments of an immunoglobulin that bind specifically to an epitope described herein. Antibodies or antibody fragments include all or a portion of polyclonal antibodies, monoclonal antibodies, human antibodies, humanized antibodies, synthetic antibodies, chimeric antibodies, bispecific antibodies, mini bodies, and linear antibodies.

A single chain variable fragment (scFv) is a fusion protein of the variable regions of the heavy and light chains of immunoglobulins connected with a short linker peptide. Fv fragments include the VL and VH domains of a single arm of an antibody. Although the two domains of the Fv fragment, VL and VH, are coded by separate genes, they can be joined, using, for example, recombinant methods, by a synthetic linker that enables them to be made as a single protein chain in which the VL and VH regions pair to form monovalent molecules (single chain Fv (scFv)). For additional information regarding Fv and scFv, see e.g., Bird, et al., Science 242 (1988) 423-426; Huston, et al., Proc. Natl. Acad. Sci. USA 85 (1988) 5879-5883; Plueckthun, in The Pharmacology of Monoclonal Antibodies, vol. 113, Rosenburg and Moore (eds.), Springer-Verlag, New York), (1994) 269-315; WO1993/16185; U.S. Pat. Nos. 5,571,894; and 5,587,458.

A Fab fragment is a monovalent antibody fragment including VL, VH, CL and CH1 domains. A F(ab')$_2$ fragment is a bivalent fragment including two Fab fragments linked by a disulfide bridge at the hinge region. For discussion of Fab and F(ab')$_2$ fragments having increased in vivo half-life, see U.S. Pat. No. 5,869,046. Diabodies include two epitope-binding sites that may be bivalent. See, for example, EP 0404097; WO1993/01161; and Holliger, et al., Proc. Natl. Acad. Sci. USA 90 (1993) 6444-6448. Dual affinity retargeting antibodies (DART™; based on the diabody format but featuring a C-terminal disulfide bridge for additional stabilization (Moore et al., Blood 117, 4542-51 (2011)) can also be used. Antibody fragments can also include isolated CDRs. For a review of antibody fragments, see Hudson, et al., Nat. Med. 9 (2003) 129-134.

The antibody fragment may be produced by any means. For example, the antibody fragment may be enzymatically or chemically produced by fragmentation of an intact antibody or it may be recombinantly produced from a gene encoding the partial antibody sequence. Alternatively, the antibody fragment may be wholly or partially synthetically produced. The antibody fragment may include a single chain antibody fragment. In another embodiment, the fragment may include multiple chains that are linked together, for example, by disulfide linkages. The fragment may also include a multimolecular complex. A functional antibody fragment may typically include at least 50 amino acids and more typically will include at least 200 amino acids.

In particular embodiments, recombinant immunoglobulins can be produced. See, Cabilly, U.S. Pat. No. 4,816,567, and Queen et al., Proc Natl Acad Sci USA, 86:10029-10033 (1989).

As indicated, in particular embodiments, binding domains of an engineered antibody or antigen binding fragment may be joined through a linker. A linker is an amino acid sequence which can provide flexibility and room for conformational movement between the binding domains of an engineered antibody or antigen binding fragment. Any appropriate linker may be used. Examples of linkers can be found in Chen et al., Adv Drug Deliv Rev. 2013 Oct. 15; 65(10): 1357-1369. Linkers can be flexible, rigid, or semi-rigid, depending on the desired functional domain presentation to a target. Commonly used flexible linkers include Gly-Ser linkers such as GGSGGGSGGSG (SEQ ID NO: 142), GGSGGGSGSG (SEQ ID NO: 143) and GGSGGGSG (SEQ ID NO: 144). Additional examples include: GGGGSGGGGS (SEQ ID NO: 145); GGGSGGGS (SEQ ID NO: 146); and GGSGGS (SEQ ID NO: 147). Linkers that include one or more antibody hinge regions and/or immunoglobulin heavy chain constant regions, such as CH3 alone or a CH2CH3 sequence can also be used.

In some situations, flexible linkers may be incapable of maintaining a distance or positioning of binding domains needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs).

It will also be understood by one of ordinary skill in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation.

A monoclonal antibody includes an antibody obtained from a population of substantially homogeneous antibodies, i.e., the individual antibodies including the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. This type of antibody is produced by the daughter cells of a single antibody-producing hybridoma. A monoclonal antibody typically displays a single binding affinity for any epitope with which it binds.

The modifier "monoclonal" indicates the character of the antibody as being obtained from a homogeneous population of antibodies and is not to be construed as requiring production of the antibody by any particular method. Monoclonal antibodies recognize only one type of antigen. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies. Techniques for the production of antibodies are well known in the art and described in, e.g., Harlow and Lane "Antibodies, A Laboratory Manual", Cold Spring Harbor Laboratory Press, 1988; Harlow and Lane "Using Antibodies: A Laboratory Manual" Cold Spring Harbor Laboratory Press, 1999; Tickle et al. JALA: Journal of the Association for Laboratory Automation. 2009; 14(5): 303-307; Babcook et al. Proc. Natl. Acad. Sci. U.S.A. 1996; 93: 7843-7848; and U.S. Pat. No. 5,627,052.

In particular embodiments "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and peptide). The affinity of a molecule X for its partner Y can generally be represented by the dissociation constant ($K_D$) or the association constant ($K_A$). Affinity can be measured by common methods known in the art.

In particular embodiments, "bind" means that the binding domain of an antibody associates with its target peptide with a dissociation constant ($K_D$) of $10^{-8}$ M or less, in particular embodiments of from $10^{-5}$ M to $10^{-13}$ M, in particular embodiments of from $10^{-5}$ M to $10^{-10}$ M, in particular embodiments of from $10^{-5}$ M to $10^{-7}$ M, in particular embodiments of from $10^{-8}$ M to $10^{-13}$ M, or in particular embodiments of from $10^{-9}$ M to $10^{-13}$ M. The term can be further used to indicate that the binding domain does not bind to other biomolecules present, (e.g., it binds to other biomolecules with a dissociation constant ($K_D$) of $10^{-4}$ M or more, in particular embodiments of from $10^{-4}$ M to 1 M).

In particular embodiments, "bind" means that the binding domain of an antibody associates with its target peptide with an affinity constant (i.e., association constant, $K_A$) of $10^7$ $M^{-1}$ or more, in particular embodiments of from $10^5$ $M^{-1}$ to $10^{13}$ $M^{-1}$, in particular embodiments of from $10^5 M^{-1}$ to $10^{10}$ $M^{-1}$, in particular embodiments of from $10^5$ $M^{-1}$ to $10^8 M^{-1}$, in particular embodiments of from $10^7$ $M^{-1}$ to $10^{13}$ $M^{-1}$, or in particular embodiments of from $10^7$ $M^{-1}$ to $10^8$ $M^{-1}$. The term can be further used to indicate that the binding domain does not bind to other biomolecules present, (e.g., it binds to other biomolecules with an association constant ($K_A$) of $10^4$ $M^{-1}$ or less, in particular embodiments of from $10^4$ $M^{-1}$ to 1 $M^{-1}$).

Antibodies of the present disclosure can be used for immunoaffinity enrichment of peptides described herein detected in SRM assays for diagnosis of SCID, WAS, XLA, cystinosis, and WD. Particular embodiments of the high affinity antibodies include anti-CD3ε 197, anti-WASp 274, anti-WASp 289, anti-BTK 407, anti-BTK 545, anti-CTNS 115, anti-CTNS 120, anti-CTNS 194, anti-CTNS 360, anti-SHPK 44, anti-SHPK 363, anti-SHPK 388, anti-ATP7B 214, anti-ATP7B 325, anti-ATP7B 466, anti-ATP7B 589, anti-ATP7B 621, anti-ATP7B 887, anti-ATP7B 1056, and anti-ATP7B 1061.

In particular embodiments, the exemplary antibodies include the CDRs presented in Table 2.

TABLE 2

Exemplary anti-peptide antibody CDRs of the present disclosure:

| Antibody/Disease | VH CDRs | VL CDRs |
| --- | --- | --- |
| Anti-CD3ε 197/SCID | CDR1: EYVIH (SEQ ID NO: 22)<br>CDR2: GFNPNIGGTNYNQRFKG (SEQ ID NO: 23)<br>CDR3: GGPYYYAMDY (SEQ ID NO: 24) | CDR1: RSSQSIVHSSGNTYLE (SEQ ID NO: 25)<br>CDR2: KVSNRFS (SEQ ID NO: 26)<br>CDR3: FQGSHVPWT (SEQ ID NO: 27) |
| Anti-WASp 274/WAS | CDR1: TYAMT (SEQ ID NO: 28)<br>CDR2: SFYIEGSASYANWANGR (SEQ ID NO: 29)<br>CDR3: GNPGGSSAV (SEQ ID NO: 30) | CDR1: QSSETVYKNNYLA (SEQ ID NO: 31)<br>CDR2: WASKLAS (SEQ ID NO: 32)<br>CDR3: AGYQSNIVDGTA (SEQ ID NO: 33) |
| Anti-BTK 407/XLA | CDR1: RNEIS (SEQ ID NO: 34)<br>CDR2: GIGSPGRAYYATWAKSR (SEQ ID NO: 35)<br>CDR3: GDI | CDR1: QSSQSVYNNNRLA (SEQ ID NO: 36)<br>CDR2: SASTLAS (SEQ ID NO: 37)<br>CDR3: LGSYDCSTADCNA (SEQ ID NO: 38) |
| Anti-CTNS 115/cystinosis | CDR1: TRDGVC (SEQ ID NO: 39)<br>CDR2: CIYRGISATTSYASWAKGR (SEQ ID NO: 40)<br>CDR3: AWDL (SEQ ID NO: 41) | CDR1: QASQSIGSDLS (SEQ ID NO: 42)<br>CDR2: KASKVET (SEQ ID NO: 43)<br>CDR3: QSIDFSKSYIGGA (SEQ ID NO: 44) |
| Anti-CTNS 360/cystinosis | CDR1: NNDGIC (SEQ ID NO: 45)<br>CDR2: CIGSTSGRIYYASWAKGR (SEQ ID NO: 46)<br>CDR3: EPYGSGSMAFDL (SEQ ID NO: 47) | CDR1: QASQSIWNNNFLS (SEQ ID NO: 48)<br>CDR2: EASKLAS (SEQ ID NO: 49)<br>CDR3: QGEFSCSIADCVA (SEQ ID NO: 50) |
| Anti-SHPK 363/cystinosis | CDR1: SNYFMC (SEQ ID NO: 51)<br>CDR2: CILVGSGRTTFASWAKGR (SEQ ID NO: 52)<br>CDR3: AWAL (SEQ ID NO: 53) | CDR1: QASQSVYNNNDLA (SEQ ID NO: 54)<br>CDR2: GASTLVS (SEQ ID NO: 55)<br>CDR3: QGGYDPRNYP (SEQ ID NO: 56) |
| Anti-ATP7B 1056/WD | CDR1: SYWII (SEQ ID NO: 57)<br>CDR2: SSGPSGSAYYTSVVVKG (SEQ ID NO: 58)<br>CDR3: AGGSDYDWFDL (SEQ ID NO: 59) | CDR1: QSSPSVANNNWLS (SEQ ID NO: 60)<br>CDR2: GASTLAS (SEQ ID NO: 61)<br>CDR3: AGGHKTAEKNP (SEQ ID NO: 62) |

In particular embodiments, the exemplary antibodies include the variable heavy and variable light domains presented in Table 3.

TABLE 3

Exemplary anti-peptide antibody variable heavy and variable light domains of the present disclosure:

| Antibody/ Disease | VH Domain | VL Domain |
|---|---|---|
| Anti-CD3ε 197/SCID | EVQLQQSGPDLVKPGASVKISCKT SGYIFIEYVIHWVKQSHGKSLEWIG GFNPNIGGTNYNQRFKGKATLTVD KSSSTAYMELRSLTSEDSAVYYCV RGGPYYYAMDYWGQGTSVTVSS (SEQ ID NO: 63) | DVLMTQNPLSLPVSLGDQASISCR SSQSIVHSSGNTYLEWYLQKPGQ SPKVLIYKVSNRFSGVPDRFSGSG SGTDFTLKISRVEAEDLGVYYCFQ GSHVPWTFGGGTKLEIK (SEQ ID NO: 64) |
| Anti-WASp 274/WAS | QSVEESGGRLVTPGTPLTLTCTVS GFSLSTYAMTWVRQAPGKGLQWI GSFYIEGSASYANWANGRFTISKTS STVNLKMTSPTVADTASYFCARGN PGGSSAVWGQGTLVTVSS (SEQ ID NO: 65) | IVLTQTPASVSAAVGGTVTISCQS SETVYKNNYLAWYQQKLGQPPKL LIYWASKLASGVPSRFKGSGSGT QFTLTISDVVCADAGTYYCAGYQS NIVDGTAFGGGTEVVVN (SEQ ID NO: 66) |
| Anti-BTK 407/XLA | QSVKESEGGLFKPTDTLTVTCTVS GFSLSRNEISWFRQAPGNGLEWIG GIGSPGRAYYATWAKSRSTITRNT NLNTVTLKMTSLTAADTATYFCAR GDIWGPGTVVTVSS (SEQ ID NO: 67) | QVLTQTVSPVSAAVGSTVTINCQS SQSVYNNNRLAVVYQQKPGQPPK GLIYSASTLASGVSSRFKGSGSGT QFTLTISDVQCDDAATYYCLGSYD CSTADCNAFGGGTEVVVK (SEQ ID NO: 68) |
| Anti-CTNS 115/cystinosis | QEQLVESGGGLVQPEGSLTLTCKA SGFSFSTRDGVCVVVRQAPGKGLE WIACIYRGISATTSYASWAKGRFTI SKTSSTTVTLQMTSLTAADTATYFC ARAWDLWGPGTLVTVSS (SEQ ID NO: 69) | DVVMTQTPASVSEPVGGTVTIKC QASQSIGSDLSWYQQKPGQPPKR LIYKASKVETGVPSRFSGSGSGTE FTLTISDLECADASTYYCQSIDFSK SYIGGAFGGGTEVVVK (SEQ ID NO: 70) |
| Anti-CTNS 360/cystinosis | QSLEESGGGLFQPGASLTLTCTAS GFSFSNNDGICWVRQAPGKGLEWI GCIGSTSGRIYYASWAKGRLTISKT SSTTVILQMTSLTAADTATYFCASE PYGSGSMAFDLWGPGTLVTVSS (SEQ ID NO: 71) | QVLTQTASSVSAAVGGTVTVNCQ ASQSIWNNNFLSWYQQKPGQPPK LLIYEASKLASGVPSRFSGSGSGT QFTLTISGVQCDDAATYYCQGEFS CSIADCVAFGGGTEVVVR (SEQ ID NO: 72) |
| Anti-SHPK 363/cystinosis | QEQIEESGGGLVKPEGSLTLTCKV SGFDFSSNYFMCWVRQAPGKGLE WIGCILVGSGRTTFASWAKGRFTIS KTSSTTVTLQMTSLTAADTATYFCA RAWALWGPGTLVTVSS (SEQ ID NO: 73) | QVLTQTPSPVSAAVGGTVTISCQA SQSVYNNNDLAWYQQKPGQPPK LLIYGASTLVSGVPSRFSGSGSGA QFTLTISDLECDDAATYYCQGGYD PRNYPFGGGTEVVVK (SEQ ID NO: 74) |
| Anti-ATP7B 1056/WD | QSLEESGGRLVTPGGSLTVTCTVS GFSLSSYWIIWVRQAPGEGLEWIG SSGPSGSAYYTSWVKGRFTISKTS TTVDLKMTGLTTEDTATYFCARAG GSDYDWFDLWGQGTLVTVSS (SEQ ID NO: 75) | QVLTQTPSPVSAAVGGTVTINCQS SPSVANNNWLSWFQQKPGQRPK LLIYGASTLASGVPSRFKGSGSGT QFTLTISDVQCDDAATYYCAGGHK TAEKNPFGGGTEVVVK (SEQ ID NO: 76) |

In particular embodiments, amino acid sequences of exemplary antibodies include: Anti-CD3ε 197 heavy chain variable domain amino acid sequence with leader sequence (SEQ ID NO: 79); Anti-CD3ε 197 light chain variable domain amino acid sequence with leader sequence (SEQ ID NO: 81); Anti-WASp 274 heavy chain amino acid sequence with leader sequence (SEQ ID NO: 83); Anti-WASp 274 heavy chain variable domain amino acid sequence with leader sequence (SEQ ID NO: 85); Anti-WASp 274 heavy chain amino acid sequence without leader sequence (SEQ ID NO: 86); Anti-WASp 274 light chain amino acid sequence with leader sequence (SEQ ID NO: 88); Anti-WASp 274 light chain variable domain amino acid sequence with leader sequence (SEQ ID NO: 90); Anti-WASp 274 light chain amino acid sequence without leader sequence (SEQ ID NO: 91); Anti-BTK 407 heavy chain amino acid sequence with leader sequence (SEQ ID NO: 93); Anti-BTK 407 heavy chain variable domain amino acid sequence with leader sequence (SEQ ID NO: 95); Anti-BTK 407 heavy chain amino acid sequence without leader sequence (SEQ ID NO: 96); Anti-BTK 407 light chain amino acid sequence with leader sequence (SEQ ID NO: 98); Anti-BTK 407 light chain variable domain amino acid sequence with leader sequence (SEQ ID NO: 100); Anti-BTK 407 light chain amino acid sequence without leader sequence (SEQ ID NO: 101); Anti-CTNS 115 heavy chain amino acid sequence with leader sequence (SEQ ID NO: 103); Anti-CTNS 115 heavy chain variable domain amino acid sequence with leader sequence (SEQ ID NO: 105); Anti-CTNS 115 heavy chain amino acid sequence without leader sequence (SEQ ID NO: 106); Anti-CTNS 115 light chain amino acid sequence with leader sequence (SEQ ID NO: 108); Anti-CTNS 115 light chain variable domain amino acid sequence with leader sequence (SEQ ID NO: 110); Anti-CTNS 115 light chain amino acid sequence without leader sequence (SEQ ID NO: 111); Anti-CTNS 360 heavy chain amino acid sequence with leader sequence (SEQ ID NO: 113); Anti-CTNS 360 heavy chain variable domain amino acid sequence with leader sequence (SEQ ID NO: 115); Anti-CTNS 360 heavy chain amino acid sequence without leader sequence (SEQ ID NO: 116); Anti-CTNS 360 light chain amino acid sequence with leader sequence (SEQ ID NO: 118); Anti-CTNS 360 light chain variable domain amino acid sequence with leader sequence (SEQ ID NO: 120); Anti-CTNS 360 light chain amino acid sequence without leader sequence (SEQ ID NO: 121); Anti-SHPK 363 heavy chain amino acid sequence with leader sequence (SEQ ID NO: 123); Anti-SHPK 363 heavy chain variable domain amino acid sequence with leader sequence (SEQ ID NO: 125); Anti-SHPK 363 heavy chain amino acid sequence without leader sequence (SEQ ID NO: 126); Anti-SHPK 363 light chain amino acid sequence with leader sequence (SEQ ID NO: 128); Anti-SHPK 363 light chain variable domain amino acid sequence with leader sequence (SEQ ID NO: 130); Anti-SHPK 363 light chain amino acid sequence without leader sequence (SEQ ID NO: 131); Anti-ATP7B 1056 heavy chain amino acid sequence with leader sequence (SEQ ID NO: 133); Anti-ATP7B 1056 heavy chain variable domain amino acid sequence with leader sequence (SEQ ID NO: 135); Anti-ATP7B 1056 heavy chain amino acid sequence without leader sequence (SEQ ID NO: 136); Anti-ATP7B 1056 light chain amino acid sequence with leader sequence (SEQ ID NO: 138); Anti-ATP7B 1056 light chain variable domain amino acid sequence with leader sequence (SEQ ID NO: 140); and Anti-ATP7B 1056 light chain amino acid sequence without leader sequence (SEQ ID NO: 141).

In particular embodiments, coding sequences of exemplary antibodies include: Anti-CD3ε 197 heavy chain variable domain coding sequence with leader sequence (SEQ ID NO: 78); Anti-CD3ε 197 light chain variable domain coding sequence with leader sequence (SEQ ID NO: 80); Anti-WASp 274 heavy chain coding sequence (EB0603-2F8-H2) with leader sequence (SEQ ID NO: 82); Anti-WASp 274 heavy chain variable domain coding sequence with leader sequence (SEQ ID NO: 84); Anti-WASp 274 light chain coding sequence (EB0603-2F8-K2) with leader sequence (SEQ ID NO: 87); Anti-WASp 274 light chain variable domain coding sequence with leader sequence (SEQ ID NO: 89); Anti-BTK 407 heavy chain coding sequence (EB0602-1G5-H2) with leader sequence (SEQ ID NO: 92); Anti-BTK 407 heavy chain variable domain coding sequence with leader sequence (SEQ ID NO: 94); Anti-BTK 407 light chain coding sequence (EB0602-1G5-K1) with leader sequence (SEQ ID NO: 97); Anti-BTK 407 light chain variable domain coding sequence with leader sequence (SEQ ID NO: 99); Anti-CTNS 115 heavy chain coding sequence (EB0606-3H8-H5) with leader sequence (SEQ ID NO: 102); Anti-CTNS 115 heavy chain variable domain coding sequence with leader sequence (SEQ ID NO: 104); Anti-CTNS 115 light chain coding sequence (EB0606-3H8-K7) with leader sequence (SEQ ID NO: 107); Anti-CTNS 115 light chain variable domain coding sequence with leader sequence (SEQ ID NO: 109); Anti-CTNS 360 heavy chain coding sequence (EB0604-4E3-H4) with leader sequence (SEQ ID NO: 112); Anti-CTNS 360 heavy chain variable domain coding sequence with leader sequence (SEQ ID NO: 114); Anti-CTNS 360 light chain coding sequence (EB0604-4E3-K1) with leader sequence (SEQ ID NO: 117); Anti-CTNS 360 light chain variable domain coding sequence with leader sequence (SEQ ID NO: 119); Anti-SHPK 363 heavy chain coding sequence (EB0605B-6G12-H1) with leader sequence (SEQ ID NO: 122); Anti-SHPK 363 heavy chain variable domain coding sequence with leader sequence (SEQ ID NO: 124); Anti-SHPK 363 light chain coding sequence (EB0605B-6G12-K1) with leader sequence (SEQ ID NO: 127); Anti-SHPK 363 light chain variable domain coding sequence with leader sequence (SEQ ID NO: 129); Anti-ATP7B 1056 heavy chain coding sequence (EB0601-H3-1) with leader sequence (SEQ ID NO: 132); Anti-ATP7B 1056 heavy chain variable domain coding sequence with leader sequence (SEQ ID NO: 134); Anti-ATP7B 1056 light chain coding sequence (EB0601-K3-2) with leader sequence (SEQ ID NO: 137); and Anti-ATP7B 1056 light chain variable domain coding sequence with leader sequence (SEQ ID NO: 139).

(V) Enrichment Strategies for Peptides

Enrichment of a desired peptide target prior to SRM can be accomplished by any means known in the art. A host of enrichment procedures are available, including immuno adsorption-based depletion of abundant protein species from samples, precipitation, chromatography, electrophoresis, solvent partitioning, immunoprecipitation, immunoelectrophoresis, and immunochromatography. In particular embodiments, a SISCAPA method for specific antibody-based capture of individual tryptic peptides from a digest of a sample can be used. Anderson et al., J. Proteome Research 2004; 3: 235-244; U.S. Pat. No. 7,632,686.

In particular embodiments, the antibodies that bind the peptide markers, such as the antibodies disclosed herein, can be attached to a solid support. Particular embodiments use an affinity column, where antibodies are covalently coupled to chromatography media. In particular embodiments, POROS (Applied Biosystems, Foster City, Calif.) nanocolumns can be used in SISCAPA enrichment and features high binding capacity, a relatively high concentration of antibodies allowing for rapid enrichment of target peptides, and the ability to prepare columns with a variety of functionalized groups. Alternatively, antibodies can be attached to beads, magnetic beads, or other solid particle. One means of attachment is conjugation of the antibody to a protein coated on the beads. For example, Protein G coated particles offer the binding of antibodies in a preferred orientation. Other means of attachment can be used, such as direct coating of a bead with the antibody. Magnetic particles are available in a wide array of chemistries allowing for coupling to antibodies. Enrichment with antibodies attached to particles can allow parallel processing of samples. Magnetic particle processing has been automated in 96 well plates for the SISCAPA enrichment step with elution in the plates for analysis by mass spectrometry. Other particular embodiments use a novel bead trap device developed to perform the bead handling steps in line with a nanoflow chromatography system. Anderson et al. Mol Cell Proteomics 2009; 8(5): 995-1005. This minimizes losses of peptides to containers between elution and analysis steps. Peptide enrichment can also be implemented by immobilizing anti-peptide antibodies in pipet tips. Nelson et al. Anal Chem. 1995; 67(7): 1153-1158. After separation of the antibody bound peptide from free peptides, the bound peptide can be eluted. Any elution means can be used. One elution means which has been found to be efficient is 5% acetic acid/3% acetonitrile.

Other elution means, including other acids, and other concentrations of acetic acid can be used, as is efficient for a particular peptide.

(VI) Liquid Chromatography (LC)

In particular embodiments, one or more LC purification steps are performed prior to SRM-MS. A mixture of enriched peptides (the mobile phase) can be passed through a column packed with material (stationary phase) to separate the peptides based on their weight and affinity for the mobile and stationary phases of the column. Traditional LC analysis relies on the chemical interactions between sample components and column packing materials, where laminar flow of the sample through the column is the basis for separation of the analyte of interest from the test sample. The skilled artisan will understand that separation in such columns is a diffusional process. A variety of column packing materials are available for chromatographic separation of samples, and selection of an appropriate separation protocol is an empirical process that depends on the sample characteristics, the analyte of interest, the interfering substances present and their characteristics, etc. Various packing chemistries can be used depending on the needs (e.g., structure, polarity, and solubility of compounds being purified). In particular embodiments the columns are polar, ion exchange (both cation and anion), hydrophobic interaction, phenyl, C-2, C-8, C-18 columns, polar coating on porous polymer, or others that are commercially available. During chromatography, the separation of materials is affected by variables such as choice of eluant (also known as a "mobile phase"), choice of gradient elution and the gradient conditions, temperature, etc. In particular embodiments, an analyte may be purified by applying a sample to a column under conditions where the analyte of interest is reversibly retained by the column packing material, while one or more other materials are not retained. In these embodiments, a first mobile phase condition can be employed where the analyte of interest is retained by the column, and a second mobile phase condition can subsequently be employed to remove retained material from the column, once the non-retained materials are washed through. Alternatively, an analyte may be purified by applying a sample to a column under mobile phase conditions where the analyte of interest elutes at a differential rate in comparison to one or more other materials. As discussed above, such procedures may enrich the amount of one or more analytes of interest relative to one or more other components of the sample. In particular embodiments, the LC is nanoflow LC (nanoLC). In nanoflow LC (nanoLC) chromatographic separations are performed using flow rates in the range of low nanoliter per minute, which result in high analytical sensitivity due to the large concentration efficiency afforded by this type of chromatography. Cutillas, Current Nanoscience, 2005; 1: 65-71.

(VII) Mass Spectrometry (MS)

A mass spectrometer includes a gas phase ion spectrometer that measures a parameter that can be translated into mass-to-charge (m/z) ratios of gas phase ions. Mass spectrometry refers to the use of a mass spectrometer to detect gas phase ions. Mass spectrometers generally include an ion source and a mass analyzer. Examples of mass spectrometers are time-of-flight (TOF), magnetic sector, quadrupole filter, ion trap, ion cyclotron resonance, electrostatic sector analyzer and hybrids of these. A laser desorption mass spectrometer includes a mass spectrometer that uses laser energy as a means to desorb, volatilize, and ionize an analyte. A tandem mass spectrometer includes any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, Fourier transform ion cyclotron resonance mass spectrometers, electrostatic sector-magnetic sector mass spectrometers, and combinations thereof.

Ionization in mass spectrometry includes the process by which analytes in a sample are ionized. Such analytes may become charged molecules used for further analysis. For example, sample ionization may be performed by electrospray ionization (ESI), laserspray ionization (LSI) atmospheric pressure chemical ionization (APCI), photoionization, electron ionization, fast atom bombardment (FAB)/liquid secondary ionization (LSIMS), matrix assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

A mass analyzer includes the component of the mass spectrometer that takes ionized masses and separates them based on m/z ratios and outputs them to the detector where they are detected and later converted to a digital output. Suitable mass analyzers for determining m/z ratios include quadrupole mass analyzer, time-of-flight (TOF) mass analyzer, magnetic or electrostatic sector mass analyzer and ion trap (e.g. ion cyclotron resonance) mass analyzer.

A selected reaction monitoring (SRM)-MS assay targets a predetermined set of peptides for a given protein of interest. SRM is a tandem mass spectrometry mode in which an ion of a particular mass, the parent or precursor ion, is selected in the first stage of tandem mass spectrometry, and an ion product of a fragmentation reaction of the precursor ion is selected in the second mass spectrometry stage for detection. The specific pair of m/z values associated with a selected precursor ion and fragment ion is referred to as a transition. For each signature peptide, those fragment ions that provide optimal signal intensity and discriminate the targeted peptide from other species present in the sample are identified. Optimized transitions contribute to an effective SRM assay. Several such transitions (precursor/fragment ion pairs) are monitored over time, yielding a set of chromatographic traces with the retention time and signal intensity for a specific transition as coordinates. SRM-MS analysis of signature peptides are generally performed on a triple quadrupole mass spectrometer (QQQ-MS), an instrument with the capability to selectively isolate precursor ions corresponding to the m/z of the signature peptides and to selectively monitor peptide-specific fragment ions. In SRM analysis, the specificity depends on multiple mass analyzers (mass filters). The first quadrupole is to select the desired parent or precursor ion. The third quadrupole is to monitor the (one or more) fragment ion(s). The fragment ion(s) is generated through collisional induced dissociation in the second quadrupole. The two levels of mass selection allow high selectivity, as co-eluting background ions are filtered out very effectively. Unlike conventional tandem mass spectrometry (MS/MS) experiments that survey all analytes in a sample, SRM analysis selectively targets (filters) particular analytes, which translates into an increased sensitivity by one or two orders of magnitude compared with conventional 'full scan' techniques. In addition, SRM provides a linear response over a wide dynamic range up to five orders of magnitude. This enables the detection of low-abundance proteins in highly complex mixtures. Therefore, SRM is a highly specific detection/monitoring method with low background interference. When multiple parent ions are monitored in a single MS run, this type of analysis is known as multiple reaction monitoring (MRM). Using MRM analysis, multiple proteins and multiple regions (signature peptides) of a protein can be monitored in a single mass spectrometry run. Selected reaction monitoring/multiple reaction monitoring mass spectrometry (SRM/MRM-MS) is described in, e.g., U.S. Pat. No. 8,383,417, WO 2013/106603, and US 2013/105684.

In particular embodiments, the following parameters can be used to specify an LC-SRM-MS assay of a protein under a particular LC-SRM-MS system: (1) an enriched for tryptic peptide of a given protein; (2) the retention time (RT) of the peptide on an LC column; (3) the m/z value of the peptide precursor ion; (4) the declustering potential used to ionize the precursor ion; (5) the m/z value of a fragment ion generated from the peptide precursor ion; and (6) the collision energy (CE) used to fragment the peptide precursor ion that is optimized for the particular peptide. RT includes the elapsed time between injection and elution of an analyte. Declustering potential (DP) includes a voltage potential to dissolvate and dissociate ion clusters. It is also known as "fragmentor voltage" or "ion transfer capillary offset voltage" depending on the manufacturer. Collision energy (CE) includes the amount of energy precursor ions receive as they are accelerated into the collision cell.

To facilitate accurate quantification of the peptides by the methods disclosed herein, a set of isotopically-labeled synthetic versions of the peptides of interest may be added in known amounts to the sample for use as internal standards. Since the isotopically-labeled peptides have physical and chemical properties identical to the corresponding surrogate peptide, they co-elute from the chromatographic column and are easily identifiable on the resultant mass spectrum. Gerber et al. Proc. Natl. Asso. Sci. 2003; 100: 6940-6945; Kirkpatrick et al. Methods 2005; 35: 265-273. The isotopes with which amino acids in a given peptide can be labeled include $^{13}C$, $^{2}H$, $^{15}N$, $^{17}O$, $^{18}O$, and $^{34}S$. In particular embodiments, a peptide is labeled with $^{13}C$ and/or $^{15}N$ heavy isotopes. The addition of the labeled standards may occur before or after proteolytic digestion. In particular embodiments, the labeled internal standard peptides are added prior to an LC-MRM-MS assay. Methods of synthesizing isotopically-labeled peptides will be known to those of skill in the art. Thus, in particular embodiments, the experimental samples contain internal standard peptides. In particular embodiments, internal standard peptides include reference signature peptides. In particular embodiments, a signature peptide concentration can be determined by combining: (i) a ratio calculated from comparing the peak area of the signature peptide to the peak area of its corresponding reference signature peptide obtained from an LC-MRM-MS assay, and (ii) the known concentration of the reference signature peptide. Peptides selected as reference standards and suitable for quantification are sometimes referred to as quantotypic peptides (Q-peptides). Q-peptides include all of the characteristics of proteotypic peptides but also place restrictions on the residues that can constitute the reference peptide to eradicate artefactual modification and/or incomplete cleavage. Holman et al. Bioanalysis 2012; 4(14): 1763-1786.

Absolute quantitative levels of a given protein, or proteins, can be determined by the SRM/MRM methodology whereby the SRM/MRM signature peak area of an individual peptide from a given protein in one biological sample is compared to the SRM/MRM signature peak area of a known amount of a "spiked" internal standard. In particular embodiments, the internal standard is a synthetic version of the same exact peptide that contains one or more amino acid residues labeled with one or more heavy isotopes. Such isotope labeled internal standards are synthesized so that mass spectrometry analysis generates a predictable and consistent SRM/MRM signature peak that is different and distinct from the native peptide signature peak, and which can be used as a comparator peak. Thus, when the internal standard is spiked in known amounts into a protein preparation from a biological sample and analyzed by mass spectrometry, the signature peak area of the native peptide is compared to the signature peak area of the internal standard peptide, and this numerical comparison indicates either the absolute molarity and/or absolute weight of the native peptide present in the original protein preparation from the biological sample. Absolute quantitative data for fragment peptides are displayed according to the amount of protein analyzed per sample. Absolute quantitation can be performed across many peptides, and thus proteins, simultaneously in a single sample and/or across many samples to gain insight into absolute protein amounts in individual biological samples and in entire cohorts of individual samples.

Another strategy for absolute quantitation of peptides is equimolarity through equalizer peptide. This methodology involves chemically synthesizing the isotopically labeled Q-peptides of interest as dipeptides. A common amino acid sequence is positioned N-terminal to the Q-peptide and is referred to as the equalizer peptide. After solubilization and proteolytic digestion, the amount of Q-peptide can be accurately determined through reference to a single light-labeled peptide. Appropriate amounts of each standard peptide can then be added to a sample of interest (either predigested or prior to proteolysis) to facilitate absolute quantification. Holzmann et al. Anal. Chem. 2009; 81: 10254-10261. Absolute quantification can also employ quantification concatemer (QconCAT) proteins. Beynon et al. Nat. Methods 2005; 2: 587-589; Johnson et al. J. Am. Soc. Mass Spectrom. 2009; 20: 2211-2220; Ding et al. J. Proteome Res. 2011; 10: 3652-3659; Carroll et al. Molecular & Cellular Proteomics 2011; September 19: mcp-M111. In this strategy, a recombinant artificial protein that is an affinity tagged, concatenation of standard peptides from several proteins of interest is heterologously produced in Escherichia coli grown in stable isotopically enriched media. The QconCAT protein is then affinity purified and co-digested with the sample, generating a stoichiometric mixture of all the 'heavy' Q-peptides of which it is composed, and the proteolytic peptides from the native proteins and internal standard are subsequently analyzed. A variant of the QconCAT approach, termed peptide-concatenated standards (PCS), uses flanking regions between the Q-peptides in the artificial protein sequence that mirror their endogenous environment. Kito et al. J. Proteome Res. 2007; 6: 792-800. Other particular embodiments use protein standards for absolute quantification (PSAQ). Brun et al. Mol. Cell. Proteomics 2007; 6: 2139-2149. PSAQ uses recombinant proteins but rather than being a concatenation of peptides from several proteins, the entire protein to be quantified is expressed in stable isotope-labeled form. One or several PSAQs can then be added to the sample pre-digestion to facilitate quantification.

Particular embodiments use label-free strategies for protein quantification such as intensity based measurements (America and Cordewener, Proteomics 2008; 8: 731-749) or spectral counting (Lundgren et al. Expert Rev. Proteomics 2010; 7: 39-53).

To obtain relative quantitative levels of a given peptide, the mass spectrometry-derived signature peak area (or the peak height if the peaks are sufficiently resolved) of an individual peptide, or multiple peptides, from a given protein, in one biological sample can be compared to the signature peak area determined for the same peptide, or peptides, from the same protein, in one or more additional and different biological samples, using the same SRM/MRM methodology. In this way, the amount of a particular peptide, or peptides, from a given protein, is determined relative to the same peptide, or peptides, from the same protein across two or more biological samples under the same experimental conditions. In addition, relative quantitation can be determined for a given peptide, or peptides, from a single protein within a single sample by comparing the signature peak area for that peptide for that given protein by SRM/MRM methodology to the signature peak area for another and different peptide, or peptides, from a different protein within the same protein preparation from the biological sample. In this way, the amount of a particular peptide from a given protein, and therefore the amount of the given protein, is determined relative to another protein within the same sample. These approaches generate quantitation of an individual peptide, or peptides, from a given protein to the amount of another peptide, or peptides, from the same protein or from a different protein between samples and within samples wherein the amounts as determined by signature peak area are relative one to another, regardless of the absolute weight to volume or weight to weight amounts of peptides in the protein preparation from the biological sample. Relative quantitative data about individual signature peak areas between different samples can be normalized to the amount of protein analyzed per sample. Relative quantitation can be performed across many peptides simultaneously in a single sample and/or across many samples to gain insight into relative protein amounts.

Signature peptide levels can be expressed in concentration units (e.g., pmol/L). In particular embodiments, the mean concentration of a signature peptide in a test sample derived from a subject being screened for SCID, WAS, XLA, cystinosis, and/or WD can be compared to the mean concentration of the corresponding peptide in a normal control sample. In particular embodiments, a normal control sample can be derived from one or more normal control subjects or from a population of normal control subjects. In particular embodiments, a normal control subject includes a subject who does not have or is not known to have SCID, WAS, XLA, cystinosis, or WD. In particular embodiments, a normal control subject includes a subject who does not have genetic mutations associated with SCID, WAS, XLA, cystinosis, or WD.

In particular embodiments, the mean concentration of a CD3ε signature peptide in DBS from a population of normal control subjects includes a concentration in a range of 70 pmol/L to 400 pmol/L, in a range of 80 pmol/L to 300 pmol/L, and in a range of 90 pmol/L to 200 pmol/L. In particular embodiments, the mean concentration of a CD3ε signature peptide in DBS from a population of normal control subjects includes a concentration of 70 pmol/L, 80 pmol/L, 90 pmol/L, 100 pmol/L, 110 pmol/L, 120 pmol/L, 130 pmol/L, 140 pmol/L, 150 pmol/L, 160 pmol/L, 170 pmol/L, 180 pmol/L, 190 pmol/L, 200 pmol/L, 210 pmol/L, 220 pmol/L, 230 pmol/L, 240 pmol/L, 250 pmol/L, 260 pmol/L, 270 pmol/L, 280 pmol/L, 290 pmol/L, 300 pmol/L, 310 pmol/L, 320 pmol/L, 330 pmol/L, 340 pmol/L, 350 pmol/L, 360 pmol/L, 370 pmol/L, 380 pmol/L, 390 pmol/L, 400 pmol/L, or more.

In particular embodiments, the mean concentration of a WASp 274 signature peptide in DBS from a population of normal control subjects includes a concentration in a range of 600 pmol/L to 5000 pmol/L, in a range of 700 pmol/L to 3000 pmol/L, and in a range of 800 pmol/L to 2500 pmol/L. In particular embodiments, the mean concentration of a WASp 274 signature peptide in DBS from a population of normal control subjects includes a concentration of 600 pmol/L, 700 pmol/L, 800 pmol/L, 900 pmol/L, 1000 pmol/L, 1100 pmol/L, 1200 pmol/L, 1300 pmol/L, 1400 pmol/L, 1500 pmol/L, 1600 pmol/L, 1700 pmol/L, 1800 pmol/L, 1900 pmol/L, 2000 pmol/L, 2100 pmol/L, 2200 pmol/L, 2300 pmol/L, 2400 pmol/L, 2500 pmol/L, 2600 pmol/L, 2700 pmol/L, 2800 pmol/L, 2900 pmol/L, 3000 pmol/L, 3100 pmol/L, 3200 pmol/L, 3300 pmol/L, 3400 pmol/L, 3500 pmol/L, 3600 pmol/L, 3700 pmol/L, 3800 pmol/L, 3900 pmol/L, 4000 pmol/L, 4100 pmol/L, 4200 pmol/L, 4300 pmol/L, 4400 pmol/L, 4500 pmol/L, 4600 pmol/L, 4700 pmol/L, 4800 pmol/L, 4900 pmol/L, 5000 pmol/L, or more.

In particular embodiments, the mean concentration of a WASp 289 signature peptide in DBS from a population of normal control subjects includes a concentration in a range of 5500 pmol/L to 15000 pmol/L, in a range of 6000 pmol/L to 14000 pmol/L, and in a range of 6500 pmol/L to 13000 pmol/L. In particular embodiments, the mean concentration of a WASp 289 signature peptide in DBS from a population of normal control subjects includes a concentration of 5500 pmol/L, 5600 pmol/L, 5700 pmol/L, 5800 pmol/L, 5900 pmol/L, 6000 pmol/L, 6100 pmol/L, 6200 pmol/L, 6300 pmol/L, 6400 pmol/L, 6500 pmol/L, 6600 pmol/L, 6700 pmol/L, 6800 pmol/L, 6900 pmol/L, 7000 pmol/L, 7100 pmol/L, 7200 pmol/L, 7300 pmol/L, 7400 pmol/L, 7500 pmol/L, 7600 pmol/L, 7700 pmol/L, 7800 pmol/L, 7900 pmol/L, 8000 pmol/L, 8100 pmol/L, 8200 pmol/L, 8300 pmol/L, 8400 pmol/L, 8500 pmol/L, 8600 pmol/L, 8700 pmol/L, 8800 pmol/L, 8900 pmol/L, 9000 pmol/L, 9800 pmol/L, 9900 pmol/L, 10000 pmol/L, 10100 pmol/L, 10200 pmol/L, 10300 pmol/L, 10400 pmol/L, 10500 pmol/L, 10600 pmol/L, 10700 pmol/L, 10800 pmol/L, 10900 pmol/L, 11000 pmol/L, 11100 pmol/L, 11200 pmol/L, 11300 pmol/L, 11400 pmol/L, 11500 pmol/L, 11600 pmol/L, 11700 pmol/L, 11800 pmol/L, 11900 pmol/L, 12000 pmol/L, 12100 pmol/L, 12200 pmol/L, 12300 pmol/L, 12400 pmol/L, 12500 pmol/L, 12600 pmol/L, 12700 pmol/L, 12800 pmol/L, 12900 pmol/L, 13000 pmol/L, 13100 pmol/L, 13200 pmol/L, 113300 pmol/L, 13400 pmol/L, 13500 pmol/L, 13600 pmol/L, 13700 pmol/L, 13800 pmol/L, 13900 pmol/L, 14000 pmol/L, 14100 pmol/L, 14200 pmol/L, 14300 pmol/L, 14400 pmol/L, 14500 pmol/L, 14600 pmol/L, 14700 pmol/L, 14800 pmol/L, 14900 pmol/L, 15000 pmol/L, or more.

In particular embodiments, the mean concentration of a BTK 407 signature peptide in DBS from a population of normal control subjects includes a concentration in a range of 350 pmol/L to 2500 pmol/L, in a range of 450 pmol/L to 2400 pmol/L, and in a range of 550 pmol/L to 2300 pmol/L. In particular embodiments, the mean concentration of a BTK 407 signature peptide in DBS from a population of normal control subjects includes a concentration of 350 pmol/L, 400 pmol/L, 450 pmol/L, 500 pmol/L, 550 pmol/L, 600 pmol/L, 650 pmol/L, 700 pmol/L, 750 pmol/L, 800 pmol/L, 850 pmol/L, 900 pmol/L, 1000 pmol/L, 1100 pmol/L, 1200 pmol/L, 1300 pmol/L, 1400 pmol/L, 1500 pmol/L, 1600 pmol/L, 1700 pmol/L, 1800 pmol/L, 1900 pmol/L, 2000 pmol/L, 2100 pmol/L, 2200 pmol/L, 2300 pmol/L, 2400 pmol/L, 2500 pmol/L, or more.

In particular embodiments, the mean concentration of a BTK 545 signature peptide in DBS from a population of normal control subjects includes a concentration in a range of 550 pmol/L to 1600 pmol/L, in a range of 650 pmol/L to 1500 pmol/L, and in a range of 750 pmol/L to 1400 pmol/L. In particular embodiments, the mean concentration of a BTK 545 signature peptide in DBS from a population of normal control subjects includes a concentration of 550 pmol/L, 600 pmol/L, 650 pmol/L, 700 pmol/L, 750 pmol/L, 800 pmol/L, 850 pmol/L, 900 pmol/L, 950 pmol/L, 1000 pmol/L, 1050 pmol/L, 1100 pmol/L, 1150 pmol/L, 1200 pmol/L, 1250 pmol/L, 1300 pmol/L, 1350 pmol/L, 1400 pmol/L, 1450 pmol/L, 1500 pmol/L, 1550 pmol/L, 1600 pmol/L, or more.

In particular embodiments, the mean concentration of a CTNS 115 signature peptide in DBS from a population of normal control subjects includes a concentration in a range of 40 pmol/L to 250 pmol/L, in a range of 50 pmol/L to 200 pmol/L, and in a range of 60 pmol/L to 150 pmol/L. In particular embodiments, the mean concentration of a CTNS 115 signature peptide in DBS from a population of normal control subjects includes a concentration of 40 pmol/L, 45 pmol/L, 50 pmol/L, 55 pmol/L, 60 pmol/L, 65 pmol/L, 70 pmol/L, 75 pmol/L, 80 pmol/L, 85 pmol/L, 90 pmol/L, 95 pmol/L, 100 pmol/L, 110 pmol/L, 120 pmol/L, 130 pmol/L, 140 pmol/L, 150 pmol/L, 160 pmol/L, 170 pmol/L, 180 pmol/L, 190 pmol/L, 200 pmol/L, 210 pmol/L, 220 pmol/L, 230 pmol/L, 240 pmol/L, 250 pmol/L, or more.

In particular embodiments, the mean concentration of a SHPK 363 signature peptide in DBS from a population of normal control subjects includes a concentration in a range of 100 pmol/L to 8000 pmol/L, in a range of 300 pmol/L to 7000 pmol/L, and in a range of 500 pmol/L to 6000 pmol/L. In particular embodiments, the mean concentration of a SHPK 363 signature peptide in DBS from a population of normal control subjects includes a concentration of 100 pmol/L, 200 pmol/L, 300 pmol/L, 400 pmol/L, 500 pmol/L, 600 pmol/L, 700 pmol/L, 800 pmol/L, 900 pmol/L, 1000 pmol/L, 1500 pmol/L, 2000 pmol/L, 2500 pmol/L, 3000 pmol/L, 3500 pmol/L, 4000 pmol/L, 4500 pmol/L, 5000 pmol/L, 5500 pmol/L, 6000 pmol/L, 6500 pmol/L, 7000 pmol/L, 7500 pmol/L, 8000 pmol/L, or more.

In particular embodiments, the mean concentration of an ATP7B 214 signature peptide in DBS from a population of normal control subjects includes a concentration in a range of 30 pmol/L to 100 pmol/L, in a range of 40 pmol/L to 90 pmol/L, and in a range of 50 pmol/L to 80 pmol/L. In particular embodiments, the mean concentration of an ATP7B 214 signature peptide in DBS in a population of normal control subjects includes a concentration of 30 pmol/L, 35 pmol/L, 40 pmol/L, 45 pmol/L, 50 pmol/L, 55 pmol/L, 60 pmol/L, 65 pmol/L, 70 pmol/L, 75 pmol/L, 80 pmol/L, 85 pmol/L, 90 pmol/L, 95 pmol/L, 100 pmol/L, or more.

In particular embodiments, the mean concentration of an ATP7B 887 signature peptide in DBS from a population of normal control subjects includes a concentration in a range of 200 pmol/L to 500 pmol/L, in a range of 250 pmol/L to 450 pmol/L, and in a range of 300 pmol/L to 400 pmol/L. In particular embodiments, the mean concentration of an ATP7B 887 signature peptide in DBS from a population of normal control subjects includes a concentration of 200 pmol/L, 210 pmol/L, 220 pmol/L, 230 pmol/L, 240 pmol/L, 250 pmol/L, 260 pmol/L, 270 pmol/L, 280 pmol/L, 290 pmol/L, 300 pmol/L, 310 pmol/L, 320 pmol/L, 330 pmol/L, 340 pmol/L, 350 pmol/L, 360 pmol/L, 370 pmol/L, 380 pmol/L, 390 pmol/L, 400 pmol/L, 410 pmol/L, 420 pmol/L, 430 pmol/L, 440 pmol/L, 450 pmol/L, 460 pmol/L, 470 pmol/L, 480 pmol/L, 490 pmol/L, 500 pmol/L, or more.

In particular embodiments, the mean concentration of an ATP7B 1056 signature peptide in DBS from a population of normal control subjects includes a concentration in a range of 90 pmol/L to 400 pmol/L, in a range of 100 pmol/L to 300 pmol/L, and in a range of 150 pmol/L to 250 pmol/L. In particular embodiments, the mean concentration of an ATP7B 1056 signature peptide in DBS from a population of normal control subjects includes a concentration of 90 pmol/L, 100 pmol/L, 110 pmol/L, 120 pmol/L, 130 pmol/L, 140 pmol/L, 150 pmol/L, 160 pmol/L, 170 pmol/L, 180 pmol/L, 190 pmol/L, 200 pmol/L, 210 pmol/L, 220 pmol/L, 230 pmol/L, 240 pmol/L, 250 pmol/L, 260 pmol/L, 270 pmol/L, 280 pmol/L, 290 pmol/L, 300 pmol/L, 310 pmol/L, 320 pmol/L, 330 pmol/L, 340 pmol/L, 350 pmol/L, 360 pmol/L, 370 pmol/L, 380 pmol/L, 390 pmol/L, 400 pmol/L, or more.

One or more standard peptides may be synthesized with any method known in the pertinent art. Such synthetic peptides may further include amino acids with one or more natural modifications. Such natural modifications may include deamination of glutamine and asparagine, amination, oxidation, and hydroxylation.

(VIII) Methods of Use

The methods of the present disclosure include identifying individuals with one or more of SCID, WAS, XLA, cystinosis, and/or WD. In particular embodiments, diagnosing individuals with SCID, WAS, XLA, cystinosis, and/or WD is performed early, for example, as part of NBS, or before symptoms of a disorder are evident in the individual.

The methods of the present disclosure include obtaining DBS samples. In particular embodiments, DBS are obtained according to a method described above. In particular embodiments, DBS are obtained from a DBS repository or lab that stores DBS for future testing.

The methods of the present disclosure include digesting proteins in DBS with digestion enzymes. In particular embodiments, one or more punches of the DBS or the whole DBS can be solubilized in an appropriate buffer, and an appropriate digestion enzyme described above can be added to digest proteins present in DBS into peptide fragments. In particular embodiments, DBS can be solubilized with 0.1% ProteaseMax™ in 50 mM ammonium biocarbonate (pH 8) and digested with trypsin.

The methods of the present disclosure include enriching for signature peptides that are used in screening for SCID, WAS, XLA, cystinosis, and/or WD. Signature peptides include CD3ε 197 for SCID; WASp 274 for WAS; WASp 289 for WAS; BTK 407 for XLA; BTK 545 for XLA; CTNS 115 for cystinosis; CTNS 120 for cystinosis; CTNS 194 for cystinosis; CTNS 360 for cystinosis; SHPK 44 for cystinosis; SHPK 363 for cystinosis; SHPK 388 for cystinosis; ATP7B 214 for WD; ATP7B 325 for WD; ATP7B 466 for WD; ATP7B 589 for WD; ATP7B 621 for WD; ATP7B 887 for WD; ATP7B 1056 for WD; and ATP7B 1061 for WD. In particular embodiments, signature peptides include the peptides disclosed in FIG. 1: CD3ε 197 for SCID; WASp 274 for WAS; WASp 289 for WAS; BTK 407 for XLA; BTK 545 for XLA; CTNS 115 for cystinosis; CTNS 360 for cystinosis; SHPK 363 for cystinosis; ATP7B 325 for WD; and ATP7B 1056 for WD. In particular embodiments, signature peptides include the peptides of Table 1: CTNS 120 for cystinosis; CTNS 194 for cystinosis; SHPK 44 for cystinosis; SHPK 388 for cystinosis; ATP7B 214 for WD; ATP7B 466 for WD; ATP7B 589 for WD; ATP7B 621 for WD; ATP7B 887 for WD; and ATP7B 1061 for WD. In particular embodiments, enriching for signature peptides include contacting mixtures of peptide fragments from digested DBS with one or more binding entities that recognize the signature peptides. In particular embodiments, the binding entities are antibodies or antigen binding fragments thereof. In particular embodiments, the antibodies include those disclosed in Tables 2 and 3 above. In particular embodiments, amino acid sequences of antibodies of the disclosure include SEQ ID NOs: 79, 81, 83, 85, 86, 88, 90, 91, 93, 95, 96, 98, 100, 101, 103, 105, 106, 108, 110, 111, 113, 115, 116, 118, 120, 121, 123, 125, 126, 128, 130, 131, 133, 135, 136, 138, 140, and 141. In particular embodiments, coding sequences of antibodies of the disclosure include SEQ ID NOs: 78, 80, 82, 84, 87, 89, 92, 94, 97, 99, 102, 104, 107, 109, 112, 114, 117, 119, 122, 124, 127, 129, 132, 134, 137, and 139. In particular embodiments, the antibodies include antibodies that bind CD3ε 197, WASp 274, WASp 289, BTK 407, BTK 545, CTNS 115, CTNS 120, CTNS 194, SHPK 44, SHPK 363, SHPK 388, ATP7B 214, ATP7B 325, ATP7B 466, ATP7B 589, ATP7B 621, ATP7B 887, ATP7B 1056, and ATP7B 1061.

In particular embodiments, antibodies including SEQ ID NOs: 22-27, 63, and 64 are used to enrich for a CD3ε peptide including SEQ ID NO: 1.

In particular embodiments, antibodies including SEQ ID NOs: 28-33, 65 and 66 are used to enrich for a WASp peptide including SEQ ID NO: 2. In particular embodiments, antibodies are used to enrich for a WASp peptide including SEQ ID NO: 3.

In particular embodiments, antibodies including SEQ ID NOs: 34-38, 67, and 68 are used to enrich for a BTK peptide including SEQ ID NO: 4. In particular embodiments, antibodies are used to enrich for a BTK peptide including SEQ ID NO: 5.

In particular embodiments, the following combination of antibodies can be used to screen for SCID, WAS, and XLA: antibodies including SEQ ID NOs: 22-27, 63, and 64 that bind to a CD3ε peptide including SEQ ID NO: 1; antibodies including SEQ ID NOs: 28-33, 65 and 66 that bind to a WASp peptide including SEQ ID NO: 2; antibodies that bind to a WASp peptide including SEQ ID NO: 3; antibodies including SEQ ID NOs: 34-38, 67, and 68 that bind to a BTK peptide including SEQ ID NO: 4; and antibodies that bind to a BTK peptide including SEQ ID NO: 5.

In particular embodiments, the following combination of antibodies can be used to screen for SCID, WAS, and XLA: antibodies including SEQ ID NOs: 22-27, 63, and 64 that bind to a CD3ε peptide including SEQ ID NO: 1; antibodies including SEQ ID NOs: 28-33, 65 and 66 that bind to a WASp peptide including SEQ ID NO: 2; antibodies that bind to a WASp peptide including SEQ ID NO: 3; and antibodies including SEQ ID NOs: 34-38, 67, and 68 that bind to a BTK peptide including SEQ ID NO: 4.

In particular embodiments, the following combination of antibodies can be used to screen for SCID, WAS, and XLA: antibodies including SEQ ID NOs: 22-27, 63, and 64 that bind to a CD3ε peptide including SEQ ID NO: 1; antibodies including SEQ ID NOs: 28-33, 65 and 66 that bind to a WASp peptide including SEQ ID NO: 2; antibodies including SEQ ID NOs: 34-38, 67, and 68 that bind to a BTK peptide including SEQ ID NO: 4; and antibodies that bind to a BTK peptide including SEQ ID NO: 5.

In particular embodiments, the following combination of antibodies can be used to screen for SCID, WAS, and XLA: antibodies including SEQ ID NOs: 22-27, 63, and 64 that bind to a CD3ε peptide including SEQ ID NO: 1; antibodies including SEQ ID NOs: 28-33, 65 and 66 that bind to a WASp peptide including SEQ ID NO: 2; and antibodies including SEQ ID NOs: 34-38, 67, and 68 that bind to a BTK peptide including SEQ ID NO: 4.

In particular embodiments, antibodies including SEQ ID NOs: 39-44, 69, and 70 are used to enrich for a CTNS peptide including SEQ ID NO: 6. In particular embodiments, antibodies including SEQ ID NOs: 45-50, 71, and 72 are used to enrich for a CTNS peptide including SEQ ID NOs: 7 and 8. In particular embodiments, antibodies are used to enrich for a CTNS peptide of SEQ ID NO: 12. In particular embodiments, antibodies are used to enrich for a CTNS peptide of SEQ ID NO: 13.

In particular embodiments, antibodies including SEQ ID NOs: 51-56, 73, and 74 are used to enrich for a SHPK peptide including SEQ ID NO: 9. In particular embodiments, antibodies are used to enrich for a SHPK peptide of SEQ ID NO: 14. In particular embodiments, antibodies are used to enrich for a SHPK peptide of SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; and antibodies that bind to a SHPK peptide including SEQ ID NO: 14.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 13; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; and antibodies that bind to a SHPK peptide including SEQ ID NO: 14.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies including SEQ ID NOs: 51-56, 73, and 74 that bind to a SHPK peptide including SEQ ID NO: 9; and antibodies that bind to a SHPK peptide including SEQ ID NO: 14.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 13; antibodies including SEQ ID NOs: 51-56, 73, and 74 that bind to a SHPK peptide including SEQ ID NO: 9; and antibodies that bind to a SHPK peptide including SEQ ID NO: 14.

In particular embodiments, the following combination of antibodies can be used to screen for cystinosis: antibodies including SEQ ID NOs: 39-44, 69, and 70 that bind to a CTNS peptide including SEQ ID NO: 6; antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; and antibodies that bind to a SHPK peptide including SEQ ID NO: 14.

In particular embodiments, the following combination of antibodies can be used to screen for cystinosis: antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; and antibodies that bind to a SHPK peptide including SEQ ID NO: 14.

In particular embodiments, the following combination of antibodies can be used to screen for cystinosis: antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 45-50, 71, and 72 that bind to a CTNS peptide including SEQ ID NOs: 7 and 8; antibodies that bind to a CTNS peptide including SEQ ID NO: 13; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies that bind to a CTNS peptide including SEQ ID NO: 13; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies that bind to a CTNS peptide including SEQ ID NO: 12; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies that bind to a CTNS peptide including SEQ ID NO: 12; antibodies that bind to a CTNS peptide including SEQ ID NO: 13; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 13; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 13; antibodies including SEQ ID NOs: 51-56, 73, and 74 that bind to a SHPK peptide including SEQ ID NO: 9; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a SHPK peptide including SEQ ID NO: 14; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies including SEQ ID NOs: 51-56, 73, and 74 that bind to a SHPK peptide including SEQ ID NO: 9; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; and antibodies that bind to a SHPK peptide including SEQ ID NO: 15.

In particular embodiments, the following combination of antibodies can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; and antibodies including SEQ ID NOs: 51-56, 73, and 74 that bind to a SHPK peptide including SEQ ID NO: 9.

In particular embodiments, the following combination of antibodies can be used to screen for cystinosis: antibodies including SEQ ID NOs: 39-44, 69, and 70 that bind to a CTNS peptide including SEQ ID NO: 6; and antibodies including SEQ ID NOs: 51-56, 73, and 74 that bind to a SHPK peptide including SEQ ID NO: 9.

One of ordinary skill in the art can recognize that other combinations of antibodies selected from the following can be used to screen for cystinosis: antibodies including SEQ ID NOs: 39-44, 69, and 70 that bind to a CTNS peptide including SEQ ID NO: 6; antibodies including SEQ ID NOs: 45-50, 71, and 72 that bind to a CTNS peptide including SEQ ID NOs: 7 and 8; antibodies that bind to a CTNS peptide including SEQ ID NO: 12; antibodies that bind to a CTNS peptide including SEQ ID NO: 13; antibodies including SEQ ID NOs: 51-56, 73, and 74 that bind to a SHPK peptide including SEQ ID NO: 9; antibodies that bind to a SHPK peptide including SEQ ID NO: 14; and antibodies that bind to a SHPK peptide including SEQ ID NO: 15.

In particular embodiments, antibodies are used to enrich for an ATP7B peptide including SEQ ID NO: 10. In particular embodiments, antibodies including SEQ ID NOs: 57-62, 75, and 76 are used to enrich for an ATP7B peptide including SEQ ID NO: 11 or 21. In particular embodiments, antibodies are used to enrich for an ATP7B peptide of SEQ ID NO: 16. In particular embodiments, antibodies are used to enrich for an ATP7B peptide of SEQ ID NO: 17. In particular embodiments, antibodies are used to enrich for an ATP7B peptide of SEQ ID NO: 18. In particular embodiments, antibodies are used to enrich for an ATP7B peptide of SEQ ID NO: 19. In particular embodiments, antibodies are used to enrich for an ATP7B peptide of SEQ ID NO: 20. In particular embodiments, antibodies are used to enrich for an ATP7B peptide of SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; and antibodies that bind to an ATP7B peptide including SEQ ID NO: 20.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 18; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; antibodies that bind to an ATP7B peptide including SEQ ID NO: 20; and antibodies that bind to an ATP7B peptide including SEQ ID NO:

In particular embodiments, the following combination of antibodies can be used to screen for WD: antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; and antibodies that bind to an ATP7B peptide including SEQ ID NO: 19.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; and antibodies that bind to an ATP7B peptide including SEQ ID NO: 20.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 19; and antibodies that bind to an ATP7B peptide including SEQ ID NO: 20, In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 18; antibodies that bind to an ATP7B peptide including SEQ ID NO: 19; and antibodies that bind to an ATP7B peptide including SEQ ID NO: 20.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; and antibodies that bind to an ATP7B peptide including SEQ ID NO: 20.

In particular embodiments, the following combination of antibodies can be used to screen for WD: antibodies that bind to an ATP7B peptide including SEQ ID NO: 10; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; and antibodies that bind to an ATP7B peptide including SEQ ID NO: 20.

In particular embodiments, the following combination of antibodies can be used to screen for WD: antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; and antibodies that bind to an ATP7B peptide including SEQ ID NO: 20.

In particular embodiments, the following combination of antibodies can be used to screen for WD: antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies including SEQ ID NOs: 57-62, 75, and 76 that bind to an ATP7B peptide including SEQ ID NO: 11 or 21; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 18; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 18; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 18; antibodies that bind to an ATP7B peptide including SEQ ID NO: 19; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 20; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 19; and antibodies that bind to an ATP7B peptide including SEQ ID NO: 21.

In particular embodiments, the following combination of antibodies can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; and antibodies that bind to an ATP7B peptide including SEQ ID NO: 21.

In particular embodiments, the following combination of antibodies can be used to screen for WD: antibodies including SEQ ID NOs: 57-62, 75, and 76 that bind to an ATP7B peptide including SEQ ID NO: 11 or 21; antibodies that bind to an ATP7B peptide including SEQ ID NO: 16; and antibodies that bind to an ATP7B peptide including SEQ ID NO: 20.

One of ordinary skill in the art can recognize that other combinations of antibodies selected from the following can be used to screen for WD: antibodies that bind to an ATP7B peptide including SEQ ID NO: 10; antibodies including SEQ ID NOs: 57-62, 75, and 76 that bind to an ATP7B peptide including SEQ ID NO: 11 or 21; antibodies that bind to an ATP7B peptide including SEQ ID NO: 16; antibodies that bind to an ATP7B peptide including SEQ ID NO: 17; antibodies that bind to an ATP7B peptide including SEQ ID NO: 18; antibodies that bind to an ATP7B peptide including SEQ ID NO: 19; antibodies that bind to an ATP7B peptide including SEQ ID NO: 20; and antibodies that bind to an ATP7B peptide including SEQ ID NO: 21.

The methods of the present disclosure include optionally performing liquid chromatography on the immunoaffinity enriched peptides to separate the peptides prior to MS analysis. Liquid chromatography can separate peptides based on their weight and affinity for the mobile and stationary phases of the column.

The methods of the present disclosure include performing SRM-MS or MRM-MS on the immunoaffinity enriched peptides to quantify the amount of a given signature peptide. In particular embodiments, the SRM-MS or MRM-MS is carried out as described above. In particular embodiments, the quantification of a signature peptide includes using a reference peptide that is introduced into an assay in known amounts. In particular embodiments, a reference peptide can be identical to the signature peptide in every respect except that the reference peptide has been differentially labeled, for example, with one or more heavy isotopes, to distinguish the reference peptide from the signature peptide.

In particular embodiments, SRM-MS or MRM-MS detects a reduction or absence in a CD3ε peptide. In particular embodiments, the CD3ε peptide includes SEQ ID NO: 1.

In particular embodiments, SRM-MS or MRM-MS detects a reduction or absence in a WASp peptide. In particular embodiments, the WASp peptide includes SEQ ID NO: 2. In particular embodiments, the WASp peptide includes SEQ ID NO: 3.

In particular embodiments, SRM-MS or MRM-MS detects a reduction or absence in a BTK peptide. In particular embodiments, the BTK peptide includes SEQ ID NO: 4. In particular embodiments, the BTK peptide includes SEQ ID NO: 5.

In particular embodiments, SRM-MS or MRM-MS detects a reduction or absence in a CTNS peptide. In particular embodiments, the CTNS peptide includes SEQ ID NO: 6. In particular embodiments, the CTNS peptide includes SEQ ID NOs: 7 and 8. In particular embodiments, the CTNS peptide includes SEQ ID NO: 12. In particular embodiments, the CTNS peptide includes SEQ ID NO: 13.

In particular embodiments, SRM-MS or MRM-MS detects a reduction or absence in a SHPK peptide. In particular embodiments, the SHPK peptide includes SEQ ID NO: 9. In particular embodiments, the SHPK peptide includes SEQ ID NO: 14. In particular embodiments, the SHPK peptide includes SEQ ID NO: 15.

In particular embodiments, SRM-MS or MRM-MS detects a reduction or absence in an ATP7B peptide. In particular embodiments, the ATP7B peptide includes SEQ ID NO: 10. In particular embodiments, the ATP7B peptide includes SEQ ID NO: 11 or 21. In particular embodiments, the ATP7B peptide includes SEQ ID NO: 16. In particular embodiments, the ATP7B peptide includes SEQ ID NO: 17. In particular embodiments, the ATP7B peptide includes SEQ ID NO: 18. In particular embodiments, the ATP7B peptide includes SEQ ID NO: 19. In particular embodiments, the ATP7B peptide includes SEQ ID NO: 20. In particular embodiments, the ATP7B peptide includes SEQ ID NO: 21.

In particular embodiments, a predetermined cut-off value is used as a threshold for a given signature peptide. A concentration of a given signature peptide above the threshold indicates that the assayed DBS is from an individual not afflicted by SCID, WAS, XLA, cystinosis, or WD. A concentration of a given signature peptide below the threshold or absent indicates that the assayed DBS is from an individual afflicted by SCID, WAS, XLA, cystinosis, or WD. In particular embodiments, the threshold can be determined by analysis of a population of normal controls and calculation of standard deviation (SD) of a concentration of a given signature peptide in this population. The threshold can be set at a certain SD from the mean concentration of the given signature peptide. In particular embodiments, the threshold is −1 SD, −1.1 SD, −1.2 SD, −1.3 SD, −1.4 SD, −1.5 SD, −1.6 SD, −1.7 SD, −1.8 SD, −1.9 SD, −2.0 SD, −2.1 SD, −2.2 SD, −2.3 SD, −2.4 SD, −2.5 SD, −2.6 SD, −2.7 SD, −2.8 SD, −2.9 SD, −3.0 SD, or more SD from the mean concentration of the given signature peptide. In particular embodiments, for diagnosis or screening of SCID, WAS, XLA, or cystinosis, the threshold can be determined by analysis of a population of normal controls and calculation of standard deviation (SD) of a ratio of a concentration of a given signature peptide to an endogenous concentration of ATP7B in this population. Peptide concentration cutoffs for each PIDD can be set at a certain SD derived from mean concentration of each signature peptide or ratio of a concentration of a given signature peptide to an endogenous concentration of ATP7B.

In particular embodiments, the threshold concentration for the CD3ε 197 peptide includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of CD3ε 197 in a population of normal controls. In particular embodiments, the threshold concentration for the CD3ε 197 peptide includes 60 pmol/L or less, 55 pmol/L or less, 50 pmol/L or less, 45 pmol/L or less, 40 pmol/L or less, 39 pmol/L or less, 38 pmol/L or less, 37 pmol/L or less, 36 pmol/L or less, 35 pmol/L or less, 34 pmol/L or less, 33 pmol/L or less, 32 pmol/L or less, 31 pmol/L or less, 30 pmol/L or less.

In particular embodiments, the threshold concentration for the WASp 274 peptide includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of WASp 274 in a population of normal controls. In particular embodiments, the threshold concentration for the WASp 274 peptide includes 220 pmol/L or less, 215 pmol/L or less, 210 pmol/L or less, 205 pmol/L or less, 200 pmol/L or less, 195 pmol/L or less, 190 pmol/L or less, 185 pmol/L or less, 180 pmol/L or less, 175 pmol/L or less, 170 pmol/L or less, 165 pmol/L or less, 160 pmol/L or less, 155 pmol/L or less, 150 pmol/L or less.

In particular embodiments, the threshold concentration for the WASp 289 peptide includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of WASp 289 in a population of normal controls. In particular embodiments, the threshold concentration for the WASp 289 peptide includes 2500 pmol/L or less, 2490 pmol/L or less, 2480 pmol/L or less, 2470 pmol/L or less, 2460 pmol/L or less, 2450 pmol/L or less, 2440 pmol/L or less, 2430 pmol/L or less, 2420 pmol/L or less, 2410 pmol/L or less, 2400 pmol/L or less.

In particular embodiments, the threshold concentration for the BTK 407 peptide includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of BTK 407 in a population of normal controls. In particular embodiments, the threshold concentration for the BTK 407 peptide includes 80 pmol/L or less, 75 pmol/L or less, 70 pmol/L or less, 65 pmol/L or less, 60 pmol/L or less, 55 pmol/L or less, 50 pmol/L or less, 49 pmol/L or less, 48 pmol/L or less, 47 pmol/L or less, 46 pmol/L or less, 45 pmol/L or less, 44 pmol/L or less, 43 pmol/L or less, 42 pmol/L or less, 41 pmol/L or less, 40 pmol/L or less, 35 pmol/L or less, 30 pmol/L or less.

In particular embodiments, the threshold concentration for the BTK 545 peptide includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of BTK 545 in a population of normal controls. In particular embodiments, the threshold concentration for the BTK 545 peptide includes 110 pmol/L or less, 109 pmol/L or less, 108 pmol/L or less, 107 pmol/L or less, 106 pmol/L or less, 105 pmol/L or less, 104 pmol/L or less, 103 pmol/L or less, 102 pmol/L or less, 101 pmol/L or less, 100 pmol/L or less.

In particular embodiments, the threshold concentration for the CTNS 115 peptide includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of CTNS 115 in a population of normal controls. In particular embodiments, the threshold concentration for the CTNS 115 peptide includes 60 pmol/L or less, 59 pmol/L or less, 58 pmol/L or less, 57 pmol/L or less, 56 pmol/L or less, 55 pmol/L or less, 54 pmol/L or less, 53 pmol/L or less, 52 pmol/L or less, 51 pmol/L or less, 50 pmol/L or less.

In particular embodiments, the threshold concentration for the SHPK 363 peptide includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of SHPK 363 in a population of normal controls. In particular embodiments, the threshold concentration for the SHPK 363 peptide includes 2000 pmol/L or less, 1950 pmol/L or less, 1900 pmol/L or less, 1850 pmol/L or less, 1800 pmol/L or less, 1750 pmol/L or less, 1700 pmol/L or less, 1650 pmol/L or less, 1600 pmol/L or less, 1550 pmol/L or less, 1500 pmol/L or less.

In particular embodiments, the threshold concentration for the ATP7B 1056 peptide includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of ATP7B 1056 in a population of normal controls. In particular embodiments, the threshold concentration for the ATP7B 1056 peptide includes 90 pmol/L or less, 85 pmol/L or less, 80 pmol/L or less, 75 pmol/L or less, 70 pmol/L or less, 65 pmol/L or less, 60 pmol/L or less, 55 pmol/L or less, 50 pmol/L or less, 45 pmol/L or less, 40 pmol/L or less, 35 pmol/L or less, 30 pmol/L or less.

In particular embodiments, the threshold concentration for the ATP7B 214 peptide includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of ATP7B 214 in a population of normal controls. In particular embodiments, the threshold concentration for the ATP7B 214 peptide includes 30 pmol/L or less, 29 pmol/L or less, 28 pmol/L or less, 27 pmol/L or less, 26 pmol/L or less, 25 pmol/L or less, 24 pmol/L or less, 23 pmol/L or less, 22 pmol/L or less, 21 pmol/L or less, 20 pmol/L or less.

In particular embodiments, the threshold concentration for the ATP7B 887 peptide includes −1.0 SD, −1.25 SD, −1.3 SD, −1.35 SD, −1.4 SD, −1.45 SD, −1.5 SD, −1.55 SD, −1.6 SD, −1.65 SD, −1.7 SD, −1.75 SD, −1.8 SD, −1.85 SD, −1.9 SD, −1.95 SD, −2.0 SD, −2.25 SD, −2.3 SD, −2.35 SD, −2.4 SD, −2.45 SD, −2.5 SD, −2.55 SD, −2.6 SD, −2.65 SD, −2.7 SD, −2.75 SD, −2.8 SD, −2.85 SD, −2.9 SD, −2.95 SD, −3.0 SD, or more from the mean concentration of ATP7B 887 in a population of normal controls. In particular embodiments, the threshold concentration for the ATP7B 887 peptide includes 190 pmol/L or less, 185 pmol/L or less, 180 pmol/L or less, 175 pmol/L or less, 170 pmol/L or less, 165 pmol/L or less, 160 pmol/L or less, 155 pmol/L or less, 150 pmol/L or less, 145 pmol/L or less, 140 pmol/L or less.

In particular embodiments, a signature peptide can be considered a primary biomarker for diagnosis or screening of a given disease. A primary signature peptide can include peptides that are used first to diagnose or screen for a given disease. In particular embodiments, a primary marker can be reproducibly obtained from a digestion of the corresponding protein, has high affinity antibodies for immunoaffinity enrichment, and/or is reproducible across independent liquid chromatography columns and/or mass spectrometry instruments. In particular embodiments, a signature peptide can be considered a secondary marker for diagnosis or screening of a given disease. A secondary signature peptide can include peptides that are used second to confirm a diagnosis or screening of a given disease with a primary marker. In particular embodiments, BTK 545 can be a secondary marker to BTK 407 in diagnosing XLA. In particular embodiments, WASp 289 can be a secondary marker to WASp 274 in diagnosing WAS.

In particular embodiments, antibodies of the present disclosure can also be used in complimentary clinical tests for the diagnosis of primary immunodeficiencies, cystinosis, and WD for those patients with ambiguous biochemical results, and for patients who carry the variants of unknown significance from genetic tests.

Methods disclosed herein include treating subjects (e.g., humans) based upon the outcome of screening for SCID, WAS, XLA, cystinosis, and/or WD with compositions and methods disclosed herein. Treating subjects includes delivering therapeutically effective amounts. Therapeutically effective amounts include those that provide effective amounts, prophylactic treatments and/or therapeutic treatments.

An "effective amount" is the amount of a composition necessary to result in a desired physiological change in the subject. For example, an effective amount can provide an alleviation of symptoms, an elimination of symptoms, or a cure for SCID, WAS, XLA, cystinosis, and/or WD. Effective amounts are often administered for research purposes. Effective amounts disclosed herein can cause a statistically-significant effect in an animal model or in vitro assay relevant to the assessment of a disease's development, progression, and/or resolution.

Particular embodiments may include administering compositions as a "prophylactic treatment." Prophylactic treatments include those administered to a subject who does not display signs or symptoms of SCID, WAS, XLA, cystinosis, and/or WD or displays only early signs or symptoms of SCID, WAS, XLA, cystinosis, and/or WD, such that treatment is administered for the purpose of diminishing or decreasing the risk of developing the disorder. Thus, a prophylactic treatment functions as a preventative treatment against SCID, WAS, XLA, cystinosis, and/or WD.

In particular embodiments, a prophylactic treatment can prevent, delay, or reduce the onset of SCID, WAS, XLA, cystinosis, and/or WD. In particular embodiments, a prophylactic treatment can be given prior, concurrently, or after other preventative measures, such as the use of antibiotics for WAS and XLA. In particular embodiments, a prophylactic treatment can prevent or reduce the severity of symptoms or complications associated with SCID, WAS, XLA, cystinosis, and/or WD. Symptoms and complications for SCID can include: poor growth; rashes that look like eczema; chronic diarrhea; recurrent thrush in the mouth; and pneumocystis pneumonia. Symptoms and complications for WAS can include: bleeding; eczema; bloody diarrhea; and recurrent infections. Symptoms and complications for XLA can include: infections; diarrhea; failure to grow; joint disease; kidney inflammation; red blood cell breakdown; and skin and muscle inflammation. Symptoms and complications for cystinosis can include: polyuria; polydipsia; dehydration; vomiting; metabolic acidosis; hypophosphatemic rickets; constipation; failure to thrive; recurrent bouts of fever; heat intolerance; and poor/loss of appetite. Symptoms and complications for WD can include: fatigue; lack of appetite or abdominal pain; jaundice; golden-brown eye discoloration (Kayser-Fleischer rings); fluid buildup in the legs or abdomen; problems with speech, swallowing or physical coordination; and uncontrolled movements or muscle stiffness.

A "therapeutic treatment" includes a treatment administered to a subject who displays symptoms or signs of SCID, WAS, XLA, cystinosis, and/or WD and is administered to the subject for the purpose of diminishing or eliminating those signs or symptoms of SCID, WAS, XLA, cystinosis, and/or WD. In particular embodiments, the therapeutic treatment can provide immune function for subjects diagnosed with SCID, WAS, and/or XLA. In particular embodiments, the therapeutic treatment can reduce cystine accumulation in the cells of subjects afflicted with cystinosis. In particular embodiments, the therapeutic treatment can reduce copper accumulation in organs of subjects afflicted with WD. In particular embodiments, the therapeutic treatment can reduce, control, or eliminate symptoms and complications of SCID, WAS, XLA, cystinosis, and/or WD such as those described above.

Prophylactic treatments and therapeutic treatments need not be mutually exclusive, and in particular embodiments, administered dosages may accomplish more than one treatment type.

In particular embodiments, therapeutically effective amounts provide immune system function for subjects diagnosed with SCID, WAS, and/or XLA. Thus, in particular embodiments, methods of treatment disclosed herein include stem cell transplants, immunoglobulin infusions, antibiotic infusions, and/or gene therapy, for disorders such as SCID, WAS, and XLA. In particular embodiments, methods of treatment include enzyme therapy for SCID. Providing immune function include: decreasing the frequency or number of bacterial, viral, or parasitic infections, increasing life expectancy, and/or increasing growth.

In particular embodiments, therapeutically effective amounts prevent accumulation of cystine in cells of subjects diagnosed with cystinosis. In particular embodiments, methods of treatment include providing cysteamine for cystinosis. In particular embodiments, providing cysteamine alleviates or eliminates symptoms of cystinosis as described above.

In particular embodiments, therapeutically effective amounts prevent accumulation of copper in organs of subjects diagnosed with WD. In particular embodiments, methods of treatment include D-penicillinamine, trientine, zinc salts, and/or liver transplants for WD. In particular embodiments, preventing accumulation of copper in organs alleviates or eliminates symptoms of WD as described above.

In particular embodiments, administration of a therapeutic composition can be accompanied with administration of a separate adjuvant. Exemplary adjuvants include alum, bentonite, latex, and acrylic particles; incomplete Freund's adjuvant, complete Freund's adjuvant; aluminum-based salts such as aluminum hydroxide; calcium-based salts; silica or any TLR biological ligand(s); Sigma Adjuvant System (SAS); Ribi adjuvants.

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including target, body weight, severity of condition, previous or concurrent therapeutic interventions, idiopathy of the subject and route of administration.

Therapeutically effective amounts of cells can range from $10^4$ cells/kg to $10^9$ cells/kg. In particular embodiments, a therapeutically effective amount of cells can include $10^4$ cells/kg, $10^5$ cells/kg, $10^6$ cells/kg, $10^7$ cells/kg, $10^8$ cells/kg, $10^9$ cells/kg, or more.

Useful doses can range from 0.1 to 5 µg/kg or from 0.5 to 1 µg/kg. In particular embodiments, a dose can include 1 µg/kg, 15 µg/kg, 30 µg/kg, 50 µg/kg, 55 µg/kg, 70 µg/kg, 90 µg/kg, 150 µg/kg, 350 µg/kg, 500 µg/kg, 750 µg/kg, 1000 µg/kg, 0.1 to 5 mg/kg or from 0.5 to 1 mg/kg. In particular embodiments, a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly).

(IX) Kits

Kits to test for congenital disorders are also provided. Kits can include lancets to prick for blood, filter cards to collect blood drops, solutions to solubilize DBS, and appropriate buffers and enzymes to digest marker proteins in the DBS. Kits can further include one or more containers including anti-peptide binding agents (e.g., antibodies) and/or reagents or supplies to assess absence or reduction in CD3ε, WASp, BTK, CTNS, SHPK and/or ATP7B. In particular embodiments, the kits include one or more containers including the following anti-peptide antibodies: anti-CD3ε 197, anti-WASp 274, anti-WASp 289, anti-BTK 407, anti-BTK 545, anti-CTNS 115, anti-CTNS 120, anti-CTNS 194, anti-CTNS 360, anti-SHPK 44, anti-SHPK 363, anti-SHPK 388, anti-ATP7B 214, anti-ATP7B 325, anti-ATP7B 466, anti-ATP7B 589, anti-ATP7B 621, anti-ATP7B 887, anti-ATP7B 1056, and/or anti-ATP7B 1061. The antibodies may be immobilized on a solid support, such as a column or beads. Kits can further include elution buffers to release peptides from antibodies. In particular embodiments, kits can include one or more labeled reference peptides to perform absolute quantification of the signature peptides. In particular embodiments, kits can also include some or all of the necessary laboratory and/or medical supplies needed to use the kit effectively, such as gauze, sterile adhesive strips, gloves, tubes, and the like. Variations in contents of any of the kits described herein can be made.

Components of the kit can be prepared for storage and later use. Associated with such container(s) can be a notice in the form prescribed by a governmental agency regulating the manufacture, use, or sale of the kit, which notice reflects approval by the agency of manufacture, use, or sale, when required.

Optionally, the kits further include instructions for using the kit in the methods. In various embodiments, the instructions can include appropriate instructions to interpret results associated with using the kit; proper disposal of the related waste; and the like. The instructions can be in the form of printed instructions provided within the kit or the instructions can be printed on a portion of the kit itself. Instructions may be in the form of a sheet, pamphlet, brochure, CD-ROM, or computer-readable device, or can provide directions to instructions at a remote location, such as a website.

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wis.) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (nonpolar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH2PO4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

(X) Exemplary Embodiments

1. A method of screening for severe combined immunodeficiency (SCID), Wiskott-Aldrich syndrome (WAS), and/or X-linked agammaglobulinemia (XLA) in a subject, the method including:
Obtaining a dried blood spot (DBS) sample derived from the subject;
Digesting proteins from blood of the DBS with an enzyme to yield one or more peptides;
Enriching for:
 a CD3ε signature peptide of SCID with an antibody or antigen-binding fragment thereof that binds to the CD3ε signature peptide;
 a first WASp signature peptide of WAS with an antibody or antigen-binding fragment thereof that binds to the first WASp signature peptide;
 a second WASp signature peptide of WAS with an antibody or antigen-binding fragment thereof that binds to the second WASp signature peptide;
 a first BTK signature peptide of XLA with an antibody or antigen-binding fragment thereof that binds to the first BTK signature peptide; and/or
 a second BTK signature peptide with an antibody or antigen-binding fragment thereof that binds to the second BTK signature peptide;
Performing liquid chromatography-multiple reaction monitoring mass spectrometry (LC-MRM-MS) on the enriched peptides to determine concentrations of the peptides; and
Diagnosing the subject with:
 SCID when the concentration of the CD3ε signature peptide is lower than a predetermined threshold concentration or when the CD3ε signature peptide is absent;
 WAS when the concentrations of the first and/or second WASp signature peptides are lower than corresponding predetermined threshold concentrations or when the first and/or second WASp signature peptides are absent; and/or
 XLA when the concentrations of the first and/or second BTK signature peptides are lower than corresponding predetermined threshold concentrations or when the first and/or second BTK signature peptides are absent.

2. A method of embodiment 1, wherein
 the CD3ε signature peptide of SCID is encoded by an amino acid sequence set forth in SEQ ID NO: 1;
 the first WASp signature peptide of WAS is encoded by an amino acid sequence set forth in SEQ ID NO: 2;
 the second WASp signature peptide of WAS is encoded by an amino acid sequence set forth in SEQ ID NO: 3;
 the first BTK signature peptide of XLA is encoded by an amino acid sequence set forth in SEQ ID NO: 4; and/or
 the second BTK signature peptide of XLA is encoded by an amino acid sequence set forth in SEQ ID NO: 5.

3. A method of embodiment 1 or 2, wherein
 the antibody or antigen-binding fragment thereof that binds to the CD3ε signature peptide includes: a heavy chain variable (VH) domain including CDR1 of SEQ ID NO: 22, CDR2 of SEQ ID NO: 23, and CDR3 of SEQ ID NO: 24, and a light chain variable (VL) domain including: CDR1 of SEQ ID NO: 25, CDR2 of SEQ ID NO: 26, and CDR3 of SEQ ID NO: 27;
 the antibody or antigen-binding fragment thereof that binds to the first WASp signature peptide includes: a heavy chain variable (VH) domain including CDR1 of SEQ ID NO: 28, CDR2 of SEQ ID NO: 29, and CDR3 of SEQ ID NO: 30, and a light chain variable (VL) domain including: CDR1 of SEQ ID NO: 31, CDR2 of SEQ ID NO: 32, and CDR3 of SEQ ID NO: 33; and/or
 the antibody or antigen-binding fragment thereof that binds to the first BTK signature peptide includes: a heavy chain variable (VH) domain including CDR1 of SEQ ID NO: 34, CDR2 of SEQ ID NO: 35, and CDR3 of sequence GDI, and a light chain variable (VL) domain including: CDR1 of SEQ ID NO: 36, CDR2 of SEQ ID NO: 37, and CDR3 of SEQ ID NO: 38.

4. A method of any one of embodiments 1-3, wherein the method is performed as part of a newborn screening (NBS) that additionally screens the subject for one or more of phenylketonuria, primary congenital hypothyroidism, cystic fibrosis, and sickle cell disease.

5. A method of any one of embodiments 1-4, wherein the method is performed in the absence of clinical symptoms of SCID, WAS, and/or XLA in the subject.

6. A method of any one of embodiments 1-5, wherein the enzyme is trypsin.

7. A method of any one of embodiments 1-6, wherein the corresponding predetermined threshold concentration for each signature peptide is calculated from a standard deviation of the mean concentration of each signature peptides in DBS from a population of normal control subjects.

8. A method of any one of embodiments 1-7, wherein the corresponding predetermined threshold concentration is −1 standard deviation (SD), −1.1 SD, −1.2 SD, −1.3 SD, −1.4 SD, −1.5 SD, −1.6 SD, −1.7 SD, −1.8 SD, −1.9 SD, −2.0 SD, −2.1 SD, −2.2 SD, −2.3 SD, −2.4 SD, −2.5 SD, −2.6 SD, −2.7 SD, −2.8 SD, −2.9 SD, −3.0 SD, or more SD from the mean concentration of each signature peptide in DBS from a population of normal control subjects.

9. A method of any one of embodiments 1-8, wherein the antibody or antigen-binding fragment thereof used for enrichment of the CD3ε signature peptide of SCID includes a VH domain of SEQ ID NO: 63.

10. A method of any one of embodiments 1-9, wherein the antibody or antigen-binding fragment thereof used for enrichment of the CD3ε signature peptide of SCID includes a VL domain of SEQ ID NO: 64.

11. A method of any one of embodiments 1-10, wherein the antibody or antigen-binding fragment thereof used for enrichment of the first WASp signature peptide of WAS includes a VH domain of SEQ ID NO: 65.

12. A method of any one of embodiments 1-11, wherein the antibody or antigen-binding fragment thereof used for enrichment of the first WASp signature peptide of WAS includes a VL domain of SEQ ID NO: 66.

13. A method of any one of embodiments 1-12, wherein the antibody or antigen-binding fragment thereof used for enrichment of the first WASp signature peptide of WAS includes a heavy chain of SEQ ID NO: 86.

14. A method of any one of embodiments 1-13, wherein the antibody or antigen-binding fragment thereof used for enrichment of the first WASp signature peptide of WAS includes a light chain of SEQ ID NO: 91.

15. A method of any one of embodiments 1-14, wherein the antibody or antigen-binding fragment thereof used for enrichment of the first BTK signature peptide of XLA includes a VH domain of SEQ ID NO: 67.

16. A method of any one of embodiments 1-15, wherein the antibody or antigen-binding fragment thereof used for enrichment of the first BTK signature peptide of XLA includes a VL domain of SEQ ID NO: 68.

17. A method of any one of embodiments 1-16, wherein the antibody or antigen-binding fragment thereof used for enrichment of the first BTK signature peptide of XLA includes a heavy chain of SEQ ID NO: 96.

18. A method of any one of embodiments 1-17, wherein the antibody or antigen-binding fragment thereof used for enrichment of the first BTK signature peptide of XLA includes a light chain of SEQ ID NO: 101.

19. A method of any one of embodiments 1-18, wherein the method further includes screening for cystinosis by enriching for:
- a first CTNS signature peptide of cystinosis with an antibody or antigen-binding fragment thereof that binds to the first CTNS signature peptide;
- a second CTNS signature peptide of cystinosis with an antibody or antigen-binding fragment thereof that binds to the second CTNS signature peptide;
- a third CTNS signature peptide of cystinosis with an antibody or antigen-binding fragment thereof that binds to the third CTNS signature peptide;
- a fourth CTNS signature peptide of cystinosis with an antibody or antigen-binding fragment thereof that binds to the fourth CTNS signature peptide;
- a first SHPK signature peptide of cystinosis with an antibody or antigen-binding fragment thereof that binds to the first SHPK signature peptide;
- a second SHPK signature peptide of cystinosis with an antibody or antigen-binding fragment thereof that binds to the second SHPK signature peptide; and/or a third SHPK signature peptide of cystinosis with an antibody or antigen-binding fragment thereof that binds to the third SHPK signature peptide;

and
Diagnosing the subject with cystinosis when the concentrations of the first CTNS, the second CTNS, the third CTNS, the fourth CTNS, the first SHPK, the second SHPK, and/or the third SHPK signature peptides are lower than corresponding predetermined threshold concentrations or when the first CTNS, the second CTNS, the third CTNS, the fourth CTNS, the first SHPK, the second SHPK, and/or the third SHPK signature peptides are absent.

20. A method of embodiment 19, wherein
the first CTNS signature peptide of cystinosis is encoded by an amino acid sequence set forth in SEQ ID NO: 6;
the second CTNS signature peptide of cystinosis is encoded by an amino acid sequence set forth in SEQ ID NO: 7 or 8;
the third CTNS signature peptide of cystinosis is encoded by an amino acid sequence set forth in SEQ ID NO: 12;
the fourth CTNS signature peptide of cystinosis is encoded by an amino acid sequence set forth in SEQ ID NO: 13;
the first SHPK signature peptide of cystinosis is encoded by an amino acid sequence set forth in SEQ ID NO: 9;
the second SHPK signature peptide of cystinosis is encoded by an amino acid sequence set forth in SEQ ID NO: 14; and/or
the third SHPK signature peptide of cystinosis is encoded by an amino acid sequence set forth in SEQ ID NO: 15.

21. A method of embodiment 19 or 20, wherein
the antibody or antigen-binding fragment thereof that binds to the first CTNS signature peptide of cystinosis includes: a heavy chain variable (VH) domain including CDR1 of SEQ ID NO: 39, CDR2 of SEQ ID NO: 40, and CDR3 of SEQ ID NO: 41, and a light chain variable (VL) domain including: CDR1 of SEQ ID NO: 42, CDR2 of SEQ ID NO: 43, and CDR3 of SEQ ID NO: 44;
the antibody or antigen-binding fragment thereof that binds to the second CTNS signature peptide includes: a heavy chain variable (VH) domain including CDR1 of SEQ ID NO: 45, CDR2 of SEQ ID NO: 46, and CDR3 of SEQ ID NO: 47, and a light chain variable (VL) domain including: CDR1 of SEQ ID NO: 48, CDR2 of SEQ ID NO: 49, and CDR3 of SEQ ID NO: 50; and/or
the antibody or antigen-binding fragment thereof that binds to the first SHPK signature peptide includes: a heavy chain variable (VH) domain including CDR1 of SEQ ID NO: 51, CDR2 of SEQ ID NO: 52, and CDR3 of SEQ ID NO: 53, and a light chain variable (VL) domain including: CDR1 of SEQ ID NO: 54, CDR2 of SEQ ID NO: 55, and CDR3 of SEQ ID NO: 56.

22. A method of any one of embodiments 19-21, wherein the antibody or antigen-binding fragment thereof used for enrichment of the first CTNS signature peptide of cystinosis includes a VH domain of SEQ ID NO: 69.

23. A method of any one of embodiments 19-22, wherein the antibody or antigen-binding fragment thereof used for enrichment of the first CTNS signature peptide of cystinosis includes a VL domain of SEQ ID NO: 70.

24. A method of any one of embodiments 19-23, wherein the antibody or antigen-binding fragment thereof used for enrichment of the first CTNS signature peptide of cystinosis includes a heavy chain of SEQ ID NO: 106.

25. A method of any one of embodiments 19-24, wherein the antibody or antigen-binding fragment thereof used for enrichment of the first CTNS signature peptide of cystinosis includes a light chain of SEQ ID NO: 111.

26. A method of any one of embodiments 19-25, wherein the antibody or antigen-binding fragment thereof used for enrichment of the second CTNS signature peptide of cystinosis includes a VH domain of SEQ ID NO: 71.

27. A method of any one of embodiments 19-26, wherein the antibody or antigen-binding fragment thereof used for enrichment of the second CTNS signature peptide of cystinosis includes a VL domain of SEQ ID NO: 72.

28. A method of any one of embodiments 19-27, wherein the antibody or antigen-binding fragment thereof used for enrichment of the second CTNS signature peptide of cystinosis includes a heavy chain of SEQ ID NO: 116.

29. A method of any one of embodiments 19-28, wherein the antibody or antigen-binding fragment thereof used for enrichment of the second CTNS signature peptide of cystinosis includes a light chain of SEQ ID NO: 121.

30. A method of any one of embodiments 19-29, wherein the antibody or antigen-binding fragment thereof used for enrichment of the first SHPK signature peptide of cystinosis includes a VH domain of SEQ ID NO: 73.

31. A method of any one of embodiments 19-30, wherein the antibody or antigen-binding fragment thereof used for enrichment of the first SHPK signature peptide of cystinosis includes a VL domain of SEQ ID NO: 74.

32. A method of any one of embodiments 19-31, wherein the antibody or antigen-binding fragment thereof used for enrichment of the first SHPK signature peptide of cystinosis includes a heavy chain of SEQ ID NO: 126.

33. A method of any one of embodiments 19-32, wherein the antibody or antigen-binding fragment thereof used for enrichment of the first SHPK signature peptide of cystinosis includes a light chain of SEQ ID NO: 131.

34. A method of any one of embodiments 1-33, wherein the method further includes screening for Wilson Disease (WD) by enriching for:
  a first ATP7B signature peptide with an antibody or antigen-binding fragment thereof that binds to the first ATP7B signature peptide;
  a second ATP7B signature peptide with an antibody or antigen-binding fragment thereof that binds to the second ATP7B signature peptide;
  a third ATP7B signature peptide with an antibody or antigen-binding fragment that binds to the third ATP7B signature peptide;
  a fourth ATP7B signature peptide with an antibody or antigen-binding fragment thereof that binds to the fourth ATP7B signature peptide;
  a fifth ATP7B signature peptide with an antibody or antigen-binding fragment thereof that binds to the fifth ATP7B signature peptide;
  a sixth ATP7B signature peptide with an antibody or antigen-binding fragment thereof that binds to the sixth ATP7B signature peptide; and/or
  a seventh ATP7B signature peptide with an antibody or antigen-binding fragment thereof;
and
Diagnosing the subject with WD when the concentrations of the first ATP7B, the second ATP7B, the third ATP7B, the fourth ATP7B, the fifth ATP7B, the sixth ATP7B, and/or the seventh ATP7B signature peptides are lower than corresponding predetermined threshold concentrations or when the first ATP7B, the second ATP7B, the third ATP7B, the fourth ATP7B, the fifth ATP7B, the sixth ATP7B, and/or the seventh ATP7B signature peptides are absent.

35. A method of embodiment 34, wherein
  the first ATP7B signature peptide of WD is encoded by an amino acid sequence set forth in SEQ ID NO: 10;
  the second ATP7B signature peptide of WD is encoded by an amino acid sequence set forth in SEQ ID NO: 11 or 21;
  the third ATP7B signature peptide of WD is encoded by an amino acid sequence set forth in SEQ ID NO: 16;
  the fourth ATP7B signature peptide of WD is encoded by an amino acid sequence set forth in SEQ ID NO: 17;
  the fifth ATP7B signature peptide of WD is encoded by an amino acid sequence set forth in SEQ ID NO: 18;
  the sixth ATP7B signature peptide of WD is encoded by an amino acid sequence set forth in SEQ ID NO: 19; and/or
  the seventh ATP7B signature peptide of WD is encoded by an amino acid sequence set forth in SEQ ID NO: 20.

36. A method of embodiment 34 or 35, wherein the antibody or antigen-binding fragment thereof that binds to the second ATP7B signature peptide includes: a heavy chain variable (VH) domain including CDR1 of SEQ ID NO: 57, CDR2 of SEQ ID NO: 58, and CDR3 of SEQ ID NO: 59, and a light chain variable (VL) domain including: CDR1 of SEQ ID NO: 60, CDR2 of SEQ ID NO: 61, and CDR3 of SEQ ID NO: 62.

37. A method of any one of embodiments 34-36, wherein the antibody or antigen-binding fragment thereof used for enrichment of the second ATP7B signature peptide of WD includes a VH domain of SEQ ID NO: 75.

38. A method of any one of embodiments 34-37, wherein the antibody or antigen-binding fragment thereof used for enrichment of the second ATP7B signature peptide of WD includes a VL domain of SEQ ID NO: 76.

39. A method of any one of embodiments 34-38, wherein the antibody or antigen-binding fragment thereof used for enrichment of the second ATP7B signature peptide of WD includes a heavy chain of SEQ ID NO: 136.

40. A method of any one of embodiments 34-39, wherein the antibody or antigen-binding fragment thereof used for enrichment of the second ATP7B signature peptide of WD includes a light chain of SEQ ID NO: 141.

41. A method of any one of embodiments 1-40, wherein the concentrations of the peptides are determined from corresponding known concentrations of reference signature peptides added prior to the LC-MRM-MS.

42. A method of any one of embodiments 7-41, wherein the mean concentration of the CD3ε signature peptide in DBS from a population of normal control subjects includes a concentration in a range of 70 pmol/L to 400 pmol/L.

43. A method of any one of embodiments 7-42, wherein the mean concentration of the first WASp signature peptide in DBS from a population of normal control subjects includes a concentration in a range of 600 pmol/L to 5000 pmol/L.

44. A method of any one of embodiments 7-43, wherein the mean concentration of the second WASp signature peptide in DBS from a population of normal control subjects includes a concentration in a range of 5500 pmol/L to 15000 pmol/L.

45. A method of any one of embodiments 7-44, wherein the mean concentration of the first BTK signature peptide in DBS from a population of normal control subjects includes a concentration in a range of 350 pmol/L to 2500 pmol/L.

46. A method of any one of embodiments 7-45, wherein the mean concentration of the second BTK signature peptide in DBS from a population of normal control subjects includes a concentration in a range of 550 pmol/L to 1600 pmol/L.

47. A method of any one of embodiments 7-46, wherein the mean concentration of the first CTNS signature peptide in DBS from a population of normal control subjects includes a concentration in a range of 40 pmol/L to 250 pmol/L.

48. A method of any one of embodiments 7-47, wherein the mean concentration of the first SHPK signature peptide in DBS from a population of normal control subjects includes a concentration in a range of 100 pmol/L to 8000 pmol/L.

49. A method of any one of embodiments 7-48, wherein the mean concentration of the second ATP7B signature peptide in DBS from a population of normal control subjects includes a concentration in a range of 90 pmol/L to 400 pmol/L.

50. A method of any one of embodiments 7-49, wherein the mean concentration of the third ATP7B signature peptide in DBS from a population of normal control subjects includes a concentration in a range of 30 pmol/L to 100 pmol/L.

51. A method of any one of embodiments 7-50, wherein the mean concentration of the seventh ATP7B signature peptide in DBS from a population of normal control subjects includes a concentration in a range of 200 pmol/L to 500 pmol/L.

52. A method of screening for severe combined immunodeficiency (SCID), Wiskott-Aldrich syndrome (WAS), and/or X-linked agammaglobulinemia (XLA) in a subject, the method including:
Obtaining a dried blood spot (DBS) sample derived from the subject;
Digesting proteins from blood of the DBS with an enzyme to yield one or more peptides;

Enriching for:
  a CD3ε signature peptide of SCID with an antibody or antigen-binding fragment thereof that binds to the CD3ε signature peptide;
  a first WASp signature peptide of WAS with an antibody or antigen-binding fragment thereof that binds to the first WASp signature peptide;
  a second WASp signature peptide of WAS with an antibody or antigen-binding fragment thereof that binds to the second WASp signature peptide;
  a first BTK signature peptide of XLA with an antibody or antigen-binding fragment thereof that binds to the first BTK signature peptide; and/or
  a second BTK signature peptide with an antibody or antigen-binding fragment thereof that binds to the second BTK signature peptide;
Enriching for an endogenous ATP7B peptide with an antibody or antigen binding fragment thereof that binds to the endogenous ATP7B peptide;
Performing liquid chromatography-multiple reaction monitoring mass spectrometry (LC-MRM-MS) on the enriched peptides to determine concentrations of the peptides;
Calculating a ratio of signature peptide concentration:endogenous ATP7B peptide concentration for each signature peptide; and
Diagnosing the subject with:
  SCID when the ratio of CD3ε signature peptide concentration:endogenous ATP7B peptide concentration is lower than a corresponding predetermined threshold ratio or when the CD3ε signature peptide is absent;
  WAS when the ratios of the first and/or second WASp signature peptide concentration:endogenous ATP7B peptide concentration are lower than corresponding predetermined threshold ratios or when the first and/or second WASp signature peptides are absent; and/or
  XLA when the ratios of the first and/or second BTK signature peptide concentration:endogenous ATP7B peptide concentration are lower than corresponding predetermined threshold ratios or when the first and/or second BTK signature peptides are absent.

53. A method of embodiment 52, wherein
  the CD3ε signature peptide of SCID is encoded by an amino acid sequence set forth in SEQ ID NO: 1;
  the first WASp signature peptide of WAS is encoded by an amino acid sequence set forth in SEQ ID NO: 2;
  the second WASp signature peptide of WAS is encoded by an amino acid sequence set forth in SEQ ID NO: 3;
  the first BTK signature peptide of XLA is encoded by an amino acid sequence set forth in SEQ ID NO: 4; and/or
  the second BTK signature peptide of XLA is encoded by an amino acid sequence set forth in SEQ ID NO: 5.

54. A method of embodiment 52 or 53, wherein
  the antibody or antigen-binding fragment thereof that binds to the CD3ε signature peptide includes: a heavy chain variable (VH) domain including CDR1 of SEQ ID NO: 22, CDR2 of SEQ ID NO: 23, and CDR3 of SEQ ID NO: 24, and a light chain variable (VL) domain including: CDR1 of SEQ ID NO: 25, CDR2 of SEQ ID NO: 26, and CDR3 of SEQ ID NO: 27;
  the antibody or antigen-binding fragment thereof that binds to the first WASp signature peptide includes: a heavy chain variable (VH) domain including CDR1 of SEQ ID NO: 28, CDR2 of SEQ ID NO: 29, and CDR3 of SEQ ID NO: 30, and a light chain variable (VL) domain including: CDR1 of SEQ ID NO: 31, CDR2 of SEQ ID NO: 32, and CDR3 of SEQ ID NO: 33; and/or
  the antibody or antigen-binding fragment thereof that binds to the first BTK signature peptide includes: a heavy chain variable (VH) domain including CDR1 of SEQ ID NO: 34, CDR2 of SEQ ID NO: 35, and CDR3 of sequence GDI, and a light chain variable (VL) domain including: CDR1 of SEQ ID NO: 36, CDR2 of SEQ ID NO: 37, and CDR3 of SEQ ID NO: 38.

55. A method of any one of embodiments 42-44, wherein the endogenous ATP7B peptide is encoded by an amino acid sequence set forth in SEQ ID NO: 10, SEQ ID NO: 11, SEQ ID NO: 16, SEQ ID NO: 17, SEQ ID NO: 18, SEQ ID NO: 19, SEQ ID NO: 20, or SEQ ID NO: 21.

56. A method of any one of embodiments 42-45, wherein the antibody or antigen-binding fragment thereof that binds to the endogenous ATP7B peptide includes: a heavy chain variable (VH) domain including CDR1 of SEQ ID NO: 57, CDR2 of SEQ ID NO: 58, and CDR3 of SEQ ID NO: 59, and a light chain variable (VL) domain including: CDR1 of SEQ ID NO: 60, CDR2 of SEQ ID NO: 61, and CDR3 of SEQ ID NO: 62.

57. A method of any one of embodiments 52-56, wherein each predetermined threshold ratio is calculated from the standard deviation of the mean ratio of each peptide concentration:endogenous ATP7B peptide concentration in a population of samples.

58. A method of any one of embodiments 52-57, wherein the method is performed as part of a newborn screening (NBS) that additionally screens the subject for one or more of phenylketonuria, primary congenital hypothyroidism, cystic fibrosis, and sickle cell disease.

59. A method of any one of embodiments 52-58, wherein the method is performed in the absence of clinical symptoms of SCID, WAS, and/or XLA in the subject.

60. A method of any one of embodiments 52-59, wherein the enzyme is trypsin.

61. A method of any one of embodiments 52-60, wherein the antibody or antigen-binding fragment thereof used for enrichment of the CD3ε signature peptide of SCID includes a VH domain of SEQ ID NO: 63.

62. A method of any one of embodiments 52-61, wherein the antibody or antigen-binding fragment thereof used for enrichment of the CD3ε signature peptide of SCID includes a VL domain of SEQ ID NO: 64.

63. A method of any one of embodiments 52-62, wherein the antibody or antigen-binding fragment thereof used for enrichment of the first WASp signature peptide of WAS includes a VH domain of SEQ ID NO: 65.

64. A method of any one of embodiments 52-63, wherein the antibody or antigen-binding fragment thereof used for enrichment of the first WASp signature peptide of WAS includes a VL domain of SEQ ID NO: 66.

65. A method of any one of embodiments 52-64, wherein the antibody or antigen-binding fragment thereof used for enrichment of the first WASp signature peptide of WAS includes a heavy chain of SEQ ID NO: 86.

66. A method of any one of embodiments 52-65, wherein the antibody or antigen-binding fragment thereof used for enrichment of the first WASp signature peptide of WAS includes a light chain of SEQ ID NO: 91.

67. A method of any one of embodiments 52-66, wherein the antibody or antigen-binding fragment thereof used for enrichment of the first BTK signature peptide of XLA includes a VH domain of SEQ ID NO: 67.

68. A method of any one of embodiments 52-67, wherein the antibody or antigen-binding fragment thereof used for enrichment of the first BTK signature peptide of XLA includes a VL domain of SEQ ID NO: 68.

69. A method of any one of embodiments 52-68, wherein the antibody or antigen-binding fragment thereof used for enrichment of the first BTK signature peptide of XLA includes a heavy chain of SEQ ID NO: 96.

70. The method of any one of embodiments 52-69, wherein the antibody or antigen-binding fragment thereof used for enrichment of the first BTK signature peptide of XLA includes a light chain of SEQ ID NO: 101.

71. A method of any one of embodiments 52-70, further including screening for cystinosis by enriching for:
   a first CTNS signature peptide of cystinosis with an antibody or antigen-binding fragment thereof that binds to the first CTNS signature peptide;
   a second CTNS signature peptide of cystinosis with an antibody or antigen-binding fragment thereof that binds to the second CTNS signature peptide;
   a third CTNS signature peptide of cystinosis with an antibody or antigen-binding fragment thereof that binds to the third CTNS signature peptide;
   a fourth CTNS signature peptide of cystinosis with an antibody or antigen-binding fragment thereof that binds to the fourth CTNS signature peptide;
   a first SHPK signature peptide of cystinosis with an antibody or antigen-binding fragment thereof that binds to the first SHPK signature peptide;
   a second SHPK signature peptide of cystinosis with an antibody or antigen-binding fragment thereof that binds to the second SHPK signature peptide; and/or
   a third SHPK signature peptide of cystinosis with an antibody or antigen-binding fragment thereof that binds to the third SHPK signature peptide;
Calculating a ratio of signature peptide concentration:endogenous ATP7B peptide concentration for each signature peptide; and
Diagnosing the subject with cystinosis when the ratio of the first CTNS peptide concentration:endogenous ATP7B peptide concentration, the second CTNS peptide concentration:endogenous ATP7B peptide concentration, the third CTNS peptide concentration:endogenous ATP7B peptide concentration, the fourth CTNS peptide concentration:endogenous ATP7B peptide concentration, the first SHPK peptide concentration:endogenous ATP7B peptide concentration, the second SHPK peptide concentration:endogenous ATP7B peptide concentration, and/or the third SHPK signature peptide concentration:endogenous ATP7B peptide concentration is lower than a corresponding predetermined threshold ratio or when the first CTNS, the second CTNS, the third CTNS, the fourth CTNS, the first SHPK, the second SHPK, and/or the third SHPK signature peptides are absent.

72. A method of embodiment 71, wherein
   the first CTNS signature peptide of cystinosis is encoded by an amino acid sequence set forth in SEQ ID NO: 6;
   the second CTNS signature peptide of cystinosis is encoded by an amino acid sequence set forth in SEQ ID NO: 7 or 8;
   the third CTNS signature peptide of cystinosis is encoded by an amino acid sequence set forth in SEQ ID NO: 12;
   the fourth CTNS signature peptide of cystinosis is encoded by an amino acid sequence set forth in SEQ ID NO: 13;
   the first SHPK signature peptide of cystinosis is encoded by an amino acid sequence set forth in SEQ ID NO: 9;
   the second SHPK signature peptide of cystinosis is encoded by an amino acid sequence set forth in SEQ ID NO: 14; and/or
   the third SHPK signature peptide of cystinosis is encoded by an amino acid sequence set forth in SEQ ID NO: 15.

73. A method of embodiment 71 or 72, wherein
   the antibody or antigen-binding fragment thereof that binds to the first CTNS signature peptide of cystinosis includes: a heavy chain variable (VH) domain including CDR1 of SEQ ID NO: 39, CDR2 of SEQ ID NO: 40, and CDR3 of SEQ ID NO: 41, and a light chain variable (VL) domain including: CDR1 of SEQ ID NO: 42, CDR2 of SEQ ID NO: 43, and CDR3 of SEQ ID NO: 44;
   the antibody or antigen-binding fragment thereof that binds to the second CTNS signature peptide includes: a heavy chain variable (VH) domain including CDR1 of SEQ ID NO: 45, CDR2 of SEQ ID NO: 46, and CDR3 of SEQ ID NO: 47, and a light chain variable (VL) domain including: CDR1 of SEQ ID NO: 48, CDR2 of SEQ ID NO: 49, and CDR3 of SEQ ID NO: 50; and/or
   the antibody or antigen-binding fragment thereof that binds to the first SHPK signature peptide includes: a heavy chain variable (VH) domain including CDR1 of SEQ ID NO: 51, CDR2 of SEQ ID NO: 52, and CDR3 of SEQ ID NO: 53, and a light chain variable (VL) domain including: CDR1 of SEQ ID NO: 54, CDR2 of SEQ ID NO: 55, and CDR3 of SEQ ID NO: 56.

74. The method of any one of embodiments 71-73, wherein the antibody or antigen-binding fragment thereof used for enrichment of the first CTNS signature peptide of cystinosis of SEQ ID NO: 6 includes a VH domain of SEQ ID NO: 69.

75. A method of any one of embodiments 71-74, wherein the antibody or antigen-binding fragment thereof used for enrichment of the first CTNS signature peptide of cystinosis includes a VL domain of SEQ ID NO: 70.

76. A method of any one of embodiments 71-75, wherein the antibody or antigen-binding fragment thereof used for enrichment of the first CTNS signature peptide of cystinosis includes a heavy chain of SEQ ID NO: 106.

77. A method of any one of embodiments 71-76, wherein the antibody or antigen-binding fragment thereof used for enrichment of the first CTNS signature peptide of cystinosis includes a light chain of SEQ ID NO: 111.

78. A method of any one of embodiments 71-77, wherein the antibody or antigen-binding fragment thereof used for enrichment of the second CTNS signature peptide of cystinosis includes a VH domain of SEQ ID NO: 71.

79. A method of any one of embodiments 71-78, wherein the antibody or antigen-binding fragment thereof used for enrichment of the second CTNS signature peptide of cystinosis includes a VL domain of SEQ ID NO: 72.

80. A method of any one of embodiments 71-79, wherein the antibody or antigen-binding fragment thereof used for enrichment of the second CTNS signature peptide of cystinosis includes a heavy chain of SEQ ID NO: 116.

81. A method of any one of embodiments 71-80, wherein the antibody or antigen-binding fragment thereof used for enrichment of the second CTNS signature peptide of cystinosis includes a light chain of SEQ ID NO: 121.

82. A method of any one of embodiments 71-81, wherein the antibody or antigen-binding fragment thereof used for enrichment of the first SHPK signature peptide of cystinosis includes a VH domain of SEQ ID NO: 73.

83. A method of any one of embodiments 71-82, wherein the antibody or antigen-binding fragment thereof used for enrichment of the first SHPK signature peptide of cystinosis includes a VL domain of SEQ ID NO: 74.

84. A method of any one of embodiments 71-83, wherein the antibody or antigen-binding fragment thereof used for enrichment of the first SHPK signature peptide of cystinosis includes a heavy chain of SEQ ID NO: 126.

85. A method of any one of embodiments 71-84, wherein the antibody or antigen-binding fragment thereof used for enrichment of the first SHPK signature peptide of cystinosis includes a light chain of SEQ ID NO: 131.

86. A method of any one of embodiments 52-85, wherein the antibody or antigen-binding fragment thereof used for enrichment of the endogenous ATP7B peptide includes a VH domain of SEQ ID NO: 75.

87. A method of any one of embodiments 52-86, wherein the antibody or antigen-binding fragment thereof used for enrichment of the endogenous ATP7B signature peptide includes a VL domain of SEQ ID NO: 76.

88. A method of any one of embodiments 52-87, wherein the antibody or antigen-binding fragment thereof used for enrichment of the endogenous ATP7B signature peptide includes a heavy chain of SEQ ID NO: 136.

89. A method of any one of embodiments 52-88, wherein the antibody or antigen-binding fragment thereof used for enrichment of the endogenous ATP7B signature peptide includes a light chain of SEQ ID NO: 141.

90. A method of any one of embodiments 52-89, wherein the concentrations of the peptides are determined from corresponding known concentrations of reference signature peptides added prior to the LC-MRM-MS.

91. A method of detecting one or more signature peptides of severe combined immunodeficiency (SCID), Wiskott-Aldrich syndrome (WAS), and/or X-linked agammaglobulinemia (XLA) in one or more dried blood spot (DBS) samples, the method including:
Obtaining the one or more dried blood spot (DBS) samples;
Digesting proteins from blood of each DBS with an enzyme to yield one or more peptides;
Enriching for:
  a CD3ε signature peptide of SCID with an antibody or antigen-binding fragment thereof that binds to the CD3ε signature peptide;
  a first WASp signature peptide of WAS with an antibody or antigen-binding fragment thereof that binds to the first WASp signature peptide;
  a second WASp signature peptide of WAS with an antibody or antigen-binding fragment thereof that binds to the second WASp signature peptide;
  a first BTK signature peptide of XLA with an antibody or antigen-binding fragment thereof that binds to the first BTK signature peptide; and/or
  a second BTK signature peptide with an antibody or antigen-binding fragment thereof that binds to the second BTK signature peptide;
Performing liquid chromatography-multiple reaction monitoring mass spectrometry (LC-MRM-MS) on the enriched peptides to determine concentrations of the peptides; and
Performing liquid chromatography-multiple reaction monitoring mass spectrometry (LC-MRM-MS) on the enriched peptides, thus detecting one or more signature peptides of SCID, WAS, and XLA in one or more DBS samples.

92. A method of embodiment 91, wherein
  the CD3ε signature peptide of SCID is encoded by an amino acid sequence set forth in SEQ ID NO: 1;
  the first WASp signature peptide of WAS is encoded by an amino acid sequence set forth in SEQ ID NO: 2;
  the second WASp signature peptide of WAS is encoded by an amino acid sequence set forth in SEQ ID NO: 3;
  the first BTK signature peptide of XLA is encoded by an amino acid sequence set forth in SEQ ID NO: 4; and/or
  the second BTK signature peptide of XLA is encoded by an amino acid sequence set forth in SEQ ID NO: 5.

93. A method of embodiment 91 or 92, wherein
  the antibody or antigen-binding fragment thereof that binds to the CD3ε signature peptide includes: a heavy chain variable (VH) domain including CDR1 of SEQ ID NO: 22, CDR2 of SEQ ID NO: 23, and CDR3 of SEQ ID NO: 24, and a light chain variable (VL) domain including: CDR1 of SEQ ID NO: 25, CDR2 of SEQ ID NO: 26, and CDR3 of SEQ ID NO: 27;
  the antibody or antigen-binding fragment thereof that binds to the first WASp signature peptide includes: a heavy chain variable (VH) domain including CDR1 of SEQ ID NO: 28, CDR2 of SEQ ID NO: 29, and CDR3 of SEQ ID NO: 30, and a light chain variable (VL) domain including: CDR1 of SEQ ID NO: 31, CDR2 of SEQ ID NO: 32, and CDR3 of SEQ ID NO: 33; and/or
  the antibody or antigen-binding fragment thereof that binds to the first BTK signature peptide includes: a heavy chain variable (VH) domain including CDR1 of SEQ ID NO: 34, CDR2 of SEQ ID NO: 35, and CDR3 of sequence GDI, and a light chain variable (VL) domain including: CDR1 of SEQ ID NO: 36, CDR2 of SEQ ID NO: 37, and CDR3 of SEQ ID NO: 38.

94. A method of any one of embodiments 91-93, wherein the enzyme is trypsin.

95. A method of any one of embodiments 91-94, wherein the antibody or antigen-binding fragment thereof used for enrichment of the CD3ε signature peptide of SCID includes a VH domain of SEQ ID NO: 63.

96. A method of any one of embodiments 91-95, wherein the antibody or antigen-binding fragment thereof used for enrichment of the CD3ε signature peptide of SCID includes a VL domain of SEQ ID NO: 64.

97. A method of any one of embodiments 91-96, wherein the antibody or antigen-binding fragment thereof used for enrichment of the first WASp signature peptide of WAS includes a VH domain of SEQ ID NO: 65.

98. A method of any one of embodiments 91-97, wherein the antibody or antigen-binding fragment thereof used for enrichment of the first WASp signature peptide of WAS includes a VL domain of SEQ ID NO: 66.

99. A method of any one of embodiments 91-98, wherein the antibody or antigen-binding fragment thereof used for enrichment of the first WASp signature peptide of WAS includes a heavy chain of SEQ ID NO: 86.

100. A method of any one of embodiments 91-99, wherein the antibody or antigen-binding fragment thereof used for enrichment of the first WASp signature peptide of WAS includes a light chain of SEQ ID NO: 91.

101. A method of any one of embodiments 91-100, wherein the antibody or antigen-binding fragment thereof used for enrichment of the first BTK signature peptide of XLA includes a VH domain of SEQ ID NO: 67.

102. A method of any one of embodiments 91-101, wherein the antibody or antigen-binding fragment thereof used for enrichment of the first BTK signature peptide of XLA includes a VL domain of SEQ ID NO: 68.

103. A method of any one of embodiments 91-102, wherein the antibody or antigen-binding fragment thereof used for enrichment of the first BTK signature peptide of XLA includes a heavy chain of SEQ ID NO: 96.

104. A method of any one of embodiments 91-103, wherein the antibody or antigen-binding fragment thereof used for enrichment of the first BTK signature peptide of XLA includes a light chain of SEQ ID NO: 101.

105. A method of any one of embodiments 91-104, further including detecting one or more signature peptides of cystinosis by enriching for:
- a first CTNS signature peptide of cystinosis with an antibody or antigen-binding fragment thereof that binds to the first CTNS signature peptide;
- a second CTNS signature peptide of cystinosis with an antibody or antigen-binding fragment thereof that binds to the second CTNS signature peptide;
- a third CTNS signature peptide of cystinosis with an antibody or antigen-binding fragment thereof that binds to the third CTNS signature peptide;
- a fourth CTNS signature peptide of cystinosis with an antibody or antigen-binding fragment thereof that binds to the fourth CTNS signature peptide;
- a first SHPK signature peptide of cystinosis with an antibody or antigen-binding fragment thereof that binds to the first SHPK signature peptide;
- a second SHPK signature peptide of cystinosis with an antibody or antigen-binding fragment thereof that binds to the second SHPK signature peptide; and/or
- a third SHPK signature peptide of cystinosis with an antibody or antigen-binding fragment thereof that binds to the third SHPK signature peptide;

and
Performing liquid chromatography-multiple reaction monitoring mass spectrometry (LC-MRM-MS) on the enriched peptides, thus detecting one or more signature peptides of cystinosis in one or more DBS samples.

106. A method of embodiment 105, wherein
the first CTNS signature peptide of cystinosis is encoded by an amino acid sequence set forth in SEQ ID NO: 6;
the second CTNS signature peptide of cystinosis is encoded by an amino acid sequence set forth in SEQ ID NO: 7 or 8;
the third CTNS signature peptide of cystinosis is encoded by an amino acid sequence set forth in SEQ ID NO: 12;
the fourth CTNS signature peptide of cystinosis is encoded by an amino acid sequence set forth in SEQ ID NO: 13;
the first SHPK signature peptide of cystinosis is encoded by an amino acid sequence set forth in SEQ ID NO: 9;
the second SHPK signature peptide of cystinosis is encoded by an amino acid sequence set forth in SEQ ID NO: 14; and/or
the third SHPK signature peptide of cystinosis is encoded by an amino acid sequence set forth in SEQ ID NO: 15.

107. A method of embodiment 105 or 106, wherein
the antibody or antigen-binding fragment thereof that binds to the first CTNS signature peptide of cystinosis includes: a heavy chain variable (VH) domain including CDR1 of SEQ ID NO: 39, CDR2 of SEQ ID NO: 40, and CDR3 of SEQ ID NO: 41, and a light chain variable (VL) domain including: CDR1 of SEQ ID NO: 42, CDR2 of SEQ ID NO: 43, and CDR3 of SEQ ID NO: 44;
the antibody or antigen-binding fragment thereof that binds to the second CTNS signature peptide includes: a heavy chain variable (VH) domain including CDR1 of SEQ ID NO: 45, CDR2 of SEQ ID NO: 46, and CDR3 of SEQ ID NO: 47, and a light chain variable (VL) domain including: CDR1 of SEQ ID NO: 48, CDR2 of SEQ ID NO: 49, and CDR3 of SEQ ID NO: 50; and/or
the antibody or antigen-binding fragment thereof that binds to the first SHPK signature peptide includes: a heavy chain variable (VH) domain including CDR1 of SEQ ID NO: 51, CDR2 of SEQ ID NO: 52, and CDR3 of SEQ ID NO: 53, and a light chain variable (VL) domain including: CDR1 of SEQ ID NO: 54, CDR2 of SEQ ID NO: 55, and CDR3 of SEQ ID NO: 56.

108. A method of any one of embodiments 105-107, wherein the antibody or antigen-binding fragment thereof used for enrichment of the first CTNS signature peptide of cystinosis includes a VH domain of SEQ ID NO: 69.

109. A method of any one of embodiments 105-108, wherein the antibody or antigen-binding fragment thereof used for enrichment of the first CTNS signature peptide of cystinosis includes a VL domain of SEQ ID NO: 70.

110. A method of any one of embodiments 105-109, wherein the antibody or antigen-binding fragment thereof used for enrichment of the first CTNS signature peptide of cystinosis includes a heavy chain of SEQ ID NO: 106.

111. A method of any one of embodiments 105-110, wherein the antibody or antigen-binding fragment thereof used for enrichment of the first CTNS signature peptide of cystinosis includes a light chain of SEQ ID NO: 111.

112. A method of any one of embodiments 105-111, wherein the antibody or antigen-binding fragment thereof used for enrichment of the second CTNS signature peptide of cystinosis includes a VH domain of SEQ ID NO: 71.

113. A method of any one of embodiments 105-112, wherein the antibody or antigen-binding fragment thereof used for enrichment of the second CTNS signature peptide of cystinosis includes a VL domain of SEQ ID NO: 72.

114. A method of any one of embodiments 105-113, wherein the antibody or antigen-binding fragment thereof used for enrichment of the second CTNS signature peptide of cystinosis includes a heavy chain of SEQ ID NO: 116.

115. A method of any one of embodiments 105-114, wherein the antibody or antigen-binding fragment thereof used for enrichment of the second CTNS signature peptide of cystinosis includes a light chain of SEQ ID NO: 121.

116. A method of any one of embodiments 105-115, wherein the antibody or antigen-binding fragment thereof used for enrichment of the first SHPK signature peptide of cystinosis includes a VH domain of SEQ ID NO: 73.

117. A method of any one of embodiments 105-116, wherein the antibody or antigen-binding fragment thereof used for enrichment of the first SHPK signature peptide of cystinosis includes a VL domain of SEQ ID NO: 74.

118. A method of any one of embodiments 105-117, wherein the antibody or antigen-binding fragment thereof used for enrichment of the first SHPK signature peptide of cystinosis includes a heavy chain of SEQ ID NO: 126.

119. A method of any one of embodiments 105-118, wherein the antibody or antigen-binding fragment thereof used for enrichment of the first SHPK signature peptide of cystinosis includes a light chain of SEQ ID NO: 131.

120. A method of any one of embodiments 91-119, further including: Enriching for an endogenous ATP7B peptide with an antibody or antigen binding fragment thereof that binds to the endogenous ATP7B peptide; and Calculating a ratio of signature peptide concentration:endogenous ATP7B peptide concentration for each signature peptide.

121. A method of embodiment 120, wherein the endogenous ATP7B peptide is encoded by an amino acid sequence set forth in SEQ ID NO: 10, SEQ ID NO: 11, SEQ ID NO: 16, SEQ ID NO: 17, SEQ ID NO: 18, SEQ ID NO: 19, SEQ ID NO: 20, or SEQ ID NO: 21.

122. A method of embodiment 120 or 121, wherein the antibody or antigen-binding fragment thereof that binds to the endogenous ATP7B peptide includes: a heavy chain variable (VH) domain including CDR1 of SEQ ID NO: 57, CDR2 of SEQ ID NO: 58, and CDR3 of SEQ ID NO: 59, and a light chain variable (VL) domain including: CDR1 of SEQ ID NO: 60, CDR2 of SEQ ID NO: 61, and CDR3 of SEQ ID NO: 62.

123. A method of any one of embodiments 91-122, further including detecting one or more signature peptides of Wilson Disease (WD) by enriching for:
- a first ATP7B signature peptide with an antibody or antigen-binding fragment thereof that binds to the first ATP7B signature peptide;
- a second ATP7B signature peptide with an antibody or antigen-binding fragment thereof that binds to the second ATP7B signature peptide;
- a third ATP7B signature peptide with an antibody or antigen-binding fragment that binds to the third ATP7B signature peptide;
- a fourth ATP7B signature peptide with an antibody or antigen-binding fragment thereof that binds to the fourth ATP7B signature peptide;
- a fifth ATP7B signature peptide with an antibody or antigen-binding fragment thereof that binds to the fifth ATP7B signature peptide;
- a sixth ATP7B signature peptide with an antibody or antigen-binding fragment thereof that binds to the sixth ATP7B signature peptide; and/or
- a seventh ATP7B signature peptide with an antibody or antigen-binding fragment thereof;

Performing liquid chromatography-multiple reaction monitoring mass spectrometry (LC-MRM-MS) on the enriched peptides, thus detecting one or more signature peptides of WD in one or more DBS samples.

124. A method of embodiment 123, wherein
the first ATP7B signature peptide of WD is encoded by an amino acid sequence set forth in SEQ ID NO: 10;
the second ATP7B signature peptide of WD is encoded by an amino acid sequence set forth in SEQ ID NO: 11 or 21;
the third ATP7B signature peptide of WD is encoded by an amino acid sequence set forth in SEQ ID NO: 16;
the fourth ATP7B signature peptide of WD is encoded by an amino acid sequence set forth in SEQ ID NO: 17;
the fifth ATP7B signature peptide of WD is encoded by an amino acid sequence set forth in SEQ ID NO: 18;
the sixth ATP7B signature peptide of WD is encoded by an amino acid sequence set forth in SEQ ID NO: 19; and/or
the seventh ATP7B signature peptide of WD is encoded by an amino acid sequence set forth in SEQ ID NO: 20.

125. A method of embodiment 123 or 124, wherein the antibody or antigen-binding fragment thereof that binds to the second ATP7B signature peptide includes: a heavy chain variable (VH) domain including CDR1 of SEQ ID NO: 57, CDR2 of SEQ ID NO: 58, and CDR3 of SEQ ID NO: 59, and a light chain variable (VL) domain including: CDR1 of SEQ ID NO: 60, CDR2 of SEQ ID NO: 61, and CDR3 of SEQ ID NO: 62.

126. A method of any one of embodiments 123-125, wherein the antibody or antigen-binding fragment thereof used for enrichment of the second ATP7B signature peptide of WD includes a VH domain of SEQ ID NO: 75.

127. A method of any one of embodiments 123-126, wherein the antibody or antigen-binding fragment thereof used for enrichment of the second ATP7B signature peptide of WD includes a VL domain of SEQ ID NO: 76.

128. A method of any one of embodiments 123-127, wherein the antibody or antigen-binding fragment thereof used for enrichment of the second ATP7B signature peptide of WD includes a heavy chain of SEQ ID NO: 136.

129. A method of any one of embodiments 123-128, wherein the antibody or antigen-binding fragment thereof used for enrichment of the second ATP7B signature peptide of WD includes a light chain of SEQ ID NO: 141.

130. A method of any one of embodiments 91-129, further including comparing the concentration of each signature peptide to a corresponding predetermined threshold concentration.

131. A method of embodiment 130, wherein the corresponding predetermined threshold concentration is −1 standard deviation (SD), −1.1 SD, −1.2 SD, −1.3 SD, −1.4 SD, −1.5 SD, −1.6 SD, −1.7 SD, −1.8 SD, −1.9 SD, −2.0 SD, −2.1 SD, −2.2 SD, −2.3 SD, −2.4 SD, −2.5 SD, −2.6 SD, −2.7 SD, −2.8 SD, −2.9 SD, −3.0 SD, or more SD from the mean concentration of each signature peptide in a population of normal control subjects.

132. A method of embodiment 130 or 131, wherein the corresponding predetermined threshold concentration for each signature peptide is calculated from a standard deviation of the mean concentration of each signature peptide in a population of normal control subjects.

133. A method of embodiment 132, wherein the mean concentration of the CD3ε signature peptide in DBS from a population of normal control subjects includes a concentration in a range of 70 pmol/L to 400 pmol/L.

134. A method of embodiment 132 or 133, wherein the mean concentration of the first WASp signature peptide in DBS from a population of normal control subjects includes a concentration in a range of 600 pmol/L to 5000 pmol/L.

135. A method of any one of embodiments 132-134, wherein the mean concentration of the second WASp signature peptide in DBS from a population of normal control subjects includes a concentration in a range of 5500 pmol/L to 15000 pmol/L.

136. A method of any one of embodiments 132-135, wherein the mean concentration of the first BTK signature peptide in DBS from a population of normal control subjects includes a concentration in a range of 350 pmol/L to 2500 pmol/L.

137. A method of any one of embodiments 132-136, wherein the mean concentration of the second BTK signature peptide in DBS from a population of normal control subjects includes a concentration in a range of 550 pmol/L to 1600 pmol/L.

138. A method of any one of embodiments 132-137, wherein the mean concentration of the first CTNS signature peptide in DBS from a population of normal control subjects includes a concentration in a range of 40 pmol/L to 250 pmol/L.

139. A method of any one of embodiments 132-138, wherein the mean concentration of the first SHPK signature peptide in DBS from a population of normal control subjects includes a concentration in a range of 100 pmol/L to 8000 pmol/L.

140. A method of any one of embodiments 132-139, wherein the mean concentration of the second ATP7B signature peptide in DBS from a population of normal control subjects includes a concentration in a range of 90 pmol/L to 400 pmol/L.

141. A method of any one of embodiments 132-140, wherein the mean concentration of the third ATP7B signature peptide in DBS from a population of normal control subjects includes a concentration in a range of 30 pmol/L to 100 pmol/L.

142. A method of any one of embodiments 132-141, wherein the mean concentration of the seventh ATP7B signature peptide in DBS from a population of normal control subjects includes a concentration in a range of 200 pmol/L to 500 pmol/L.

143. A method of any one of embodiments 91-142, wherein the concentrations of the peptides are determined from corresponding known concentrations of reference signature peptides added prior to the LC-MRM-MS.

144. An assay for the screening of severe combined immunodeficiency (SCID), Wiskott-Aldrich syndrome (WAS), X-linked agammaglobulinemia (XLA), cystinosis, or Wilson Disease (WD) in a subject, the assay including:

(I) (i) an antibody or antigen-binding fragment thereof that binds to a CD3ε signature peptide of SCID;
  (ii) an antibody or antigen-binding fragment thereof that binds to a first WASp signature peptide of WAS;
  (iii) an antibody or antigen-binding fragment thereof that binds to a second WASp signature peptide of WAS;
  (iv) an antibody or antigen-binding fragment thereof that binds to a first BTK signature peptide of XLA;
  (v) an antibody or antigen-binding fragment thereof that binds to a second BTK signature peptide of XLA;
  (vi) an antibody or antigen-binding fragment thereof that binds to a first CTNS signature peptide of cystinosis;
  (vii) an antibody or antigen-binding fragment thereof that binds to a second CTNS signature peptide of cystinosis;
  (viii) an antibody or antigen-binding fragment thereof that binds to a third CTNS signature peptide of cystinosis;
  (ix) an antibody or antigen-binding fragment thereof that binds to a fourth CTNS signature peptide of cystinosis;
  (x) an antibody or antigen-binding fragment thereof that binds to a first SHPK signature peptide of cystinosis;
  (xi) an antibody or antigen-binding fragment thereof that binds to a second SHPK signature peptide of cystinosis;
  (xii) an antibody or antigen-binding fragment thereof that binds to a third SHPK signature peptide of cystinosis;
  (xiii) an antibody or antigen-binding fragment thereof that binds to a first ATP7B signature peptide of WD;
  (xiv) an antibody or antigen-binding fragment thereof that binds to a second ATP7B signature peptide of WD;
  (xv) an antibody or antigen-binding fragment thereof that binds to a third ATP7B signature peptide of WD;
  (xvi) an antibody or antigen-binding fragment thereof that binds to a fourth ATP7B signature peptide of WD;
  (xvii) an antibody or antigen-binding fragment thereof that binds to a fifth ATP7B signature peptide of WD;
  (xviii) an antibody or antigen-binding fragment thereof that binds to a sixth ATP7B signature peptide of WD; and/or
  (xix) an antibody or antigen-binding fragment thereof that binds to a seventh ATP7B signature peptide of WD; and/or
(II) the corresponding reference signature peptides.

145. An assay of embodiment 144, wherein
  (i) the CD3ε signature peptide and/or its reference signature peptide is encoded by an amino acid sequence set forth in SEQ ID NO: 1;
  (ii) the first WASp signature peptide and/or its reference signature peptide is encoded by an amino acid sequence set forth in SEQ ID NO: 2;
  (iii) the second WASp signature peptide and/or its reference signature peptide is encoded by an amino acid sequence set forth in SEQ ID NO: 3;
  (iv) the first BTK signature peptide and/or its reference signature peptide is encoded by an amino acid sequence set forth in SEQ ID NO: 4; and/or
  (v) the second BTK signature peptide and/or its reference signature peptide is encoded by an amino acid sequence set forth in SEQ ID NO: 5.
  (vi) the first CTNS signature peptide and/or its reference signature peptide is encoded by an amino acid sequence set forth in SEQ ID NO: 6;
  (vii) the second CTNS signature peptide and/or its reference signature peptide is encoded by an amino acid sequence set forth in SEQ ID NO: 7 or 8;
  (viii) the third CTNS signature peptide and/or its reference signature peptide is encoded by an amino acid sequence set forth in SEQ ID NO: 12;
  (ix) the fourth CTNS signature peptide and/or its reference signature peptide is encoded by an amino acid sequence set forth in SEQ ID NO: 13;
  (x) the first SHPK signature peptide and/or its reference signature peptide is encoded by an amino acid sequence set forth in SEQ ID NO: 9;
  (xi) the second SHPK signature peptide and/or its reference signature peptide is encoded by an amino acid sequence set forth in SEQ ID NO: 14;
  (xii) the third SHPK signature peptide and/or its reference signature peptide is encoded by an amino acid sequence set forth in SEQ ID NO: 15;
  (xiii) the first ATP7B signature peptide and/or its reference signature peptide is encoded by an amino acid sequence set forth in SEQ ID NO: 10;
  (xiv) the second ATP7B signature peptide and/or its reference signature peptide is encoded by an amino acid sequence set forth in SEQ ID NO: 11 or 21;
  (xv) the third ATP7B signature peptide and/or its reference signature peptide is encoded by an amino acid sequence set forth in SEQ ID NO: 16;
  (xvi) the fourth ATP7B signature peptide and/or its reference signature peptide is encoded by an amino acid sequence set forth in SEQ ID NO: 17;
  (xvii) the fifth ATP7B signature peptide and/or its reference signature peptide is encoded by an amino acid sequence set forth in SEQ ID NO: 18;
  (xviii) the sixth ATP7B signature peptide and/or its reference signature peptide is encoded by an amino acid sequence set forth in SEQ ID NO: 19; and/or
  (xix) the seventh ATP7B signature peptide and/or its reference signature peptide is encoded by an amino acid sequence set forth in SEQ ID NO: 20.

146. An assay of embodiment 144 or 145, wherein
  the antibody or antigen-binding fragment thereof that binds to the CD3ε signature peptide includes: a heavy chain variable (VH) domain including CDR1 of SEQ ID NO: 22, CDR2 of SEQ ID NO: 23, and CDR3 of SEQ ID NO: 24, and a light chain variable (VL) domain including: CDR1 of SEQ ID NO: 25, CDR2 of SEQ ID NO: 26, and CDR3 of SEQ ID NO: 27;
  the antibody or antigen-binding fragment thereof that binds to the first WASp signature peptide includes: a heavy chain variable (VH) domain including CDR1 of SEQ ID NO: 28, CDR2 of SEQ ID NO: 29, and CDR3 of SEQ ID NO: 30, and a light chain variable (VL) domain including: CDR1 of SEQ ID NO: 31, CDR2 of SEQ ID NO: 32, and CDR3 of SEQ ID NO: 33;
  the antibody or antigen-binding fragment thereof that binds to the first BTK signature peptide includes: a heavy chain variable (VH) domain including CDR1 of SEQ ID NO: 34, CDR2 of SEQ ID NO: 35, and CDR3 of sequence GDI, and a light chain variable (VL) domain including: CDR1 of SEQ ID NO: 36, CDR2 of SEQ ID NO: 37, and CDR3 of SEQ ID NO: 38;

the antibody or antigen-binding fragment thereof that binds to the first CTNS signature peptide of cystinosis includes: a heavy chain variable (VH) domain including CDR1 of SEQ ID NO: 39, CDR2 of SEQ ID NO: 40, and CDR3 of SEQ ID NO: 41, and a light chain variable (VL) domain including: CDR1 of SEQ ID NO: 42, CDR2 of SEQ ID NO: 43, and CDR3 of SEQ ID NO: 44;

the antibody or antigen-binding fragment thereof that binds to the second CTNS signature peptide includes: a heavy chain variable (VH) domain including CDR1 of SEQ ID NO: 45, CDR2 of SEQ ID NO: 46, and CDR3 of SEQ ID NO: 47, and a light chain variable (VL) domain including: CDR1 of SEQ ID NO: 48, CDR2 of SEQ ID NO: 49, and CDR3 of SEQ ID NO: 50;

the antibody or antigen-binding fragment thereof that binds to the first SHPK signature peptide includes: a heavy chain variable (VH) domain including CDR1 of SEQ ID NO: 51, CDR2 of SEQ ID NO: 52, and CDR3 of SEQ ID NO: 53, and a light chain variable (VL) domain including: CDR1 of SEQ ID NO: 54, CDR2 of SEQ ID NO: 55, and CDR3 of SEQ ID NO: 56; and/or the antibody or antigen-binding fragment thereof that binds to the second ATP7B signature peptide includes: a heavy chain variable (VH) domain including CDR1 of SEQ ID NO: 57, CDR2 of SEQ ID NO: 58, and CDR3 of SEQ ID NO: 59, and a light chain variable (VL) domain including: CDR1 of SEQ ID NO: 60, CDR2 of SEQ ID NO: 61, and CDR3 of SEQ ID NO: 62.

147. An assay of any one of embodiments 144-146, wherein the antibody or antigen-binding fragment thereof that binds to the CD3ε signature peptide of SCID includes a VH domain of SEQ ID NO: 63.

148. An assay of any one of embodiments 144-147, wherein the antibody or antigen-binding fragment thereof that binds to the CD3ε signature peptide of SCID includes a VL domain of SEQ ID NO: 64.

149. An assay of any one of embodiments 144-148, wherein the antibody or antigen-binding fragment thereof that binds to the first WASp signature peptide of WAS includes a VH domain of SEQ ID NO: 65.

150. An assay of any one of embodiments 144-149, wherein the antibody or antigen-binding fragment thereof that binds to the first WASp signature peptide of WAS includes a VL domain of SEQ ID NO: 66.

151. An assay of any one of embodiments 144-150, wherein the antibody or antigen-binding fragment thereof that binds to the first WASp signature peptide of WAS includes a heavy chain of SEQ ID NO: 86.

152. An assay of any one of embodiments 144-1551, wherein the antibody or antigen-binding fragment thereof that binds to the first WASp signature peptide of WAS includes a light chain of SEQ ID NO: 91.

153. An assay of any one of embodiments 144-152, wherein the antibody or antigen-binding fragment thereof that binds to the first BTK signature peptide of XLA includes a VH domain of SEQ ID NO: 67.

154. An assay of any one of embodiments 144-153, wherein the antibody or antigen-binding fragment thereof that binds to the first BTK signature peptide of XLA includes a VL domain of SEQ ID NO: 68.

155. An assay of any one of embodiments 144-154, wherein the antibody or antigen-binding fragment thereof that binds to the first BTK signature peptide of XLA includes a heavy chain of SEQ ID NO: 96.

156. An assay of any one of embodiments 144-155, wherein the antibody or antigen-binding fragment thereof that binds to the first BTK signature peptide of XLA includes a light chain of SEQ ID NO: 101.

157. An assay of any one of embodiments 144-156, wherein the antibody or antigen-binding fragment thereof that binds to the first CTNS signature peptide of cystinosis of SEQ ID NO: 6 includes a VH domain of SEQ ID NO: 69.

158. An assay of any one of embodiments 144-157, wherein the antibody or antigen-binding fragment thereof that binds to the first CTNS signature peptide of cystinosis of SEQ ID NO: 6 includes a VL domain of SEQ ID NO: 70.

159. An assay of any one of embodiments 144-158, wherein the antibody or antigen-binding fragment thereof that binds to the first CTNS signature peptide of cystinosis of SEQ ID NO: 6 includes a heavy chain of SEQ ID NO: 106.

160. An assay of any one of embodiments 144-159, wherein the antibody or antigen-binding fragment thereof that binds to the first CTNS signature peptide of cystinosis of SEQ ID NO: 6 includes a light chain of SEQ ID NO: 111.

161. An assay of any one of embodiments 144-160, wherein the antibody or antigen-binding fragment thereof that binds to the second CTNS signature peptide of cystinosis of SEQ ID NO: 7 or 8 includes a VH domain of SEQ ID NO: 71.

162. An assay of any one of embodiments 144-161, wherein the antibody or antigen-binding fragment thereof that binds to the second CTNS signature peptide of cystinosis of SEQ ID NO: 7 or 8 includes a VL domain of SEQ ID NO: 72.

163. An assay of any one of embodiments 144-162, wherein the antibody or antigen-binding fragment thereof that binds to the second CTNS signature peptide of cystinosis of SEQ ID NO: 7 or 8 includes a heavy chain of SEQ ID NO: 116.

164. An assay of any one of embodiments 144-163, wherein the antibody or antigen-binding fragment thereof that binds to the second CTNS signature peptide of cystinosis of SEQ ID NO: 7 or 8 includes a light chain of SEQ ID NO: 121.

165. An assay of any one of embodiments 144-164, wherein the antibody or antigen-binding fragment thereof that binds to the first SHPK signature peptide of cystinosis of SEQ ID NO: 9 includes a VH domain of SEQ ID NO: 73.

166. An assay of any one of embodiments 144-165, wherein the antibody or antigen-binding fragment thereof that binds to the first SHPK signature peptide of cystinosis of SEQ ID NO: 9 includes a VL domain of SEQ ID NO: 74.

167. An assay of any one of embodiments 144-166, wherein the antibody or antigen-binding fragment thereof that binds to the first SHPK signature peptide of cystinosis of SEQ ID NO: 9 includes a heavy chain of SEQ ID NO: 126.

168. An assay of any one of embodiments 144-167, wherein the antibody or antigen-binding fragment thereof that binds to the first SHPK signature peptide of cystinosis of SEQ ID NO: 9 includes a light chain of SEQ ID NO: 131.

169. An assay of any one of embodiments 144-168, wherein the antibody or antigen-binding fragment thereof that binds to the second ATP7B signature peptide of WD of SEQ ID NO: 11 or 21 includes a VH domain of SEQ ID NO: 75.

170. An assay of any one of embodiments 144-169, wherein the antibody or antigen-binding fragment thereof that binds to the second ATP7B signature peptide of WD of SEQ ID NO: 11 or 21 includes a VL domain of SEQ ID NO: 76.

171. An assay of any one of embodiments 144-170, wherein the antibody or antigen-binding fragment thereof that binds to the second ATP7B signature peptide of WD of SEQ ID NO: 11 or 21 includes a heavy chain of SEQ ID NO: 136.

172. An assay of any one of embodiments 144-171, wherein the antibody or antigen-binding fragment thereof that binds to the second ATP7B signature peptide of WD of SEQ ID NO: 11 or 21 includes a light chain of SEQ ID NO: 141.

173. An assay of any one of embodiments 144-172, wherein the reference signature peptides are isotopically labeled.

174. An assay of any one of embodiments 144-173, wherein the antibodies or antigen-binding fragments thereof are attached to magnetic beads.

175. An isolated antibody or antigen binding fragment thereof including: a heavy chain variable (VH) domain including CDR1 of SEQ ID NO: 22, CDR2 of SEQ ID NO: 23, and CDR3 of SEQ ID NO: 24, and a light chain variable (VL) domain including: CDR1 of SEQ ID NO: 25, CDR2 of SEQ ID NO: 26, and CDR3 of SEQ ID NO: 27.

176. The isolated antibody or antigen binding fragment thereof of embodiment 175, wherein the VH domain includes SEQ ID NO: 63.

177. The isolated antibody or antigen binding fragment thereof of embodiment 175 or 176, wherein the VL domain includes SEQ ID NO: 64.

178. An isolated antibody or antigen binding fragment thereof including: a heavy chain variable (VH) domain including CDR1 of SEQ ID NO: 28, CDR2 of SEQ ID NO: 29, and CDR3 of SEQ ID NO: 30, and a light chain variable (VL) domain including: CDR1 of SEQ ID NO: 31, CDR2 of SEQ ID NO: 32, and CDR3 of SEQ ID NO: 33.

179. The isolated antibody or antigen binding fragment thereof of embodiment 178, wherein the VH domain includes SEQ ID NO: 65.

180. The isolated antibody or antigen binding fragment thereof of embodiment 178 or 179, wherein the VL domain includes SEQ ID NO: 66.

181. The isolated antibody or antigen binding fragment thereof of any one of embodiments 178-180, wherein the heavy chain includes SEQ ID NO: 86.

182. The isolated antibody or antigen binding fragment thereof of any one of embodiments 178-181, wherein the light chain includes SEQ ID NO: 91.

183. An isolated antibody or antigen binding fragment thereof including: a heavy chain variable (VH) domain including CDR1 of SEQ ID NO: 34, CDR2 of SEQ ID NO: 35, and CDR3 of sequence GDI, and a light chain variable (VL) domain including: CDR1 of SEQ ID NO: 36, CDR2 of SEQ ID NO: 37, and CDR3 of SEQ ID NO: 38.

184. The isolated antibody or antigen binding fragment thereof of embodiment 183, wherein the VH domain includes SEQ ID NO: 67.

185. The isolated antibody or antigen binding fragment thereof of embodiment 183 or 184, wherein the VL domain includes SEQ ID NO: 68.

186. The isolated antibody or antigen binding fragment thereof of any one of embodiments 183-185, wherein the heavy chain includes SEQ ID NO: 96.

187. The isolated antibody or antigen binding fragment thereof of any one of embodiments 183-186, wherein the light chain includes SEQ ID NO: 101.

188. An isolated antibody or antigen binding fragment thereof including: a heavy chain variable (VH) domain including CDR1 of SEQ ID NO: 39, CDR2 of SEQ ID NO: 40, and CDR3 of SEQ ID NO: 41, and a light chain variable (VL) domain including: CDR1 of SEQ ID NO: 42, CDR2 of SEQ ID NO: 43, and CDR3 of SEQ ID NO: 44.

189. The isolated antibody or antigen binding fragment thereof of embodiment 188, wherein the VH domain includes SEQ ID NO: 69.

190. The isolated antibody or antigen binding fragment thereof of embodiment 188 or 189, wherein the VL domain includes SEQ ID NO: 70.

191. The isolated antibody or antigen binding fragment thereof of any one of embodiments 188-190, wherein the heavy chain includes SEQ ID NO: 106.

192. The isolated antibody or antigen binding fragment thereof of any one of embodiments 188-191, wherein the light chain includes SEQ ID NO: 111.

193. An isolated antibody or antigen binding fragment thereof including: a heavy chain variable (VH) domain including CDR1 of SEQ ID NO: 45, CDR2 of SEQ ID NO: 46, and CDR3 of SEQ ID NO: 47, and a light chain variable (VL) domain including: CDR1 of SEQ ID NO: 48, CDR2 of SEQ ID NO: 49, and CDR3 of SEQ ID NO: 50.

194. The isolated antibody or antigen binding fragment thereof of embodiment 193, wherein the VH domain includes SEQ ID NO: 71.

195. The isolated antibody or antigen binding fragment thereof of embodiment 193 or 194, wherein the VL domain includes SEQ ID NO: 72.

196. The isolated antibody or antigen binding fragment thereof of any one of embodiments 193-195, wherein the heavy chain includes SEQ ID NO: 116.

197. The isolated antibody or antigen binding fragment thereof of any one of embodiments 193-196, wherein the light chain includes SEQ ID NO: 121.

198. An isolated antibody or antigen binding fragment thereof including: a heavy chain variable (VH) domain including CDR1 of SEQ ID NO: 51, CDR2 of SEQ ID NO: 52, and CDR3 of SEQ ID NO: 53, and a light chain variable (VL) domain including: CDR1 of SEQ ID NO: 54, CDR2 of SEQ ID NO: 55, and CDR3 of SEQ ID NO: 56.

199. The isolated antibody or antigen binding fragment thereof of embodiment 198, wherein the VH domain includes SEQ ID NO: 73.

200. The isolated antibody or antigen binding fragment thereof of embodiment 198 or 199, wherein the VL domain includes SEQ ID NO: 74.

201. The isolated antibody or antigen binding fragment thereof of any one of embodiments 198-200, wherein the heavy chain includes SEQ ID NO: 126.

202. The isolated antibody or antigen binding fragment thereof of any one of embodiments 198-201, wherein the light chain includes SEQ ID NO: 131.

203. An isolated antibody or antigen binding fragment thereof including: a heavy chain variable (VH) domain including CDR1 of SEQ ID NO: 57, CDR2 of SEQ ID NO: 58, and CDR3 of SEQ ID NO: 59, and a light chain variable (VL) domain including: CDR1 of SEQ ID NO: 60, CDR2 of SEQ ID NO: 61, and CDR3 of SEQ ID NO: 62.

204. The isolated antibody or antigen binding fragment thereof of embodiment 203, wherein the VH domain includes SEQ ID NO: 75.

205. The isolated antibody or antigen binding fragment thereof of embodiment 203 or 204, wherein the VL domain includes SEQ ID NO: 76.

206. The isolated antibody or antigen binding fragment thereof of any one of embodiments 203-205, wherein the heavy chain includes SEQ ID NO: 136.

207. The isolated antibody or antigen binding fragment thereof of any one of embodiments 203-206, wherein the light chain includes SEQ ID NO: 141.

208. A kit including:
(I) (i) an antibody or antigen-binding fragment thereof that binds to a CD3ε signature peptide of SCID;
(ii) an antibody or antigen-binding fragment thereof that binds to a first WASp signature peptide of WAS;
(iii) an antibody or antigen-binding fragment thereof that binds to a second WASp signature peptide of WAS;

(iv) an antibody or antigen-binding fragment thereof that binds to a first BTK signature peptide of XLA;
(v) an antibody or antigen-binding fragment thereof that binds to a second BTK signature peptide of XLA;
(vi) an antibody or antigen-binding fragment thereof that binds to a first CTNS signature peptide of cystinosis;
(vii) an antibody or antigen-binding fragment thereof that binds to a second CTNS signature peptide of cystinosis;
(viii) an antibody or antigen-binding fragment thereof that binds to a third CTNS signature peptide of cystinosis;
(ix) an antibody or antigen-binding fragment thereof that binds to a fourth CTNS signature peptide of cystinosis;
(x) an antibody or antigen-binding fragment thereof that binds to a first SHPK signature peptide of cystinosis;
(xi) an antibody or antigen-binding fragment thereof that binds to a second SHPK signature peptide of cystinosis;
(xii) an antibody or antigen-binding fragment thereof that binds to a third SHPK signature peptide of cystinosis;
(xiii) an antibody or antigen-binding fragment thereof that binds to a first ATP7B signature peptide of WD;
(xiv) an antibody or antigen-binding fragment thereof that binds to a second ATP7B signature peptide of WD;
(xv) an antibody or antigen-binding fragment thereof that binds to a third ATP7B signature peptide of WD;
(xvi) an antibody or antigen-binding fragment thereof that binds to a fourth ATP7B signature peptide of WD;
(xvii) an antibody or antigen-binding fragment thereof that binds to a fifth ATP7B signature peptide of WD;
(xviii) an antibody or antigen-binding fragment thereof that binds to a sixth ATP7B signature peptide of WD; and/or
(xix) an antibody or antigen-binding fragment thereof that binds to a seventh ATP7B signature peptide of WD; and/or
(II) the corresponding reference signature peptides; and
(III) use instructions on use of contents in the kit.
209. A kit of embodiment 208, wherein
  (i) the CD3ε signature peptide and/or its reference signature peptide is encoded by an amino acid sequence set forth in SEQ ID NO: 1;
  (ii) the first WASp signature peptide and/or its reference signature peptide is encoded by an amino acid sequence set forth in SEQ ID NO: 2;
  (iii) the second WASp signature peptide and/or its reference signature peptide is encoded by an amino acid sequence set forth in SEQ ID NO: 3;
  (iv) the first BTK signature peptide and/or its reference signature peptide is encoded by an amino acid sequence set forth in SEQ ID NO: 4; and/or
  (v) the second BTK signature peptide and/or its reference signature peptide is encoded by an amino acid sequence set forth in SEQ ID NO: 5.
  (vi) the first CTNS signature peptide and/or its reference signature peptide is encoded by an amino acid sequence set forth in SEQ ID NO: 6;
  (vii) the second CTNS signature peptide and/or its reference signature peptide is encoded by an amino acid sequence set forth in SEQ ID NO: 7 or 8;
  (viii) the third CTNS signature peptide and/or its reference signature peptide is encoded by an amino acid sequence set forth in SEQ ID NO: 12;
  (ix) the fourth CTNS signature peptide and/or its reference signature peptide is encoded by an amino acid sequence set forth in SEQ ID NO: 13;
  (x) the first SHPK signature peptide and/or its reference signature peptide is encoded by an amino acid sequence set forth in SEQ ID NO: 9;
  (xi) the second SHPK signature peptide and/or its reference signature peptide is encoded by an amino acid sequence set forth in SEQ ID NO: 14;
  (xii) the third SHPK signature peptide and/or its reference signature peptide is encoded by an amino acid sequence set forth in SEQ ID NO: 15;
  (xiii) the first ATP7B signature peptide and/or its reference signature peptide is encoded by an amino acid sequence set forth in SEQ ID NO: 10;
  (xiv) the second ATP7B signature peptide and/or its reference signature peptide is encoded by an amino acid sequence set forth in SEQ ID NO: 11 or 21;
  (xv) the third ATP7B signature peptide and/or its reference signature peptide is encoded by an amino acid sequence set forth in SEQ ID NO: 16;
  (xvi) the fourth ATP7B signature peptide and/or its reference signature peptide is encoded by an amino acid sequence set forth in SEQ ID NO: 17;
  (xvii) the fifth ATP7B signature peptide and/or its reference signature peptide is encoded by an amino acid sequence set forth in SEQ ID NO: 18;
  (xviii) the sixth ATP7B signature peptide and/or its reference signature peptide is encoded by an amino acid sequence set forth in SEQ ID NO: 19; and/or
  (xix) the seventh ATP7B signature peptide and/or its reference signature peptide is encoded by an amino acid sequence set forth in SEQ ID NO: 20.
210. A kit of embodiment 208 or 209, wherein
  the antibody or antigen-binding fragment thereof that binds to the CD3ε signature peptide includes: a heavy chain variable (VH) domain including CDR1 of SEQ ID NO: 22, CDR2 of SEQ ID NO: 23, and CDR3 of SEQ ID NO: 24, and a light chain variable (VL) domain including: CDR1 of SEQ ID NO: 25, CDR2 of SEQ ID NO: 26, and CDR3 of SEQ ID NO: 27;
  the antibody or antigen-binding fragment thereof that binds to the first WASp signature peptide includes: a heavy chain variable (VH) domain including CDR1 of SEQ ID NO: 28, CDR2 of SEQ ID NO: 29, and CDR3 of SEQ ID NO: 30, and a light chain variable (VL) domain including: CDR1 of SEQ ID NO: 31, CDR2 of SEQ ID NO: 32, and CDR3 of SEQ ID NO: 33;
  the antibody or antigen-binding fragment thereof that binds to the first BTK signature peptide includes: a heavy chain variable (VH) domain including CDR1 of SEQ ID NO: 34, CDR2 of SEQ ID NO: 35, and CDR3 of sequence GDI, and a light chain variable (VL) domain including: CDR1 of SEQ ID NO: 36, CDR2 of SEQ ID NO: 37, and CDR3 of SEQ ID NO: 38;
  the antibody or antigen-binding fragment thereof that binds to the first CTNS signature peptide of cystinosis includes: a heavy chain variable (VH) domain including CDR1 of SEQ ID NO: 39, CDR2 of SEQ ID NO: 40, and CDR3 of SEQ ID NO: 41, and a light chain variable (VL) domain including: CDR1 of SEQ ID NO: 42, CDR2 of SEQ ID NO: 43, and CDR3 of SEQ ID NO: 44;
  the antibody or antigen-binding fragment thereof that binds to the second CTNS signature peptide includes: a heavy chain variable (VH) domain including CDR1 of SEQ ID NO: 45, CDR2 of SEQ ID NO: 46, and CDR3 of SEQ ID NO: 47, and a light chain variable (VL) domain including: CDR1 of SEQ ID NO: 48, CDR2 of SEQ ID NO: 49, and CDR3 of SEQ ID NO: 50;
  the antibody or antigen-binding fragment thereof that binds to the first SHPK signature peptide includes: a heavy chain variable (VH) domain including CDR1 of SEQ ID NO: 51, CDR2 of SEQ ID NO: 52, and CDR3 of SEQ ID NO: 53, and a light chain variable (VL) domain including: CDR1 of SEQ ID NO: 54, CDR2 of SEQ ID NO: 55, and CDR3 of SEQ ID NO: 56; and/or the antibody or antigen-binding fragment thereof that binds to the second ATP7B signature peptide includes: a heavy chain variable (VH) domain including CDR1 of SEQ ID NO: 57, CDR2 of SEQ ID NO: 58, and CDR3 of SEQ ID NO: 59, and a light chain variable (VL) domain including: CDR1 of SEQ ID NO: 60, CDR2 of SEQ ID NO: 61, and CDR3 of SEQ ID NO: 62.

211. A kit of any one of embodiments 208-210, wherein the antibody or antigen-binding fragment thereof that binds to the CD3ε signature peptide of SCID includes a VH domain of SEQ ID NO: 63.

212. A kit of any one of embodiments 208-211, wherein the antibody or antigen-binding fragment thereof that binds to the CD3ε signature peptide of SCID includes a VL domain of SEQ ID NO: 64.

213. A kit of any one of embodiments 208-212, wherein the antibody or antigen-binding fragment thereof that binds to the first WASp signature peptide of WAS includes a VH domain of SEQ ID NO: 65.

214. A kit of any one of embodiments 208-213, wherein the antibody or antigen-binding fragment thereof that binds to the first WASp signature peptide of WAS includes a VL domain of SEQ ID NO: 66.

215. A kit of any one of embodiments 208-214, wherein the antibody or antigen-binding fragment thereof that binds to the first WASp signature peptide of WAS includes a heavy chain of SEQ ID NO: 86.

216. A kit of any one of embodiments 208-215, wherein the antibody or antigen-binding fragment thereof that binds to the first WASp signature peptide of WAS includes a light chain of SEQ ID NO: 91.

217. A kit of any one of embodiments 208-216, wherein the antibody or antigen-binding fragment thereof that binds to the first BTK signature peptide of XLA includes a VH domain of SEQ ID NO: 67.

218. A kit of any one of embodiments 208-217, wherein the antibody or antigen-binding fragment thereof that binds to the first BTK signature peptide of XLA includes a VL domain of SEQ ID NO: 68.

219. A kit of any one of embodiments 208-218, wherein the antibody or antigen-binding fragment thereof that binds to the first BTK signature peptide of XLA includes a heavy chain of SEQ ID NO: 96.

220. A kit of any one of embodiments 208-219, wherein the antibody or antigen-binding fragment thereof that binds to the first BTK signature peptide of XLA includes a light chain of SEQ ID NO: 101.

221. A kit of any one of embodiments 208-220, wherein the antibody or antigen-binding fragment thereof that binds to the first CTNS signature peptide of cystinosis of SEQ ID NO: 6 includes a VH domain of SEQ ID NO: 69.

222. A kit of any one of embodiments 208-221, wherein the antibody or antigen-binding fragment thereof that binds to the first CTNS signature peptide of cystinosis of SEQ ID NO: 6 includes a VL domain of SEQ ID NO: 70.

223. A kit of any one of embodiments 208-222, wherein the antibody or antigen-binding fragment thereof that binds to the first CTNS signature peptide of cystinosis of SEQ ID NO: 6 includes a heavy chain of SEQ ID NO: 106.

224. A kit of any one of embodiments 208-223, wherein the antibody or antigen-binding fragment thereof that binds to the first CTNS signature peptide of cystinosis of SEQ ID NO: 6 includes a light chain of SEQ ID NO: 111.

225. A kit of any one of embodiments 208-224, wherein the antibody or antigen-binding fragment thereof that binds to the second CTNS signature peptide of cystinosis of SEQ ID NO: 7 or 8 includes a VH domain of SEQ ID NO: 71.

226. A kit of any one of embodiments 208-225, wherein the antibody or antigen-binding fragment thereof that binds to the second CTNS signature peptide of cystinosis of SEQ ID NO: 7 or 8 includes a VL domain of SEQ ID NO: 72.

227. A kit of any one of embodiments 208-226, wherein the antibody or antigen-binding fragment thereof that binds to the second CTNS signature peptide of cystinosis of SEQ ID NO: 7 or 8 includes a heavy chain of SEQ ID NO: 116.

228. A kit of any one of embodiments 208-227, wherein the antibody or antigen-binding fragment thereof that binds to the second CTNS signature peptide of cystinosis of SEQ ID NO: 7 or 8 includes a light chain of SEQ ID NO: 121.

229. A kit of any one of embodiments 208-228, wherein the antibody or antigen-binding fragment thereof that binds to the first SHPK signature peptide of cystinosis of SEQ ID NO: 9 includes a VH domain of SEQ ID NO: 73.

230. A kit of any one of embodiments 208-229, wherein the antibody or antigen-binding fragment thereof that binds to the first SHPK signature peptide of cystinosis of SEQ ID NO: 9 includes a VL domain of SEQ ID NO: 74.

231. A kit of any one of embodiments 208-230, wherein the antibody or antigen-binding fragment thereof that binds to the first SHPK signature peptide of cystinosis of SEQ ID NO: 9 includes a heavy chain of SEQ ID NO: 126.

232. A kit of any one of embodiments 208-231, wherein the antibody or antigen-binding fragment thereof that binds to the first SHPK signature peptide of cystinosis of SEQ ID NO: 9 includes a light chain of SEQ ID NO: 131.

233. A kit of any one of embodiments 208-232, wherein the antibody or antigen-binding fragment thereof that binds to the second ATP7B signature peptide of WD of SEQ ID NO: 11 or 21 includes a VH domain of SEQ ID NO: 75.

234. A kit of any one of embodiments 208-233, wherein the antibody or antigen-binding fragment thereof that binds to the second ATP7B signature peptide of WD of SEQ ID NO: 11 or 21 includes a VL domain of SEQ ID NO: 76.

235. A kit of any one of embodiments 208-234, wherein the antibody or antigen-binding fragment thereof that binds to the second ATP7B signature peptide of WD of SEQ ID NO: 11 or 21 includes a heavy chain of SEQ ID NO: 136.

236. A kit of any one of embodiments 208-235, wherein the antibody or antigen-binding fragment thereof that binds to the second ATP7B signature peptide of WD of SEQ ID NO: 11 or 21 includes a light chain of SEQ ID NO: 141.

237. A kit of any one of embodiments 208-236, further including one or more of filter paper card, punch tool, digestion enzymes, digestion buffers, solid support for the antibodies or antigen-binding fragments thereof; and elution buffers.

238. A kit of any one of embodiments 208-237, wherein the reference signature peptides are isotopically labeled.

239. A kit of any one of embodiments 208-238, wherein the antibodies or antigen-binding fragments thereof are attached to magnetic beads.

(XI) Experimental Examples

Example 1. Summary. A study was undertaken to evaluate whether a multiplex assay based on peptide immunoaffinity enrichment coupled with selected reaction monitoring mass spectrometry (immuno-SRM) can reliably and precisely distinguish affected patients with CD3ε-associated severe combined immunodeficiency (SCID), Wiskott-Aldrich Syndrome (WAS), and X-linked agammaglobulinemia (XLA) from one another and from unaffected normal control dried blood spot (DBS) samples. A blinded, multiplexed analysis of proteolytically-generated peptides from CD3ε, WASp, and BTK (for SCID, WAS, and XLA, respectively) in DBS samples from 42 primary immunodeficiency disorders (PIDD) patients, 40 normal adult controls, and 62 normal newborns was performed. The immuno-SRM assays reliably quantified the target peptides in DBS, including intra- and inter-assay precision (11-22% and 11-43%), linearity (1.39-2000 fmol peptide), and stability (≤0.09% difference in 72 h). Analysis of signature peptides found a statistically significant reduction (or absence) of peptide levels in affected patients compared to control groups (SCID: p=0.05, WAS and BTK: p=0.0001). Immuno-SRM-based quantification of proteotypic peptides from CD3ε, WASp, and BTK in DBS distinguishes relevant PIDD cases from controls. The approach can be employed to conduct large-scale multiplexed newborn screening of selective PIDDs.

Materials and Methods. Patient Samples. PIDD and normal control blood samples were obtained from Seattle Children's Immunology Diagnostic Laboratory. Newborn DBS were retrieved from the Washington State Newborn Screening Laboratory (Shoreline, Wash.) after Institutional Review Board approval. XLA DBS were collected from 20 suspected Vietnamese patients and shipped per regular mail to Seattle Children's Hospital. Genotypes of these patients by Sanger sequencing was previously reported in Segundo et al. Front Immunol. Frontiers; 2018; 9: 289. In total, DBS samples from 42 PIDD patients and 40 normal controls were obtained. Normal control and PIDD patient DBS were prepared by pipetting 70 µL of blood/12 mm spot onto filter paper cards (Protein Saver 903 Card, Whatman, Piscataway, N.J.), allowed to dry at room temperature overnight, and stored in sealed plastic bags at −80° C. until use. Affected patient samples were shipped from collection locations and stored at −80° C. until use.

Selection of Surrogate Peptides and Antibody Production. Surrogate peptides for CD3ε, WASp, and BTK were selected by in silico trypsin digestion and NCBI BLAST tools. Final peptide selections were made according to accepted major criteria for immuno-SRM development including peptide length, lack of post-transcriptional modifications, and uniqueness in the human genome by BLAST searching as previously described. Kerfoot et al. Proteomics Clin Appl. 2012; 6: 394-402; Abbatiello et al. Mol. Cell Proteomics. American Society for Biochemistry and Molecular Biology; 2015; 14: 2357-2374; Hoofnagle et al. Clin. Chem. 2016; 62: 48-69. Peptide selection and monoclonal antibody production for ATP7B signature peptides have been previously reported. Jung et al. 2017, supra. Crude peptides were then screened empirically to determine suitability for detection and quantification by liquid chromatography-tandem mass spectrometry (LC-MS/MS).

Affinity-purified rabbit polyclonal antibodies (pAb), or monoclonal antibodies (mAb), were successfully generated against five peptides by Pacific Immunology (Ramona, Calif.) or Fred Hutchinson Cancer Research Center Immunology lab (Seattle, Wash.). Briefly, signature peptides were synthesized with a C-terminal extension (GSGC, SEQ ID NO: 77) or an N-terminal cysteine extension and conjugated to keyhole limpet hemocyanin (KHL) for immunization. Two New Zealand white rabbits or five mice were injected per peptide. pAbs or mAbs for all selected peptides successfully underwent affinity-purification from 25 mL of antiserum.

Immuno-SRM Assay Reagents. ProteaseMAX™ Surfactant (no. V2072) and proteomics grade trypsin (no. V5113) were purchased from Promega (Madison, Wis.). Bovine serum albumin standard (200 mg/m L), and (3-[3-cholamidopropyl)=dimethylammonio]-1-propanesulfonate) (Pierce™ CHAPS, no. P128300) detergent were obtained from Thermo Fisher Scientific (Waltham, Mass.). Ammonium bicarbonate (40867-50G-F) was purchased from Fluka Analytical (Munich, Germany). Acetonitrile (no. A955), water (no. W6, LCMS optima grade), formic acid (no. P128905), and phosphate-buffered saline (PBS, no. 10010-023) were obtained from Thermo Fisher Scientific (Waltham, Mass.).

Heavy stable isotope-labeled peptides were obtained from Anaspec (Fremont, Calif.). The stable isotope-labeled peptides were purified >95% by HPLC and the C-terminal arginine or lysine was labeled with $^{13}C$ and $^{15}N$ atoms, resulting in a mass shift of +8 or +10 Da, respectively. Aliquots were stored in 5% acetonitrile/0.1% formic acid at −20° C. until use.

Antibodies were immobilized on 2.8 µm Dynabeads Protein G magnetic beads (no. 10004D, Invitrogen, Carlsbad, Calif.) in a 1 µg antibody-to-2.5 µL of beads ratio. In brief, 250 µL of the beads were added to 1.5 mL Eppendorf tubes (022363204 Eppendorf) and washed twice with 250 µL of 1×PBS, followed by the addition of 100 µg of antibody and 1×PBS+0.03% CHAPS (no. 28300, Thermo Scientific, Waltham, Mass.) to yield a total 250 µL of volume. The antibodies were allowed to couple to the beads overnight with tumbling at 4° C. The next day, the antibodies were immobilized onto the beads with chemical cross-linking. Briefly, antibody beads were collected using magnetic pulldown, excess PBS was discarded, and 300 µL of freshly prepared 20 mM DMP (dimethyl pimelimidate dihydrochloride, no. D8388, Sigma Aldrich, St. Louis, Mo.) in 200 mM triethanolamine, pH 8.5 (no. T58300, Sigma Aldrich, St. Louis, Mo.) was added. The samples were tumbled for 30 min at room temperature, and the DMP in triethanolamine was discarded. 250 µL of 150 mM monoethanolamine (no. 411000, Sigma Aldrich, St. Louis, Mo.) was added and the beads were tumbled at room temperature for 30 min. The antibody beads were washed twice using 250 µL of 5% acetic acid+0.03% CHAPS (5 min of tumbling at room temperate each time), and washed once more using 250 µL of 1×PBS+0.03% CHAPS. The CD3ε, WASp, and BTK antibody-linked beads were then washed and incubated in 5% acetic acid +3% acetonitrile (ACN), washed with 250 µL of 1×PBS+0.03% CHAPS, and the latter two steps were repeated once. All antibody-linked beads were washed with 250 µL of 1×PBS+0.03% CHAPS until neutral pH (7.0) was achieved. The washed antibody-linked beads were then resuspended in 250 µL of 1×PBS+0.03% CHAPS and 2.5 µL of $NaN_3$ (52002-5G Sigma Aldrich) for anti-fungal properties and stored at 4° C. until use.

DBS Protein Extraction and Trypsin Digestion. For each sample (blinded normal controls or patients), one entire DBS spot (13 mm) containing 70 µL blood was perforated into 17 punches at 3-mm diameter with a standard leather punch tool. Final sample representation was SCID: n=3, WAS: n=11, XLA: n=26, and normal controls (n=40). The punches were placed in a 1.5 mL eppendorf tube, and 490 µL of 0.1% ProteaseMax™ in 50 mM ammonium biocarbonate (pH 8) was added into each tube. The tubes were vortexed for 1 h on the Eppendorf MixMate (Eppendorf, Hamburg, Germany), after which 10 µL of each sample were aliquoted and diluted 200-fold for Bradford assay to determine protein concentration. Disulfide bond reduction was performed with 2 M DTT at 5 mM, and an additional 490 µL of 0.1% ProteaseMax™ in 50 mM ammonium biocarbonate (pH 8) was added into each tube before incubation in 37° C. water bath for 30 minutes. Trypsin was then added at a 1:50 enzyme to protein ratio (w/w), and acetonitrile was added to a final concentration of 15%. The mixture was incubated in a 37° C. water bath overnight for digestion before centrifugation for 10 minutes at 13,000 RPM before each supernatant was transferred to a new tube and dried in the Savant™ SpeedVac™ High Capacity Concentrator (Thermo Fisher Scientific, Waltham, Mass.). All trypsinized DBS digests were stored at −80° C. until use.

For samples analyzed from the Washington State NBS laboratory, 5 or 6 3-mm punches were used for protein extraction and digestion (n=62). Procedures were identical to those for previous samples except that volumes were reduced as follows: 150 µL of 0.1% ProteaseMax™ and 0.78 µL DTT for each addition.

Peptide Immunoaffinity Enrichment. DBS digests were resuspended in 1×PBS+0.03% CHAPS to yield a 1 µg/µL nominal protein digest concentration. Cross-linked, antibody-coated beads were added to a total mass of 2 µg pAb for each target. Then 20 µL of 1M Tris pH 8.0 (15568-025 UltraPure, Invitrogen, Carlsbad, Calif.) was added. Isotope-labeled peptides were added as internal standards (IS). This suspension was incubated overnight with tumbling at 4° C. to achieve peptide capture. The next day, the antibody bead:peptide complexes were washed twice with 100 µL PBS+0.01% CHAPS and once in 100 µL 0.01% PBS+0.01% CHAPS. Finally, the peptides were eluted by incubation in 30 µL of 5% acetic acid/3% ACN. Released peptides were stored at −80° C. until analysis. For samples analyzed from the WA State NBS laboratory, procedures were identical to those for previous samples except that volumes were reduced as follows: 58.1 µL of 1×PBS+0.03% CHAPS, 0.59 µg pAb for each peptide, 3.13 µL internal standard (IS), and 12.5 µL TRIS.

Liquid Chromatography-Tandem Mass Spectrometry. Enriched samples were analyzed at two laboratory sites to examine the inter-laboratory variability in data acquisition, utilizing two separate LC-MS/MS systems and instrument configurations (described below). Measured peptide concentrations were then compared for method validation. Peptide parent and daughter ion spectra have been previously reported. Kerfoot et al. Proteomics Clin Appl. 2012; 6: 394-402.

Laboratory Site 1: Instruments included a Waters Xevo TQ-XS MS with ionkey source technology connected to Waters M-Class Gradient and Loading pumps (Waters, Milford, Mass.). Chromatographic solvents were A: $H_2O$+0.1% Formic Acid (FA) and B: ACN+0.1% FA. Initially, peptide mixtures were loaded onto a M-Class Trap Symmetry 300 µm×50 mm C18 column (100 Å, 5 µm) utilizing a constant flow of 98:2 A:B at 20 µL/min for 3 minutes. Subsequently, the flow was reversed and peptides were separated using gradient flow across a 150 µm×100 mm BEH C18 ikey (130 Å, 1.7 µm). Gradient method programming is shown in Table 4. The peptides monitored in this location were CD3ε 197, WASp 274, WASp 289, BTK 407, and ATP7B 1056.

TABLE 4

LC method setup for signature peptide separation at Laboratory Site 1 and Laboratory Site 2.

| Lab site 1 | | Lab site 2 | |
|---|---|---|---|
| Time | % B | Time | % B |
| 0 | 5 | 0 | 1 |
| 1 | 5 | 4 | 1 |
| 11 | 45 | 24 | 40 |
| 13 | 85 | 25 | 90 |
| 15 | 85 | 26 | 90 |
| 17 | 5 | 27 | 1 |
| 20 | 5 | 35 | 1 |

A = $H_2O$ + 0.1% Formic Acid,
B = B: ACN + 0.1% Formic Acid

Parameters for transitions and collision energy (CE) were taken from a linear regression of previously optimized values in Skyline and those generated using Waters intellistart technology to identify the most intense fragments upon ionization. SRM transitions were acquired at unit/unit resolution in both the Q1 and Q3 quadrupoles with 5 ms dwell time and 3 ms pause between mass ranges, resulting in a cycle time of 1.5 s. All samples were run in a blinded fashion.

Laboratory Site 2: LC-MS was conducted on a SCIEX 5500 QTRAP mass spectrometer interfaced with an Eksigent 425 LC and Nanoflex Chip system. Chromatographic solvents were A: $H_2O$+0.1% FA and B: 90% ACN+0.1% FA. Peptides were loaded on a 0.2×0.5 mm trap column (Reprosil-Pur AQ C18, 3 µm, 120 A) at 2% B using a flow rate of 4 µL/min for 4 minutes. Peptides were eluted on a 0.075×150 mm column (Reprosil-Pur AQ C18, 3 µm, 120 A) at 300 nL/min. The gradient program is shown in Table 4. Collision energy settings were taken from Skyline. MacLean et al. Bioinformatics. 2010; 26: 966-968. Transitions were acquired at unit/unit resolution with a 10 ms dwell time and 5 ms pause between mass ranges resulting in a cycle time of 0.75 sec. All data were acquired in a blinded fashion.

Method Performance Assessment. A response curve was performed to determine assay linearity and sensitivity in a background matrix of DBS. Punches from normal control DBS (4 punches per sample) were extracted using extraction buffer (ProteaseMax™, ammonium bicarbonate) in triplicate. Trypsin digestion was performed on the extracted protein, and the digests were pooled to create a common background matrix. Heavy stable isotope standards were spiked into the digest and serially diluted to create samples with varying peptide amounts (2000, 200, 12.5, 4.17, 1.39, 0.69 fmol). Two micrograms of each antibody, covalently coupled to magnetic Protein G beads, were added to the background matrix and incubated overnight. The antibody beads were washed with PBS, and the eluate was analyzed by SRM.

Repeatability and intra- and inter-assay precision were characterized by performing measurement of endogenous (light) peptide signal over 5 separate days. Each sample was analyzed in 5 complete process replicates (including punches, extraction, digestion, enrichment, and mass spectrometry) per day.

Finally, stability was assessed by comparing the endogenous (light) peptide detected in DBS stored at room temperature for 1 day and 3 days to peptide detected in DBS at −80° C. in a sealed container. Each sample was processed as described above in process triplicate. Percent difference was calculated at each timepoint.

Interlaboratory Validation of the Analytical Assay. DBS extractions, trypsin digestion, and peptide captures for patient samples were all performed at Laboratory Site 1. Peptide solutions eluted from antibody-beads were split into two 15 µl aliquots for analysis at Laboratory Site 1 and Laboratory Site 2 for inter-laboratory validation of the analytical performance of the assay.

Data Analysis. All SRM data were analyzed and plotted using Skyline (MacCoss Lab Software, open source, Seattle, Wash.). MacLean et al. Bioinformatics. 2010; 26: 966-968. Endogenous target peptide concentrations were quantified by comparing the ratio of the peak area of the signature peptide to its IS added at a known concentration (100 fmol). Statistics were generated using Graphpad Prism (San Diego, Calif.). Receiver operating characteristic (ROC) curves were constructed using Graphpad Prism and a 95% confidence interval.

Results. Peptide Selection and Antibody Development. Selected peptide sequences, molecular weights, parent, and daughter ions are listed in FIG. 1. Fragmentation patterns for the peptides of interest have been previously reported. Kerfoot et al. Proteomics Clin Appl. 2012; 6: 394-402. Affinity-purified polyclonal antibodies (Pacific Immunology, Ramona, Calif.) were generated against all five peptides and pursued for use in human samples because of their ability to successfully capture their target sequences and the absence of background signals brought on by copurified peptide contaminants. Kuhn et al. Clin. Chem. 2009; 55: 1108-1117; Hoofnagle et al. Clin. Chem. 2008; 54: 1796-1804; Whiteaker et al. Mol. Cell Proteomics. American Society for Biochemistry and Molecular Biology; 2011; 10: M110.005645.

Method Performance Assessment. Analytical figures of merit are reported in Table 5. Overall, the linear response spanned a range from 1.39 to 2000 fmol of peptide (FIGS. 2A-2E). The median coefficient of variation (CV) for all points on the response curve was 11%. Lower limits of quantification (LLOQ) were defined by the lowest point to yield a CV <20%. LLOQs ranged from 0.69 to 12.5 fmol. There were five peptides detected above LLOQ in the DBS samples. Across all peptides, the mean intra-assay (i.e. within-day) variability ranged from 11 to 22% while the inter-assay (i.e. between-day) variability ranged from 11 to 43%. Of note, a single peptide (BTK 545-558) showed variability greater than 20% CV

TABLE 5

Analytical performance of signature peptides

| Protein | Peptide | (fmol) | | | Median CV | % Intra-assay CV | Inter-assay CV | Relative Difference | |
|---------|---------|--------|--|--|-----------|------------------|----------------|---------------------|--|
| | | LLOD | ULOD | LLOQ | | | | 24 h | 72 h |
| CD3ε | CD3ε 197-205 | 0.69 | 2000 | 0.69 | 13 | 12 | 11 | 0.17 | 0.09 |
| BTK | BTK 407-417 | 0.69 | 2000 | 1.39 | 10 | 14 | 25 | 0.32 | −0.05 |
| | BTK 545-558 | 0.69 | 2000 | 1.39 | 12 | 22 | 43 | 0.61 | 0.06 |
| WASp | WASp 274-288 | 0.69 | 2000 | 0.69 | 17 | 11 | 12 | −0.04 | 0.01 |
| | WASp 289-304 | 1.39 | 2000 | 4.17 | 7 | 13 | 17 | −0.19 | 0.03 |

Finally, stability was assessed by comparing the endogenous (light) peptide detected in DBS stored at room temperature for 1 day and 3 days to peptide detected in DBS preserved at −80° C. in a sealed container. Results are reported in Table 5. All five peptides had endogenous signal above the LLOQ and little variability over time. Representative multiple reaction monitoring (MRM) chromatograms for each peptide are shown in FIGS. 3A-3E.

Figure 4A:
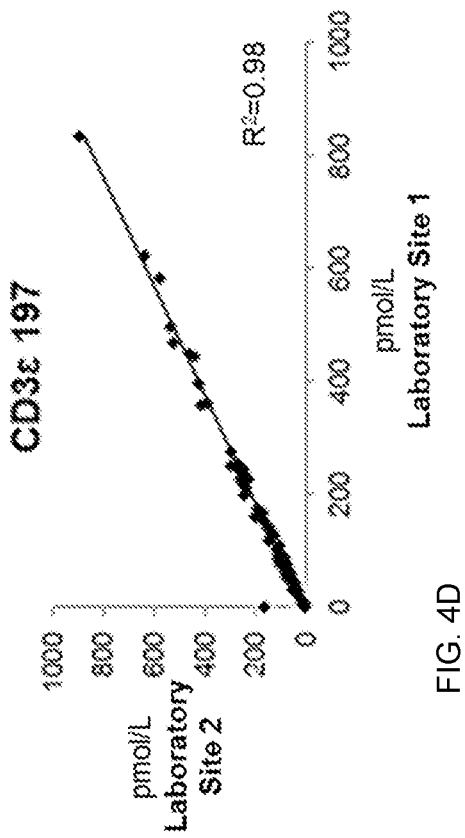
FIGS. 4A-4D. Inter-laboratory correlation in measured PIDD peptide concentrations.
Figure 4B:
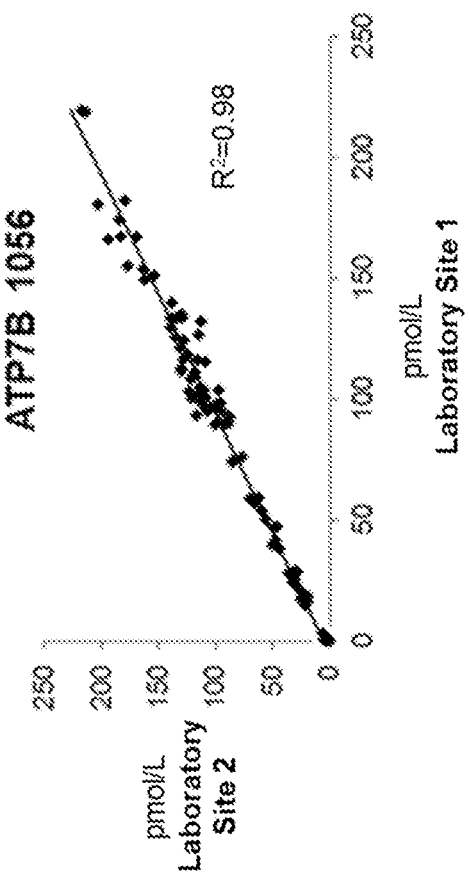
Figure 4C:
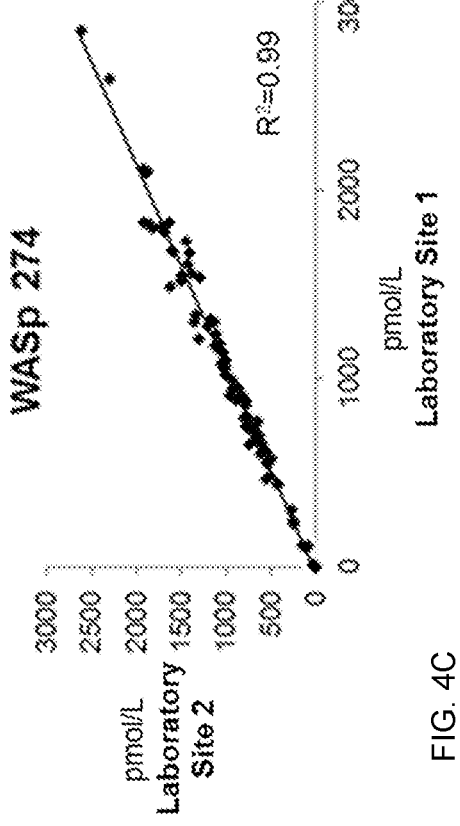
Figure 4D:
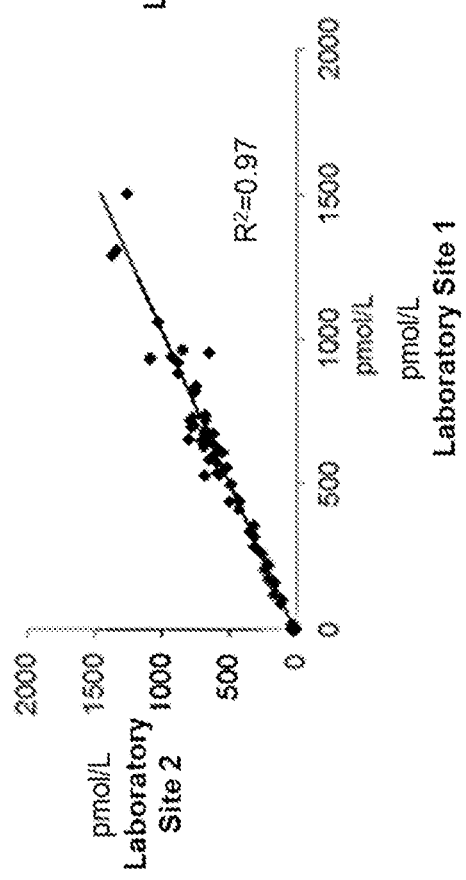
Figure 5:
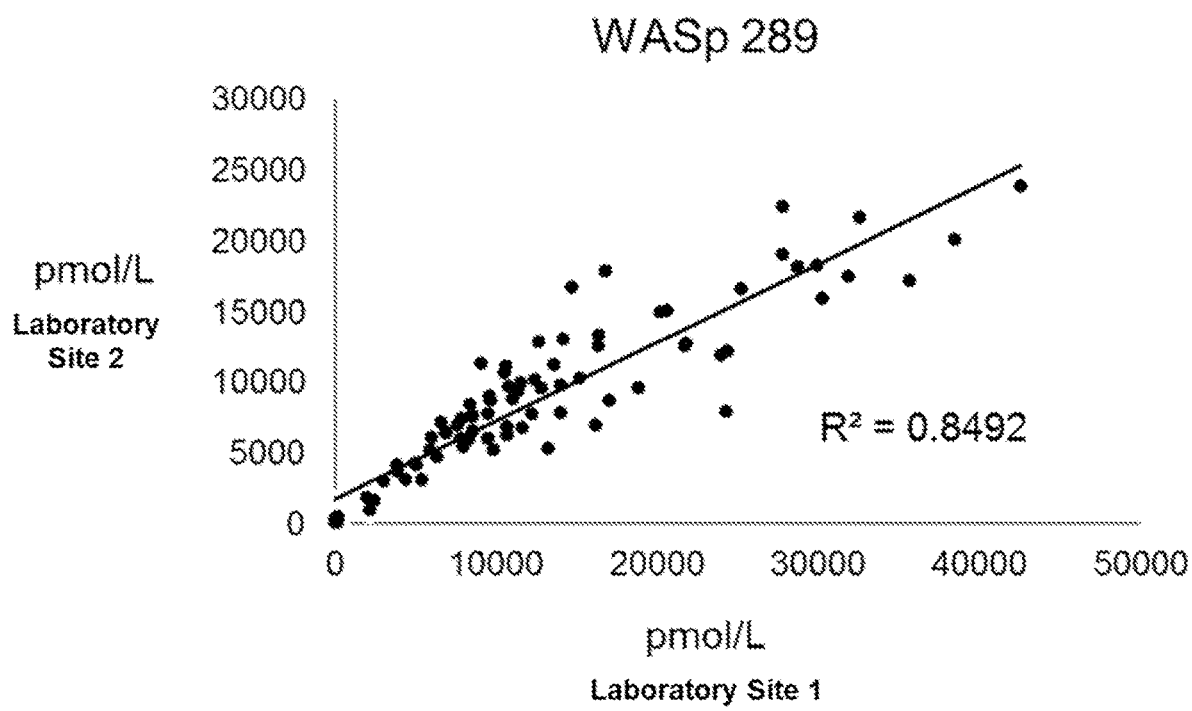
FIG. 5. Inter-laboratory analytical validation of WASp 289.

Overall, there was high level of agreement between the concentrations determined by two separate instrumental analyses. Correlation plots comparing the two measurements, FIGS. 4A-4D, show the linearity of measured concentrations with $R^2$ values 0.97 in the cases of primary peptides CD3ε 197 (FIG. 4B), WASp 274 (FIG. 4A), BTK 407 (FIG. 4C), and ATP7B 1056 (FIG. 4D). The measurements of WASp 289 was found to correlate with $R^2=0.85$ and could therefore be useful as a secondary marker to WASp 274 (FIG. 5).

Peptide Concentrations. After analysis, normal controls were unblinded to define normal ranges for affected patient comparison. The average peptide concentrations from normal controls were as follows (average ±SD): CD3ε=228.68±150.98 pmol/L, WASp 274=1176.96±456.68 pmol/L, WASp 289=10326.98±4513.13 pmol/L, BTK 407=635.09±260.40 pmol/L, and BTK 545=1038.44±465.77 pmol/L. Analysis of signature peptides found statistically significant ($p<0.05$-0.0001) reductions in patient peptide levels relative to control groups in each case (FIGS. 6A-6E). Peptide levels in the majority of affected patients were significantly diminished or absent. For each patient, the concentration of ATP7B 1056 was also determined using previously developed immuno-SRM methodology. Jung et al. 2017, supra. These protein concentrations serve as quality control (QC) measurements and their consistency across samples is used to assess digestion and process reproducibility (FIGS. 3A-3E).

Peptide concentration cutoffs for each PIDD diagnosis were arbitrarily set at −1.25 SD (CD3ε), −2.15 SD (WASp 274), −1.75 SD (WASp 289), −2 SD (BTK 545), and −2.25 SD (BTK 407). Use of these ranges resulted in 2 false positive indications in the normal controls. NC4 and NC20 were indicated to be WAS and SCID patients respectively. NC signature peptide values are shown in FIG. 8. Cutoffs for positive identification of PIDDs are shown in Table 6.

TABLE 6

Cutoffs for signature peptides by concentration

| | BTK 545 (pmol/L) | BTK 407 (pmol/L) | WASp 274 (pmol/L) | WASp 289 (pmol/L) | CD3ε 197 (pmol/L) |
| --- | --- | --- | --- | --- | --- |
| Average | 1038.44 | 635.09 | 1176.96 | 10326.98 | 228.68 |
| SD | 465.77 | 260.40 | 456.68 | 4513.13 | 150.98 |
| Cutoff | 106.90 | 49.19 | 195.10 | 2428.99 | 39.96 |

Using these cutoffs, the specific PIDD diagnosis was predicted for each patient. Predicted diagnoses showed excellent agreement with clinical or genetic diagnoses as shown in FIG. 9. Every molecularly-confirmed case of WAS and BTK was also diagnosed by immuno-SRM analysis. Two patients, Patient 10 and 13, who were clinically diagnosed as agammaglobulinemia, had normal levels of BTK protein by immuno-SRM. Molecularly, no mutations in BTK were identified in these patients. Segundo et al. Front Immunol. Frontiers; 2018; 9: 289. Interestingly, patient 12 with agammaglobulinemia had low levels of BTK protein but no mutations were found in the coding regions of BTK.

Figure 10A:
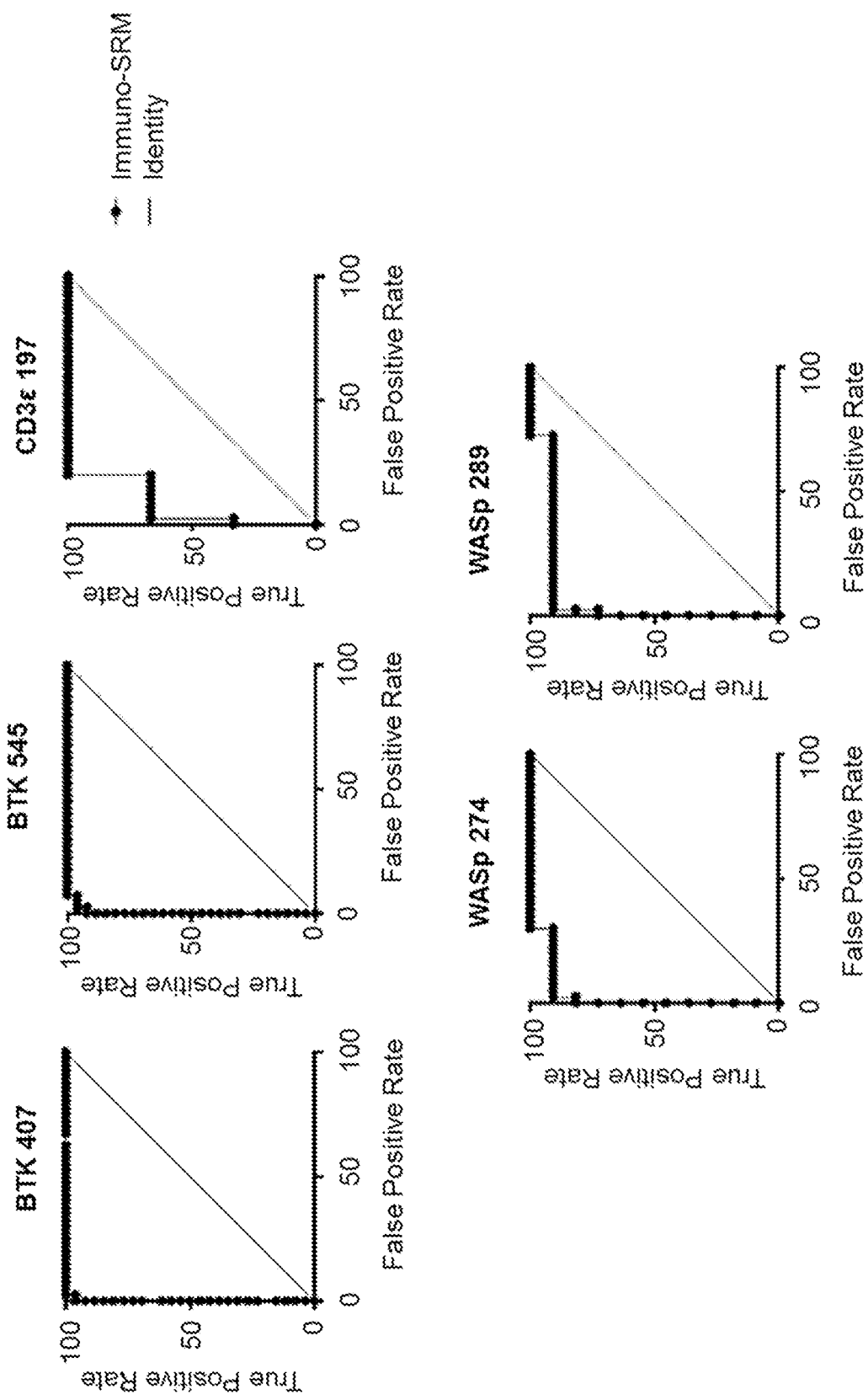

In addition, one case of X-linked hypomorphic SCID, patient 41, was identified as normal by immuno-SRM. For each signature peptide utilized, area under the curve (AUC) analysis of the ROC plots reveal areas from 0.925 to 0.999 with p-values ranging from 0.015-0.0001 (FIGS. 10A, 10B). Overall 97.6% of cases had concordance between the clinical diagnosis and the immuno-SRM assay results. Interesting outlier and discordant cases are discussed further below.

Signature peptide concentrations for NBS lab samples are shown in FIG. 11. Each DBS sample had significant measured peptide concentrations above the previously set diagnostic cutoffs for PIDDs, indicating unaffected status.

Immuno-SRM as a sensitive and specific proteomic screening method for the multiplex detection of patients with three life-threatening PIDD (i.e., SCID, WAS, and XLA) from DBS has been demonstrated. The results clearly differentiate patients with PIDD from normal controls, with low levels of endogenous peptides of transmembrane protein CD3ε and intracellular proteins WASp and BTK correlating with the target diseases (SCID, WAS, and XLA, respectively). These diagnoses can be made in a single run with a total runtime of 20 min or 6.67 min per disease target. The disclosed results also demonstrate peptide stability in DBS, with minimal variability in concentrations after 72 hours of storage at room temperature (Table 5).

The immuno-SRM platform reliably detected endogenous peptide from normal control DBS in this highly multiplexed fashion. Normal control DBS (N=40) were unblinded and utilized to define the normal ranges and potential screen-positive cutoffs (FIG. 8). In clinical laboratories, reference ranges for diagnostic tests are determined by the normal distribution in the general population. Initial cutoffs for screening tests are typically conservative, aiming to detect all true positives without creating an excessively high screen positive rate relative to the incidence of disease (Table 6). However, these cutoffs are continually validated and adjusted in accordance with population-based studies. Given these parameters, the definition of screen-positive results ranged from 1.25-2.25 standard deviation (SD) below the mean for the peptides in this example. The chosen cutoffs generated 2 false positive normal controls, one WAS (NC4) and one SCID (NC20) (FIG. 8). In the case of NC4, rescreening showed WASp levels in the normal range. These preliminary cutoffs are not static and will become better defined as higher numbers of normal controls and patient samples are screened.

Using these cutoffs, every molecularly-confirmed WAS and BTK patient covering a broad range of mutations were positively identified (FIG. 9). As hypothesized, peptide concentrations are reduced in the majority of BTK and WAS cases, independent of genotype. Qasim et al. Br. J. Haematol. 2001; 113: 861-865; Jin et al. Blood. American Society of Hematology; 2004; 104: 4010-4019; Futatani et al. British Journal of Haematology. 2001; 114(1): 141-9. These peptides therefore provide biomarkers for diagnosis and screening. Of the 3 SCID patients available for testing, 2 were positively identified by CD3ε analysis. The third patient, while having low CD3ε levels relative to the majority of the normal controls, was within the defined cutoffs and had a "hypomorphic" mutation in IL2RG known to generate a partially functional protein. This is reflected by the patients total CD3+ T-cell count that was mildly low (800 cells/μL) but not absent as in the classical form of SCID. Since CD3ε is exclusively expressed by CD3+ T cells in peripheral blood, the amount of CD3ε protein present is reflective of total CD3+ T cell counts. Therefore, patients with hypomorphic forms of SCID, patients with "leaky" forms of SCID who have expanded oligoclonal T cell populations, or patients who have expanded maternally-derived T cells, may be missed by the Immuno-SRM approach.

ROC curves were constructed to assess the diagnostic ability of immuno-SRM analysis. These plots relate the true positive rate to the false positive rate with increasingly stringent cutoff values. As diagnostic cutoffs are lowered, the test will have greater ability to note true positives, but this process is also more likely to lead to false positives. A screening test maintaining a high true positive rate and a low false positive rate will therefore lead to graphs lying close to the y axis and a large AUC (FIGS. 10A, 10B). These values indicate high diagnostic accuracy for immuno-SRM analysis of signature peptides of PIDDs.

QC monitoring of digestion and process performance is included in the current immuno-SRM multiplex in the form of ATP7B signature peptide measurements. As not all detected metabolites are helpful NBS targets, the calculation of metabolite ratios and secondary metabolite analysis are employed to improve the sensitivity and specificity of NBS for certain diseases, such as the C3:C2 ratio and 2-methylcitric acid analysis in methylmalonic aciduria. Lindner et al. J. Inherit. Metab. Dis. 2nd ed. 2008; 31: 379-385. In addition, target ratioing can account for variability between samples brought on by a number of factors including sample collection quality, storage, extraction and digestion efficiency, and blood characteristics. Razavi et al. Bioanalysis. Future Science Ltd London, UK; 2016; 8: 1597-1609. Here, ATP7B concentrations were found to be largely consistent across the screened samples (FIG. 7). Absent ATP7B could serve to flag improperly processed or handled specimens. As an initial experiment, each PIDD peptide was compared by ratio to the endogenous concentration of ATP7B in the same sample. The resulting predictions based on peptide concentrations showed complete agreement with the clinical diagnosis, demonstrating immuno-SRM and ATP7B ratioing is an effective and complementary tool for PIDD diagnosis (FIG. 12 and Table 7). These types of ratios have utility in clinical immuno-SRM screening, provided the chosen peptide is proven to be a ubiquitous and significantly invariant signal across a large cohort of samples.

TABLE 7

Cutoffs for Signature Peptides by the Ratios against ATP7B peptide

| | BTK 545 ATP7B Ratio | BTK 407 ATP7B Ratio | WASp 274 ATP7B Ratio | WASp 289 ATP7B Ratio | CD3ε 197 ATP7B Ratio |
|---|---|---|---|---|---|
| Average | 9.31 | 5.71 | 10.71 | 92.47 | 2.12 |
| SD | 4.62 | 2.68 | 5.10 | 48.79 | 1.55 |
| Cutoff | 1.23 | 1.16 | 2.04 | 24.16 | 0.33 |

One case demonstrated the importance of having both primary and secondary signature peptides for proteins of interest. Patient 18 was found to have a positive BTK diagnosis after the analysis of BTK 545 instead of primary marker BTK 407. Levels of BTK 407 were significantly reduced relative to the average, 167.86 versus 642.16 pmol/L, but not quite low enough to trigger a positive screen. In contrast, BTK 545 levels were nearly absent (FIG. 9) because the patient harbors the p.Y551N mutation, which is located within the amino acid sequence 545-558 encompassed by the signature peptide itself. In this case, the multiplexed peptides allowed for confirmation of a positive diagnosis that was initially borderline.

It was notable that normal levels of BTK were found in two clinically defined agammaglobulinemic patients (sample #10 and #13) who lacked mutations in BTK by Sanger sequencing (FIG. 9). These patients therefore likely do not have XLA but may have other autosomal forms of agammaglobulinemia, although broader genetic testing was not performed. Another patient (sample #12) had diminished levels of BTK protein but no identifiable mutation in BTK. This suggests the mutation may have been missed during sequencing of the coding region and intron-exon junctions or the patient may harbor a BTK mutation affecting either the regulatory elements, Poly-adenylation signal, or intronic regions. These cases highlight the clinical utility of immuno-SRM.

Additionally, two samples obtained from the same WAS patient pre- and post-bone marrow transplant (BMT) (samples #29 and 30 in FIG. 9, respectively). Pre-BMT, immuno-SRM analysis identified the patient as having WAS. Post-BMT, the patient was identified as normal. This case highlights the ability of immuno-SRM to follow the therapeutic course of BMT and confirm successful reconstitution of the immune system. A similar principle can be applied to patients with monogenetic disorders undergoing gene therapy.

Overall, the analysis demonstrates that the disclosed assay has a broad linear range and acceptable precision to determine the concentrations of target peptides in DBS (Table 5). Correlation plots show significant concordance of sample analysis by different MS instruments in two separate laboratory facilities (FIGS. 4A-4D and 5). Four of the five peptides, CD3ε 197, WASp 274, BTK 407, and ATP7B 1056 were nearly identical upon analysis with $R^2$ values >0.97. WASp 289 showed slightly more variable performance with an overlap of $R^2=0.85$ and would therefore likely be a secondary marker to WASp 274 when conducting clinical analysis. Additionally, BTK 545 showed a variability greater than 20% CV, which would make it suitable as a secondary marker to BTK 407. These results show that immuno-SRM analysis has clinical application and transferability. In a clinical setting, the use of reference standards and/or calibrators will aid inter-laboratory validation of findings.

Randomly selected samples provided by the NBS laboratory of Washington State were used to test the feasibility of utilizing immuno-SRM analysis in the context of NBS. Due to limited sample availability and to test the utility of signature peptide analysis from a smaller sample, the amount of DBS used was reduced from 1 whole spot to 5 or 6 3-mm punches. Peptides of interest were readily enriched and analyzed with minimal change to sample processing. The concentrations of signature peptides were all greater than the pre-defined cutoffs obtained from analysis of known normal controls (FIG. 11). These patients would therefore be designated as normal. The ability to robustly perform this analysis with a greatly reduced sample input makes immuno-SRM analysis more amenable to translation into NBS. This high-throughput multiplexed method may effectively decrease run time per disease, making it suitable for NBS where current automated methods have a typical run time of less than three minutes. Rashed et al. Clin. Chem. 1997; 43: 1129-1141; Khalid et al. J Med Screen. SAGE Publications, Sage UK: London, England; 2008; 15:112-117. The successful prediction of BTK patients using DBS shipped at ambient temperature via traditional post from Vietnam also highlights the potential utility for diagnostic testing in resource poor settings where collection and shipping of DBS is economical.

NBS has been one of the most successful public health initiatives in modern times but relies on the detection of accumulated metabolites due to downstream enzyme deficiency. However, many genetic disorders including PIDD are characterized by absent or decreased proteins, limiting the scope of current NBS methods. Qasim et al. Br. J. Haematol. 2001; 113: 861-865; Jin et al. Blood. American Society of Hematology; 2004; 104: 4010-4019. By being able to detect PIDD-related peptides from DBS, immuno-SRM bridges this gap in current coverage, allowing for the expansion of NBS to treatable diseases currently without metabolite biomarkers. Immuno-SRM would rapidly provide quantified evidence of protein deficiency and could be performed simultaneously with initial screening and molecular analysis from DBS without further invasive procedures. Quantification of these signature peptides lays the foundation for immuno-SRM as a highly multiplexable screening and diagnostic tool for various congenital diseases.

Example 2. Development of a quantitative assay for NBS of cystinosis using DBS. An immuno-SRM assay was performed as described in Example 1 but using signature peptides for cystinosis. Antibodies recognizing CTNS 115 peptide were developed and used for screening in patient samples. This peptide biomarker provides robust and specific detection of CTNS down to 16.9 pmol/L in DBS (Table 8). Measured concentrations for CTNS range from 5.5-79.8 pmol/L. Levels of SHPK range from 922.3-5787.6 pmol/L. Samples CTNS 00001-CTNS 00013 are blinded and predicted mutational status is based on protein levels evidenced by immuno-SRM. The most common form of cystinosis results from a 57 kb-deletion mutation that results in the loss of CTNS protein as well as the adjacent protein SHPK. Samples in bold are either confirmed or predicted to contain homozygous 57-kb deletion mutations. ND: Not Detected (Table 8).

TABLE 8

Concentrations of CTNS and SHPK proteins in patients and normal control samples.

| Samples | pmol/L CTNS | pmol/L SHPK | Status | Mutation |
| --- | --- | --- | --- | --- |
| CTNS 209 | ND | 1026.193 | Confirmed | 57kb del/c.838A>G; p.K280R |
| CTNS 211 | ND | 3577.042 | Confirmed | c.DNA 18656C<G/ c.DNA 21635C<T |
| CTNS 212 | ND | 4563.733 | Confirmed | c.473T>C; p.L158P/ c.530A>G; p.N177S |
| CTNS 213 | ND | 3717.015 | Confirmed | c.473T>C; p.L158P/ c.530A>G; p.N177S |
| CTNS 243 | ND | ND | Confirmed | 57kb del/57kb del |
| CTNS 252 | ND | ND | Confirmed | 57kb del/57kb del |
| CTNS 00001 | ND | 1426.654 | Blinded | |
| CTNS 00002 | ND | 3941.397 | Blinded | |
| CTNS 00003 | ND | 2736.816 | Blinded | |
| CTNS 00004 | ND | 5787.633 | Blinded | |
| CTNS 00005 | ND | ND | Blinded | Predicted—57kb del/57kb del |
| CTNS 00006 | ND | 991.878 | Blinded | |
| CTNS 00007 | ND | 922.330 | Blinded | |
| CTNS 00008 | 71.87953553 | 469.439 | Blinded | Predicted—Normal Control |
| CTNS 00009 | ND | ND | Blinded | Predicted—57kb del/57kb del |
| CTNS 0010 | ND | ND | Blinded | Predicted—57kb del/57kb del |
| CTNS 00011 | ND | ND | Blinded | Predicted—57kb del/57kb del |
| CTNS 00012 | ND | 1087.535 | Blinded | |
| CTNS 00013 | 79.79928237 | 3401.707 | Blinded | Predicted—Normal Control |
| Normal Controls | | | | |
| NM1 | 46.23052899 | 1177.935 | Confirmed | |
| NM2 | ND | 2000.437 | Confirmed | |
| NM3 | 46.63169607 | 1226.747 | Confirmed | |
| NF1 | ND | 1784.461 | Confirmed | |

Figure 13:
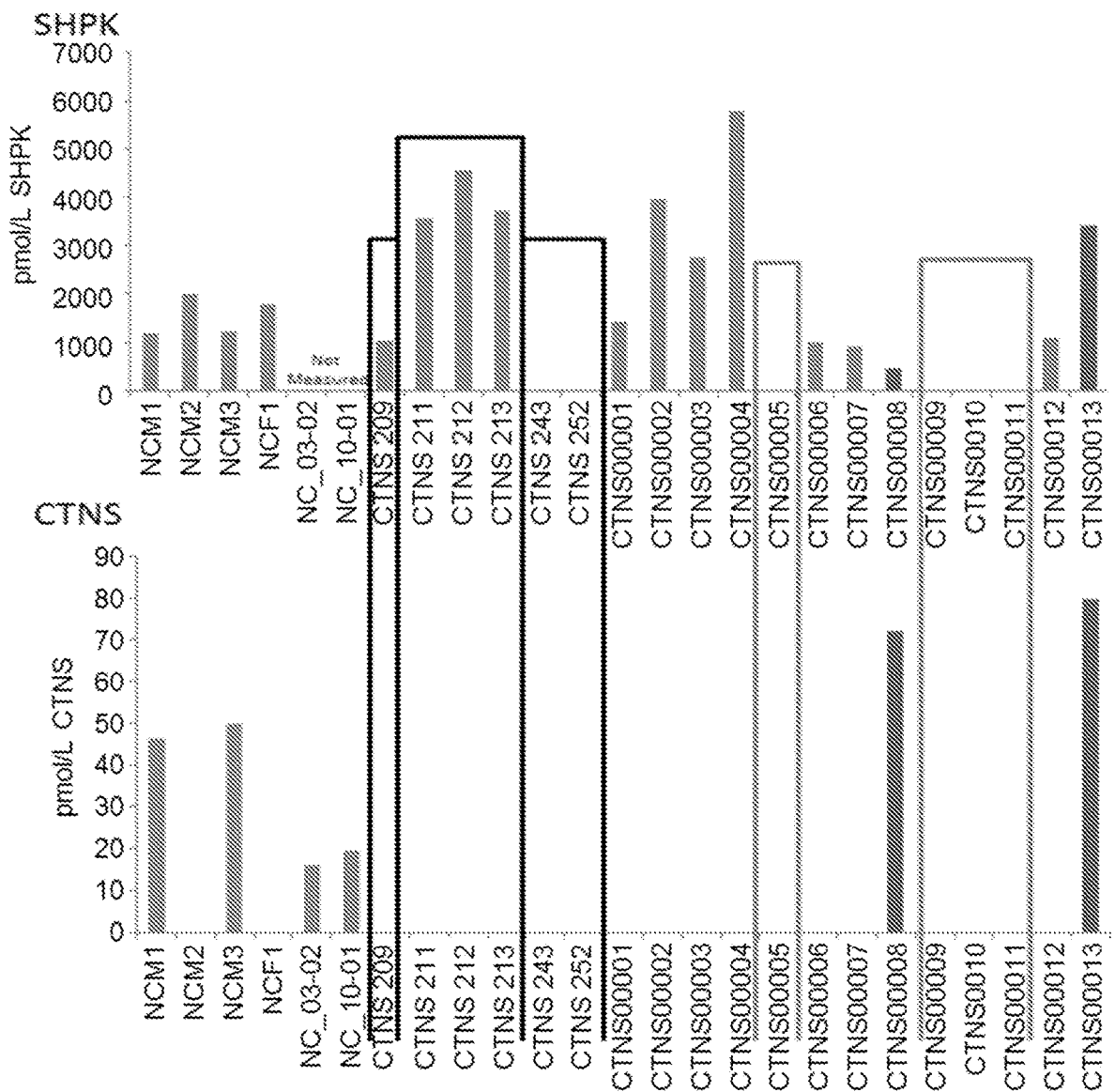
FIG. 13. Concentrations of CTNS and SHPK proteins in patients and normal control samples. Samples outlined in black have confirmed mutational status while samples outlined in gray are predicted to be homozygous for the 57-kb deletion. Samples CTNS 00001-CTNS 00013 are blinded and predicted genotype is based on protein levels evidenced by immuno-SRM.

Example 3. Multiplex immuno-SRM assay of CTNS and SHPK peptides for diagnosis of cystinosis. Multiplexed quantification of peptide biomarkers for CTNS and SHPK from affected and normal control DBS has been achieved in a single experiment, and the results are consistent with underlying patients' genotypes. CTNS 115 peptide was joined with a signature peptide biomarker for sedoheptulokinase (SHPK), SHPK 363, for a multiplexed analysis of cystinosis patient samples. These assays involved the combined use of antibodies for both CTNS 115 and SHPK 363 in the immuno-SRM workflow. Four micrograms of CTNS 115 mAb and 0.25 micrograms of SHPK 363 mAb were used in this analysis. The multiplexed analysis was performed on 4 normal controls, 6 confirmed cystinosis patients, and 13 blinded samples (Table 8). CTNS 115 is completely absent from the known patient samples. In addition, patient samples confirmed to be homozygous for the 57-kb deletion lack SHPK 363 while heterozygous patient samples have varying levels of SHPK protein present. Interestingly, sample CTNS 209 (compound heterozygous for the 57 kb del and c.838A>G; p.K280R) has reduced levels of SHPK relative to samples CTNS 211-213, where no deletion is present (FIG. 13), suggesting correlation between genotype and peptide levels. Of the 13 blinded samples, only two have detectable concentrations of CTNS. These samples are predicted to be normal controls. The assay also accurately predicted that samples 00005 and 00009-00010 were from patients with homozygous deletions as they were lacking in both CTNS and SHPK peptides (Table 8).

Figure 14:
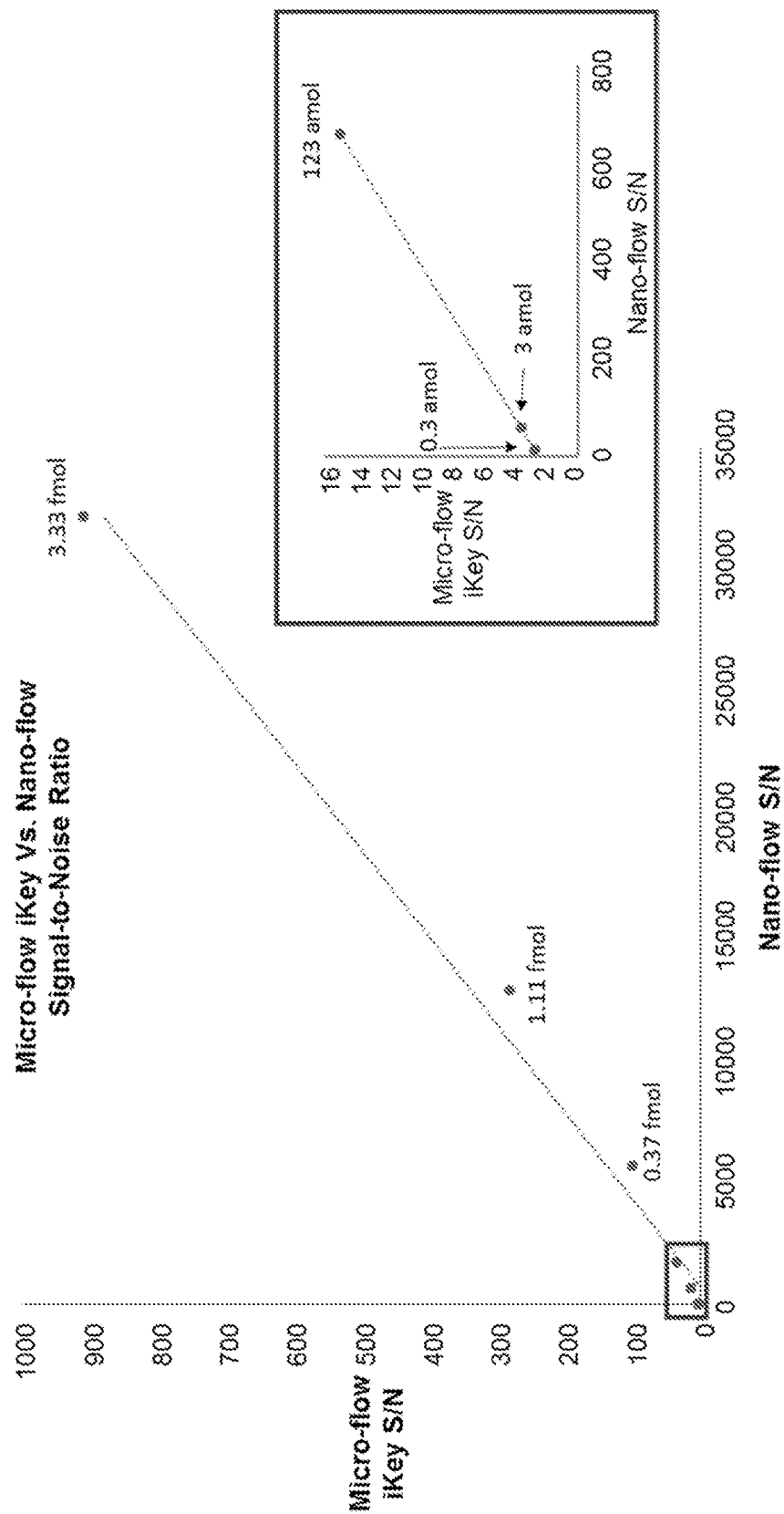
FIG. 14. Comparison of the signal-to-noise (S/N) ratios achieved using both micro-flow ionkey detection methods and new nano-flow methods for CTNS 115. Nano-liter per minute flow rates boost the signal produced by CTNS 115 target peptide.

Based on an initial multiplexed quantification of CTNS 115 and SHPK 363, it was determined that enhanced sensitivity was necessary to increase CTNS 115 signal. This prompted a transition from microliter per minute flow rates during LC-MS/MS detection using a Waters Ionkey system to a more sensitive nanoliter per minute LC-MS/MS assay. This change has greatly enhanced the analytical sensitivity of the measurement. Direct comparison of CTNS 115 when analyzed on both systems finds that nano-flow analysis boosts peptide signal-to-noise (S/N) ratios by 44-fold at 123 amol, 16-fold at 3 amol and 5-fold at 0.3 amol (FIG. 14). This lowers the limit of quantification for CTNS 115 in DBS significantly. In addition, the increased signal was obtained using ½ of the sample typically injected for LC-MS/MS analysis. This allows for a reduction in the amount of DBS sample necessary for future screening.

With this improved assay, 9 blinded samples and 4 normal controls were screened (FIG. 15). Seven of the nine samples were found to be lacking CTNS 115 entirely. Six of those seven were additionally lacking SHPK 363 and were predicted to harbor the 57-kb homozygous deletion mutation which would impair the production of both proteins. The remaining three patients were predicted to be heterozygotes. Two of the predicted heterozygotes were found to have levels of CTNS 115 that were moderately to significantly reduced relative to controls. These predictions were confirmed in six cases, including the three compound heterozygotes. The sequencing of the remaining three patients is ongoing but are predicted to be 57-kb deletion homozygotes by immuno-SRM. Normal controls were found to have appreciable levels of both CTNS 115 and SHPK 363.

Incorporation of validated peptide biomarkers from other proteins will allow for the development of robust clinical reference ranges for process monitoring and analytical quality control downstream. Antibodies for WD (ATP7B protein) and primary immunodeficiency disorders (BTK and WAS proteins) are being incorporated. These ranges will inform the clinical validity of any sample run in a population screening environment, while simultaneously serving as diagnostic screens of their own associated disease states.

Example 4. Additional CTNS and SHPK peptide biomarkers are being developed. Peptides CTNS 120, CTNS 194, SHPK 44, and SHPK 388 showed robust immune response and high polyclonal antibody titer generation. Therefore, anti-CTNS 120, anti-CTNS 194, anti-SHPK 44, and/or anti-SHPK 388 antibodies may be used in the disclosed methods to screen for cystinosis. Polyclonal antibodies for SHPK 388 have been utilized previously to show the presence of this peptide in normal control DBS and its absence in patients' DBS. Monoclonal antibodies for the CTNS 120, CTNS 194, SHPK 44, and SHPK 388 peptide biomarkers will be produced. These markers will be incorporated into existing multiplexed assays.

Example 5. Polyclonal antibodies or monoclonal antibodies were used to enrich for WASp 274 or BTK 407 peptides. Internal standard peptide peak areas were generated upon peptide capture of both WASp 274 (FIGS. 16B and 16D) and BTK 407 (FIGS. 16A and 16C). Peak areas were measured in blank control samples only (i.e. no patient blood, FIGS. 16C, 16D) and in an aggregated set of both patient and blank control samples (FIGS. 16A and 16B). Monoclonal antibodies showed comparable or superior ability to capture and enrich target peptides regardless of sample matrix.

Figure 17:
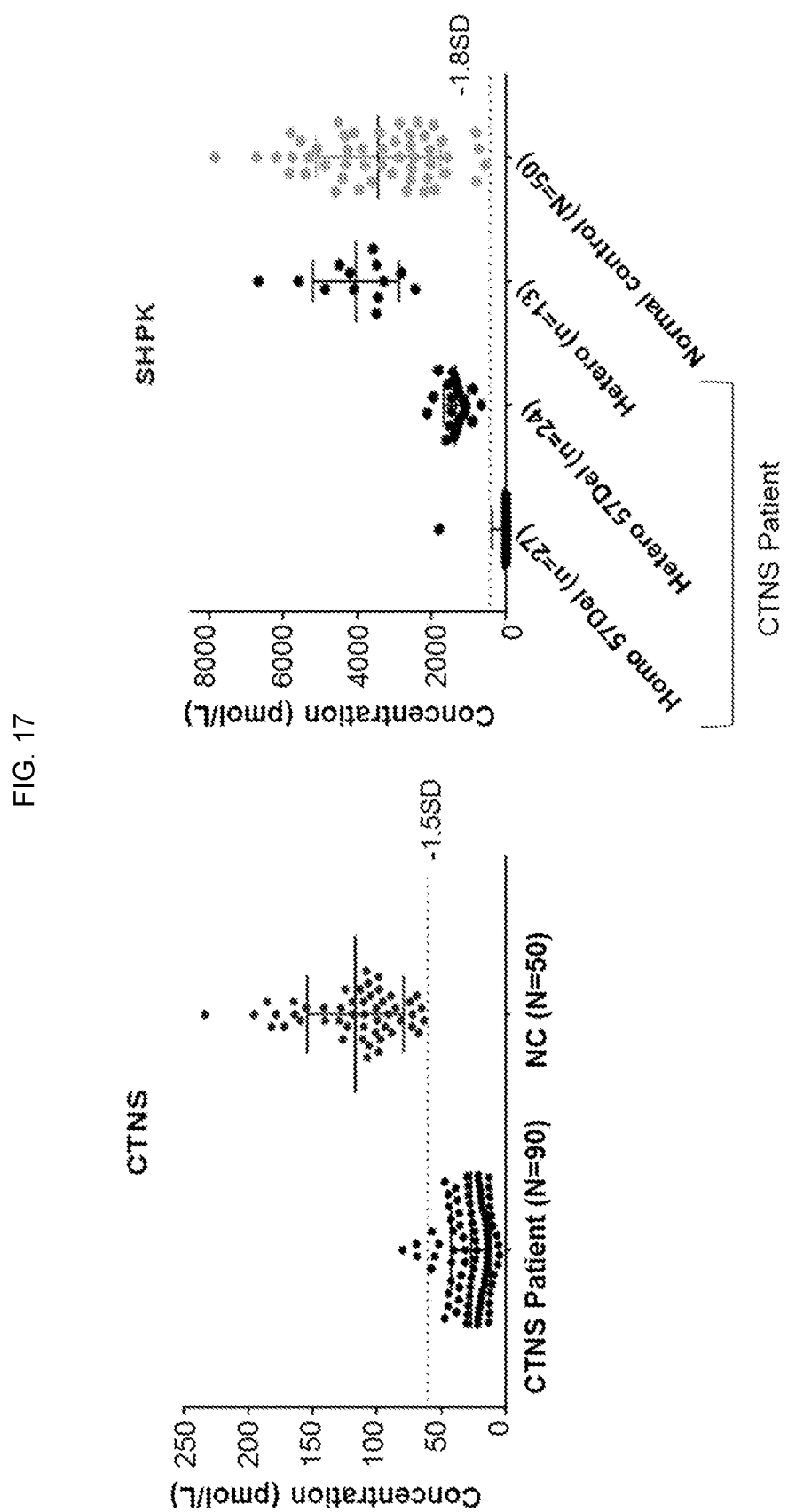
FIG. 17. Signature CTNS 115 and SHPK 363 peptide levels in patients and normal control (NC) samples in a screen for cystinosis. The study is an extension of that shown in FIG. 13 and Table 8.

Example 6. Extension of cystinosis screen. The screen for cystinosis using signature peptide biomarkers CTNS 115 and SHPK 363 as described in Examples 2 and 3 (FIG. 13 and Table 8) was extended to include 90 patients in total. After analysis, cystinosis patients were unblinded to find that CTNS levels were markedly reduced relative to control. The vast majority (87/90, 96.7%) have levels of CTNS 115 below the diagnostic cutoff of 1.5 standard deviations below the normal mean regardless of mutation (FIG. 17). In addition, cystinosis patient mutations could be stratified based on SHPK concentration. Of patients with a known homozygous 57-kb deletion genetic background, 26/27 (96.3%) had non-detectable levels of SHPK 363. These patients fell below a diagnostic cutoff set at 1.8 standard deviations below the normal mean. In addition, compound heterozygous patients with a single 57-kb deletion mutation were found to have significantly lower SHPK 363 levels than those patients with no copies of this deletion mutation. As expected, these patients successfully produced SHPK in proportion to their genotype (FIG. 17).

Figure 18A:
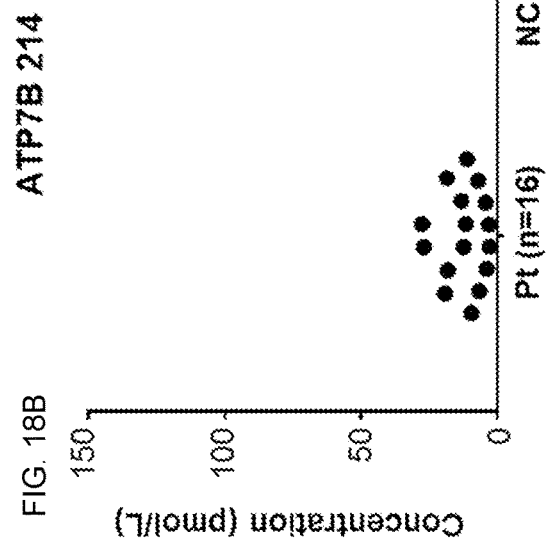
FIGS. 18A-18C. A study of 16 WD patients (NC: normal control; Pt: Wilson disease patients).
Figure 18B:
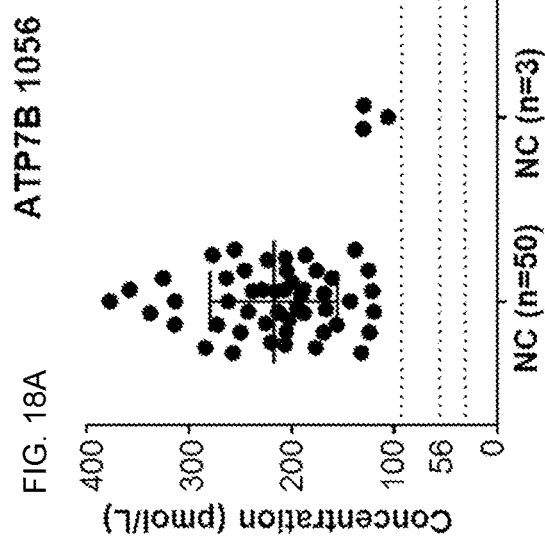
Figure 18C:
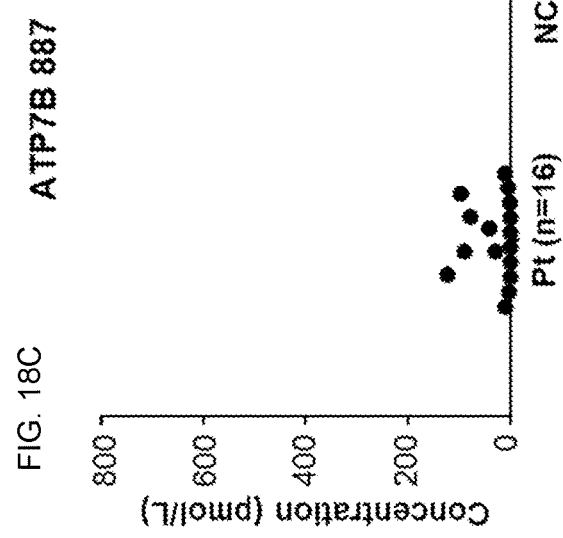

Example 7. A study on WD patients. An immuno-SRM assay was performed as described in Example 1 but using DBS samples from normal controls and 16 WD patients and monoclonal antibodies binding to the following signature peptides for WD: ATP7B 1056, ATP7B 214, and ATP7B 887 (FIGS. 18A-18O). In this study, all 16 WD patients showed reduced or absent level of ATP7B 1056 (less than 2.6 SD below the average of normal control; FIG. 18A). Both ATP7B 214 and ATP7B 887 peptide levels were reduced as well compared to the normal controls (FIGS. 18B, 18C). In each case, every WD patient was identified as having levels of the ATP7B peptide biomarkers that are below that of normal controls. Each has potential utility as an NBS screening tool and together they provide a robust complimentary confirmation of WD status.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the ability to reliably diagnose SCID, WAS, XLA, cystinosis, or Wilson Disease utilizing DBS obtained from a newborn, the antibodies disclosed herein, and immuno-SRM.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

The invention claimed is:

1. A method of detecting signature peptides of severe combined immunodeficiency (SCID), Wiskott-Aldrich syndrome (WAS), and/or X-linked agammaglobulinemia (XLA) in a dried blood spot (DBS) sample, the method comprising: obtaining a DBS sample; digesting proteins from the DBS sample with an enzyme to yield a digested DBS sample comprising peptides; enriching for:
 a CD3ε signature peptide of SCID having the sequence of SEQ ID NO: 1 with an antibody or antigen-binding fragment thereof that binds the CD3ε signature peptide and comprises: a heavy chain variable (VH) domain comprising a complementarity determining region (CDR) 1 of SEQ ID NO: 22, a CDR2 of SEQ ID NO: 23, and a CDR3 of SEQ ID NO: 24, and a light chain variable (VL) domain comprising a CDR1 of SEQ ID NO: 25, a CDR2 of SEQ ID NO: 26, and a CDR3 of SEQ ID NO: 27;
 a first WASp signature peptide of WAS having the sequence of SEQ ID NO: 2 with an antibody or antigen-binding fragment thereof that binds the first WASp signature peptide and comprises: a VH domain comprising a CDR1 of SEQ ID NO: 28, a CDR2 of SEQ ID NO: 29, and a CDR3 of SEQ ID NO: 30, and a VL domain comprising a CDR1 of SEQ ID NO: 31, a CDR2 of SEQ ID NO: 32, and a CDR3 of SEQ ID NO: 33; and
 a BTK signature peptide of XLA having the sequence of SEQ ID NO: 4 with an antibody or antigen-binding fragment thereof that binds the first BTK signature peptide and comprises: a VH domain comprising a CDR1 of SEQ ID NO: 34, a CDR2 of SEQ ID NO: 35, and a CDR3 of sequence GDI, and a VL domain comprising a CDR1 of SEQ ID NO: 36, a CDR2 of SEQ ID NO: 37, and a CDR3 of SEQ ID NO: 38; and
performing liquid chromatography-multiple reaction monitoring mass spectrometry (LC-MRM-MS) on the enriched peptides to determine a concentration for each signature peptide, thereby detecting signature peptides of SCID, WAS, and XLA in the DBS sample.

2. The method of claim 1, wherein the method further comprises detecting signature peptides of cystinosis by enriching for:
 a first cystinosin (CTNS) signature peptide of cystinosis having the sequence of SEQ ID NO: 6 with an antibody or antigen-binding fragment thereof that binds the first CTNS signature peptide and comprises: a VH domain comprising a CDR1 of SEQ ID NO: 39, a CDR2 of SEQ ID NO: 40, and a CDR3 of SEQ ID NO: 41, and a VL domain comprising a CDR1 of SEQ ID NO: 42, a CDR2 of SEQ ID NO: 43, and a CDR3 of SEQ ID NO: 44;
 a second CTNS signature peptide of cystinosis having the sequence of SEQ ID NO: 7 or 8 with an antibody or antigen-binding fragment thereof that binds the second CTNS signature peptide and comprises: a VH domain comprising a CDR1 of SEQ ID NO: 45, a CDR2 of SEQ ID NO: 46, and a CDR3 of SEQ ID NO: 47, and a VL domain comprising a CDR1 of SEQ ID NO: 48, a CDR2 of SEQ ID NO: 49, and a CDR3 of SEQ ID NO: 50;
 a SHPK signature peptide of cystinosis having the sequence of SEQ ID NO: 9 with an antibody or antigen-binding fragment thereof that binds the first SHPK signature peptide and comprises: a VH domain comprising a CDR1 of SEQ ID NO: 51, a CDR2 of SEQ ID NO: 52, and a CDR3 of SEQ ID NO: 53, and a VL domain comprising aCDR1 of SEQ ID NO: 54, a CDR2 of SEQ ID NO: 55, and a CDR3 of SEQ ID NO: 56; and
performing liquid chromatography-multiple reaction monitoring mass spectrometry (LC-MRM-MS) on the enriched first CTNS signature peptide, the enriched second CTNS signature peptide, the enriched SHPK signature peptide to determine a concentration for each signature peptide, thereby detecting signature peptides of cystinosis.

3. The method of claim 2, wherein the method further comprises detecting signature peptides of Wilson Disease (WD) by enriching for:
 an ATP7B signature peptide of WD having the sequence of SEQ ID NO: 11 or 21 with an antibody or antigen-binding fragment thereof that binds the ATP7B signature peptide and comprises: a VH domain comprising a CDR1 of SEQ ID NO: 57, a CDR2 of SEQ ID NO: 58, and a CDR3 of SEQ ID NO: 59, and a VL domain comprising a CDR1 of SEQ ID NO: 60, a CDR2 of SEQ ID NO: 61, and a CDR3 of SEQ ID NO: 62; and
performing liquid chromatography-multiple reaction monitoring mass spectrometry (LC-MRM-MS) on the enriched ATP7B signature peptide, to determine a concentration for the signature peptide, thereby detecting signature peptides of WD.

4. The method of claim 3, further comprising comparing the concentration of each signature peptide to that of a corresponding predetermined threshold concentration.

5. The method of claim 4, further comprising diagnosing the subject with:
 SCID when the concentration of the CD3ε signature peptide is lower than a predetermined threshold concentration or when the CD3ε signature peptide is absent;
 WAS when the concentration of the first WASp signature peptide is lower than corresponding predetermined threshold concentration or when the first WASp signature peptide is absent;
 XLA when the concentration of the BTK signature peptide is lower than corresponding predetermined threshold concentration or when the first BTK signature peptide is absent;
 cystinosis when the concentrations of the first CTNS and/or the second CTNS signature peptides are lower than corresponding predetermined threshold concentrations or when the first CTNS, the second CTNS, and/or the SHPK peptides are absent; and/or WD when the concentration of the ATP7B-signature peptides is lower than corresponding predetermined threshold concentration or when the ATP7B signature peptides is absent.

6. The method of claim 4, wherein the corresponding predetermined threshold concentration for each signature peptide is calculated from a standard deviation of a mean concentration of each signature peptide in DBS from a population of normal control subjects.

7. The method of claim 6, wherein a mean concentration of the CD3ε signature peptide of SCID having the sequence of SEQ ID NO: 1 in DBS from a population of normal control subjects comprises a concentration in a range of 70 pmol/L to 400 pmol/L.

8. The method of claim 6, wherein a mean concentration of the first WASp signature peptide of WAS having the sequence of SEQ ID NO: 2 in DBS from a population of normal control subjects comprises a concentration in a range of 600 pmol/L to 5000 pmol/L.

9. The method of claim 6, wherein a mean concentration of the BTK signature peptide of XLA having the sequence of SEQ ID NO: 4 in DBS from a population of normal control subjects comprises a concentration in a range of 350 pmol/L to 2500 pmol/L.

10. The method of claim 6, wherein a mean concentration of the first CTNS signature peptide of cystinosis having the sequence of SEQ ID NO: 6 in DBS from a population of normal control subjects comprises a concentration in a range of 40 pmol/L to 250 pmol/L.

11. The method of claim 6, wherein a mean concentration of the SHPK signature peptide of cystinosis having the sequence of SEQ ID NO: 9 in DBS from a population of normal control subjects comprises a concentration in a range of 100 pmol/L to 8000 pmol/L.

12. The method of claim 6, wherein a mean concentration of the ATP7B signature peptide of WD having the sequence of SEQ ID NO: 11 or 21 in DBS from a population of normal control subjects comprises a concentration in a range of 90 pmol/L to 400 pmol/L.

13. An assay for screening severe combined immunodeficiency (SCID), Wiskott-Aldrich syndrome (WAS), and/or X-linked agammaglobulinemia (XLA) in a subject, the assay comprising: (i) (A) an antibody or antigen-binding fragment thereof comprising: a heavy chain variable (VH) domain comprising a complementarity determining region (CDR) 1 of SEQ ID NO: 22, a CDR2 of SEQ ID NO: 23, and a CDR3 of SEQ ID NO: 24, and a light chain variable (VL) domain comprising a CDR1 of SEQ ID NO: 25, a CDR2 of SEQ ID NO: 26, and a CDR3 of SEQ ID NO: 27;
  an antibody or antigen-binding fragment thereof comprising: a VH domain comprising a CDR1 of SEQ ID NO: 28, a CDR2 of SEQ ID NO: 29, and a CDR3 of SEQ ID NO: 30, and a VL domain comprising a CDR1 of SEQ ID NO: 31, a CDR2 of SEQ ID NO: 32, and a CDR3 of SEQ ID NO: 33;
  an antibody or antigen-binding fragment thereof that binds a WASp signature peptide of WAS having the sequence of SEQ ID NO: 3; and
  an antibody or antigen-binding fragment thereof comprising: a VH domain comprising a CDR1 of SEQ ID NO: 34, a CDR2 of SEQ ID NO: 35, and a CDR3 of sequence GDI, and a VL domain comprising a CDR1 of SEQ ID NO: 36, a CDR2 of SEQ ID NO: 37, and a CDR3 of SEQ ID NO: 38; or
  (B) the antibody or antigen-binding fragment thereof comprising: a VH domain comprising a CDR1 of SEQ ID NO: 22, a CDR2 of SEQ ID NO: 23, and a CDR3 of SEQ ID NO: 24, and a VL domain comprising a CDR1 of SEQ ID NO: 25, a CDR2 of SEQ ID NO: 26, and a CDR3 of SEQ ID NO: 27;
  the antibody or antigen-binding fragment thereof comprising: a VH domain comprising a CDR1 of SEQ ID NO: 28, a CDR2 of SEQ ID NO: 29, and a CDR3 of SEQ ID NO: 30, and a VL domain comprising a CDR1 of SEQ ID NO: 31, a CDR2 of SEQ ID NO: 32, and a CDR3 of SEQ ID NO: 33; and the antibody or antigen-binding fragment thereof comprising: a VH domain comprising a CDR1 of SEQ ID NO: 34, a CDR2 of SEQ ID NO: 35, and a CDR3 of sequence GDI, and a VL domain comprising a CDR1 of as set forth in SEQ ID NO: 36, a CDR2 of SEQ ID NO: 37, and a CDR3 of SEQ ID NO: 38; and
  (ii) reference signature peptides comprising:
  a CD3ε peptide of SCID having the sequence of SEQ ID NO: 1;
  a WASp peptide of WAS having the sequence of SEQ ID NO: 2;
  a WASp peptide of WAS having the sequence of SEQ ID NO: 3;
  a BTK peptide of XLA having the sequence of SEQ ID NO: 4; and/or
  a BTK peptide of XLA having the sequence of SEQ ID NO: 5.

14. The assay of claim 13 to further screen for cystinosis, the assay further comprising: (iii) an antibody or antigen-binding fragment thereof comprising:
  a VH domain comprising a CDR1 of SEQ ID NO: 39, a CDR2 of SEQ ID NO: 40, and a CDR3 of SEQ ID NO: 41, and a VL domain comprising a CDR1 of SEQ ID NO: 42, a CDR2 of SEQ ID NO: 43, and a CDR3 of SEQ ID NO: 44;
  a VH domain comprising a CDR1 of SEQ ID NO: 45, a CDR2 of SEQ ID NO: 46, and a CDR3 of SEQ ID NO: 47, and a VL domain comprising a CDR1 of SEQ ID NO: 48, a CDR2 of SEQ ID NO: 49, and a CDR3 of SEQ ID NO: 50; and/or
  a VH domain comprising a CDR1 of SEQ ID NO: 51, a CDR2 of SEQ ID NO: 52, and a CDR3 of SEQ ID NO: 53, and a VL domain comprising a CDR1 of SEQ ID NO: 54, a CDR2 of SEQ ID NO: 55, and a CDR3 of SEQ ID NO: 56; and/or (iv) reference signature peptides comprising:
  a CTNS peptide of cystinosis having the sequence of SEQ ID NO: 6;
  a CTNS peptide of cystinosis having the sequence of SEQ ID NO: 7 or 8;
  a CTNS peptide of cystinosis having the sequence of SEQ ID NO: 12;
  a CTNS peptide of cystinosis having the sequence of SEQ ID NO: 13;
  a SHPK peptide of cystinosis having the sequence of SEQ ID NO: 9;
  a SHPK peptide of cystinosis having the sequence of SEQ ID NO: 14; and/or
  a SHPK peptide of cystinosis having the sequence of SEQ ID NO: 15.

15. The assay of claim 14 to further screen for Wilson Disease, the assay further comprising:
  (v) an antibody or antigen-binding fragment thereof comprising: a VH domain comprising a CDR1 of SEQ ID NO:57, of SEQ ID NO: 58, and a CDR3 of SEQ ID NO: 59, and a VL domain comprising a CDR1 of SEQ ID NO: 60, a CDR2 of SEQ ID NO: 61, and a CDR3 of SEQ ID NO: 62; and/or (vi) reference signature peptides comprising:
  an ATP7B peptide of WD having the sequence of SEQ ID NO: 10;
  an ATP7B peptide of WD having the sequence of SEQ ID NO: 11;
  an ATP7B peptide of WD having the sequence of SEQ ID NO: 16;
  an ATP7B peptide of WD having the sequence of SEQ ID NO: 17;
  an ATP7B peptide of WD having the sequence of SEQ ID NO: 18;
  an ATP7B peptide of WD having the sequence of SEQ ID NO: 19;
  an ATP7B peptide of WD having the sequence of SEQ ID NO: 20; and/or
  an ATP7B peptide of WD having the sequence of SEQ ID NO: 21.

16. A recombinant antibody or antigen binding fragment thereof, wherein:
  (A) a variable heavy (VH) domain comprises a complementary determining region (CDR) 1 of SEQ ID NO: 22, a CDR2 of SEQ ID NO: 23, and a CDR3 of SEQ ID NO: 24, and a variable light (VL) domain comprises a CDR1 of SEQ ID NO: 25, a CDR2 of SEQ ID NO: 26, and a CDR3 of SEQ ID NO: 27;
  (B) a VH domain comprises a CDR1 of SEQ ID NO: 28, a CDR2 of SEQ ID NO: 29, and a CDR3 of SEQ ID NO: 30, and a VL domain comprises a CDR1 of SEQ ID NO: 31, a CDR2 of SEQ ID NO: 32, and a CDR3 of SEQ ID NO: 33;
  (C) a VH domain comprises a CDR1 of SEQ ID NO: 34, a CDR2 of SEQ ID NO: 35, and a CDR3 of sequence GDI, and a VL domain comprises a CDR1 of SEQ ID NO: 36, a CDR2 of SEQ ID NO: 37, and a CDR3 of SEQ ID NO: 38;
  (D) a VH domain comprises a CDR1 of SEQ ID NO: 39, a CDR2 of SEQ ID NO: 40, and a CDR3 of SEQ ID NO: 41, and a VL domain comprises a CDR1 of SEQ ID NO: 42, a CDR2 of SEQ ID NO: 43, and a CDR3 of SEQ ID NO: 44;
  (E) a VH domain comprises a CDR1 of SEQ ID NO: 45, a CDR2 of SEQ ID NO: 46, and a CDR3 of SEQ ID NO: 47, and a VL domain comprises a CDR1 of SEQ ID NO: 48, a CDR2 of SEQ ID NO: 49, and a CDR3 of SEQ ID NO: 50;
  (F) a VH domain comprises a CDR1 of SEQ ID NO: 51, a CDR2 of SEQ ID NO: 52, and a CDR3 of SEQ ID NO: 53, and a VL domain comprises a CDR1 of SEQ ID NO: 54, a CDR2 of SEQ ID NO: 55, and a CDR3 of SEQ ID NO: 56; or
  (G) a VH domain comprises a CDR1 of SEQ ID NO: 57, a CDR2 of SEQ ID NO: 58, and a CDR3 of SEQ ID NO: 59, and a VL domain comprises a CDR1 of SEQ ID NO: 60, a CDR2 of SEQ ID NO: 61, and a CDR3 of SEQ ID NO: 62, each according to Kabat numbering.

* * * * *